US012577608B2

(12) United States Patent
Aksel et al.

(10) Patent No.: US 12,577,608 B2
(45) Date of Patent: Mar. 17, 2026

(54) AFFINITY REAGENTS HAVING ENHANCED BINDING AND DETECTION CHARACTERISTICS

(71) Applicant: Nautilus Subsidiary, Inc., Seattle, WA (US)

(72) Inventors: Tural Aksel, Redwood City, CA (US); Torri Rinker, San Francisco, CA (US); Markus Burns, Palo Alto, CA (US); Michael Dorwart, San Jose, CA (US); Rachel Galimidi, Belmont, CA (US); Dmitriy Gremyachinskiy, San Diego, CA (US); Stephen Hendricks, Los Gatos, CA (US); Elvis Ikwa, San Leandro, CA (US); Gregory Kapp, San Carlos, CA (US); Joshua Simon Klein, Pacifica, CA (US); Julia Robinson, East Palo Alto, CA (US); Cassandra Stawicki, Foster City, CA (US); Sonal Tonapi, Santa Clara, CA (US); Parag Mallick, San Mateo, CA (US)

(73) Assignee: Nautilus Subsidiary, Inc., Seattle, WA (US)

( * ) Notice: Subject to any disclaimer, the term of this patent is extended or adjusted under 35 U.S.C. 154(b) by 3 days.

(21) Appl. No.: 18/328,489

(22) Filed: Jun. 2, 2023

(65) Prior Publication Data

US 2024/0018574 A1 Jan. 18, 2024

Related U.S. Application Data

(63) Continuation of application No. 17/523,869, filed on Nov. 10, 2021, now Pat. No. 11,692,217.

(60) Provisional application No. 63/227,080, filed on Jul. 29, 2021, provisional application No. 63/132,170, filed on Dec. 30, 2020, provisional application No. 63/112,607, filed on Nov. 11, 2020.

(51) Int. Cl.
| | |
|---|---|
| *C12Q 1/6832* | (2018.01) |
| *C12Q 1/6834* | (2018.01) |
| *C12Q 1/6876* | (2018.01) |

(52) U.S. Cl.
CPC ......... *C12Q 1/6832* (2013.01); *C12Q 1/6834* (2013.01); *C12Q 1/6876* (2013.01)

(58) Field of Classification Search
CPC .... C12Q 1/68; C12Q 2665/518; C07H 21/00; G01N 33/53
See application file for complete search history.

(56) References Cited

U.S. PATENT DOCUMENTS

| | | | |
|---|---|---|---|
| 5,445,934 A | 8/1995 | Fodor et al. | |
| 6,255,469 B1 | 7/2001 | Seeman et al. | |
| 6,737,236 B1 | 5/2004 | Pieken et al. | |
| 7,252,954 B2 | 8/2007 | Wang et al. | |
| 7,259,258 B2 | 8/2007 | Kozlov et al. | |
| 7,375,234 B2 | 5/2008 | Sharpless et al. | |
| 7,427,678 B2 | 9/2008 | Pieken et al. | |
| 7,598,363 B2 | 10/2009 | Seeman et al. | |
| 7,763,736 B2 | 7/2010 | Sharpless et al. | |
| 7,842,793 B2 | 11/2010 | Rothemund | |
| 8,445,194 B2 | 5/2013 | Drmanac et al. | |
| 9,275,871 B2 | 3/2016 | Sandhu | |
| 9,330,932 B1 | 5/2016 | Sills et al. | |
| 9,466,504 B1 | 10/2016 | Sills et al. | |
| 9,528,984 B2 | 12/2016 | Mitra et al. | |
| 9,717,685 B2 | 8/2017 | Shih et al. | |
| 9,796,749 B2 | 10/2017 | Yin et al. | |
| 9,880,175 B2 | 1/2018 | Mitra et al. | |
| 9,975,916 B2 | 5/2018 | Yin et al. | |
| 10,099,920 B2 | 10/2018 | Shen et al. | |
| 10,175,248 B2 | 1/2019 | Mitra et al. | |
| 10,473,654 B1 * | 11/2019 | Mallick .................. C40B 30/04 | |
| 10,550,145 B2 | 2/2020 | Han et al. | |
| 10,571,473 B2 | 2/2020 | Mitra et al. | |
| 10,604,543 B2 | 3/2020 | Yin et al. | |
| 10,741,382 B2 | 8/2020 | Sills et al. | |
| 10,829,816 B2 | 11/2020 | Staker et al. | |
| 10,921,317 B2 * | 2/2021 | Mallick ................ C12Q 1/6804 | |
| 10,948,488 B2 * | 3/2021 | Mallick .................. C40B 30/04 | |
| 11,125,748 B2 | 9/2021 | Gopinath et al. | |
| 11,282,586 B2 * | 3/2022 | Patel ...................... G16B 40/10 | |
| 11,448,647 B2 * | 9/2022 | Mallick ............ G01N 33/54353 | |
| 11,505,796 B2 * | 11/2022 | Aksel ................... C12Q 1/6834 | |
| 11,545,234 B1 * | 1/2023 | Patel ........................ G16B 5/20 | |
| 11,549,942 B2 * | 1/2023 | Mallick .................. C40B 30/04 | |

(Continued)

FOREIGN PATENT DOCUMENTS

| | | |
|---|---|---|
| WO | 03/095469 A1 | 11/2003 |
| WO | WO-2005065814 A1 | 7/2005 |

(Continued)

OTHER PUBLICATIONS

Anderson et al. Fluorescent structural DNA nanoballs functionalized with phosphate-linked nucleotide triphosphates. Nano Letters 10:788 (Year: 2010).*

Gopinath and Rothemund et al. Engineering and mapping nanocavity emission via precision placement of DNA origami. Nature 535:401—hereinafter "Rothemund" (Year: 2016).*

Lou et al. Antibody-oriented strategy and mechanism for the preparation of fluorescent nanoprobes for fast and sensitive immunodetection. Langmuir et al. (Year: 2019).*

Hattori et al., Next-generation antibodies for post-translational modifications. Current Opinions in Structural Biology 51:145-148 (Year: 2018).*

(Continued)

*Primary Examiner* — Ethan C Whisenant

(74) *Attorney, Agent, or Firm* — Orrick, Herrington & Sutcliffe LLP

(57) ABSTRACT

An affinity reagent, having: (a) a retaining component such as a structured nucleic acid particle; and (b) one or both of (i) one or more label components attached to the retaining component, and (ii) one or more binding components attached to the retaining component.

23 Claims, 76 Drawing Sheets

Specification includes a Sequence Listing.

(56) References Cited

U.S. PATENT DOCUMENTS

| | | | |
|---|---|---|---|
| 11,579,144 B2* | 2/2023 | Mallick | G01N 33/6803 |
| 11,692,217 B2* | 7/2023 | Aksel | C12Q 1/6832 |
| | | | 435/6.11 |
| 11,721,412 B2* | 8/2023 | Patel | G16B 20/20 |
| | | | 702/19 |
| 11,758,201 B2* | 9/2023 | Iguchi | H04N 21/231 |
| | | | 725/115 |
| 11,760,997 B2* | 9/2023 | Aksel | C12Q 1/6834 |
| | | | 506/16 |
| 11,893,807 B2* | 2/2024 | Petrov | G08B 21/06 |
| 11,970,693 B2* | 4/2024 | Mallick | C07K 16/00 |
| 11,993,865 B2* | 5/2024 | Klein | G01N 33/6878 |
| 12,148,509 B2* | 11/2024 | Patel | G16B 40/10 |
| 12,306,093 B2* | 5/2025 | Indermuhle | C12Q 1/6837 |
| 2001/0014668 A1 | 8/2001 | Cassels et al. | |
| 2001/0053519 A1* | 12/2001 | Fodor | G03F 7/265 |
| | | | 536/24.1 |
| 2002/0004587 A1* | 1/2002 | Miller | A61P 35/00 |
| | | | 435/325 |
| 2002/0048823 A1 | 4/2002 | Hu | |
| 2003/0032203 A1* | 2/2003 | Sabatini | G01N 33/543 |
| | | | 436/518 |
| 2003/0049626 A1 | 3/2003 | Jendoubi | |
| 2003/0082560 A1 | 5/2003 | Wang | |
| 2003/0170613 A1 | 9/2003 | Straus | |
| 2005/0095602 A1* | 5/2005 | West | B01F 33/30 |
| | | | 435/6.19 |
| 2007/0218503 A1* | 9/2007 | Mitra | G01N 33/54306 |
| | | | 435/7.1 |
| 2008/0032310 A1 | 2/2008 | Shannon et al. | |
| 2008/0081330 A1* | 4/2008 | Kahvejian | C12Q 1/6869 |
| | | | 435/6.12 |
| 2009/0018028 A1 | 1/2009 | Lindsay et al. | |
| 2010/0069621 A1 | 3/2010 | Maune et al. | |
| 2010/0081134 A1 | 4/2010 | Mirkin et al. | |
| 2010/0151472 A1 | 6/2010 | Nolan et al. | |
| 2010/0298163 A1* | 11/2010 | Juncker | B01L 3/5085 |
| | | | 506/30 |
| 2013/0078226 A1 | 3/2013 | Nakauchi et al. | |
| 2013/0224859 A1 | 8/2013 | Bachelet | |
| 2015/0004193 A1 | 1/2015 | Chang et al. | |
| 2015/0104880 A1 | 4/2015 | Tagawa et al. | |
| 2015/0330974 A1 | 11/2015 | Staker et al. | |
| 2016/0102344 A1* | 4/2016 | Niemeyer | C12Q 1/6837 |
| | | | 536/23.1 |
| 2016/0161472 A1 | 6/2016 | Jungmann | |
| 2017/0327888 A1 | 11/2017 | Ong et al. | |
| 2018/0044663 A1 | 2/2018 | Yan | |
| 2018/0148514 A1 | 5/2018 | Williams | |
| 2019/0032050 A1 | 1/2019 | Guo et al. | |
| 2019/0323002 A1 | 10/2019 | Gopinath et al. | |
| 2019/0331676 A1* | 10/2019 | Hingwing | B01L 3/502715 |
| 2019/0352401 A1* | 11/2019 | de Kruif | C07K 16/18 |
| 2020/0025757 A1* | 1/2020 | Gopinath | G01N 33/54373 |
| 2020/0082914 A1 | 3/2020 | Patel et al. | |
| 2020/0090785 A1 | 3/2020 | Patel et al. | |
| 2020/0232994 A1 | 7/2020 | Mitra et al. | |
| 2020/0286584 A9 | 9/2020 | Patel et al. | |
| 2020/0318101 A1 | 10/2020 | Mallick et al. | |
| 2021/0032775 A1 | 2/2021 | Gopinath et al. | |
| 2021/0071237 A1 | 3/2021 | Taylor et al. | |
| 2021/0101930 A1 | 4/2021 | Gremyachinskiy et al. | |
| 2021/0132053 A1 | 5/2021 | Chandradoss et al. | |
| 2021/0239705 A1 | 8/2021 | Mallick | |
| 2021/0355483 A1 | 11/2021 | Chee et al. | |
| 2021/0356757 A1 | 11/2021 | Weigel et al. | |
| 2021/0390705 A1* | 12/2021 | Egertson | G06T 7/0012 |
| 2022/0050049 A1 | 2/2022 | Indermuhle et al. | |
| 2022/0162684 A1 | 5/2022 | Aksel et al. | |
| 2022/0290218 A1 | 9/2022 | Aksel et al. | |
| 2022/0333215 A1 | 10/2022 | Xu et al. | |
| 2023/0090454 A1 | 3/2023 | Kapp et al. | |

FOREIGN PATENT DOCUMENTS

| | | |
|---|---|---|
| WO | WO-2008016644 A1 | 2/2008 |
| WO | WO-2014078855 A1 | 5/2014 |
| WO | WO-2019059961 A1 | 3/2019 |
| WO | WO-2019133892 A1 | 7/2019 |
| WO | WO-2019211631 A1 | 11/2019 |
| WO | WO-2020106889 A1 | 5/2020 |
| WO | WO-2020223368 A1 | 11/2020 |
| WO | WO-2020254684 A1 | 12/2020 |
| WO | WO-2021074087 A1 | 4/2021 |
| WO | WO-2021087402 A1 | 5/2021 |

OTHER PUBLICATIONS

Jones et al., A procedure for the immunoanalysis of samples containing oneor more members of a group of cross-reacting analytes. Analytica Chimica Acta 336:175-183 (Year: 1996).*

Liang et al.,Development of pan-specific antibody against trimethyllysine for protein research. Proteome Science 6:2 pp. 1-8 (Year: 2008).*

Li et al., Production and Characterization of Monoclonal Antibodies Specific for a Conserved Epitope within Hepatitis C Virus Hypervariable Region 1. Journal of Virology 75, No. 24 (Year: 2001).*

Maerkl, S., Next generation microfluidic platforms for high-throughput protein biochemistry. Current Opinion in Biotechnology 22 :59-65 (Year: 2011).*

Goldman et al.,, Conjugation of Luminescent Quantum Dots with Antibodies Using an Engineered Adaptor Protein To Provide New Reagents for Fluoroimmunoassays. Analytical Chemistry 74: 841-847 (Year: 2002).*

Niemeyer et al.. Detecting antigens by quantitative immuno-PCR. Nature Protocols 2(8) : 1918 (Year: 2007).*

Vasudevan et al., Core-shell quantum dots :Properties and applications . Journal of Alloys and Compunds 636 :395-404 (Year: 2015).*

Yi et al., Silica-Coated Nanocomposites of Magnetic Nanoparticles and Quantum Dots. JACS 127:4990-4991 (Year: 2005).*

Zajac et al.,Protein microarrays and quantum dot probes for early cancer detection. . Colloids and Surfaces B: Biointerfaces 58:309-314 (Year: 2007).*

Ayoglu et al., "Systematic antibody and antigen-based proteomic profiling with microarrays," Expert Reviews, 2011, vol. 11, No. 2, pp. 219-228.

Cahill, D., "Protein and antibody arrays and their medical applications," Journal of Immunological Methods, 2001, vol. 250, pp. 81-91.

Gallotta et al., "Biomarkers Quantification with Antibody Arrays in Cancer Early Detection," Clinics in Laboratory Medicine, 2012, vol. 32, pp. 33-45.

Haab, B., "Antibody Arrays in Cancer Research," Molecular & Cellular Proteomics, 2005, vol. 4, No. 4, pp. 377-383.

Herbath et al., "Exploiting fluorescence for multiplex immunoassays on protein microarrays," Methods and Applications in Fluorescence, 2014, vol. 2, p. 26.

Poetz et al., "Protein microarrays: catching the proteome," Mechanisms of Ageing and Development, 2005, vol. 126, pp. 161-170.

Tomizaki et al., "Protein-Detecting Microarrays: Current Accomplishments and Requirements," ChemBioChem, 2005, vol. 6, pp. 782-799.

Williams et al., "DNA-Origami-Based Fluorescence Brightness Standards for Convenient and Fast Protein Counting in Live Cells," NANO Letters, 2020, vol. 20, pp. 8890-8896.

WO, International Search Report and Written Opinion for International Application No. PCT/US2021/058851, 12 pages, Mar. 4, 2022.

Asseline, U. et al. "Development and Applications of Fluorescent Oligonucleotides" Curr. Org. Chem. (2006) 10:491-518.

Bauer et al., "Anything You Can Do, I Can Do Better: Can Aptamers Replace Antibodies in Clinical Diagnostic Applications?", Molecules 24:4377 (2019).

Bruno, "Predicting the Uncertain Future of Aptamer-Based Diagnostics and Therapeutics", Molecules2015, 20, 6866-6887; doi:10.3390/molecules20046866.

(56) References Cited

OTHER PUBLICATIONS

Chen et al., "Protein Microarrays", BioTechniques, vol. 40, Issue 4, Apr. 2006, pp. 423-429.

Choi, Youngeun et al. "A new reporter design based on DNA origami nanostructures for quantification of short oligonucleotides using microbeads", Scientific Reports, vol. 9, No. 1, Mar. 18, 2019.

Clever, G.H. et al. "DNA-Metal Base Pairs" Angew. Chem. Int. Ed. (2007) 46:6226-6236.

Cox, W.G. et al. "Fluorescent DNA Hybridization Probe Preparation Using Amine Modification and Reactive Dye Coupling" Biotechniques (2004) 36:114-122.

Evanko, D. et al. "Hybridization Chain Reaction" Nat. Methods (2004) 1:186-187.

Fodor er al., Light-Directed Spatially Addressable Parallel Chemical Synthesis, Science, vol. 251, 767-773, 1991.

Galimidi, R.P. et al. "Intra-Spike Crosslinking Overcomes Antibody Evasion by HIV-1" Cell (2015) 160:433-446.

Gardner, A.F. et al. "Therminator DNA Polymerase: Modified Nucleotides and Unnatural Substrates" Front. Mol. Biosci. (2019) 6:28.

Garmendia, C. et al. "The Bacteriophage Phi29 DNA Polymerase, a Proofreading Enzyme" J. Bio. Chem. (1992) 267:2594-2599.

Gyssels, E. et al. "Interstrand Cross-Linking of Nucleic Acids: From History to Recent and Future Applications" Modified Nucleic Acids in Biology and Medicine (2016) pp. 339-369.

He et al., "In situ synthesis of protein arrays", Current Opinions in Biotechnology 19: 4-9 (2008).

He, et al. Fluorescence aptameric sensor for strand displacement amplification detection of cocaine. Analytical chemistry 82.4 (2010): 1358-1364.

Itzkovitz, S. et al. "Validating Transcripts with Probes and Imaging Technology" Nat. Methods (2011) 8:512-519.

Jaekel, A. et al., "Manipulating Enzymes Properties with DNA Nanostructures" Molecules 24(20):3694 (2019).

Janssen, et al. Nucleic acids for ultra-sensitive protein detection. Sensors (Basel). Jan. 21, 2013;13(1):1353-84.

Jensen, J.O. et al. "Nanoengineered Bioplatforms Based on DNA Origami [Point of View]" Proceedings of the IEEE 102:1046-1049 (2014).

Kolb, H.C. et al., "Click Chemistry: Diverse Chemical Function from a Few Good Reactions" Angewandte Chemie International Edition. 40 (11): 2004-2021 (2001).

Krufczik, M. et al. "Combining Low Temperature Fluorescence DNA-Hybridization, Immunostaining, and Super-Resolution Localization Microscopy for Nano-Structure Analysis of ALU Elements and Their Influence on Chromatin Structure" Int. J. Mol. Sci. (2017) 18:1005-1020.

Li Weiping et al., "Multiplex electrochemical origami immunodevice based on cuboid silver-paper electrode and metal ions tagged nanoporous silver chitosan", (2014) Biosensors & Bioelectronics, vol. 56, pp. 167-173.

Lian et al., "Ultrasensitive detection of biomolecules with fluorescent dye-doped nanoparticles", Analytical Biochemistry, vol. 334, 2004, pp. 135-144.

Lundberg, E.P. et al. "A New Fixation Strategy for Addressable Nano-Network Building Blocks" Chem. Comm. (2010) 46:3714-3716.

Musumeci, et al. Fluorescence sensing using DNA aptamers in cancer research and clinical diagnostics. Cancers 9.12 (2017): 174.

Nakamura, S. et al. "Creation of DNA Array Structure Equipped with Heat Resistance by Ultrafast Photocrosslinking" J. Chem. Technol. Biotechnol. (2013) 89:1086-1090.

Nam et al., "Nanoparticle-Based Bio-Bar Codes for the Ultraseneitive Detection of Proteins", Science 301:1884, Sep. 26, 2003.

O'Flaherty, D.K. et al. "Site-Specific Covalent Capture of Human 06-alkylguanine-DNA-alkyltransferase Using Single-Stranded Intrastrand Cross-Linked DNA" Org. Biomol. Chem. (2016) 15:189-196.

Rajendran, A. et al. "Photo-Cross-Linking-Assisted Thermal Stability of DNA Origami Structures and Its Application for Higher-Temperature Self-Assembly" JACS (2011) 133:14488-14491.

Randolph, J.B. et al. "Stability, Specificity, and Fluorescence Brightness of Mulitply-Labeled Fluorescent DNA Probes" Nuc. Acids Res. (1997) 25:2923-2929.

Rothemund, P.W.K., "Folding DNA to create nanoscale shapes and patterns" Nature 440:297-302 (2006).

Sacca et al., "Orthogonal Protein Decoration of DNA Origami", Agnew. Chem. Intl. Ed. 49:9378, 2010.

Sacca et al., "Orthogonal Protein Decoration of DNA Origami", Supporting Information, Agnew. Chem. Intl. Ed. 49:9378, 2010.

Sakamoto et al., "Magnetically Promoted Rapid Immunoreactions Using Functionalized Fluorescent Magnetic Beads: A Proof of Principle", Clinical Chemistry 60(4) : 610-620 et al. (2014).

Schweitzer et al. Immunoassays with rolling circle DNA amplification: a versatile platform for ultrasensitive antigen detection. Proceedings of the National Academy of Sciences. USA. 97(18) (Aug. 2000):10113-10119.

Sinkeldam, R.W. et al. "Fluorescent Analogs of Biomolecular Building Blocks: Design, Properties and Applications" Chem. Rev. (2010) 110:2579-2619.

Spicer, C.D. et al. "Achieving Controlled Biomolecule-Biomaterial Conjugation" Chem. Rev. (2018) 118(16):7702-7743.

Stawicki, C.M. et al., "Modular fluorescent nanoparticle DNA probes for detection of peptides and proteins" Scientific Reports 11:19921 (2021) [doi.org/10.1038/s41598-021-99084-4].

Sun, H. et al. "Coumarin-Induced DNA Ligation, Rearrangement to DNA Interstrand Crosslinks, and Photorelease of Coumarin Moiety" Chem BioChem (2016) 17:1-9.

Tagawa, M. et al. "Stabilization of DNA Nanostructures by Photo-Cross-Linking" Soft Matter (2011) 7:10931-10934.

Tsourkas et al., "Hybridization kinetics and thermodynamics of molecular beacons", Nucleic Acids Research, 2003, vol. 31, No. 4, pp. 1319-1330.

Vauquelin, G. et al., "Exploring avidity: understanding the potential gains in functional affinity and target residence time of bivalent and heterobivalent ligands" British Journal of Pharmacology 168:1771ñ1785 (2013).

Wang, L. et al. "DNA Nanostructures in Cell Biology and Medicine" DNA Nanotechnology for Bioanalysis (2017) pp. 99-127.

Wojcezewski et al., "Fluorescent Oligonucleotides-Versatile Tools as Probes and Primers for DNA and RNA Analysis", Snylett No. 10:1667-1678 (1999).

Zakeri, B. et al., "Peptide tag forming a rapid covalent bond to a protein, through engineering a bacterial adhesin" PNAS 109 (12): E690-E697 (2012).

Zhang, P. et al., "Capturing transient antibody conformations with DNA origami epitopes" Nature Communications 11:3114 (2020).

Zhao, Z. et al., "Organizing DNA origami tiles into larger structures using preformed scaffold frames" NanoLetters 11:2997-3002 (2011).

Zlauddin et al., "Microarray of cells expressing defined cDNAs", Science, 411:107 (2001).

Office Action in EP21820758.7, mailed Sep. 24, 2024, 6 pages.

Examination Report issued by the EPO on Oct. 15, 2025, in corresponding EP application No. 21820758.7, 6 pages.

* cited by examiner

210

220

215

225

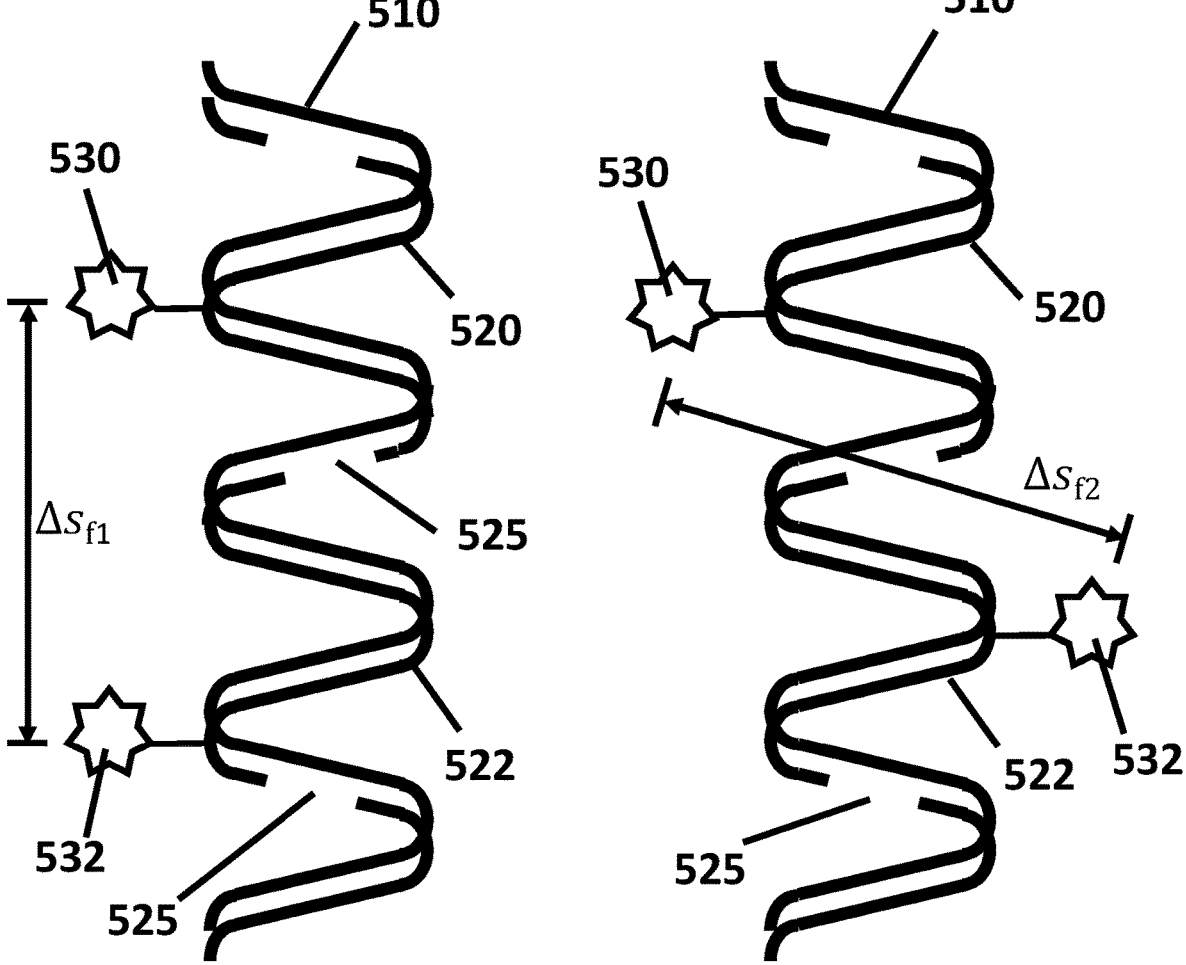
FIG. 5A                              FIG. 5B

620

630          610

630

610

620

630          610          620

630          610

620

610

630                                                            620

630

610

620

1170

1160

1150

1140

1130

1190

1110

1120

1140

1130

1190

1170

1160

1150

1110

1120

| | | |
|---|---|---|
| 20 | 26 | 23 |
| 22 | 36 | 15 |
| 22 | 18 | 27 |

| | | |
|---|---|---|
| 64 | 83 | 68 |
| 73 | 225 | 59 |
| 66 | 78 | 67 |

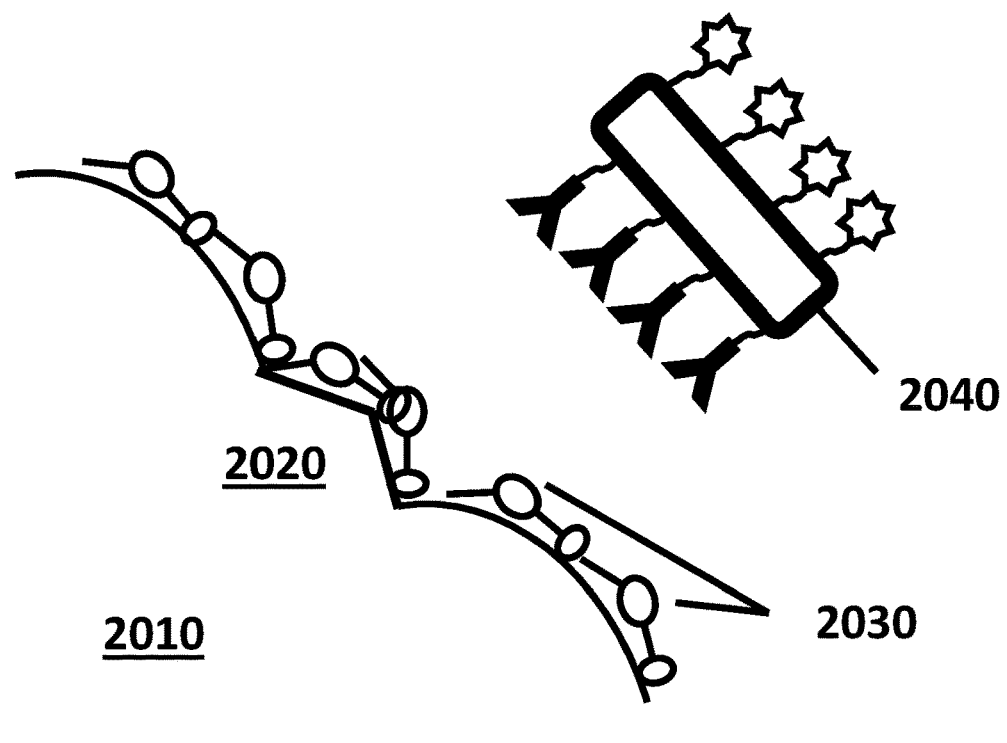
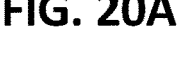
FIG. 20A
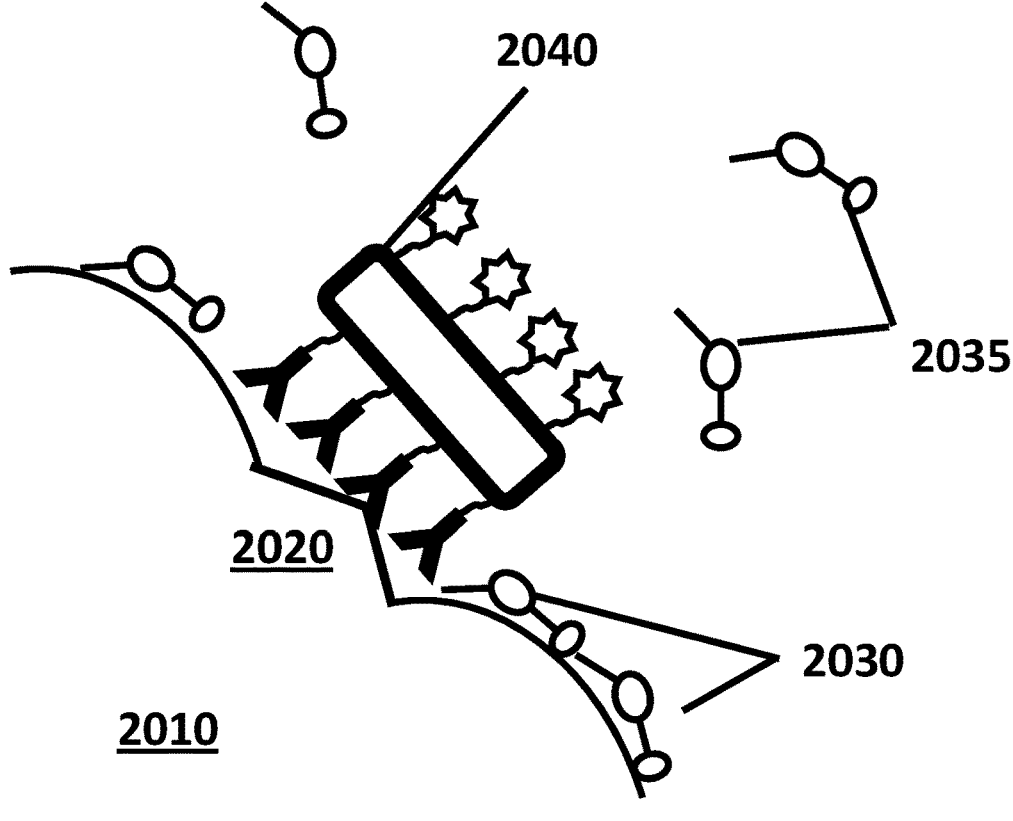
FIG. 20B

2110

2140

2130

2120

2150

EC50 = 60 nM

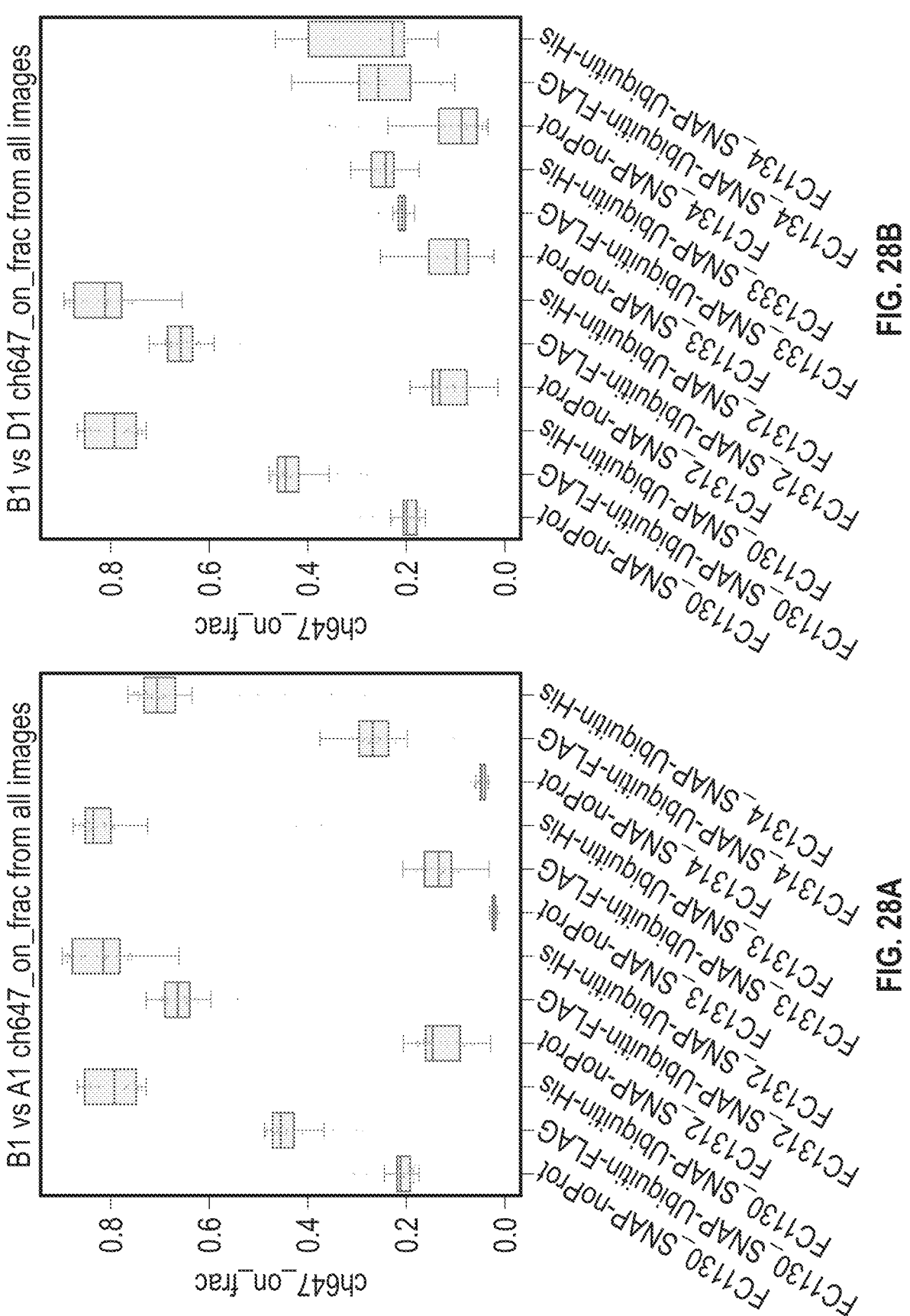

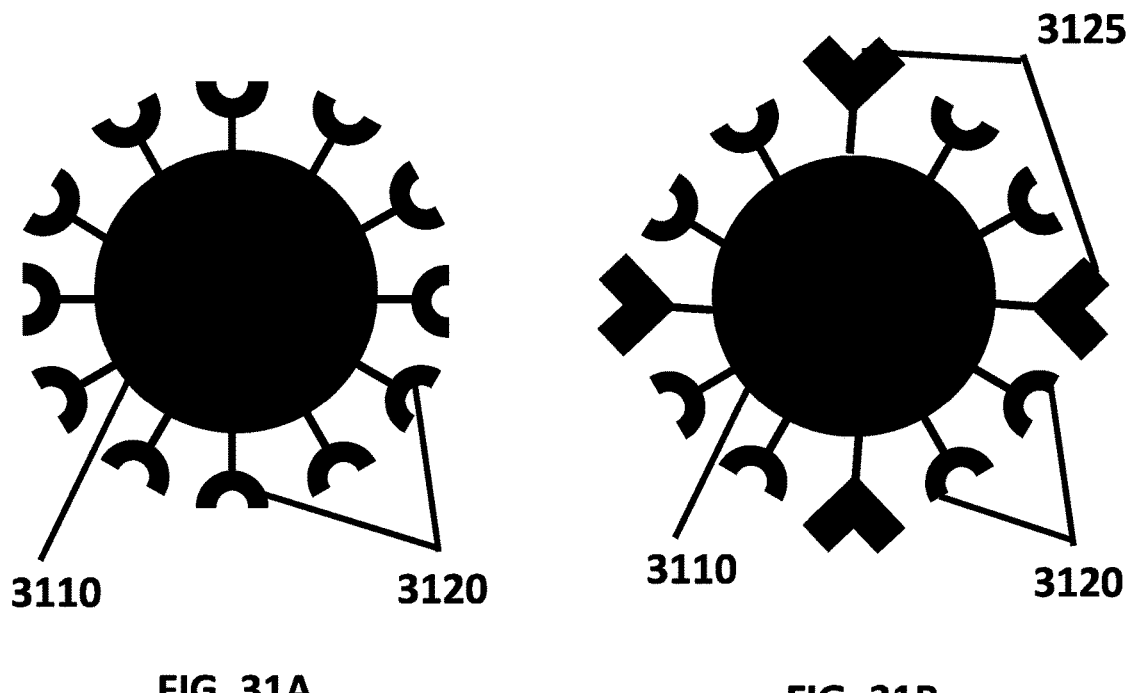
3125
3110                    3120                    3110                    3120
FIG. 31A                              FIG. 31B
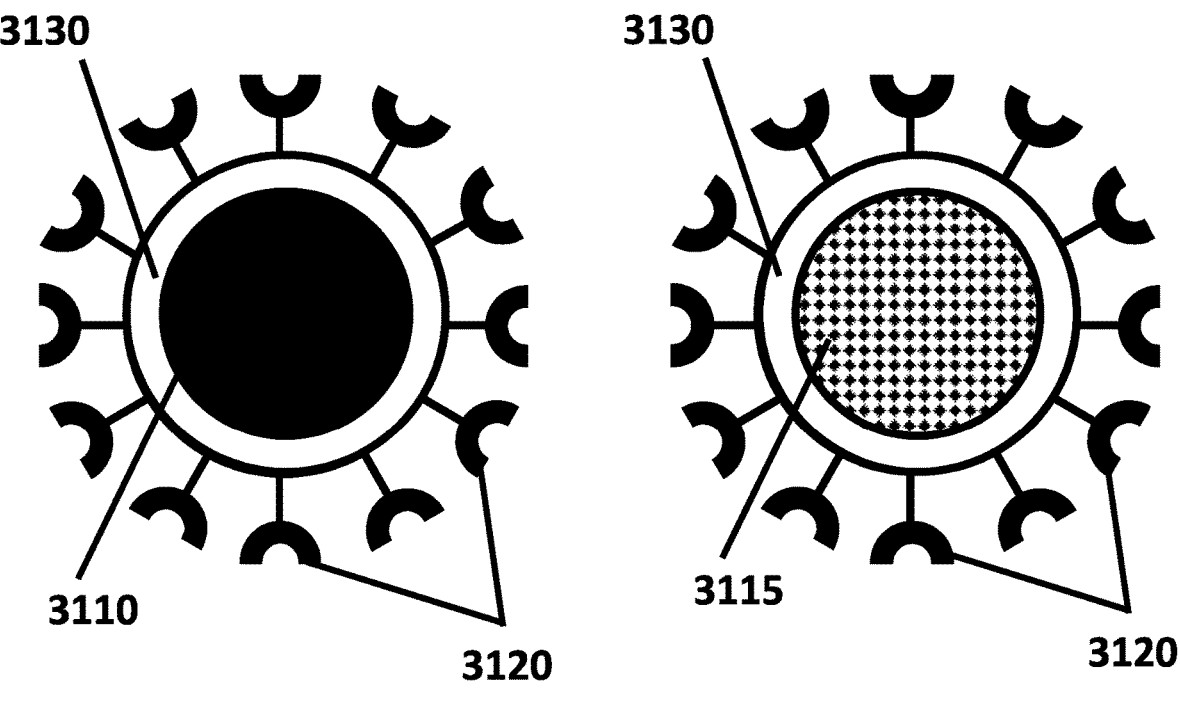
3130                                  3130
3110                                  3115
3120                                  3120
FIG. 31C                              FIG. 31D

3222

3224                                                                    3220

3222          3235

3235

3224                                                                    3220

3230

3240

3226

3240

3235                    3235

3240

3230

3520

3510

3520

3510

3515

3930

3910

3920

3930          3910

3920

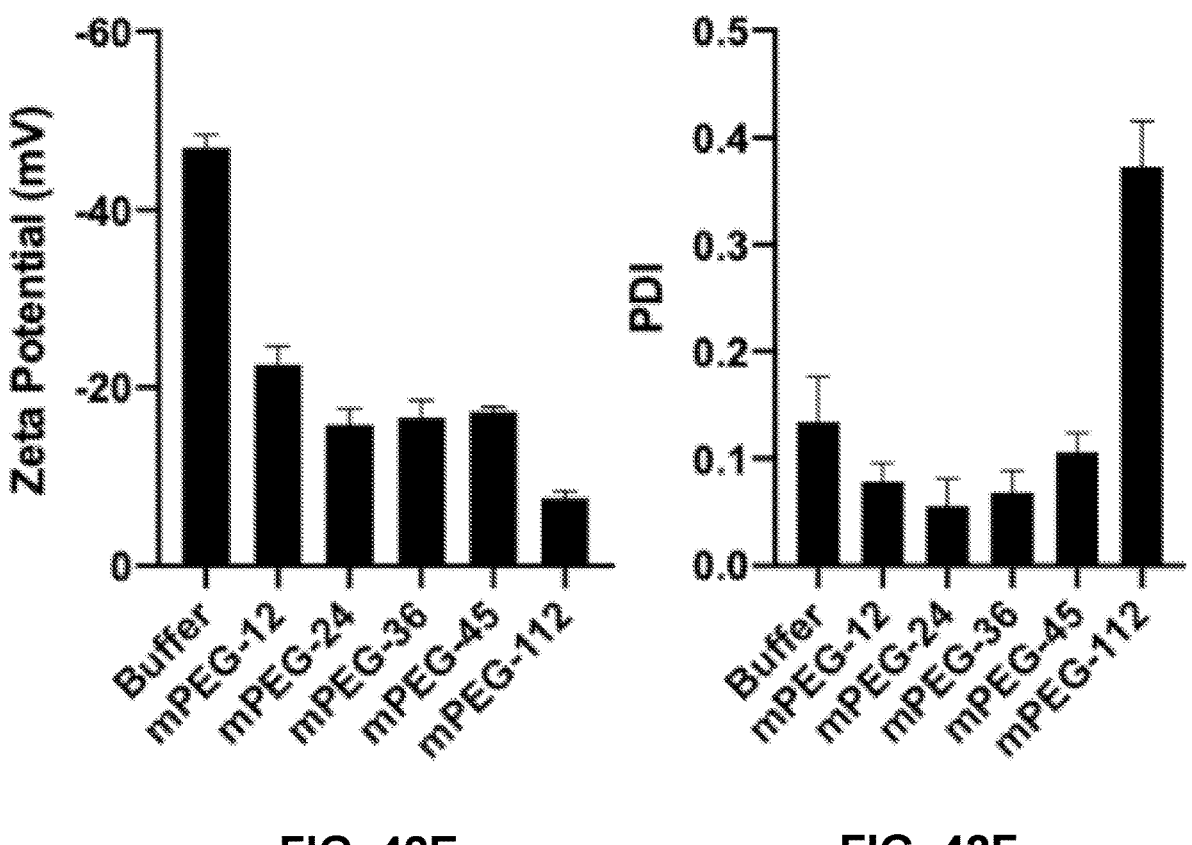
FIG. 42E                    FIG. 42F

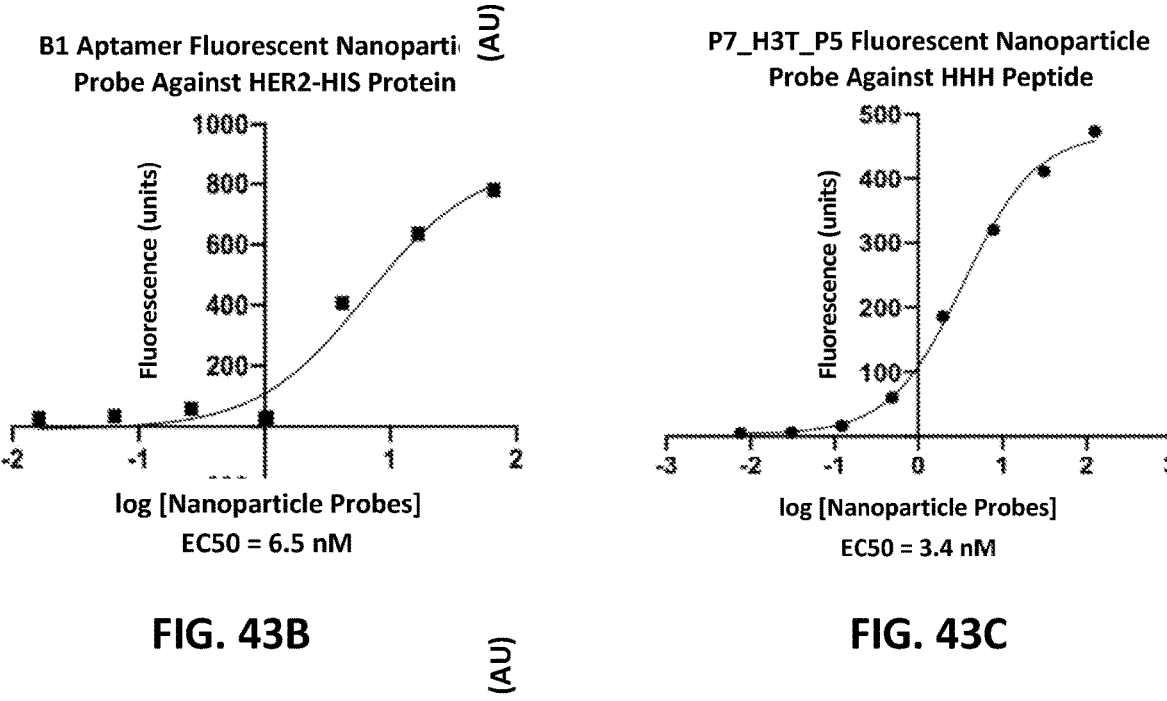
FIG. 43B
FIG. 43C
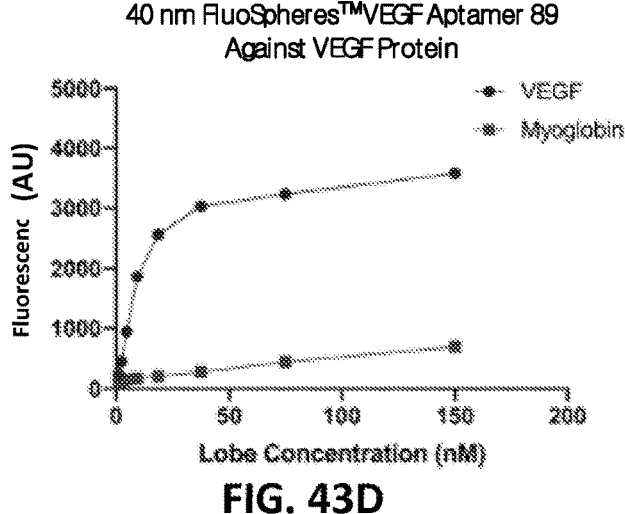
FIG. 43D

Streptavidin, Alexa Fluor™Conjugate
with B1 Against HHH Peptide
0, 21 Days at 4°C
B1 Aptamer Fluorescent Nanoparticle Probe
Against HHH Peptide
1, 8, 12, 16 Weeks at 4°C
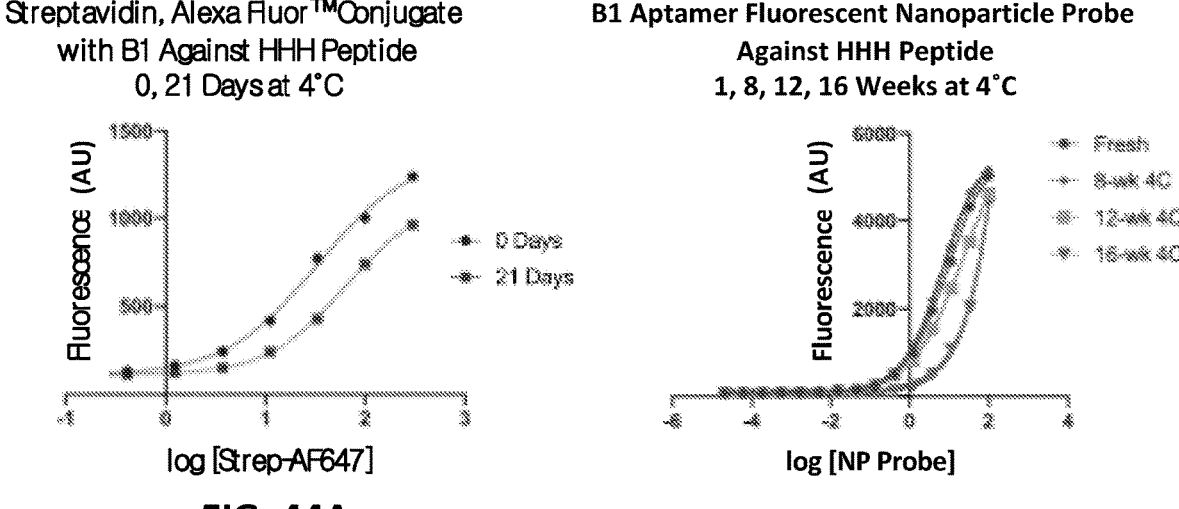
log [Strep-AF647]
FIG. 44A
log [NP Probe]
FIG. 44B
Streptavidin, APC Labeled B1
Against HHH Peptide
0, 21 Days at 4°C
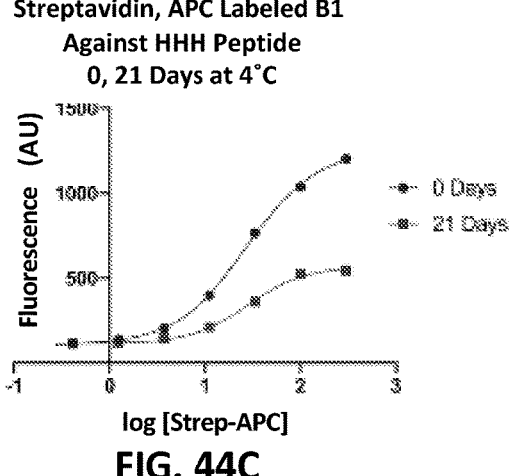
log [Strep-APC]
FIG. 44C

1

Streptavidin, APC Labeled B1
Against HHH Peptide log [Strep-APC]
EC50 = 29.9 nM

SureLight™ APC Labeled B1
Against HHH  Peptide log [SureLight-P3]
EC50 = 2.3 nM

A dsDNA-647 Lobe Concentration

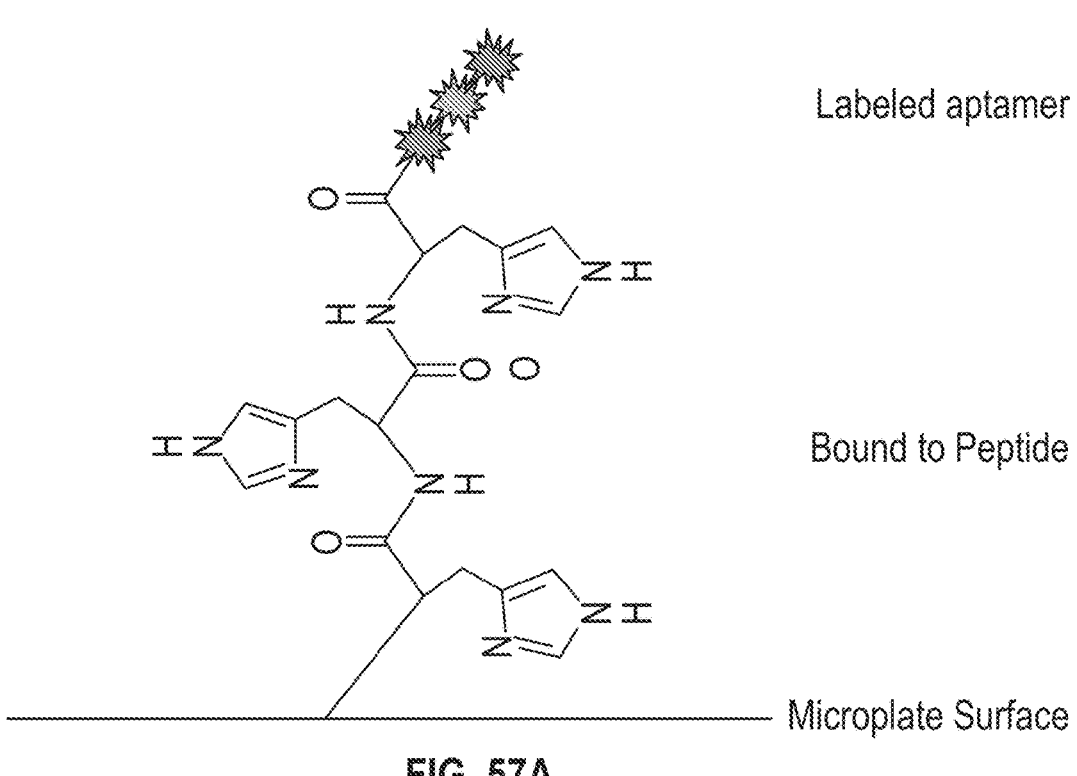
Labeled aptamer
Bound to Peptide
Microplate Surface
FIG. 57A
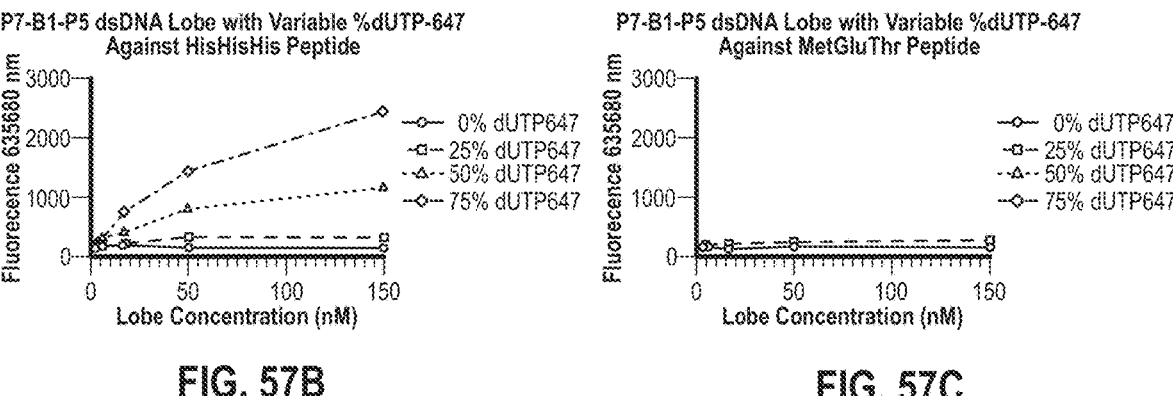
P7-B1-P5 dsDNA Lobe with Variable %dUTP-647 Against HisHisHis Peptide
0% dUTP647
25% dUTP647
50% dUTP647
75% dUTP647
FIG. 57B
P7-B1-P5 dsDNA Lobe with Variable %dUTP-647 Against MetGluThr Peptide
0% dUTP647
25% dUTP647
50% dUTP647
75% dUTP647
FIG. 57C
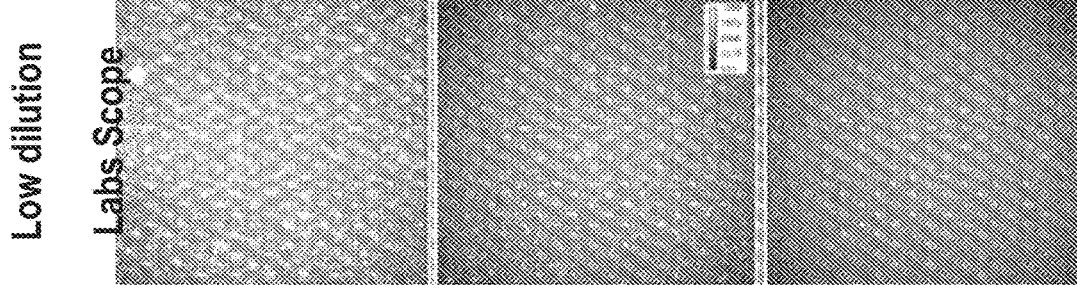
Low dilution          Labs Scope
FIG. 57D

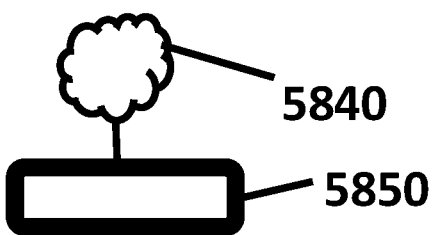
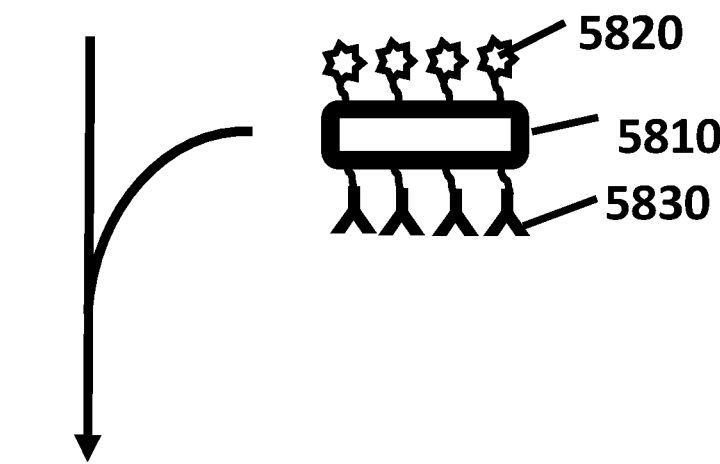
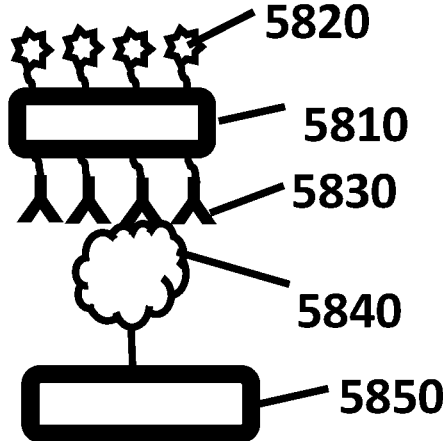
FIG. 58A

AFFINITY REAGENTS HAVING ENHANCED BINDING AND DETECTION CHARACTERISTICS

CROSS-REFERENCE

This application is a continuation of U.S. application Ser. No. 17/523,869, filed Nov. 10, 2021, which claims the benefit of priority to U.S. Provisional Application No. 63/112,607, filed on Nov. 11, 2020, U.S. Provisional Application No. 63/132,170, filed on Dec. 30, 2020, and U.S. Provisional Application No. 63/227,080, filed on Jul. 29, 2021, each of which is incorporated herein in its entirety by reference.

SEQUENCE LISTING

The instant application contains a Sequence Listing which has been submitted electronically in XML format and is hereby incorporated by reference in its entirety. Said XML copy, created on Mar. 1, 2023, is named 50109_4003.xml and is 22,530 bytes in size.

BACKGROUND

Affinity reagents include a broad class of chemical reagents that form detectable interactions with other molecules. Affinity reagents may include binding reagents that form temporary or reversible binding pairs with other molecules. Affinity reagents may be utilized to characterize the structure and properties of biomolecules, such as polypeptides, nucleic acids, and polysaccharides. Affinity reagents may include detectable labels for the purpose of visualizing the affinity reagent. Frequently these detectable labels are fluorescent labels. There is a need for labeled affinity reagents that produce strong and reliable signals including, for example, signals strong enough for single molecule detection, and reliable enough for accurate quantification. There is also a need for affinity reagents that bind avidly to target molecules, for example, with sufficient avidity to support detection of target molecules at single molecule resolution.

SUMMARY

The present disclosure provides an affinity reagent, having: (a) a retaining component; and (b) one or both of (i) one or more label components, and (ii) one or more binding components. Optionally, one or more of the label components is attached to the retaining component. As an alternative or additional option, one or more of the binding components is attached to the retaining component. The retaining component can include a structured nucleic acid such as a nucleic acid origami.

An affinity reagent can include: (a) a retaining component; (b) one or more label components, and (ii) a plurality of binding components. Optionally, the affinity reagent has an equilibrium dissociation constant that is less than the equilibrium dissociation constant of any one of the plurality binding components for the binding partner, or wherein the detectable probe has a dissociation rate constant that is less than the dissociation rate constant of any of the plurality of binding components for the binding partner.

An affinity reagent can include: (a) a retaining component; (b) a plurality of label components, and (ii) one or more binding components.

An affinity reagent of the present disclosure can be configured as a detectable probe. A detectable probe can include: (a) a retaining component; (b) one or more label components; and (c) two or more binding components attached to the retaining component, wherein the detectable probe has an equilibrium dissociation constant for a binding partner that is less than the equilibrium dissociation constant of any of the two or more binding components for the binding partner, or wherein the detectable probe has a dissociation rate constant for a binding partner that is less than the dissociation rate constant of any of the two or more binding components for the binding partner.

The present disclosure further provides a method of detecting an analyte, including the steps of: (a) contacting an analyte with a detectable probe, wherein the detectable probe comprises (i) a retaining component; (ii) one or more label components, and (iii) one or more binding components; and (b) acquiring a signal from the one or more label components, thereby detecting the analyte.

Also provided is a method of detecting an analyte, including steps of (a) contacting an analyte with a first detectable probe, the first detectable probe including: (i) a first retaining component, (ii) one or more label components, and (iii) a first set of two or more binding components attached to the retaining component, wherein at least one of the binding components in the first set binds to a first epitope in the analyte; (b) acquiring a signal from the one or more label components of the first detectable probe; (c) contacting the analyte with a second detectable probe, the second detectable probe including: (i) a second retaining component (ii) one or more label components, and (iii) a second set of two or more binding components attached to the retaining component, wherein at least one of the binding components in the second set binds to a second epitope in the analyte, the second epitope having a different chemical composition compared to the first epitope; and (d) acquiring a signal from the one or more label components of the second detectable probe, thereby detecting the analyte. Optionally, the second retaining component has a structure that is substantially the same as the first retaining component.

The present disclosure also provides a composition, including: (a) a probe having a first structured nucleic acid particle attached to a binding component; and (b) an analyte having a second structured nucleic acid particle attached to an epitope for the binding component, wherein the probe is attached to the analyte via binding of the binding component to the epitope. In particular configurations one or both of the structured nucleic acid particles include nucleic acid origami.

Also provided is a composition, including: (a) a plurality of different probes, each of the different probes having a first structured nucleic acid particle attached to a binding component, each of the different probes having a different binding component; and (b) a plurality of different analytes, each of the different analytes having a second structured nucleic acid particle attached to an epitope for a different binding component, wherein the different probes are attached to the different analytes via binding of a different binding component of the plurality of different probes to an epitope of the plurality of different analytes. Optionally, the first structured nucleic acid particle is substantially the same for the different probes. As a further option, the second structured nucleic acid particle can be substantially the same for the different analytes. In particular configurations one or both of the structured nucleic acid particles include nucleic acid origami. The nucleic acid origami of the different probes can optionally include the same scaffold nucleic acid structure, whether or not staple structures are the same or different for the different probes. Alternatively or additionally, the nucleic acid origami of the different analytes can optionally include the same scaffold nucleic acid structure, whether or not staple structures are the same or different for the different analytes.

Described herein is a detectable probe comprising a retaining component including one or more label components (e.g. detectable labels), and two or more binding components coupled to the retaining component, where the detectable probe has a dissociation constant for a binding partner that is less than a dissociation constant of any of the two or more binding components for the binding partner.

In some configurations, one or more label components of a detectable probe are coupled to the retaining component of the detectable probe. In some embodiments, the retaining component includes a scaffold having a closed single-stranded nucleic acid, and a plurality of oligonucleotides hybridized to the scaffold.

In some configurations, a retaining component in a detectable probe or affinity reagent includes a scaffold nucleic acid. A scaffold can include a strand from a phage genome or a plasmid, for example, from an M13 phage genome. Optionally, a retaining component can further include a plurality of oligonucleotides. The oligonucleotides can be annealed to the scaffold, for example, to form staples in an origami structure. In some configurations, an oligonucleotide of the plurality of oligonucleotides can include at least one non-natural nucleotide. Optionally, a non-natural nucleotide in an oligonucleotide can have a functional group, such as a functional group used in a bioorthogonal or click reaction. In some configurations, one, two or more binding components are attached to one or more oligonucleotides of the plurality of oligonucleotides. In some configurations, one, two or more label components are attached to one or more oligonucleotides of the plurality of oligonucleotides. In some configurations, a scaffold can include at least one non-natural nucleotide. Optionally, a non-natural nucleotide in a scaffold can have a functional group, such as a functional group used in a bioorthogonal or click reaction. In some configurations, one, two or more binding components are attached to a scaffold. In some configurations, one, two or more label components are attached to a scaffold.

In some configurations, a detectable probe or affinity regent having two or more binding components has a dissociation constant for a binding partner that is less than the dissociation constant for any of the two or more binding components for the binding partner. For example, the detectable probe or affinity regent can have a dissociation constant for a binding partner that is less than or equal to 50%, 25%, 10% or less of the dissociation constant for any of the two or more binding components for the binding partner. In some configurations, the off-rate of a detectable probe or affinity reagent when bound to a binding partner is lower than an individual off-rate for any of the two or more binding components when bound to a binding partner. In some configurations, the on-rate of a detectable probe or affinity reagent for a binding partner is higher than an individual on-rate for any of the two or more binding components for the binding partner.

In some configurations, a detectable probe or affinity reagent has non-zero binding affinity for a first type of epitope and non-zero binding affinity for a second type of epitope. For example, the detectable probe or affinity reagent can have a first non-zero binding probability to a first type of epitope and a second non-zero binding probability to a second type of epitope. In some configurations, a first binding component of two or more binding components of the detectable probe or affinity reagent has the first non-zero binding probability to the first type of epitope and also has the second non-zero binding probability to the second type of target moiety. In other configurations, a first binding component of the two or more binding components includes the first non-zero binding probability to the first type of target moiety, and a second binding component of the two or more binding components includes the second non-zero binding probability to the second type of target moiety.

In some configurations, at least one of the binding components in a detectable probe or affinity reagent includes an antibody or functional fragment thereof, wherein a binding partner of the detectable probe or affinity reagent has an epitope for the antibody or functional fragment thereof. In some configurations, at least one of the binding components in a detectable probe or affinity reagent includes an aptamer, wherein a binding partner of the detectable probe or affinity reagent has an epitope for the aptamer.

In some configurations, a detectable probe or affinity reagent is bound to a binding partner via at least one binding component. Optionally, the binding partner can bound to the detectable probe or affinity reagent via two or more binding components. The binding partner can be a polypeptide. At least one of the binding components can be configured to recognize dimer, trimer or tetramer amino acid sequences in polypeptides. Optionally, the polypeptide can include a post-translational modification, for example, present within an epitope recognized by a binding component or outside of the epitope. In some embodiments, the binding partner includes a non-polypeptide material such as a polysaccharide, polymer, metal, ceramic, or a combination thereof. In some embodiments, the non-polypeptide material includes a nanoparticle of a polysaccharide, polymer, metal, or ceramic. A detectable probe or affinity reagent can be non-covalently bound to a binding partner or covalently bound to a binding partner. A binding partner that is bound to a detectable probe or affinity reagent, can be in solution phase or attached to a solid support. Optionally, the binding partner can be attached to a structured nucleic acid particle other than a structured nucleic acid particle that is a component of the detectable probe or affinity reagent to which it binds. A structured nucleic acid particle can optionally mediate attachment of a binding partner to a solid support, for example, at a site of an array.

A retaining component of a detectable probe or affinity reagent having two or more binding components can be configured to constrain a first binding component of the two or more binding components from contacting a second binding component of the two or more binding components. A retaining component of a detectable probe or affinity reagent having two or more label components can be configured to constrain a first label component of the two or more label components from contacting a second label component of the two or more label components. A retaining component of a detectable probe or affinity reagent having a label component and a binding component can be configured to constrain the label component from contacting the binding component. Optionally, a retaining component can constrain a first component of two or more components from coming within a specified distance of a second component of the two or more components, for example, a distance of no more than 1 nm, 5 nm, 10 nm, 20 nm or more. In some configurations, the constraint is due to an angular offset. For example, the angular offset can be at least about 90° or 180°. In some configurations, the constraint is due to a blocking moiety, for example, a blocking moiety attached to the retaining component. Exemplary blocking moieties include but are not limited to polyethylene glycol (PEG), polyethylene oxide (PEO), linear or. branched alkane chains, or dextran.

A retaining component of a detectable probe or affinity reagent can include a three-dimensional structure having a first side that is offset from a second side. For example, the first side can have an offset from the second side that is an angular offset of at least about 90° or 180°. Optionally, one, some or all binding components of a detectable probe or affinity reagent are constrained to residing on the first side and constrained from residing on the second side. In some configurations, the first side and the second side can each include one or more binding components. As a further option, one, some or all label components of a detectable probe or affinity reagent can be constrained to residing on the first side of a retaining component and constrained from residing on a second side of the retaining component. In some configurations, the first side and the second side can each include one or more label components. Accordingly, a detectable probe or affinity reagent can be configured to retain binding components on a first side of a retaining component while retaining label components on another side of the retaining component. A detectable probe or affinity reagent can be configured to constrain one, some, or all binding components from residing on the side of a retaining component where one, some, or all label components reside. Moreover, a detectable probe or affinity reagent can be configured to constrain one, some, or all label components from residing on the side of a retaining component where one, some, or all binding components reside. A retaining component of a detectable probe or affinity reagent can include a structured nucleic acid particle (SNAP) such as a nucleic acid nanoball or nucleic acid origami.

One or more label components of a detectable probe or affinity reagent can include any of a variety of labels including, for example, optical labels (e.g. fluorophore, luminophore), radiolabels, or nucleic acid based labels (e.g. sequence tags). In some configurations, two or more label components of a detectable probe or affinity reagent can produce overlapping or indistinguishable signals. For example, two or more label components can be fluorophores that are configured to emit at the same wavelength. In some configurations, two or more label components of a detectable probe or affinity reagent produce signals that are resolved from each other. For example, two or more label components can be fluorophores that are configured to emit at different wavelengths from each other.

In some configurations, two or more label components of a detectable probe or affinity reagent include a donor and acceptor in a Forster resonant energy transfer mechanism. Alternatively, two or more label components of a detectable probe or affinity reagent can be separated from each other by a distance that precludes quenching or Forster resonant energy transfer. Two or more label components of a detectable probe or affinity reagent can have a relative orientation that precludes quenching or Forster resonant energy transfer. For configurations that include a SNAP, a first fluorescent label can be attached at a first nucleotide position in the SNAP and a second fluorescent label is attached at a second nucleotide position in the SNAP, wherein the first nucleotide position is separated from the second nucleotide position by at least 3, 4, 5, 6, 7, 8 or 9 nucleotide positions in the primary sequence of the structured nucleic acid particle. Alternatively or additionally, the first nucleotide position can be separated from the second nucleotide position by at most 9, 8, 7, 6, 5, 4, 3, 2, or 1 nucleotide positions in the primary sequence of the structured nucleic acid particle.

A binding component or label component can be attached to a detectable probe or affinity reagent by a linker. The linker can be a rigid linker or a flexible linker. Exemplary flexible linkers include, but are not limited to, PEG, PEO, an alkane chain, a single stranded nucleic acid, or a combination thereof. A double-stranded nucleic acid or branched alkane chain can be used as a rigid linker.

In some configurations, the major diameter of a detectable probe or affinity reagent is larger than the major diameter of a binding partner to which it binds. Optionally, the volume of a detectable probe or affinity reagent is larger than the volume of a binding partner to which it binds.

In particular configurations, a detectable probe or affinity reagent can include an optically detectable retaining component. For example, one, two or more binding components can be attached to the optically-detectable retaining component. In such configurations, the detectable probe or affinity reagent need not include label components and detection can be carried out based on observation of signals produced by the optically detectable retaining component. Particularly useful optically detectable retaining components include, but are not limited to, fluorescent nanoparticles, Fluo-Spheres™, or quantum dots.

In another aspect, described herein is a detectable probe or affinity reagent including an optically detectable retaining component, and two or more binding components coupled to the optically-detectable retaining component, where the detectable probe or affinity reagent has a dissociation constant for a binding partner that is less than the dissociation constant of any of the two or more binding components for the binding partner.

In another aspect, described herein is a detectable probe or affinity reagent including an optically detectable retaining component, and two or more binding components coupled to the optically-detectable retaining component, where the detectable probe or affinity reagent has a binding on-rate for a binding partner that is higher than the binding on-rate of any of the two or more binding components for the binding partner.

In another aspect, described herein is a detectable probe or affinity reagent including an optically detectable retaining component, and two or more binding components coupled to the optically-detectable retaining component, where the detectable probe or affinity reagent has a binding off-rate for a binding partner that is lower than the binding off-rate of any of the two or more binding components for the binding partner.

In another aspect, described herein is a method including contacting an analyte with a detectable probe, wherein the analyte is a binding partner of the detectable probe, and acquiring a signal from the detectable probe, thereby detecting the analyte. The method can further include identifying the analyte from the acquired signal, or determining the chemical composition of the analyte from the acquired signal. In some embodiments, the analyte includes a polypeptide and the chemical composition that is determined includes the presence or absence of an amino acid sequence of at least a portion of the polypeptide, or the presence or absence of a post translationally modified amino acid in the polypeptide. In some embodiments, the method further includes quantifying the analyte from the acquired signal. In some embodiments, the method further includes determining the location of the analyte on a solid support from the acquired signal, for example, identifying a site in an array where the analyte resides. In some embodiments, the signal is acquired from an optically detectable retaining component of the detectable probe. In some embodiments, the signal is acquired from one or more label components of the detectable probe.

In another aspect, described herein is a method including (a) contacting a plurality of different analytes with a first plurality of detectable probes, wherein detectable probes from the first plurality of detectable probes bind to a first subset of different analytes from the plurality of different analytes, (b) acquiring signals from the first plurality of detectable probes, (c) contacting the plurality of different analytes with a second plurality of detectable probes, wherein detectable probes from the second plurality of detectable probes bind to a second subset of different analytes from the plurality of different analytes, where the first subset of different analytes is different from the second subset of analytes, (d) acquiring signals from the second plurality of detectable probes, and (e) identifying analytes based on the signals acquired in step (b) and step (d). Optionally, the first plurality of detectable probes include substantially the same two or more binding components as the second plurality of detectable probes. Alternatively, the first plurality of detectable probes can include two or more binding components that are different from the two or more binding components of the second plurality of detectable probes. As a further option, one, some or all the detectable probes in the first plurality can include a retaining component. Optionally, the retaining components can have a common structure for some or all the detectable probes in the first plurality. For example, the retaining components for some or all the detectable probes can include an origami structure, such as a scaffold folding structure, that is the same. Similarly, the retaining component for one, some or all the detectable probes in the first plurality can have a structure in common with the retaining component for one, some or all the detectable probes in the second plurality. For example, the retaining components for some or all the detectable probes in the first and second pluralities can include an origami structure, such as a scaffold folding structure, that is the same.

In some configurations, the above method can further include a step of removing the first plurality of detectable probes from the plurality of different analytes prior to step (c). In some configurations of the above method, the first plurality of detectable probes produce the same signal as a signal produced one or more label components as the second plurality of detectable probes. For example, the first plurality of detectable probes can include the same one or more label components as the second plurality of detectable probes. In some configurations of the above method, the first plurality of detectable probes include one or more label components that are different from the one or more label components of the second plurality of detectable probes. In some configurations of the above method, the first plurality of detectable probes include the same optically detectable retaining component as the second plurality of detectable probes. In some configurations of the above method, the first plurality of detectable probes include a different optically detectable retaining component from the optically detectable retaining component of the second plurality of detectable probes.

One or more different analytes that are bound to an affinity agent or detected by a detectable probe in a method set forth herein can be attached to a solid support. For example, individual analytes of a plurality of different analytes can be attached at respective sites on a solid support, whereby the solid support includes an array of analytes.

Further provided by the present disclosure is a method of locating a binding partner, including (a) providing a material (e.g. a solid support) including a binding partner at a discrete location in the material; (b) contacting the material with a detectable probe, wherein the detectable probe includes (i) a retaining component, (ii) one or more label components that are configured to produce a detectable signal, and (iii) two or more binding components coupled to the retaining component, wherein the retaining component and two or more binding components form a detectable probe; (c) detecting the detectable signals from the one or more label components; and (d) identifying the discrete location of the detectable signal, thereby locating the binding partner in the material. Optionally, the detectable probe binds the binding partner with a dissociation constant that is less than or equal to half of a dissociation constant for binding of the binding partner to any of the binding components, individually.

Also provided is a method of forming a detectable probe or affinity reagent, including (a) providing a retaining component including a plurality of coupling groups, and (b) attaching coupling groups of the plurality of coupling groups to a plurality of binding components. Optionally, the method further includes (c) attaching coupling groups of the plurality of coupling groups to a plurality of label components.

Attachment between components of a detectable probe or affinity reagent can be covalent or non-covalent. Nucleic acids provide a particularly useful coupling group. For example, the coupling groups in the above method can include single-stranded nucleic acid moieties that anneal to complementary nucleic acids attached to the binding components and/or label components. The retaining component can include nucleic acid origami that is engineered to position the single-stranded nucleic acid moieties at known positions. For example, the single-stranded nucleic acid moieties can be included in staple strands or oligonucleotides that are annealed to a scaffold strand. Other useful non-covalent attachments include, for example, those mediated by receptor-ligand pairs such as streptavidin-biotin, SpyCatcher-SpyTag, SdyCatcher-SdyTag, and Snoop-Catcher-SnoopTag.

Any of a variety of functional groups can be used to covalently attach components of a detectable probe or affinity reagent. Bioorthogonal reactions and Click reactions are particularly useful.

A method for making a detectable probe or affinity reagent can include a step of forming a passivating layer on a retaining component. Passivation of a retaining component can be carried out, for example, prior to attaching functional groups (e.g. coupling groups), label components or binding components to the retaining component. Optionally, the passivating layer can include a metal, metal oxide, organic functional group, or polymer. For example, the metal can include gold, silver, copper, titanium, or iron. Optionally, the metal oxide includes titanium oxide, alumina, silicon dioxide, or magnesium oxide. Optionally, the organic functional group includes a phosphate, a phosphonate, a carboxylate, an epoxide, or a silane. In some embodiments, the polymer includes a hydrocarbon polymer or a biopolymer. In some embodiments, the hydrocarbon polymer includes polyethylene glycol (PEG), polyethylene oxide (PEO), or an alkane chain. In some embodiments, the biopolymer includes a polysaccharide, a polynucleotide, or a polypeptide.

A detectable probe of the present disclosure can include a double stranded region and an aptamer; wherein the double stranded region includes two or more label components. For example, the label components can be fluorescently labeled nucleotides in one or both of the strands. Optionally, the fluorescently labeled nucleotide can be separated from each other, for example, by at least 5, 6, 7, 8, 9, 10, 15, 20, 25, 30, 35, 40, 45, 50 or more nucleotides. Optionally, the double stranded region can include at least 3, 4, 5, 6, 7, 8, 9, 10 or more fluorophores or other label components. Two or more label components of a detectable probe can be the same as each other or different from each other.

Optionally an aptamer, or other binding component, that is included in a detectable probe or affinity reagent can recognize or bind to some or all sequences of the form $\alpha X\beta$, wherein X is a desired epitope and $\alpha$ and $\beta$ are any amino acid residues. Optionally, the aptamer can recognize or bind to at least 10%, 20%, 30%, 50%, 80% or 90% of sequences of the form $\alpha X\beta$.

In some configurations, an aptamer or other binding component, that is included in a detectable probe or affinity reagent can recognize or bind to a desired three amino acid epitope, without specifically binding any other three amino acid sequences, and binds the desired three amino acid epitope with substantially similar affinity regardless of flanking sequence surrounding the desired epitope.

In another aspect, described herein is a switchable aptamer which binds to between 5% and 10% of all proteins in the human proteome; and wherein the switchable aptamer includes two or more fluorescent moieties.

The present disclosure further provides a method of manufacturing a fluorescently labeled aptamer, the method including synthesizing an aptamer with a primer sequence at the 3' end, hybridizing a template DNA strand to the primer sequence, wherein the template DNA strand includes a segment complementary to the primer and a template region, and using a polymerase to extend the 3' end of the aptamer molecule along the template. Optionally, the polymerase reaction is performed with a nucleotide mix including labeled nucleotides. For example, one or more species of nucleotide can include a label, whereas the other species of nucleotide lack labels. For example the polymerase reaction can be carried out with four nucleotides (adenine, cytosine, guanine, and thymine or uracil) of which three nucleotides are non-labeled and the fourth nucleotide is fluorescently labeled, and wherein the template is designed such that the base complementary to the fluorescently labeled nucleotide occurs in a predetermined pattern. Optionally, the base complementary to the fluorescently labeled nucleotide can occur in every $2^{nd}$, $3^{rd}$, $4^{th}$, $5^{th}$, $6^{th}$, $7^{th}$, $8^{th}$, $9^{th}$, $10^{th}$, $15^{th}$, $20^{th}$, $25^{th}$, $30^{th}$, $35^{th}$, $40^{th}$, $45^{th}$, or $50^{th}$ position along the template.

In another aspect, described herein is a method of manufacturing the above-described fluorescently labeled aptamer, the method including ligating an aptamer to a fluorescently labeled oligonucleotide. In another configuration, a method of manufacturing a fluorescently labeled aptamer, can include synthesizing an aptamer with an extension sequence at the 3' end, hybridizing a splint nucleic acid strand to the extension sequence, and hybridizing a labeled oligonucleotide to the splint nucleic acid strand such that an end of the labeled oligonucleotide is adjacent to an end of the extension sequence, and using a ligase to ligate the labeled oligonucleotide to the aptamer via the extension sequence.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 5A shows configurations for spacing label components on a retaining component.

FIG. 5B shows configurations for spacing label components on a retaining component.

FIG. 20A shows a method of altering a binding interaction utilizing a binding competitor.

FIG. 20B shows a method of altering a binding interaction utilizing a binding competitor.

FIG. 28A shows binding data for a detectable probe against a polypeptide target.

FIG. 28B shows binding data for a detectable probe against a polypeptide target.

FIG. 31A shows a configuration of a non-nucleic acid retaining component.

FIG. 31B shows a configuration of a non-nucleic acid retaining component.

FIG. 31C shows a configuration of a non-nucleic acid retaining component.

FIG. 31D shows a configuration of a non-nucleic acid retaining component.

FIG. 42E shows characterization data for FluoSphere™-based detectable probes.

FIG. 42F shows characterization data for FluoSphere™-based detectable probes.

FIG. 43B shows binding characterization data for Fluo-Sphere™-based detectable probes.

FIG. 43C shows binding characterization data for Fluo-Sphere™-based detectable probes.

FIG. 43D shows binding characterization data for Fluo-Sphere™-based detectable probes.

FIG. 44A shows stability characterization data for Fluo-Sphere™-based detectable probes.

FIG. 44B shows stability characterization data for Fluo-Sphere™-based detectable probes.

FIG. 44C shows stability characterization data for Fluo-Sphere™-based detectable probes.

FIG. 47 shows binding data for fluorescent nanoparticle B1 probes fabricated with direct attachment or with pre-annealing protocol to his-tagged Her2 (on target) and myoglobin (off-target).

FIG. 48 shows an immobilized target for selection of affinity reagents, along with an exemplary list of peptides which include the target. Figure discloses SEQ ID NOS 10-12, 1-2, 13, 3-4 and 14-17, respectively, in order of appearance.

Figure 49A:
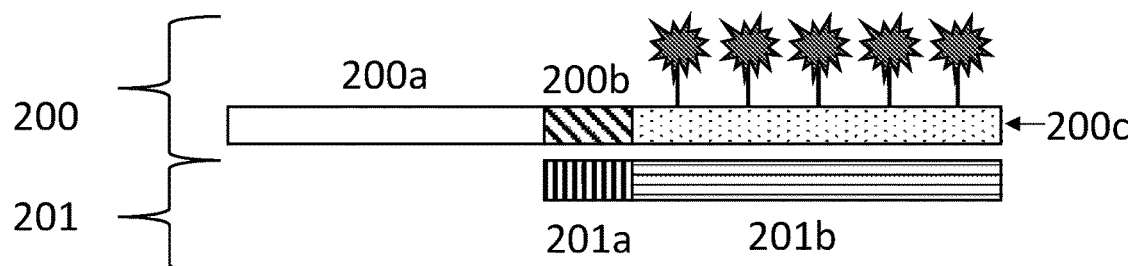

FIG. 49A provides a schematic illustration of a labeled affinity reagent as described herein.

Figure 49B:
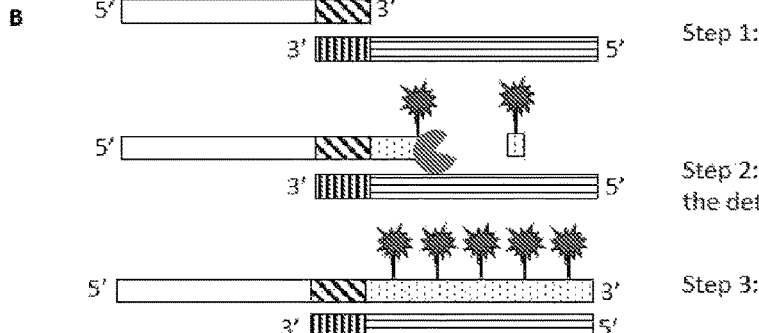

FIG. 49B shows a method of attaching label components to a nucleic acid probe by enzymatic extension.

Figure 50A:
Figure 50B:
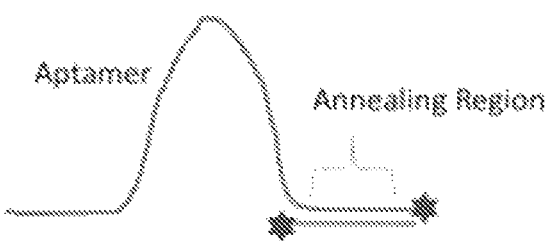
Figure 50C:
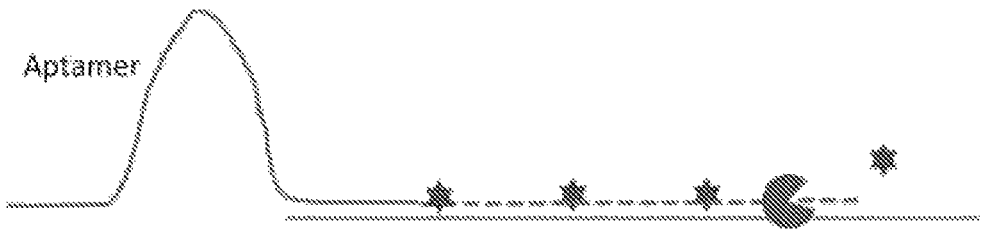

FIGS. 50A-50C diagram some exemplary ways to fluorescently label an affinity reagent. FIG. 50A shows an aptamer with a single fluorophore attached. FIG. 50B shows an aptamer with a double stranded nucleic acid label region, the label region having two fluorophores attached. FIG. 50C shows attachment of multiple regularly spaced fluorophores to an aptamer using a template.

Figure 51:
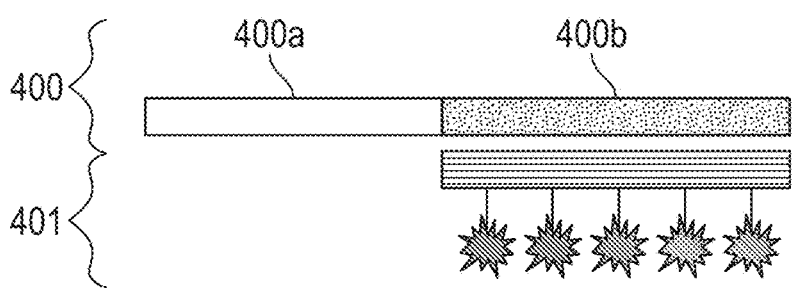

FIG. 51 shows a labeled probe including a single strand of nucleic acid including an aptamer, hybridized to a single strand of nucleic acid including fluorophores.

Figure 52:
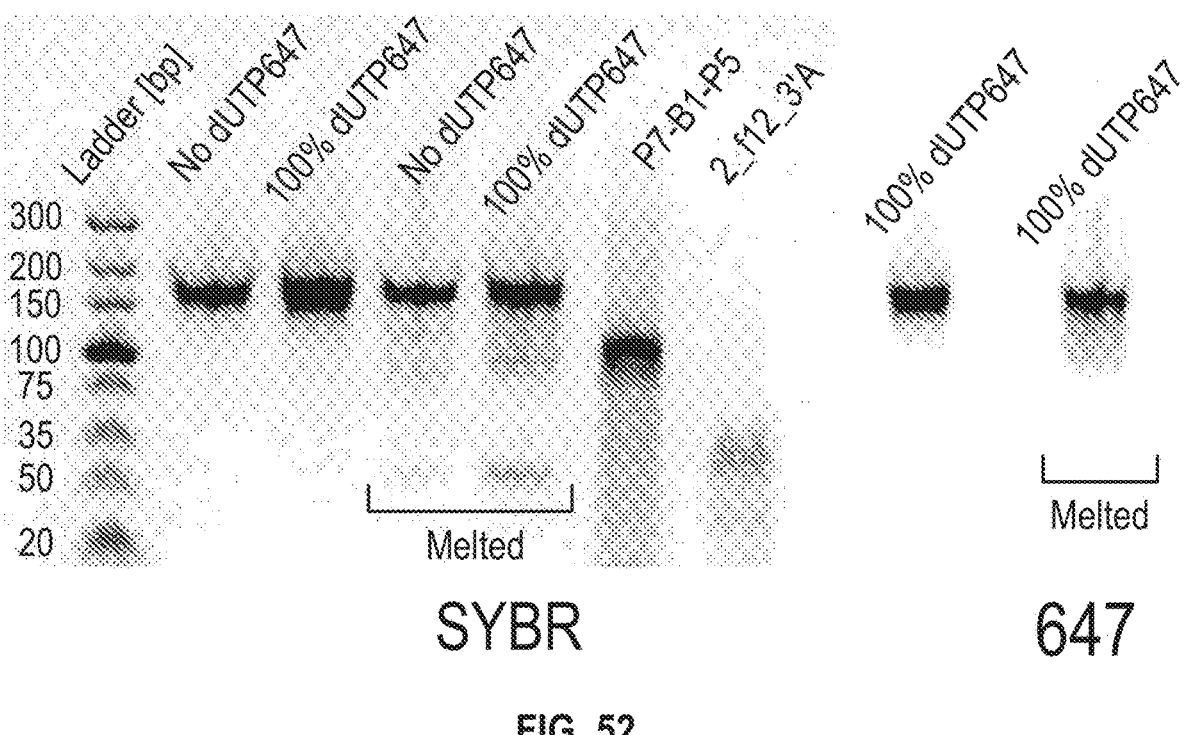

FIG. 52 shows a gel visualized at 488 nm to show double stranded DNA and 647 nm to show incorporated fluorophores. These labeled affinity reagents were produced via enzymatic extension and incorporation of fluorophore-modified nucleotides.

Figure 53A:
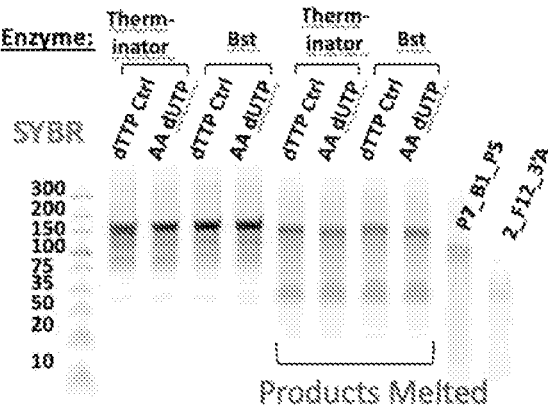

FIG. 53A shows a gel visualized at 488 nm to show double stranded DNA.

Figure 53B:
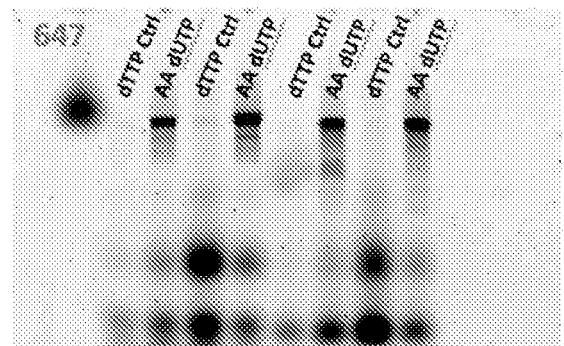

FIG. 53B shows a gel visualized at 647 nm to show incorporated fluorophores. These labeled affinity reagents were produced via enzymatic extension and incorporation of chemically-modified nucleotides. Subsequently, chemical conjugation was used to incorporated fluorophores, in accordance with some embodiments.

Figure 54:
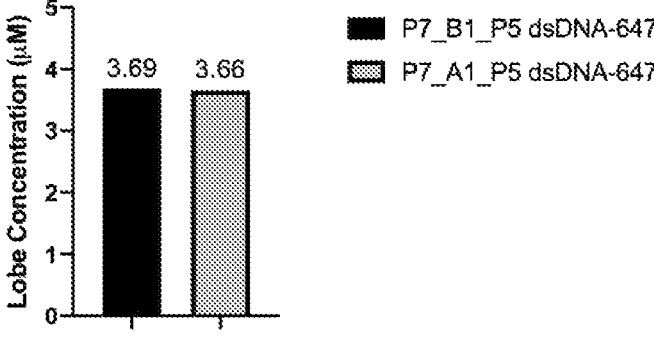

FIG. 54 shows labeled aptamer concentration.

Figure 55A:
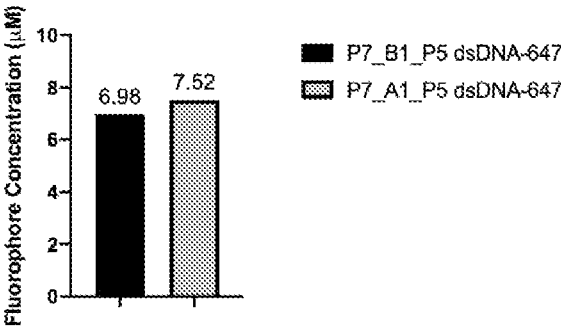

FIG. 55A shows fluorophore concentration in the labeled aptamers of FIG. 54.

Figure 55B:
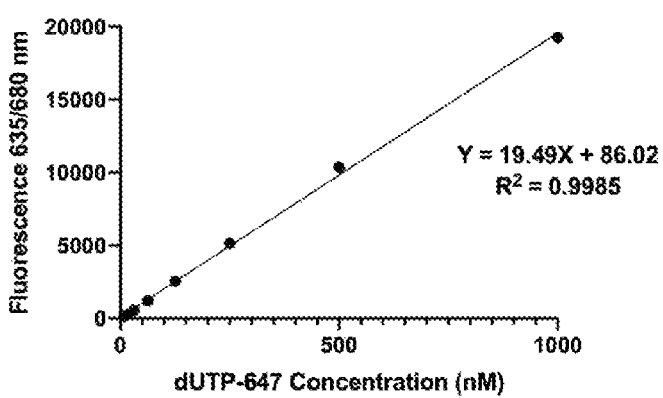

FIG. 55B shows a dUTP-647 standard curve used to determine the fluorophore concentration in FIG. 8A.

Figure 56:
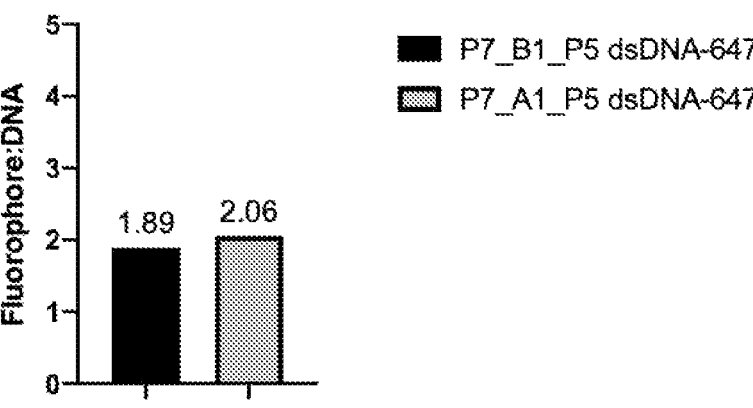

FIG. 56 shows the fluorophore:DNA ratio calculated from FIGS. 54 and 55.

FIG. 57A shows a labeled aptamer bound to an immobilized peptide.

FIG. 57B shows binding of a labeled aptamer to an immobilized target peptide.

FIG. 57C shows binding of a labeled aptamer to an immobilized non target peptide.

FIG. 57D shows microscopy of a labeled aptamer at limiting dilution on an amine-coated coverslip.

FIG. 58A shows a binding reaction between a detectable probe and a SNAP-attached polypeptide.

Figure 58B:
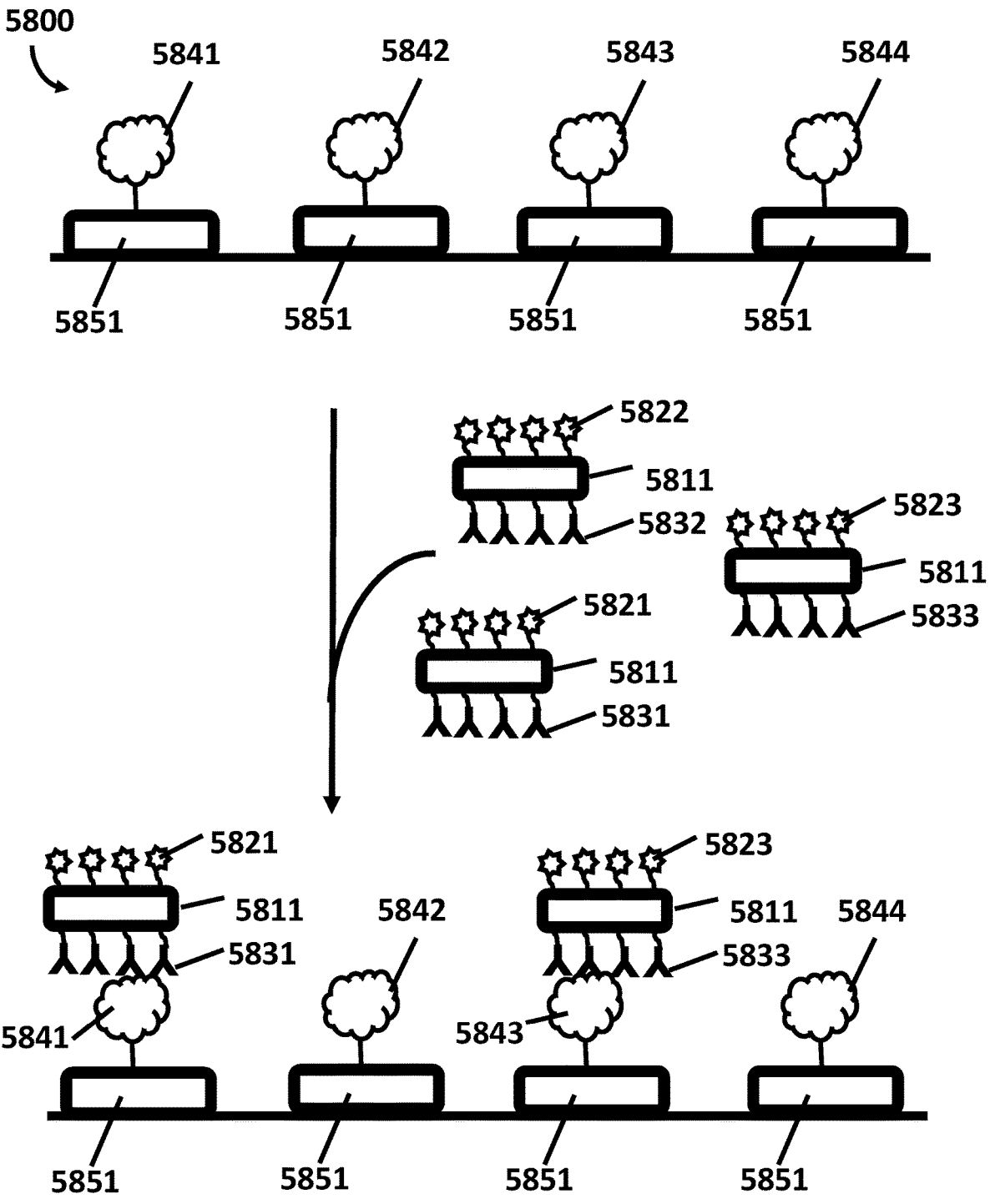

FIG. 58B shows a binding reaction between a plurality of detectable probes and an array of SNAP-attached polypeptides.

DETAILED DESCRIPTION

Detection of interactions between affinity reagents and binding targets can be useful for providing spatial and/or temporal characterization and/or quantitation of physical systems. For example, affinity reagent-based methods such as enzyme linked immunosorbent assay (ELISA) may be used to determine the presence and potentially the quantity of a biomarker within a biochemical sample. Affinity reagents can display complex behaviors, such as interactions with unexpected or unlikely targets, or failure to interact with an expected target. In bulk or large-scale characterizations, affinity reagents may be engineered to a sufficient degree that the complex aspects of their behavior fall within the experimental error, thereby producing usable interaction data. However, for single-molecule assays that utilize affinity reagents, complex affinity reagent behaviors may produce anomalous results (e.g., "false" negatives, false positives) that complicate the interpretation of single molecule affinity reagent interaction data.

Due to a variety of factors that influence binding interaction between an affinity reagent and a binding partner, binding may be transient. In some cases, an affinity reagent may associate and disassociate freely with a binding partner. In other cases, an affinity reagent may interact with a binding partner with sufficient strength to create a stable or quasi-stable complex. Furthermore, in some cases an affinity reagent may associate with an unexpected or unlikely binding partner.

Due to the complex nature of the interactions between affinity reagents and binding partners, some affinity reagent interactions may not fit within a conventional binary interaction framework (i.e., single binding partner, binding or no binding). For example, an affinity reagent may not be observed interacting with an available binding partner for various reasons, including 1) failure of the affinity reagent to come within a sufficient proximity of the binding partner; 2) failure of the affinity reagent to remain associated with the binding partner during the time interval when an observation of association is made; or 3) environmental changes that interrupt or weaken the affinity interaction (e.g., a conformational change of the binding partner or affinity reagent). Likewise, an affinity reagent may be observed binding to an unexpected or unlikely target for various reasons, such as 1) environmental changes that strengthen an affinity interaction; or 2) a transient association that occurs during the time interval when an observation of association is made.

Consequently, some affinity reagent interactions may best be described within a probabilistic or stochastic framework (e.g., multiple binding partners, non-zero probability of binding to each target). Probabilistic or stochastic models for affinity reagent binding may be especially useful for single-molecule assays where single interaction measurement may not necessarily provide a definitive characterization. In such situations, multiple rounds or cycles of measurement may increase measurement confidence.

Although affinity reagents may not always behave optimally in particular conditions, affinity reagents may be engineered to increase or improve their behavior for certain purposes. Two aspects of affinity reagent behavior that may be modified include avidity and observability.

Avidity may be understood as the tendency of an affinity reagent to remain bound to a binding partner due to the presence of multiple, often synergistic, binding interactions between the affinity reagent and binding partner. Multiple binding interactions can occur, for example, due to the binding partner having a plurality of different epitopes that are recognized by the affinity reagent and/or due to the probe having a plurality of binding components that recognize an epitope in the binding partner. A common example of such a phenomenon is the avidity of antibodies, where avidity is often achieved through the weak binding of multiple binding sites on a single antibody to a particular target to create an apparent binding strength that is greater than the binding strength between the binding partner and any individual binding site on the antibody.

Observability may be understood as the ability to detect binding interaction between an affinity reagent and its binding partner. For example, observability may refer to the tendency of an affinity reagent to be detected during an interaction between the affinity reagent and its binding partner. In some configurations, observability may refer to the tendency of an affinity reagent to create a signal or signal generating tag (e.g. a nucleic acid tag) that can be detected after an interaction between the affinity reagent and its binding partner. Observability may be affected by both the ability of the affinity reagent to maintain an interaction for a sufficient time interval during detection and the resistance of the affinity to mechanisms that may diminish a detectable signal of the interaction (e.g., photobleaching, cleavage of a label component).

Described herein are compositions including probes with enhanced avidity for a binding partner. In some configurations, the probe is detectable and, optionally, has enhanced observability. Compositions described herein, such as affinity reagents and detectable probes, can be especially useful for single-molecule characterization assays including, for example, in configurations in which multiple rounds or cycles of affinity reagent interactions are measured. The compositions optionally have the property of enhanced avidity for one or more binding partners while also being configured for reversible binding, for example, to allow removal from a binding partner to permit multiple cycles or rounds of binding measurements. The compositions can optionally possess tunable detection labels that permit observation and measurement of the labels at signal levels that sufficiently exceed the background signal of the system in which affinity agent interactions are measured.

In some configurations, detectable probes or affinity reagents described herein may be characterized as including a retaining component that is associated with one or both of a plurality of binding components and a plurality of label components (e.g. detection labels). The plurality of binding components may be displayed on the retaining component in a configuration that permits enhanced avidity for binding of the detectable probe or affinity reagent to a particular binding partner. The affinity of the detectable probe or affinity reagent can exceed the affinity of any one of the individual binding components for that particular binding partner. In some configurations, the avidity of the detectable probe or affinity reagent for the binding partner may exceed the sum of the affinities of the plurality of binding components for the binding partner. Moreover, a plurality of label components may be displayed on the retaining component of a detectable probe or affinity reagent in a manner that enhances the detectable signal produced by the detection labels. For example, signal can be enhanced with regard to intensity, duration or specificity. In particular configurations, a detectable probe or affinity reagent can further possess the property of being stable in the presence of chemical species (e.g., surfactants, denaturants) that would otherwise disrupt interactions between an affinity reagent and its binding partner, thereby permitting removal of the detectable probe or affinity reagent from the binding partner without damaging or disrupting the structure of the detectable probe or affinity reagent.

In some configurations, the described detectable probes or affinity reagents employ nucleic acid origami as a retaining component that is coupled to a plurality of binding components (e.g. antibodies, antibody fragments, mini proteins, DARPins, DNA aptamers, RNA aptamers, etc.) and/or a plurality of label components (e.g., fluorophores, nucleic acid tags, quantum dots, fluorescent nanoparticles, fluorescent proteins). In some configurations, a nucleic acid origami-based retaining component may possess a regular or symmetric shape that permits attachment of a plurality of binding components and/or a plurality of label components at predetermined positions. For example, the components can be separated from each other by predefined distances, the components can be oriented to achieve synergistic function, or the components can be oriented to reduce or prevent inhibition of each other's activity. The ability to adjust spacing and orientation can yield desired detection properties such as reduced quenching between fluorophore labels or enhanced Forster resonant energy transfer (FRET) between fluorophore labels. Alternatively or additionally, spacing and orientation can be adjusted to tune the affinity of the affinity reagent for one or more binding partner.

In particular configurations, a detectable probe can employ an optically detectable particle. The particle can have a modifiable surface to which a plurality of binding components may be attached. The optically detectable particle may include a fluorescent or luminescent nanoparticle (e.g., a FluoSphere™, or quantum dot). The modifiable surface coating may include a hydrogel or polymer. In such configurations, the optically detectable particle may serve as both a retaining component for the attachment of binding components to the detectable probe and as a label component for detection of the probe. In some configurations, a surface coating of an optically detectable particle may serve as a retaining component for the attachment of binding components to the detectable probe.

In further configurations, two or more detectable probes may be combined to form a complex of detectable probes. A similar complex can be made between two affinity reagents or between an affinity reagent and a detectable probe. A complex of probes and/or reagents may possess binding components of alike affinity (e.g., a univalent probe or reagent) or differing affinity (e.g., a plurivalent probe).

In some configurations, a detectable probe or affinity reagent is combined with or coupled to a competitor affinity reagent. The competitor affinity reagent may be configured as a free molecule, or as a binding component that is attached to the detectable probe or affinity reagent. Competitor affinity reagents have a decreased affinity or specificity for a binding partner of interest in some cases resulting in higher levels of promiscuity than a non-competitor affinity reagent. The presence of the competitor affinity reagent may enhance the avidity of a detectable probe or affinity reagent for a particular binding partner.

The present disclosure provides methods for detecting analytes using compositions including detectable probes or affinity reagents with enhanced avidity for a binding partner and enhanced observability. Methods are exemplified herein for use in detecting polypeptides. It will be understood that any of a variety of analytes can be used, such as those that are targeted by analytical chemistry assays, biochemistry assays, molecular diagnostic assays, molecular forensic assays, quality control assays or the like.

Characterization and quantitation of heterogeneous polypeptide samples is often hindered by the co-existence of proteins and/or peptides in widely varying quantities. For example, the signal from a low-copy number protein may be drowned out by the signal from a high-copy number protein in a quantitative characterization assay. Accuracy of a polypeptide characterization assay that is performed at a proteomic level (e.g. tens of thousands of unique protein species) can benefit from a combination of high-sensitivity analysis techniques and high-confidence prediction techniques.

Biological analyses can greatly benefit from advances in the tools available for examining the molecular operations of biological systems. Advances in genomics technologies, single cell analysis platforms, and highly sensitive chemical analysis systems can greatly improve researcher's and clinician's view into how biological systems function, and in turn, improve understanding, treatment and prevention of disease and other human health conditions.

Many of these advanced tools benefit from the use of detectable reagents that are able to bind, or otherwise associate with different biological molecules, where the binding allows for the identification of the presence and/or the quantification of such molecules in a given system, where that presence and/or quantity provides insight into the functioning of the system. As an example, many of these tools provide for the immobilization of different molecular species from a biological system, such as proteins, nucleic acids or the like, on a supporting structure, such as a fixed substrate or bead. Molecules that have a level of binding affinity for different molecular species, also called affinity reagents, may then be used to interrogate the bound molecules by contacting the two together to see if, where, and/or for how long the affinity reagents bind, indicating the potential presence of particular molecules in the biological sample.

Detection of binding can typically be accomplished through the detection of a label component of the affinity reagent. While the label component may be an inherent part of the affinity reagent, in many cases, the label component may be an exogenous chemical or structural moiety attached to the affinity reagent. An affinity reagent having a label component can function as a detectable probe.

A wide variety of exogenous detectable labels may generally be useful for such purposes, including, for example, optically detectable labels, such as fluorescent dye labels, enzymes (for example enzymes which catalyze reactions with colored reagents or products), electrochemical labels, such as highly charged label groups, or even groups that are detected through subsequent processing, such as nucleic acid barcode labels that can be subsequently identified through nucleic acid amplification processes, sequencing processes or hybridization assays. Fluorescent labels are useful for visualization of binding interactions between affinity reagents and other molecules, such as proteins or peptides.

Depending on the applications for which affinity reagents or detectable probes will be used, different degrees of signal intensity may be desirable, or even required. By way of example, in many applications amplification of a binding signal may be achieved through the binding of many affinity reagents or detectable probes. For example a sample may be separated such that multiple molecules of a single detectable moiety are aggregated in a single location, and are thus, more readily observed or detected. Alternatively or additionally, secondary binding systems may be used to present multiple additional binding sites to which separate label components may be subsequently bound and detected.

In some cases, however, it may be useful to visualize binding of a single molecule of an affinity reagent or detectable probe to a single molecule in a sample in a quantitative manner. As will be appreciated, detection of individual molecules presents many challenges in terms of detection. One such challenge is the ability to present a detectable signal from the binding of a single molecule of reagent or probe to a single molecule that has sufficient signal strength (e.g. signal intensity and duration) as to be detected by available analytical systems, both in terms of raw signal strength, as well as signal strength relative to strength of background noise of the system.

The signal strength challenge may be addressed through a number of approaches, alone or in combination. For example, use of highly sensitive microscopy techniques can enhance abilities to detect very low level signals, including single molecule signals having low intensity and/or short duration. Additionally, signal strength may be increased through the incorporation of multiple label components (e.g., multiple label components on a single molecule such as an affinity reagent molecule or detectable probe molecule) to significantly increase the signal associated with that single molecule, and thus improve its detectability. Again, by way of example, for fluorescent labels, increasing signal intensity may be accomplished by attaching several fluorescent moieties in a single affinity reagent or detectable probe. However, simply loading up a probe or reagent with fluorescent dye labels can raise its own set of challenges. Care may be taken to configure a probe or reagent such that one fluorescent moiety on the probe or reagent does not quench another fluorescent moiety on the probe or reagent, that the number of fluorescent moieties on a probe or reagent can be controlled, and that the chemistry of attaching these labeling groups to the probe or reagent does not interfere with the binding affinity of the probes themselves.

Particularly useful affinity reagents and detectable probes are able to bind to specific proteins, metabolites, cells or cell interfaces. Examples of such affinity reagents and detectable probes may include protein-based probes composed of naturally occurring amino acids, small molecule probes, nucleic acid-based probes composed of naturally occurring bases, and probes composed of non-natural nucleotides and amino acids. The reagents can be configured to bind exclusively to a given epitope or other target.

Exclusivity of binding is often considered to be a desirable trait in an affinity reagent or detectable probe. Substantial efforts are made to ensure that the affinity reagent or probe binds to just one target species, with minimal binding to other targets. For example, the target species may be a particular sequence of amino acids. If that sequence is unique to a protein that is found in a biological sample, then a reagent or probe that is specific for the sequence will be specific for the protein in the milieu of the sample. As such, the reagent or probe can be used to identify or even quantify the protein in the sample. As set forth in further detail herein, there are particular use cases in which it may be useful to have affinity reagents or detectable probes that bind to one or more different proteins in a sample. For example, a useful affinity reagent or detectable probe may bind to an epitope that is common to two or more different proteins. Alternatively or additionally, the probe or reagent may bind to two or more different epitopes, the epitopes being present in different proteins or in different regions of the same protein. Affinity probes and detectable probes that bind to multiple targets in a sample can be employed to useful effect in compositions and methods set forth herein.

Terms used herein will be understood to take on their ordinary meaning in the relevant art unless specified otherwise. Several terms used herein and their meanings are set forth below.

As used herein, the term "affinity reagent" refers to a molecule or other substance that is capable of binding to a binding partner specifically, reproducibly or with high probability. Specific binding can be characterized in terms of a binding constant such as dissociation constant ($K_D$) that is less $10^{-4}$M, $10^{-6}$ M, $10^{-8}$ M, $10^{-10}$ M, $10^{-12}$ M, $10^{-14}$ M or lower. High probability can be characterized as a probability that is at least 0.25, 0.5, 0.51, 0.75, 0.9, 0.99 or higher (on a scale of 0 to 1). An affinity reagent can optionally be larger than, smaller than or the same size as its binding partner. An affinity reagent may form a reversible or irreversible interaction with a binding partner. An affinity reagent may bind with a binding partner in a covalent or non-covalent manner. An affinity reagent is typically non-catalytic and chemically non-reactive, thereby not permanently altering the chemical structure of the binding partner it binds in a method set forth herein. Alternatively, an affinity reagent may be configured to catalyze or participate in a chemical modification (e.g., ligation, cleavage, concatenation, etc.) that produces a detectable change in a binding partner to which it binds. Optionally, the product of the reaction can permit detection of the interaction. Affinity reagents may include reactive affinity reagents (e.g., kinases, ligases, proteases, nucleases, etc.) or non-reactive affinity reagents (e.g., antibodies, antibody fragments, aptamers, DARPins, peptamers, etc.). An affinity reagent may include one or more known and/or characterized binding components or binding sites (e.g., complementarity-defining regions) that mediate or facilitate binding with a binding partner. Accordingly, an affinity reagent can be monovalent (e.g. having only a single binding component), bivalent (e.g. having only two binding components), trivalent (e.g. having only three binding components), tetravalent (e.g. having only four binding components) or multivalent (e.g. having two or more binding components). Exemplary affinity reagents include detectable probes and probes as set forth in U.S. Provisional Application No. 63/112,607, which is incorporated herein by reference.

As used herein, the term "antibody" refers to an immunoglobulin molecule, or functional fragment thereof that specifically binds a binding partner. An antibody may have specificity for one or more epitopes within a binding partner. An antibody may be naturally-occurring, engineered, or evolved. An antibody may include complementarity determining region (CDR) fragments, single-chain antibodies (scFv), single domain antibodies, chimeric antibodies, diabodies, and polypeptides that contain at least a portion of an immunoglobulin that is sufficient to confer specific epitope binding to the polypeptide. Linear antibodies are also included for the purposes described herein. Exemplary antibodies include immunoglobulin isotypes such as IgM, IgA, IgG, IgD, and IgE. Exemplary antibody fragments include F(ab')2 fragments, Fab' fragments, Fab fragments, Fv fragments, scFV fragments, rlgG fragments, and Fc fragments.

Figure 2A:
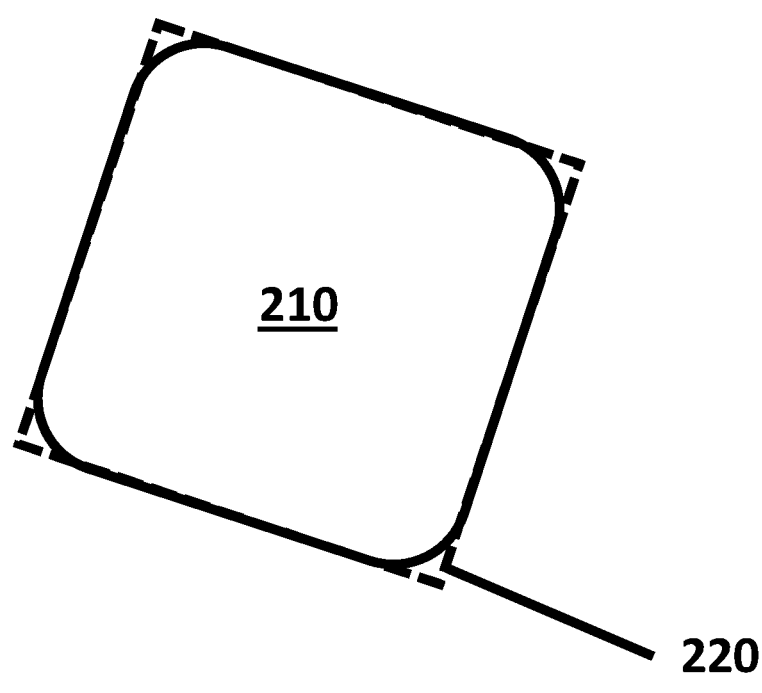
FIG. 2A shows an approximate two-dimensional projection of a square retaining component.
Figure 2B:
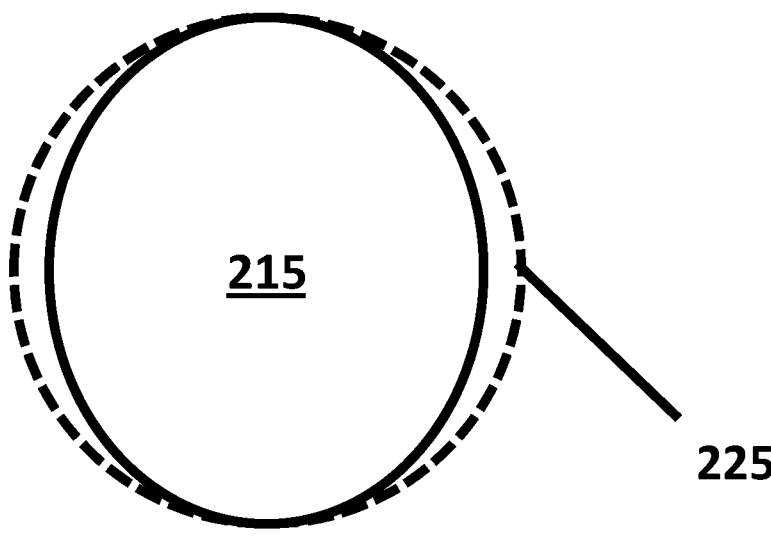
FIG. 2B shows an approximate two-dimensional projection of a circular retaining component.

As used herein, the term "approximately," when used in connection with shapes, may mean a shape that is within 20% of an ideal shape with reference to two or more measures of the shape. For example, FIGS. 2A-2B show an approximately square and approximately circular 2-dimensional bodies, 210 and 215 respectively, with ideal boundaries for the square 220 or circle 225 shown in dashed lines. As used herein, the term "approximate," when used in connection with a length, area, or volume may mean a length, area, or volume that is within 10% of the given measurement. For example, a length of 10 millimeters (mm) may refer to any length between 9 mm and 11 mm.

As used herein, the term "array" refers to a population of analytes (e.g. proteins) that are associated with unique identifiers such that the analytes can be distinguished from each other. A unique identifier can be a solid support (e.g. particle or bead), structured nucleic acid particle, retaining component, site (e.g. spatial address) on a solid support, tag, label (e.g. luminophore), or barcode (e.g. nucleic acid barcode) that is associated with an analyte and that is distinct from other identifiers in the array. Analytes can be associated with unique identifiers by attachment, for example, via covalent or non-covalent (e.g. ionic bond, hydrogen bond, van der Waals forces, electrostatics etc.) bonds. An array can include different analytes that are each attached to different unique identifiers. An array can include different unique identifiers that are attached to the same or similar analytes. An array can include separate solid supports or separate addresses that each bear a different analyte, wherein the different analytes can be identified according to the locations of the solid supports or addresses. Analytes or other molecules that can be included in an array can be, for example, nucleic acids such as SNAPs, polypeptides, enzymes, affinity reagents, biding partners, ligands, or receptors.

As used herein, the term "attached" refers to the state of two things being joined, fastened, adhered, connected or bound to each other. For example, a binding component can be attached to a retaining component by a covalent or non-covalent bond. A covalent bond is characterized by the sharing of pairs of electrons between atoms. A non-covalent bond is a chemical bond that does not involve the sharing of pairs of electrons and can include, for example, hydrogen bonds, ionic bonds, van der Waals forces, hydrophilic interactions and hydrophobic interactions.

As used herein, the term "binding affinity" or "affinity" refers to the strength or extent of binding between an affinity reagent and a binding partner, epitope or target moiety. In some cases, the binding affinity of an affinity reagent for a binding partner, epitope, or target moiety may be vanishingly small or effectively zero. A binding affinity of an affinity reagent-of an affinity reagent for a binding partner, epitope, or target moiety may be qualified as being a "high affinity," "medium affinity," or "low affinity." A binding affinity-of an affinity reagent for a binding partner, epitope, or target moiety may be quantified as being "high affinity" if the interaction has an equilibrium dissociation constant ($(K_D)$ of less than about 100 nM, "medium affinity" if the interaction has a dissociation constant between about 100 nM and 1 mM, and "low affinity" if the interaction has a dissociation constant of greater than about 1 mM. Binding affinity—can be described in terms known in the art of biochemistry such as equilibrium dissociation constant, equilibrium association constant ($K_A$), association rate constant ($k_{on}$), dissociation rate constant ($k_{off}$) and the like. See, for example, Segel, *Enzyme Kinetics* John Wiley and Sons, New York (1975), which is incorporated herein by reference in its entirety.

As used herein, the term "binding component" refers to a moiety of an affinity reagent, the moiety being capable of binding to a binding partner specifically, reproducibly or with high probability. Exemplary binding components include, but are not limited to, antibodies or functional fragments thereof (e.g., Fab' fragments, F(ab')$_2$ fragments, single-chain variable fragments (scFv), di-scFv, tri-scFv, microantibodies, intrabodies, affibodies, affilins, affimers, affitins, alphabodies, anticalins, avimers, DARPins, Kunitz domain peptides, monobodies, nanoCLAMPs, mini-peptide binders, etc.), lectins or functional fragments thereof, avidin, streptavidin, aptamers, nucleic acids that are either single- or double-stranded, or other affinity reagents set forth herein or known in the art. Exemplary binding components include probes, as set forth in U.S. Provisional Application No. 63/112,607, which is incorporated herein by reference.

As used herein, the term "binding context" refers to the environmental conditions in which an affinity reagent-binding partner interaction is observed. Environmental conditions may include any factors that may influence an interaction between an affinity reagent and a binding partner, such as temperature, fluid properties (e.g., ionic strength, pH), relative concentrations, absolute concentrations, fluid composition, binding partner conformation, affinity reagent conformation, and combinations thereof. Environmental conditions may include structural features of a binding partner that, although being outside of an epitope, have an influence interaction of the epitope with a binding reagent. The structural features can include, for example, amino acids or regions of a polypeptide that are proximal to an epitope in the primary, secondary, tertiary or quaternary structure of the polypeptide.

As used herein, the term "binding partner" refers to molecule or other substance that is recognized by an affinity reagent or binding component. An affinity reagent may specifically or reproducibly recognize a particular binding partner relative to other molecules or substances in a sample. Alternatively, an affinity reagent may recognize a plurality of different binding partners in a sample, for example, binding promiscuously to a subset of different polypeptide sequences among a larger set of different polypeptides. A binding partner may be capable of forming an interaction with an affinity reagent, regardless of whether such an interaction occurs. A binding partner may include one or more epitopes. A binding partner may have a rigid structure, such as a nanoparticle or a microparticle. A binding partner may have a molten or dynamic structure (e.g., a globular protein, a globular polymer). A binding partner may be solution phase or solid phase. For example a binding partner can be free within a solution containing an affinity reagent, or may be localized at a surface or interface that an affinity reagent can access. A binding partner can be attached to a structured nucleic acid particle (e.g. nucleic acid origami) or retaining component.

As used herein, the term "binding probability" refers to the probability that an affinity reagent may be observed to interact with a binding partner and/or an epitope, for example, within a fixed binding context. A binding probability may be expressed as a discrete number (e.g., 0.4 or 40%) a matrix of discrete numbers, or as mathematical model (e.g., a theoretical or empirical model). A binding probability may include one or more factors, including binding specificity, likelihood of locating a target epitope, or the likelihood of binding for a sufficient amount of time for a binding interaction to be detected. An overall binding probability may include binding probability when all factors have been weighted relative to the binding context.

As used herein, the term "binding specificity" refers to the tendency of an affinity reagent to preferentially interact with a binding partner or epitope relative to other biding partners or epitopes. An affinity reagent may have a calculated, observed, known, or predicted binding specificity for any possible binding partner or epitope. Binding specificity may refer to selectivity for a single binding partner, epitope, or target moiety in a sample over all, some or at least one other analyte in the sample. Moreover, binding specificity may refer to selectivity for a subset of binding partners, epitopes, or target moieties in a sample over at least one other analyte in the sample.

As used herein, the term "bioorthogonal reaction" refers to a chemical reaction that can occur within a biological system (in vitro and/or in vivo) without interfering with some or all native biological processes, functions, or activities of the biological system. A bioorthogonal reaction may be further characterized as being inert to components of a biological system other than those targeted by the bioorthogonal reaction. A bioorthogonal reaction may include a click reaction. Bioorthogonal or click reactions may include Staudinger ligation, copper-free click reactions, nitrone dipole cycloaddition, norbornene cycloaddition, oxanobornadiene cycloaddition, tetrazine ligation, [4+1] cycloaddition, tetrazole photoclick reactions, or quadricyclane ligation. A bioorthogonal reaction may utilize an enzymatic approach, such as attachment between a first molecule and a second molecule by an enzyme such as a sortase, a ligase, or a subtiligase. A bioorthogonal reaction may utilize an irreversible peptide capture system, such as SpyCatcher/SpyTag, SnoopCatcher/SnoopTag, or Sdy-Catcher/SdyTag.

As used herein, the term "click reaction" refers to single-step, thermodynamically-favorable conjugation reaction utilizing biocompatible reagents. A click reaction may be configured to not utilize toxic or biologically incompatible reagents (e.g., acids, bases, heavy metals) or to not generate toxic or biologically incompatible byproducts. A click reaction may utilize an aqueous solvent or buffer (e.g., phosphate buffer solution, Tris buffer, saline buffer, MOPS, etc.). A click reaction may be thermodynamically favorable if it has a negative Gibbs free energy of reaction, for example a Gibbs free energy of reaction of less than about −5 kilo-Joules/mole (kJ/mol), −10 kJ/mol, −25 kJ/mol, −50 kJ/mol, −100 kJ/mol, −200 kJ/mol, −300 kJ/mol, −400 kJ/mol, or less than −500 kJ/mol. Exemplary bioorthogonal and click reactions are described in detail in WO2019/195633A1, which is incorporated herein by reference.

The term "comprising" is intended herein to be open-ended, including not only the recited elements, but further encompassing any additional elements.

As used herein, the term "each," when used in reference to a collection of items, is intended to identify an individual item in the collection but does not necessarily refer to every item in the collection. Exceptions can occur if explicit disclosure or context clearly dictates otherwise.

As used herein, the term "epitope" refers to a molecule or part of a molecule, which is recognized by or binds specifically to an affinity reagent. Epitopes may include amino acid sequences that are sequentially adjacent in the primary structure of a polypeptide or amino acids that are structurally adjacent in the secondary, tertiary or quaternary structure of a polypeptide. An epitope can optionally be recognized by or bound to an antibody. However, an epitope need not necessarily be recognized by any antibody, for example, instead being recognized by an aptamer, miniprotein or other affinity agent. An epitope can optionally bind an antibody to elicit an immune response. However, an epitope need not necessarily participate in, nor be capable of, eliciting an immune response. The term "affinity target" is used herein synonymously with the term "epitope."

As used herein, the term "exogenous," when used in reference to a moiety of a molecule, means a moiety that is not present in a natural analog of the molecule. For example, an exogenous label of an amino acid is a label that is not present on a naturally occurring amino acid. Similarly, an exogenous label that is present on an antibody is not found on the antibody in its native milieu.

As used herein, the term "functional group" refers to a moiety or group of atoms in a molecule that confer a chemical property, such as reactivity, polarity, hydrophobicity, hydrophilicity, solubility, binding affinity etc., to the molecule. Functional groups may include organic moieties or may include inorganic atoms. Exemplary functional groups may include bioorthogonal reactants, click reactants, alkyl, alkenyl, alkynyl, phenyl, halide, hydroxyl, carbonyl, aldehyde, acyl halide, ester, carboxylate, carboxyl, carboalkoxy, methoxy, hydroperoxy, ether, hemiacetal, hemiketal, acetal, ketal, orthoester, epoxide, carboxylic anhydride, carboxamide, amine, ketimine, aldimine, imide, azide, azo, cyanate, isocyanate, nitrate, nitrile, isonitrile, nitrosoxy, nitro, nitroso, oxime, pyridyl, carbamate, sulfhydryl, sulfide, disulfide, sulfinyl, sulfonyl, sulfinom, sulfo, thiocyanate, isothiocyanate, carbonothioyl, thioester, thionoester, phosphino, phosphono, phosphonate, phosphate, borono, boronate, and borinate functional groups.

As used herein, the term "label" refers to a molecule, or moiety thereof, that provides a detectable characteristic. The detectable characteristic can be, for example, an optical signal such as absorbance of radiation, luminescence emission, luminescence lifetime, luminescence polarization, fluorescence emission, fluorescence lifetime, fluorescence polarization, or the like; Rayleigh and/or Mie scattering; binding affinity for a ligand or receptor; magnetic properties; electrical properties; charge; mass; radioactivity or the like. Exemplary labels include, without limitation, a fluorophore, luminophore, chromophore, nanoparticle (e.g., gold, silver, carbon nanotubes), heavy atoms, radioactive isotope, mass label, charge label, spin label, receptor, ligand, or the like. A label may produce a signal that is detected in real-time (e.g., fluorescence, luminescence, radioactivity). A label component may produce a signal that is detected off-line (e.g., a nucleic acid barcode) or in a time-resolved manner (e.g., time-resolved fluorescence). A label component may produce a signal with a characteristic frequency, intensity, polarity, duration, wavelength, sequence, or fingerprint.

As used herein, the term "label component" refers to a moiety of an affinity reagent or other substance that provides a detectable characteristic. The detectable characteristic can be, for example, any of those set forth herein in the context of labels. A label component can be attached to or capable of being attached to another molecule or substance. Exemplary molecules that can be attached to a label component include an affinity reagent or a binding partner.

As used herein, the term "nucleic acid nanoball" refers to a globular or spherical nucleic acid structure. A nucleic acid nanoball may include a concatemer of sequence regions that arranges in a globular structure. A nucleic acid nanoball may include DNA, RNA, PNA, modified or non-natural nucleic acids, or combinations thereof.

As used herein, the term "nucleic acid origami" refers to a nucleic acid construct including an engineered tertiary or quaternary structures in addition to the naturally-occurring helical structure of nucleic acid(s). A nucleic acid origami may include DNA, RNA, PNA, modified or non-natural nucleic acids, or combinations thereof. A nucleic acid origami may include a plurality of oligonucleotides that hybridize via sequence complementarity to produce the engineered structuring of the origami particle. A nucleic acid origami may include sections of single-stranded or double-stranded nucleic acid, or combinations thereof. Exemplary nucleic acid origami structures may include nanotubes, nanowires, cages, tiles, nanospheres, blocks, and combinations thereof. A nucleic acid origami can optionally include a relatively long scaffold nucleic acid to which multiple smaller nucleic acids hybridize, thereby creating folds and bends in the scaffold that produce an engineered structure. The scaffold nucleic acid can be circular or linear. The scaffold nucleic acid can be single stranded but for hybridization to the smaller nucleic acids. A smaller nucleic acid (sometimes referred to as a "staple") can hybridize to two regions of the scaffold, wherein the two regions of the scaffold are separated by an intervening region that does not hybridize to the smaller nucleic acid.

As used herein, the term "oligonucleotide" refers to a molecule including two or more nucleotides joined by a phosphodiester bond. An oligonucleotide may include DNA, RNA, PNA, modified nucleotides, non-natural nucleotides, or combinations thereof. An oligonucleotide may include a limited number of nucleotide subunits, such as, for example, less than about 200, 190, 180, 170, 160, 150, 140, 130, 120, 110, 100, 90, 80, 70, 60, 50, 40, 30, 25, 20, 15, 10, or less than 5 nucleotides.

Figure 1A:
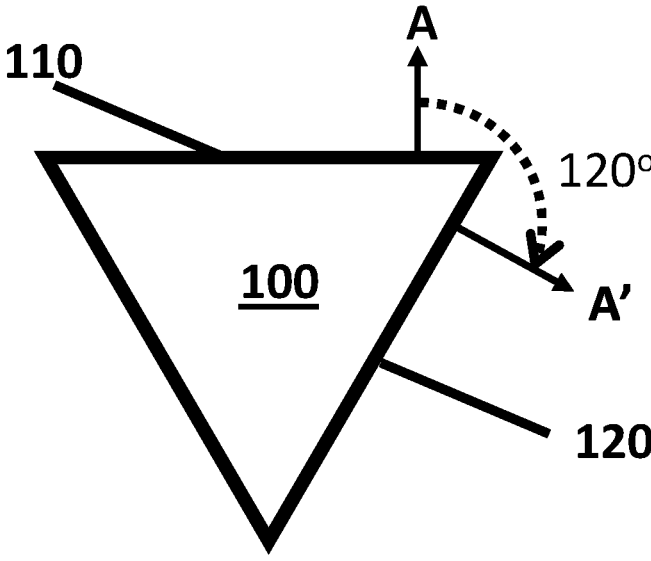
FIG. 1A shows an object with an angular offset between two faces of the object.
Figure 1B:
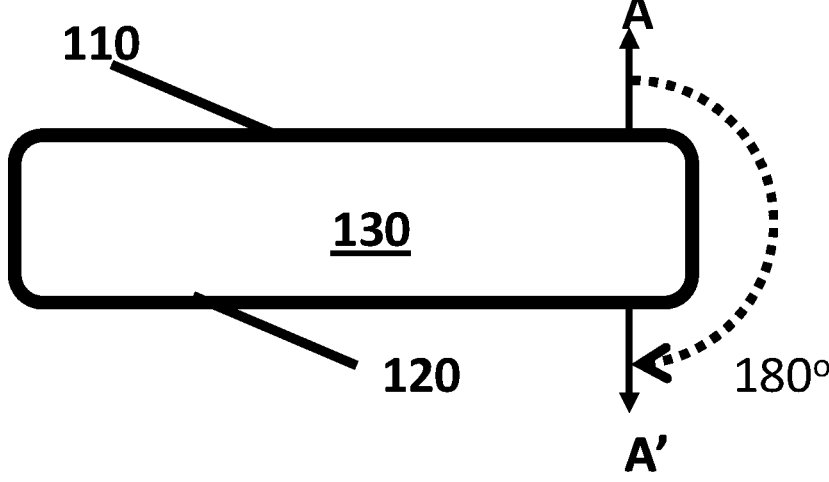
FIG. 1B shows an object with an angular offset between two faces of the object.

As used herein, the term "offset," when used in reference to molecular structures, refers to the spatial difference in orientation between two lines (2-dimensional) or two planes (3-dimensional). The planes can approximate a surface of a molecular structure such as a face of an origami tile. An offset may include a distance offset and/or an angular offset. FIGS. 1A and 1B depict examples of angular offset for differing two-dimensional shapes (which could be two-dimensional projections of three-dimensional structures). The isosceles triangle 100 of FIG. 1A has an angular offset of 120° between the first face 110 and the second face 120 whose relative orientations are depicted by orthogonal vectors A and A'. The rectangle 130 of FIG. 1B has an angular offset of 180° between the first face 110 and the second face 120, whose relative orientations are depicted by orthogonal vectors A and A'.

As used herein, the term "polypeptide" refers to a molecule including two or more amino acids joined by a peptide bond. A polypeptide may also be referred to as a protein, oligopeptide or peptide. Although the terms "protein," "polypeptide," "oligopeptide" and "peptide" may optionally be used to refer to molecules having different characteristics, such as amino acid sequence composition or length, molecular weight, origin of the molecule or the like, the terms are not intended to inherently include such distinctions in all contexts. A polypeptide can be a naturally occurring molecule, or synthetic molecule. A polypeptide may include one or more non-natural amino acids, modified amino acids, or non-amino acid linkers. A polypeptide may contain D-amino acid enantiomers, L-amino acid enantiomers or both. Amino acids of a polypeptide may be modified naturally or synthetically, such as by post-translational modifications.

As used herein, the term "promiscuity," when used in reference to an affinity reagent, refers to the binding agent binding to, or having the capability of binding to, two or more different binding partners. For example, a promiscuous binding agent may: 1) bind to a plurality of different binding partners due to the presence of a common epitope within the structures of the different binding partner; or 2) bind to a plurality of different epitopes; or 3) a combination of both properties. A promiscuous binding agent may bind to a plurality of binding partners due to the presence of a particular epitope or target moiety, regardless of the binding context of the epitope or target moiety. The binding context may include, for example, the local chemical environment surrounding an epitope or target moiety, such as flanking, adjacent, or neighboring chemical entities (e.g., for a polypeptide epitope, flanking amino acid sequences, or adjacent or neighboring non-contiguous amino acid sequences relative to the epitope). A plurality of different epitopes that is bound by a promiscuous affinity reagent may include structurally- or chemically-related epitopes that nonetheless have different amino acid content. For example, an affinity reagent may be considered promiscuous if it possesses a binding affinity for trimer peptide sequences having the form WXK, where X is any possible amino acid. Additional concepts pertaining to binding promiscuity are discussed in WO 2020/106889A1, which is incorporated herein by reference.

As used herein, the term "retaining component" refers to a moiety of an affinity reagent, detectable robe or other substance that links at least two other components. A retaining component can maintain two other components within a particular distance of each other. For example, the two other components can be maintained at a distance of at most 1000 nm, 500 nm, 100 nm, 50 nm, 10 nm, 5 nm, 1 nm or less. Alternatively or additionally, a retaining component can separate the two other moieties at a minimum distance from each other. For example, the two other components can be maintained at a distance of at least 1 nm, 5 nm, 10 nm, 50 nm, 100 nm, 500 nm, 1000 nm or more. A retaining component can include, for example, a structured nucleic acid particle, nucleic acid nanoball, nucleic acid origami, protein nucleic acid, polypeptide, synthetic polymer, polysaccharide, organic particle, inorganic particle, gel, hydrogel, coated particle, or the like. A retaining component can optionally have a polymeric structure. Alternatively, a retaining component need not have a polymeric structure. In some embodiments, a retaining component has a composition that is similar to other components to which it is attached. For example, a plurality of binding components that are composed of polypeptide material can be attached to a polypeptide retaining component. Alternatively, a retaining component can have a composition that differs substantially from the composition of other components to which it is attached. For example, a plurality of binding components that are composed of polypeptide material can be attached to a retaining component that is composed partially or entirely of a material other than polypeptide, such as nucleic acid material, or an organic or inorganic nanoparticle (e.g., carbon nanosphere, silicon dioxide nanosphere, etc.). A retaining component may include one or more attachment sites that permit attachment of another component, such as a label component or binding component, to the retaining component. Attachment sites may include functional groups, active sites, binding ligands, binding receptors, nucleic acid sequences, or any other entity capable of forming a covalent or non-covalent attachment to a binding component, label component, or other detectable probe component. A retaining component may include an organic or inorganic particle or nanoparticle. A scaffold may include a coating or surface layer that permits attachment of another component, for example, as occurs in a polymer-coated FluoSphere™ or polymer-coated quantum dot. Examples of retaining components include scaffolds as set forth in U.S. Provisional Application No. 63/112,607, which is incorporated herein by reference.

As used herein, the term "site," when used in reference to an array, means a location in an array occupied by, or configured to be occupied by, a particular molecule or analyte such as a polypeptide, nucleic acid, structured nucleic acid or functional group. A site can contain only a single molecule, or it can contain a population of several molecules of the same species (i.e. an ensemble of the molecules). Alternatively, a site can include a population of molecules that are different species. Sites of an array are typically discrete. The discrete sites can be contiguous, or they can have interstitial spaces between each other. An array useful herein can have, for example, sites that are separated by less than 100 microns, 10 microns, 1 micron, or 0.5 micron, 0.1 micron, 0.01 micron or less. Alternatively or additionally, an array can have sites that are separated by at least 0.01 micron, 0.1 micron, 0.5 micron, 1 micron, 10 microns, 100 microns or more. The sites can each have an area of less than 1 square millimeter, 500 square microns, 100 square microns, 25 square microns, 1 square micron or less. An array can include at least about $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$, $1 \times 10^{12}$, or more sites.

As used herein, the term "solid support" refers to a rigid substrate that is insoluble in aqueous liquid. The substrate can be non-porous or porous. The substrate can optionally be capable of taking up a liquid (e.g. due to porosity) but will typically be sufficiently rigid that the substrate does not swell substantially when taking up the liquid and does not contract substantially when the liquid is removed by drying. A nonporous solid support is generally impermeable to liquids or gases. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefins, poly-imides etc.), nylon, ceramics, resins, Zeonor™, silica or silica-based materials including silicon and modified silicon, carbon, metals, inorganic glasses, optical fiber bundles, and polymers.

As used herein, the term "species" is used to identify molecules or moieties that share the same chemical struc-ture. For example, individual epitope moieties that have the same sequence of amino acids are the same species of epitope, whereas epitope moieties with different sequences are different species of epitope. Proteins expressed from the same gene are the same species of gene product, proteins expressed from the same gene and having the same post-translational modifications are the same proteoform or iso-form. Two proteins can be expressed from the same gene but have different protein modifications, in which case the two proteins are the same species of gene product but different proteoforms or isoforms.

As used herein, the term "structured nucleic acid particle" (or "SNAP") refers to a single- or multi-chain polynucle-otide molecule having a compacted three-dimensional struc-ture. The compacted three-dimensional structure can option-ally be characterized in terms of hydrodynamic radius or Stoke's radius of the SNAP relative to a random coil or other non-structured state for a nucleic acid having the same sequence length as the SNAP. The compacted three-dimen-sional structure can optionally be characterized with regard to tertiary structure. For example, a SNAP can be configured to have an increased number of internal binding interactions between regions of a polynucleotide strand, less distance between the regions, increased number of bends in the strand, and/or more acute bends in the strand, as compared to the same nucleic acid molecule in a random coil or other non-structured state. Alternatively or additionally, the com-pacted three-dimensional structure can optionally be char-acterized with regard to quaternary structure. For example, a SNAP can be configured to have an increased number of interactions between polynucleotide strands or less distance between the strands, as compared to the same nucleic acid molecule in a random coil or other non-structured state. In some configurations, the secondary structure (i.e. the helical twist or direction of the polynucleotide strand) of a SNAP can be configured to be more dense than the same nucleic acid molecule in a random coil or other non-structured state. A SNAP can optionally be modified to permit attachment of additional molecules to the SNAP. A SNAP may comprise DNA, RNA, PNA, modified or non-natural nucleic acids, or combinations thereof. A SNAP may include a plurality of oligonucleotides that hybridize to form the SNAP structure. The plurality of oligonucleotides in a SNAP may include oligonucleotides that are attached to other molecules (e.g., affinity reagents, binding partners, functional groups, or detectable labels) or are configured to be attached to other molecules (e.g., by functional groups). A SNAP may include engineered or rationally-designed structures, such as nucleic acid origami.

As used herein, the term "substantially the same," when used in reference to two or more structures, refers to the structures performing, or being capable of performing, sub-stantially the same function in substantially the same way to obtain the same result. For example, two structured nucleic acid particles that are substantially the same can have the same primary structure. Optionally, they may differ in pri-mary structure so long as they do not differ in tertiary or quaternary structure. Optionally, they may differ in one or more of primary, secondary, tertiary or quaternary structure, so long as they perform substantially the same function in substantially the same way to obtain the same result in a method set forth herein.

As used herein, the term "target moiety" refers to a specific chemical structure within an epitope that mediates or facilitates a binding interaction. A target moiety may include a functional group, sidechain, active site, or other chemical entity with a characterizable structure. For example, a target moiety can be one or more amino acids, or sidechain(s) thereof, that form a portion of a polypeptide epitope. A target moiety may specifically interact with a binding site of an affinity reagent to facilitate or mediate the interaction that causes binding of the affinity reagent to the binding partner.

As used herein the term "tunable" refers to adjustability of the specific, precise, and/or rational location of components or attachment sites in the structure of a retaining component, scaffold or molecule. Tunable retaining components may refer to the ability to attach other components at specific sites or within specific regions of the retaining component structure, or to generate attachment sites for the attaching of other components at specific sites or specific regions of the retaining component structure. As used herein, "tunability" refers to the property of a probe or retaining component having a tunable structure or architecture.

Other than in the operating examples, or where otherwise indicated, all numbers expressing quantities of ingredients or reaction conditions used herein should be understood as modified in all instances by the term "about." As used herein, the term "about," when used in connection with percentages, may mean ±5% of the value being referred to. For example, about 90% would mean from 85% to 95%.

As used herein, the term "two-dimensional projection" refers to the area or shape that would be occupied by the projection of a three-dimensional structure onto a planar two-dimensional surface without substantial geometric or spatial distortion. For example, the two-dimensional projec-tion of a sphere onto a planar two-dimensional surface would produce a circular area on the surface with a diameter equivalent to the diameter of the sphere. A two-dimensional projection may be formed from any frame of reference, including a frame of reference that is orthogonal to any surface of the three-dimensional structure.

Structure and Function of Detectable Probes and Affinity Reagents

Described herein are detectable probes or affinity reagents having an increased binding avidity for a binding partner, increased observability or both. Structural and functional characteristics exemplified herein for detectable probes can be present in other affinity reagents. Conversely, structural and functional characteristics exemplified herein for affinity reagents can be present in detectable probes. Accordingly, the compositions, structures and methods set forth herein in the context of detectable probes can be applied to other affinity reagents and vice versa.

Detectable probes or affinity reagents may include a plurality of binding components that, collectively, increase the overall binding affinity of the probe for a binding partner as compared to any individual binding component of the plurality of binding components contained within the detectable probe or affinity reagent structure. Any of a variety of affinity reagents known in the art or set forth herein can function as binding components when attached to a detectable probe or affinity reagent of the present disclosure. Detectable probes or affinity reagents of the present disclosure may further include one or more label components that permit observation of a binding interaction between the detectable probe (or affinity reagent) and a binding partner. Any of a variety of detectable labels known in the art or set forth herein can function as label components when attached to a detectable probe or affinity reagent of the present disclosure.

A detectable probe or affinity reagent of the present disclosure may include (a) a retaining component; (b) a label component, and (c) one, two or more binding components attached to the retaining component. Of particular interest are retaining components that are spatially and/or orientationally tunable to provide precise, predetermined and/or rational display of other components attached thereto. For example, binding components can be attached in configurations that increase the binding avidity and/or observability of the detectable probe or affinity reagent. A detectable probe or affinity reagent may include a retaining component that provides sufficient sites to attach at least one binding component and/or at least one label component. In some configurations, the retaining component may be a natural, artificial, or synthetic particle including a plurality of functional groups, reactive sites, nucleic acids, or functional groups that permit attachment of other molecules to the retaining component. A retaining component may have an amorphous, globular, or irregular structure (e.g., a DNA nanoball, a fluorescent nanoparticle such as a FluoSphere™ or a quantum dot). A retaining component may have a regular or symmetric structure (e.g., carbon nanospheres, carbon nanotubes, metal nanotubes, ceramic nanoparticles). A retaining component may include a shell or scaffold that is formed by a templating particle, such as a particle or nanoparticle. In some configurations, a templating particle may include a label component, such as a FluoSphere™ or a quantum dot. A retaining component may include any appropriate material, including, but not limited to polymers, metals, semiconductors, ceramics, glasses, and biomolecules (e.g., nucleic acids such as DNA or RNA, proteins, polysaccharides).

In some cases, a retaining component may include a partially or substantially completely double stranded nucleic acid. A double stranded nucleic acid may impart additional structural rigidity to the retaining component, in order to provide better spacing between label components. In such cases, the label components may be coupled to one or both strands of the double stranded nucleic acid. A retaining component may include a structured particle or rationally-designed particle. A retaining component may include a structured nucleic acid particle (SNAP) that is configured to attach one or more binding components and/or one or more label components. In some configurations, the SNAP may include a DNA origami particle or a DNA nanoball.

A retaining component may include a plurality of sites for attaching other components (e.g. a binding component, label component or another retaining component). A retaining component may include unique or dedicated sites for coupling binding components and/or label components. For example, a retaining component may include nucleic acids with first sequences that are complementary to nucleic acids coupled to binding components, and may further include nucleic acids with second sequences that are complementary to nucleic acids coupled to label components. The first sequences can differ from the second sequences such that the different types of components are appropriately directed to a subset of the coupling sites. Alternatively, the first and second sequences can be the same. Optionally, a retaining component may include one or more first functional groups that are configured to form covalent bonds with functional groups coupled to binding components, and may further include one or more second functional groups that are configured to form covalent bonds with functional groups coupled to label components. The first functional group(s) can differ from the second functional group(s) such that the different types of components are appropriately directed to a subset of the coupling sites. For example, the first plurality of functional groups may participate in a bond-forming reaction that is orthogonal to the bond-forming reaction in which the second plurality of functional groups participates. Alternatively, the first and second functional groups can be the same. In some configurations, a retaining component may include a mixture of attachment site types, such as nucleic acids and functional groups, where each type of attachment site is configured to attach a different type of component.

A retaining component may include one or more other components (e.g. a binding component, label component or another retaining component) that is attached to the retaining component. A retaining component may be attached to another component by a covalent bond (e.g., via a click reaction), a coordination bond (e.g., a silane linker to a silicon nanoparticle), or a non-covalent bond (e.g., nucleic acid hybridization). A retaining component may be attached to another component by a chemical reaction that forms a covalent bond between a functional group on the retaining component and a functional group on the other component. The reaction may occur by any suitable method, including nucleophilic substitution, electrophilic substitution, and elimination reactions. In some configurations, a covalent bond between a retaining component and another component may be formed by a bioorthogonal or click reaction. A retaining component and/or other component may be modified to include a functional group that is configured to participate in a bioorthogonal or click reaction. Exemplary functional groups and linkages that may be used to attach a retaining component to one or more other components are set forth in further detail herein, for example, in the context of making detectable probes or affinity reagents.

In some configurations, a retaining component may include a nucleic acid structure, such as a SNAP. In some cases, the nucleic acid structure may include regions of single-stranded nucleic acid that provide targeted, site-specific hybridization sites for the attachment of other components (e.g. a binding component, label component or another retaining component) to the retaining component. In such configurations, other components attached to complementary oligonucleotides can be annealed to single stranded sequences on a retaining component to form an attachment at the targeted sites on the retaining component. In other configurations, oligonucleotides including functional groups may be annealed to a retaining component, thereby permitting subsequent attachment of another component via a chemical reaction (e.g., a click reaction) between the functional group on the oligonucleotide and a functional group on the other component.

A detectable probe or affinity reagent may include a retaining component attached to a plurality of binding components. The plurality of binding components attached to the retaining component may be chosen to increase the avidity of the detectable probe or affinity reagent. In some configurations, a detectable probe or affinity reagent may contain a plurality of binding components that is homogeneous with regard to species (e.g., only antibodies, only aptamers, only nanobodies, only mini-peptide binders, only DARPins etc.). In other configurations, a detectable probe or affinity reagent may contain a plurality of binding components that is heterogeneous with regard to species (e.g., a mixture of antibodies, nanobodies, mini-protein binders, DARPins and/or aptamers). In some configurations, a detectable probe or affinity reagent may contain a plurality of binding components that have essentially the same binding specificity for a particular binding partner, epitope, or target moiety. In other configurations, a detectable probe or affinity reagent may contain a plurality of binding component that have a mixture of binding specificities for a particular binding partner, epitope, or target moiety.

The quantity and/or variety of binding components attached to a detectable probe or affinity reagent may be chosen to increase the avidity of the detectable probe or affinity reagent. A detectable probe or affinity reagent may have a total of at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, or more, whether being different from each other (e.g. a heterogeneous mixture of binding components) or the same (e.g. a homogenous set of binding components). Alternatively or additionally, a detectable probe or affinity reagent may have a total of no more than about 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or less, whether being different from each other or the same.

A detectable probe or affinity reagent may include a heterogeneous mixture of binding components at a chosen ratio, heterogeneity being based upon binding component species and/or binding specificity. For example, a detectable probe or affinity reagent for a particular epitope may include a high specificity binding component and a medium specificity binding component at a ratio of about 3:1 on a molar basis. A detectable probe or affinity reagent may include a first binding component and a differing second binding component at a ratio of at least about 1:1, 1.5:1, 2:1, 3:1, 4:1, 5:1, 6:1, 7:1, 8:1, 9:1, 10:1, 25:1, 50:1, 100:1, 250:1, 500:1, 1000:1, 2500:1, 5000:1, 10000:1, 25000:1, 50000:1, 100000:1, 250000:1, 500000:1, 1000000:1, or more. Alternatively or additionally, a detectable probe or affinity reagent may include a first binding component and a differing second binding component at a ratio of no more than about 1000000:1, 500000:1, 250000:1, 100000:1, 50000:1, 25000:1, 10000:1, 5000:1, 2500:1, 1000:1, 500:1, 250:1, 100:1, 50:1, 25:1, 10:1, 9:1, 8:1, 7:1, 6:1, 5:1, 4:1, 3:1, 2:1, 1.5:1, or less.

An affinity reagent, probe or binding component of the present disclosure may have a characterized binding probability for a binding partner, epitope, or target moiety. For example, an affinity reagent, probe or binding component may be known to bind to a certain polypeptide epitope and may be known to show a high probability of binding (e.g., fails to show evidence of binding 1 out of every 100 observations). In another example, an affinity reagent, probe or binding component may be characterized as binding to a certain epitope with a low, but non-zero, binding probability (e.g., 0.00001% chance of binding for a given observation). A probabilistic characterization may include two aspects regarding binding probability: 1) the structure-dependent likelihood of binding to a binding partner, epitope, or target moiety; and 2) the environmentally-dependent likelihood of binding to a binding partner, epitope, or target moiety.

The binding probability of an affinity reagent, probe or binding component for a binding partner, epitope, or target moiety may be extended beyond polypeptides to include non-polypeptide or heterogeneous systems (e.g., soil, crude cell lysates, bodily fluids). For example, an affinity reagent, probe or binding component may have a characterized binding probability for a component of a composite (e.g., metal nanoparticles embedded in a polymer matrix) or may preferentially bind to structural subunits within a polysaccharide (e.g., glycosylations, hemicelluloses, celluloses, lignins, pectins, etc.). The skilled person will recognize from the present disclosure that an affinity reagent, probe or binding component intended for a non-polypeptide or heterogeneous system may show the analogous property of possessing a non-zero probability of binding to a non-polypeptide binding partner, epitope, or target moiety for which the affinity reagent, probe or binding component possesses a low binding affinity.

The binding affinity or binding promiscuity of an affinity reagent, probe or binding component may pertain to the effect that polypeptide primary, secondary, tertiary, or quaternary structure (i.e. amino acid sequence) has on binding. For example, an affinity reagent, probe or binding component may be characterized as binding with increased or decreased preference for particular polypeptide epitope sequences (e.g., amino acid trimers, tetramers, pentamers, etc.). The structure-dependent likelihood of an affinity reagent, probe or binding component binding to an epitope may also be affected by sequence context (e.g., amino acids that flank the amino terminus and/or carbonyl terminus of a peptide epitope; amino acid residues that are proximal to a peptide epitope in the secondary or tertiary structures of a polypeptide, the presence or absence of post-translational modifications in or around a peptide epitope, etc.). An affinity reagent, probe or binding component of the present disclosure may have substantial affinity or promiscuity for a family of amino acid epitopes (e.g., AXA, where A represents alanine and X represents any of the 20 naturally-occurring amino acids). The structure-dependent likelihood of binding may be calculated for each affinity reagent, probe or binding component used for polypeptide characterization, such as by an empirical binding model or a database of binding probabilities. An affinity reagent, probe or binding component may have a sequence-specific likelihood of binding to a binding partner, epitope, or target moiety of at least about 0.000001%, 0.00001%, 0.0001%, 0.001%, 0.01%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.9999%, 99.99999%, 99.999999% or more. Alternatively or additionally, an affinity reagent, probe or binding component may have a sequence-specific likelihood of binding to a binding partner, epitope, or target moiety of no more than about 99.999999%, 99.99999%, 99.9999%, 99.999%, 99.99%, 99.9%, 99.5%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less.

The environmentally-dependent likelihood of binding an affinity reagent, probe or binding component to an epitope in a polypeptide may pertain to the effect of variables other than the structure of the epitope and/or the polypeptide on binding. For example, binding of an affinity reagent, probe or binding component to a particular epitope may vary based upon solvent chemical composition (e.g., solvent identity, solvent polarity, ionic strength of the solvent, buffer concentration, pH, presence of surfactants or denaturants, etc.). Other non-polypeptide variables may include the time duration of binding; concentration of affinity reagent, probe or binding component; concentration of binding partner, epitope or target moiety; and the presence of externally-applied fields, such as heat, electrical fields, magnetic fields, and fluid velocity fields. An affinity reagent, probe or binding component may have an environmentally-dependent likelihood of binding to a binding partner, epitope, or target moiety of at least about 0.000001%, 0.00001%, 0.0001%, 0.001%, 0.01%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.9999%, 99.99999%, 99.999999% or more. Alternatively or additionally, an affinity reagent, probe or binding component may have an environmentally-dependent likelihood of binding to a binding partner, epitope, or target moiety of no more than about 99.999999%, 99.99999%, 99.9999%, 99.999%, 99.99%, 99.9%, 99.5%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less.

In some configurations, the structure-dependent binding likelihood and the environmentally-dependent binding likelihood may be combined to determine an overall likelihood or probability of an affinity reagent, probe or binding component binding to a binding partner, epitope, or target moiety. Overall likelihoods or probabilities may be compiled for some or all known binding partners, epitopes, or target moieties to create a probabilistic binding profile for an affinity reagent, probe or binding component. In some configurations, an affinity agent, probe or binding component may be characterized as binding to a set of N binding partners, epitopes, or target moieties with an overall binding probability of at least about 20%, and a set of M binding partners, epitopes, or target moieties with an overall binding probability of no more than 0.1%, where $N \geq 1$, $M \geq 1$, and $M \geq 10$ N. An affinity reagent, probe or binding component may have an overall likelihood or probability of binding to a binding partner, epitope, or target moiety of at least about 0.000001%, 0.00001%, 0.0001%, 0.001%, 0.01%, 0.1%, 0.5%, 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.5%, 99.9%, 99.99%, 99.999%, 99.9999%, 99.99999%, 99.999999% or more. Alternatively or additionally, an affinity reagent, probe or binding component may have an overall likelihood or probability of binding to a binding partner, epitope, or target moiety of no more than about 99.999999%, 99.99999%, 99.9999%, 99.999%, 99.99%, 99.9%, 99.5%, 99%, 98%, 97%, 96%, 95%, 90%, 85%, 80%, 75%, 70%, 65%, 60%, 55%, 50%, 45%, 40%, 35%, 30%, 25%, 20%, 15%, 10%, 5%, 4%, 3%, 2%, 1%, 0.5%, 0.1%, 0.01%, 0.001%, 0.0001%, 0.00001%, 0.000001%, or less.

A retaining component may include one or more label components that are associated with the retaining component. In some configurations, the one or more label components may be attached to the retaining component of the detectable probe or affinity reagent. In some configurations, the one or more label components may be non-covalently associated with the detectable probe (e.g., nucleic acid intercalation dyes) or affinity reagent. In some configurations, a retaining component may surround or enclose a label component (e.g., a polymer coating on a FluoSphere™ or quantum dot). A label component may be attached to a retaining component by a covalent bond (e.g., via a click reaction), a coordination bond (e.g., a silane linker to a silicon nanoparticle), or a non-covalent bond (e.g., nucleic acid hybridization). A label component may be attached to a retaining component by a chemical reaction that forms a covalent bond between a functional group on the retaining component and a functional group on the label components. The reaction may occur by any suitable method, including those set forth herein or known in the art.

A retaining component may include a particle (e.g. microparticle or nanoparticle) that provides one or more attachment sites for other components (e.g. a binding component, label component or another retaining component). In some configurations, a particle may include a surface that is functionalized, can be functionalized, or is otherwise modifiable to provide attachment sites for other components. In some configurations, a particle may provide a template for a shell or coating (e.g., a polymer or hydrogel coating) that contains or can be modified to contain attachment sites for components. In some configurations, a retaining component may effectively function as a label component (e.g., a FluoSphere™ or quantum dot). A particle may include a surrounding or concentric shell, layer, or coating that provides attachment sites or modifiable sites for the attachment of components. The shell, coating, or layer may include a polymer or hydrogel that has been covalently or non-covalently joined to the particle surface. The shell, coating, or layer may include a plurality of functional groups that can form a covalent bond or can be modified to form a covalent bond with another molecule. The shell, coating, or layer may be modified with additional groups that provide attachment sites or otherwise modify the surface (e.g., providing steric hindrance by PEGylation of the surface).

Any of a variety of detectable moieties may be used as label components for an affinity reagent or detectable probe described herein. For example, in some cases, the labels may be electrochemical labels and may be detected by electrochemical detection. These may be charged moieties, for example large nucleic acids, polylysine, and other highly charged chemical structures, and detection regions may be ChemFET type sensors. Alternatively or additionally, in some cases, the detectable moieties may be optically detectable moieties, i.e., detectable based upon observation of differential light energy that comes from the label.

A detectable probe may include one or more retaining components attached to one or more label components. The one or more label components attached to the retaining component may be chosen to increase the observability of the detectable probe. In some configurations, a detectable probe may contain a plurality of label components that are homogeneous with regard to species of label (e.g., a single type of fluorophore, homogeneous nucleic acid barcodes, etc.). In other configurations, a detectable probe may contain a heterogeneous plurality of label component species (e.g., a mixture of fluorophores with differing emissions wavelengths, a mixture of fluorophores and nucleic acid barcodes). Optionally, a detectable probe may contain a plurality of label components that produce overlapping signals or signals that are indistinguishable when detected in a method or apparatus set forth herein. For example, a plurality of fluorophores present in a detectable probe may emit fluorescence at a common wavelength whether the fluorophores are excited at the same wavelength as each other or different wavelengths form each other. Alternatively, a detectable probe may contain a plurality of label components that produce different signals from each other, for example, signals that are distinguishable or distinguished when detected in a method or apparatus set forth herein.

A detectable label or label component may produce a detectable signal that permits identification of an interaction between an affinity reagent (e.g. detectable probe) and a binding partner, epitope, or target moiety. A detectable label or label component may be configured to provide spatial information, such as providing a detectable signal at a spatially-resolved location. A detectable label or label component may be configured to provide temporal information, such as providing an evanescent or decaying signal, optionally at a spatially-resolved location. A detectable label or label component may emit a detectable signal in the presence of an excitation source (e.g., radiation, heat, a chemical substrate). A detectable label or label component may emit a detectable signal in the absence of an excitation source (e.g., a radiolabel or chemiluminescent label). A detectable label or label component may contain an encoded signal, such as a nucleic acid or polypeptide barcode.

In some configurations, a label component may include an attached enzyme, protein, or a sequence of enzymes that create a detectable chemical signal. Exemplary enzymes may include horseradish peroxidase (HRP) or alkaline phosphatase. An enzyme or protein may be chosen that converts a substrate molecule into a detectable molecule (e.g., a fluorescent compound) or binds a substrate molecule that in turn produces a fluorescent or luminescent effect in the enzyme or protein. For example, HRP may convert a substrate molecule such as ABTS, OPD, AmplexRed, DAB, AEC, TMB, homovanillic acid, or luminol into a fluorescent or luminescent molecule. In some configurations, a detectable probe or affinity reagent may interact with a binding partner, epitope, or target moiety in the presence of a substrate molecule to produce a deposited fluorescent or luminescent molecule that provides a spatial signal of the location of the detectable probe or affinity reagent binding interaction. In an alternative configuration, a detectable probe or affinity reagent binding interaction may be detected by a reactive pathway or reaction sequence that produces a detectable signal through a succession of reactions of a substrate molecule. For example, an enzyme such as HRP or alkaline phosphatase may be colocalized with a binding partner, epitope, or target moiety. A detectable probe or affinity reagent may include one or more enzymes that convert a substrate molecule from a substrate that cannot be processed or altered by the colocalized enzyme to a product that is a substrate for the colocalized enzyme. A detectable probe or affinity reagent may include a plurality of differing enzymes or an enzymatic complex (e.g., a polyketide synthase) that converts a substrate into a detectable product.

A detectable label or label component may be detected by a signal detection source as would be appropriate for the chosen label species. Optical labels and optical detectors are particularly useful. Examples of optical detection apparatus and components thereof that can be used herein include those commercialized for nucleic acid sequencing such as those provided by Illumina™, Inc. (e.g. HiSeq™, MiSeq™, NextSeq™, or NovaSeq™ systems), Life Technologies™ (e.g. ABI PRISM™, or SOLID™ Systems), Pacific Biosciences (e.g. systems using SMRT™ Technology such as the Sequel™ or RS II™ systems), or Qiagen (e.g. Genereader™ system) or those described in US Pat. App. Pub. No. 2010/0111768 A1 or U.S. Pat. Nos. 7,329,860; 8,951,781 or 9,193,996, each of which is incorporated herein by reference. Other useful detectors are described in U.S. Pat. Nos. 5,888,737; 6,175,002; 5,695,934; 6,140,489; or 5,863,722; or US Pat. Pub. Nos. 2007/007991 A1, 2009/0247414 A1, or 2010/0111768; or WO2007/123744, each of which is incorporated herein by reference in its entirety.

Other detection techniques that can be used in a method set forth herein include, for example, mass spectrometry which can be used to perceive mass; surface plasmon resonance which can be used to perceive binding to a surface; absorbance which can be used to perceive the wavelength of the energy a label absorbs; calorimetry which can be used to perceive changes in temperature due to presence of a label; electrical conductance or impedance which can be used to perceive electrical properties of a label, or other known analytic techniques. For example, charged labels can be detected using electronic detectors such as chemFET detectors used for detection of protons or pyrophosphate (see, for example, US Pat. App. Pub. Nos. 2009/0026082 A1; 2009/0127589 A1; 2010/0137143 A1; or 2010/0282617 A1, each of which is incorporated herein by reference in its entirety, or detectors commercialized in the Ion Torrent™ systems commercially available from ThermoFisher, Waltham, Mass.) A FET detector can be used such as one or more of those described in US Pat. App. Pub. Nos. 2017/0240962 A1, 2018/0051316 A1, 2018/0112265 A1, 2018/0155773 A1 or 2018/0305727 A1; or U.S. Pat. Nos. 9,164,053, 9,829,456, 10,036,064, or 10,125,391, each of which is incorporated herein by reference.

A label component may include a moiety or molecule that is luminescent (e.g. a luminophore or fluorophore). Luminophores, which emit light of one wavelength in response to being excited by a light of another wavelength, are particularly useful as optically detectable labels given their ability to provide readily detectable light signals, as well as their ability to be tailored to a variety of different excitation and emission light spectra, providing great flexibility in their deployment and use.

Any of a variety of luminophores may be used herein. In some cases, the luminophore may be a small molecule. In some cases, the luminophore may be a protein. Luminophores may include labels that emit in the ultraviolet spectrum, visible spectrum, or infrared spectrum. In some cases, the luminophore may be selected from the group consisting of FITC, Alexa Fluor® 350, Alexa Fluor® 405, Alexa Fluor® 488, Alexa Fluor® 532, Alexa Fluor® 546, Alexa Fluor® 555, Alexa Fluor® 568, Alexa Fluor® 594, Alexa Fluor® 647, Alexa Fluor® 680, Alexa Fluor® 750, Pacific Blue, Coumarin, BODIPY FL, Pacific Green, Oregon Green, Cy3, Cy5, Pacific Orange, TRITC, Texas Red, R-Phycoerythrin, Allophcocyanin (APC). In some cases, the label may be an Atto dye, for example Atto 390, Atto 425, Atto 430, Atto 465, Atto 488, Atto 490, Atto 495, Atto 514, Atto 520, Atto 532, Atto 540, Atto 550, Atto 565, Atto 580, Atto 590, Atto 594, Atto 610, Atto 611, Atto 612, Atto 620, Atto 633, Atto 635, Atto 647, Atto 655, Atto 680, Atto 700, Atto 725, Atto 740, Atto MB2, Atto Oxa12, Atto Rho101, Atto Rho12, Atto Rho13, Atto Rho14, Atto Rho3B, Atto Rho6G, or Atto Thio12. In some cases, the luminophore may be a fluorescent protein, for example a fluorescent protein selected from the group consisting of green fluorescent protein (GFP), cyan fluorescent protein (CFP), red fluorescent protein (RFP), blue fluorescent protein (BFP), orange fluorescent protein (OFP), and yellow fluorescent protein (YFP). A wide range of effective luminophores are commercially available, for example, from the Molecular Probes division of ThermoFisher Scientific and/or generally described in the *Molecular Probes Handbook* (11$^{th}$ Edition) which is hereby incorporated by reference. Label components may also include intercalation dyes, such as ethidium bromide, propidium bromide, crystal violet, 4',6-diamidino-2-phenylindole (DAPI), 7-aminoactinomycin D (7-AAD), Hoescht 33258, Hoescht 33342, Hoescht 34580, YOYO-1, DiYO-1, TOTO-1, DiTO-1, or combinations thereof.

Specific fluorescent labels or other luminophores may be chosen depending upon the desired use, and in some cases, selected based on their absorption/emission spectra, for example, to optimize multiplexed detection. Likewise, in some cases, luminophores may include pairs of fluorescent dyes that interact to provide advantageous fluorescent properties. For example paired dyes can function as Forster resonant energy transfer (FRET) pairs, where excitation of one member of the pair (i.e. "donor") results in an energy transfer that excites or is transferred to the other member (i.e. "acceptor"). The acceptor then emits luminescence at a wavelength that is shifted from the emission that would have occurred from the donor alone.

In some cases, optically detectable labels may include other types of detectable moieties. For example, in some cases, luminescent particles (e.g. microparticles or nanoparticles), such as semiconductor nanoparticles, "quantum dots", or FluoSphere™ particles, may be included as label components.

A luminophore may be characterized by a characteristic excitation or absorbance wavelength. An excitation source may include a light source that is tuned to a characteristic excitation or absorbance wavelength of a luminophore. A luminophore may absorb light over a range of wavelengths, with maximum absorbance of light occurring at a peak wavelength. A luminophore can be excited at or near peak excitation. In particular configurations of methods set forth herein a luminophore can be excited by radiation in the ultraviolet (UV), visible (VIS) or infrared (IR) region of the spectrum. Excitation in the VIS region may occur at one or more of the red, orange, yellow, green, blue or violet regions of the spectrum. A luminophore may be characterized by a characteristic emission wavelength. A luminophore may emit light over a range of wavelengths, with maximum emission of light occurring at a peak wavelength. A luminophore can be detected at or near peak emission. In particular configurations of methods set forth herein emission from a luminophore can be detected in the ultraviolet (UV), visible (VIS) or infrared (IR) region of the spectrum. Detection in the VIS region may occur at one or more of the red, orange, yellow, green, blue or violet regions of the spectrum.

The presence of multiple label components in a detectable probe may increase the observability of the detectable probe, for example, by 1) increasing the likelihood of detection; 2) providing redundancy in case of label loss (e.g., photobleaching, chemical damage, cleavage of labels, etc.); and/or 3) increasing the signal strength generated by a detectable probe. The quantity of label components associated with a detectable probe may be decided by various factors, including probe size, desired label spacing, signal intensity, measurement length, measurement environments, and label size.

A detectable probe may have a chosen number of associated label components. A detectable probe may have at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, or more, whether being different from each other (e.g. a heterogeneous mixture of labels that produce signals that are distinguishable from each other in a method or apparatus set forth herein) or the same (e.g. a mixture of labels that produce signals that are indistinguishable in a method or apparatus set forth herein). Alternatively or additionally, a detectable probe may have no more than about 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or less, whether being different from each other (e.g. a heterogeneous mixture of labels that produce signals that are distinguishable from each other in a method or apparatus set forth herein) or the same (e.g. a mixture of labels that produce signals that are indistinguishable in a method or apparatus set forth herein).

The chosen variety or quantity of label components on a detectable probe may provide a signal that exceeds a background signal. For example, probes that are detected by fluorescence may produce a fluorescent signal that exceeds the existing background from sources such as autofluorescence, signal cross-talk, and impinging external sources. A detectable probe may include a variety or quantity of label components that is configured to produce a detectable signal intensity that exceeds a signal background intensity (e.g., maximum, minimum, or average) by at least 2×, 5×, 10×, 25×, 50×, 100×, or more. Additionally or alternatively, a detectable probe may include a quantity of label components that is configured to produce a detectable signal intensity that exceeds a signal background intensity (e.g., maximum, minimum, or average) by no more than about 100×, 50×, 25×, 10×, 5×, 2×, or less.

A detectable probe may include more than one type and/or species of label component. For example, a detectable probe may include at least one luminophore and at least one nucleic acid barcode sequence. In another example, a detectable probe may include two or more different luminophores (e.g., Alexa-Fluor® 488 and Alexa-Fluor® 647). The different luminophores can differ with respect to one or more signal properties such as their excitation spectra, emission spectra, luminescence lifetime, or luminescence polarity. In some configurations the different luminophores can be similar with regard to one or more signal properties. For example, two luminophores can be excited at the same wavelength, but emit at different wavelengths. As such, a single excitation source can be used to excite two different luminophores that are nonetheless distinguished based on differences in their emission properties. A detectable probe may include more than one type and/or species of label component for various purposes, including creating unique signal fingerprints, enabling multi-label detection methods (e.g., FRET or luminescence quenching), and/or generating signal redundancy to reduce false positive or false negative detections.

A detectable probe may include a heterogeneous mixture of label components, based upon label type and/or species. A detectable probe may have at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, or more label components, whether being the same as each other or different from each other. Alternatively or additionally, a detectable probe may have no more than about 100, 95, 90, 85, 80, 75, 70, 65, 60, 55, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or fewer label components, whether being the same as each other or different from each other.

A detectable probe may include a heterogeneous mixture of label components at a chosen ratio, based upon detectable label species. For example, a detectable probe for a particular epitope may include Alexa-Fluor® 488 and Alexa-Fluor®-647 dyes at a ratio of about 3:1 on a molar basis, respectively. A detectable probe may include a first label component and a differing second label component at a ratio of at least about 1:1, 1.5:1, 2:1, 3:1, 4:1, 5:1, 6:1, 7:1, 8:1, 9:1, 10:1, 25:1, 50:1, 100:1, 250:1, 500:1, 1000:1, 2500:1, 5000:1, 10000:1, 25000:1, 50000:1, 100000:1, 250000:1, 500000:1, 1000000:1, or more. Alternatively or additionally, a detectable probe may include a first label component and a differing second label component at a ratio of no more than about 1000000:1, 500000:1, 250000:1, 100000:1, 50000:1, 25000:1, 10000:1, 5000:1, 2500:1, 1000:1, 500:1, 250:1, 100:1, 50:1, 25:1, 10:1, 9:1, 8:1, 7:1, 6:1, 5:1, 4:1, 3:1, 2:1, 1.5:1, or less.

FIG. 49A provides a schematic representation of a detectable probe. Each detectable probe consists of two parts: the labeled affinity probe (200) and template (201). As shown, the labeled affinity probe 200 includes a binding component 200*a*, an annealing region 200*b* which provides a retaining component, and an enzymatically extended label component 200*c*. The template 201 includes 201*a*, a complimentary sequence to annealing region 200*b*, and 201*b*, the template for enzymatic extension of 200*c*. FIG. 49B shows a step by step demonstration of enzymatic extension off of an aptamer probe to form the label component.

In some cases, a label component may include or be attached to a retaining component (e.g. a scaffold as set forth in U.S. Provisional Application No. 63/112,607). Multiple label components may be provided randomly spaced along the retaining component, or in some cases, may be positioned at regular or semi-regular intervals along the length of the retaining component. In other cases, a single label component may be attached to a retaining component, e.g., at the 5' terminus of a nucleic acid, see FIG. 50A. In yet other cases, a nucleic acid of a retaining component can be designed to include an annealing region, and may have a single label component (e.g. a fluorophore) at the end of the annealing region. A second strand of nucleic acid with an additional single fluorophore can anneal to this region, see FIG. 50B.

It will be understood that an affinity reagent of the present disclosure need not include any label components. Accordingly, an affinity reagent can be configured to omit or be devoid of one or more label components or species of label components set forth herein. Moreover, exemplary affinity reagents or detectable probes set forth herein as having one or more label components may be reconfigured to omit one or more of the exemplified label components. It will also be understood that an affinity reagent or detectable probe of the present disclosure can be configured to omit or be devoid of one or more binding components or species of binding components set forth herein.

A retaining component may form a central structural element of a detectable probe or affinity reagent. In some configurations, a retaining component may be structured to provide constraint or control of the physical positioning of other components, such as binding components, label components or other retaining components. For example, a detectable probe or affinity reagent may include binding components that are attached at sufficiently spaced positions on a retaining component to prevent contact or cross-reactivity between the binding components. In another example, a detectable probe may include luminophores that are attached at sufficiently spaced positions on a retaining component to reduce or prevent quenching between adjacent luminophores. In a third example, a detectable probe may include luminophores that are attached at positions on a retaining component that are spaced and oriented to facilitate FRET. A retaining component may be engineered or rationally designed to control the location and/or positioning of components attached thereto. Factors that may influence the design of a retaining component include: 1) nature of a likely interaction between adjacent components; 2) likelihood of interaction between adjacent components; 3) critical scales (e.g., distance, volume, time) for likely interactions between adjacent components; 4) physical properties of the retaining component (e.g., shape, conformation, size, rigidity, etc.); 5) physical properties of the attached probe components (shape, conformation, size, hydrodynamic radius, etc.); 6) nature and properties of optional linkers that bind components to the retaining component; and 7) nature of a likely interaction between a detectable probe or affinity reagent and a binding partner.

In some configurations, a detectable probe or affinity reagent may include a retaining component including one or more nucleic acids. For example, the one or more nucleic acids that form the retaining component may take the form of a nucleic acid origami structure, nucleic acid nanoball structure or other structured nucleic acid particle. A nucleic acid retaining component can contain a single nucleic acid strand or a plurality of nucleic acid strands, such as a plurality of oligonucleotide strands. A retaining component including a plurality of nucleic acid strands may be formed by hybridization between the plurality of strands to form nucleic acid structures with increased structural complexity beyond the natural helical structure. A nucleic acid may include nucleic acids such as DNA, RNA, PNA, or combinations thereof. Nucleic acids may include non-natural nucleotides, such as luminescently modified nucleotides. Nucleic acids may include non-nucleotide residues within their structures such as photocleavable linkers (e.g., nitrobenzyl, carbonyl, or benzyl-based photocleavable linker). A retaining component including a nucleic acid may be structured to break up or destabilize under certain conditions. A retaining component may be broken up or destabilized to, for example, facilitate removal of a detectable probe or affinity reagent from a binding partner. A retaining component including a nucleic acid may include a plurality of restriction sites that can be cleaved by a restriction enzyme, thereby facilitating break up or destabilization of the nucleic acid retaining component. A retaining component including a nucleic acid may include a plurality of photocleavable, chemically cleavable or otherwise reactive bonds, thereby facilitating break up or destabilization of the retaining component.

A retaining component can include a nucleic acid nanoball. The nanoball can contain a single strand of nucleic acid that folds in on itself to form a compact structure. Optionally, the nanoball can be crosslinked to constrain the nanoball to a relatively compact structure. Exemplary crosslinks include chemical crosslinks such as psoralen or oligonucleotides that hybridize to different regions of the single strand. Nucleic acid nanoballs can be created by rolling circle amplification of a circular template to yield a concatemeric amplification product in which each unit of sequence in the concatemer has a sequence that complements the circular template. Exemplary sequence elements that can be incorporated into a nucleic acid nanoball include tag sequences that provide information about the nanoball such as its source or history of use, sequences that complement oligonucleotides used as intrastrand crosslinkers, sequences that complement oligonucleotides that are attached to functional groups or components such as binding components or label components, or the like. Exemplary nucleic acid nanoballs and methods for their manufacture and use are set forth in U.S. Pat. No. 8,445,194, which is incorporated herein by reference.

A nucleic acid nanoball may be formed by a method such as rolling circle amplification (RCA) or ligation of repeated concatemer units. A nucleic acid nanoball may include a particular number of repeated concatemer units. A nucleic acid nanoball may include at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000 or more concatemer units. Alternatively or additionally, a nucleic acid nanoball may include no more than about 1000, 900, 800, 700, 600, 500, 450, 400, 350, 300, 250, 200, 190, 180, 170, 160, 150, 140, 130, 120, 110, 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, or fewer concatemer units. A concatemer unit in a nucleic acid nanoball may have a nucleotide sequence length of at least about 20, 25, 30, 35, 40, 45, 50, 55, 60, 65, 70, 75, 80, 85, 90, 95, 100, 110, 120, 130, 140, 150, 160, 170, 180, 190, 200, or more nucleotides. Alternatively or additionally, a concatemer unit in a nucleic acid nanoball may have a nucleotide sequence length of no more than about 200, 190, 180, 170, 160, 150, 140, 130, 120, 110, 100, 95, 90, 85, 80, 75, 70, 65, 60, 55, 50, 45, 40, 35, 30, 25, 20, or fewer nucleotides.

A retaining component can include a nucleic acid origami. Accordingly, a retaining component can include one or more nucleic acids having tertiary or quaternary structures such as spheres, cages, tubules, boxes, tiles, blocks, trees, pyramids, wheels, combinations thereof, and any other possible structure. Examples of such structures formed with DNA origami are set forth in Zhao et al. *Nano Lett.* 11, 2997-3002 (2011), which is incorporated herein by reference. In some configurations, a nucleic acid origami may include a scaffold and a plurality of staples, where the scaffold is a single, continuous strand of nucleic acid, and the staples are oligonucleotides that are configured to hybridize, in whole or in part, with the scaffold nucleic acid. Examples of nucleic acid origami structures formed using a continuous scaffold strand and several staple strands are set forth in *Rothemund Nature* 440:297-302 (2006) or U.S. Pat. No. 8,501,923 or 9,340, 416, each of which is incorporated herein by reference. A retaining component including one or more nucleic acids (e.g. as found in origami or nanoball structures) may include regions of single-stranded nucleic acid, regions of double-stranded nucleic acid, or combinations thereof.

In some embodiments, a nucleic acid origami includes a scaffold having a closed nucleic acid strand, and a plurality of oligonucleotides hybridized to the scaffold. A nucleic acid scaffold may include a continuous strand of nucleic acids that, absent complementary oligonucleotides, is a circular or joined strand (i.e., no 5' or 3' termini). In some configurations, a nucleic acid scaffold is derived from a natural source, such as a viral genome or a bacterial plasmid. In other configurations, a nucleic acid scaffold may be engineered, rationally designed, or synthetic. A scaffold may include one or more modified nucleotides. Modified nucleotides may provide functional groups or attachment sites for attaching additional components (e.g. binding component, label component or another retaining component) before, during, or after assembly of a detectable probe or affinity reagent. A modified nucleotide may include a linking group or a functional group (e.g., a functional group configured to perform a click reaction). In some configurations, a nucleic acid scaffold may include a single strand of an M13 viral genome. The size of a nucleic acid scaffold may vary depending upon the desired size of the retaining component. A nucleic acid scaffold may include at least about 1000, 2000, 3000, 4000, 5000, 6000, 7000, 8000, 9000, 10000, or more nucleotides. Alternatively or additionally, a nucleic acid scaffold may include at most about 10000, 9000, 8000, 7000, 6000, 5000, 4000, 3000, 2000, 1000 or fewer nucleotides.

A retaining component, such as a nucleic acid origami, may include a plurality of oligonucleotides (e.g. staples). Staples may include oligonucleotides that are configured to hybridize with a nucleic acid scaffold, other staples, or a combination thereof. A staple may include one or more modified nucleotides. Staples may be modified to include additional chemical entities, such as binding components, label components, chemically-reactive groups (e.g. functional groups or handles), or other groups (e.g., polyethylene glycol (PEG) moieties). Staples may include linear or circular nucleic acids. Staples may include regions of single-stranded nucleic acids, double-stranded nucleic acids, or combinations thereof. A staple may be configured to bind with other nucleic acids by complementary base pair hybridization or ligation. A staple may be configured to act as a primer for a complementary nucleic acid strand and the priming staple may be extended by an enzyme (e.g., a polymerase such as a template directed polymerase or non-template directed polymerase such as terminal transferase) to form lengthened regions of double-stranded nucleic acid.

A staple may be any length depending upon the design of the retaining component. Staples may be designed by a software package, such as CADNANO, ATHENA, or DAEDALUS. A staple may have a length of at least about 10, 25, 50, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2500, 3000, 3500, 4000, 4500, 5000, or more nucleotides. Alternatively or additionally, a staple may have a length of no more than about 5000, 4500, 4000, 3500, 3000, 2500, 2000, 1900, 1800, 1700, 1600, 1500, 1400, 1300, 1200, 1100, 1000, 950, 900, 850, 800, 750, 700, 650, 600, 550, 500, 450, 400, 350, 300, 250, 200, 150, 100, 50, 25, 10, or fewer nucleotides.

A staple may include one or more modified nucleotides. Modified nucleotides may provide attached sites for attaching additional components, such as binding components or label components. A modified nucleotide may be utilized as an attachment site for an additional component before, during, or after assembly of a detectable probe or affinity reagent. A staple may include at least about 1, 2, 3, 4, 5, 6, 7, 8, 9, 10, 20, 30, 40, 50, 75, 100 or more modified nucleotides. Alternatively or additionally, a staple may include no more than about 100, 75, 50, 40, 30, 20, 10, 9, 8, 7, 6, 5, 4, 3, 2, or 1 modified nucleotides.

A staple may be designed or modified to achieve desired stability of a detectable probe, affinity reagent or nucleic acid origami. Stability may be affected by the dissociation of individual oligonucleotides from the assembled origami. Loss of oligonucleotides could have various destabilizing effects, including loss of functionality for a detectable probe or affinity reagent (e.g., loss of component attachment sites, loss of binding components, loss of label components, etc.) or destabilization of secondary or tertiary structures, thereby promoting further destabilization of other oligonucleotides. A scaffold or staple in a nucleic acid retaining component may include one or more modified nucleotides that are configured to form covalent or non-covalent bonds that promote the stability of the nucleic acid retaining component. For example, an oligonucleotide may include one or more modified nucleotides that form covalent bonds or cross-links with modified nucleotides in other oligonucleotides or in the scaffold strand. Alternatively or additionally, an oligonucleotide may be designed to have a minimum hybridization length or minimum melting temperature to decrease the likelihood of dissociation.

An oligonucleotide in a detectable probe or affinity reagent may hybridize with another oligonucleotide or a scaffold strand forming a particular number of base pairs. An oligonucleotide may form a hybridization region of at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more consecutive or total base pairs. Alternatively or additionally, an oligonucleotide may form a hybridization region of no more than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or fewer consecutive or total base pairs.

An oligonucleotide in a detectable probe, affinity reagent or nucleic acid origami may have a characterized melting temperature. The melting temperature may refer to the temperature at which nucleotide base-pair binding interactions become interrupted, thereby causing dissociation of the oligonucleotide. An oligonucleotide in a nucleic acid retaining component may have a characterized melting temperature of at least about 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 81° C., 82° C., 83° C., 84° C., 85° C., 86° C., 87° C., 88° C., 89° C., 90° C., or higher. Alternatively or additionally, an oligonucleotide in a nucleic acid retaining component may have a characterized melting temperature of no more than about 90° C., 89° C., 88° C., 87° C., 86° C., 85° C., 84° C., 83° C., 82° C., 81° C., 80° C., 79° C., 78° C., 77° C., 76° C., 75° C., 74° C., 73° C., 72° C., 71° C., 70° C., 69° C., 68° C., 67° C., 66° C., 65° C., 64° C., 63° C., 62° C., 61° C., 60° C., 59° C., 58° C., 57° C., 56° C., 55° C., 54° C., 53° C., 52° C., 51° C., 50° C., or lower.

A detectable probe or affinity reagent may include a retaining component that is configured to position a plurality of binding components at specific locations on the retaining component. The relative positioning may be determined in part by the potential for positive or negative interactions between adjacent binding components. For example, some adjacent binding components (e.g., aptamers, peptamers) may be prone to misfolding or conformational changes when brought into close proximity with particular species of binding components. Such binding components may benefit from sufficient separation to minimize the likelihood of such negative interactions. In another example, some binding components may experience an increase in avidity when multiple binding components are brought within a close proximity. In some configurations, the positioning of binding components at specific locations on a retaining component may be determined by optimizing a balance between positive avidity effects and negative inter-affinity reagent interactions.

Positioning of binding components on a detectable probe or affinity reagent may be determined, in whole or in part, by the structural properties of a retaining component. In some configurations, retaining components may include an inherently rigid, inelastic, or non-deformable material (e.g., carbon or metal nanoparticles) that is not prone to deformation when used in particular compositions or methods, for example, in solution or on a solid support. In other configurations, retaining components may include a flexible or deformable material (e.g., polymers, nucleic acids, etc.) that is prone to some degree of deformation, such as stretching, compression, or bending (e.g., torsional or lateral bending). The natural deformation of a retaining component may produce conformational changes that increase or decrease the relative proximity of adjacent binding components attached to the retaining component.

Figures 3A, 3B, 3C:
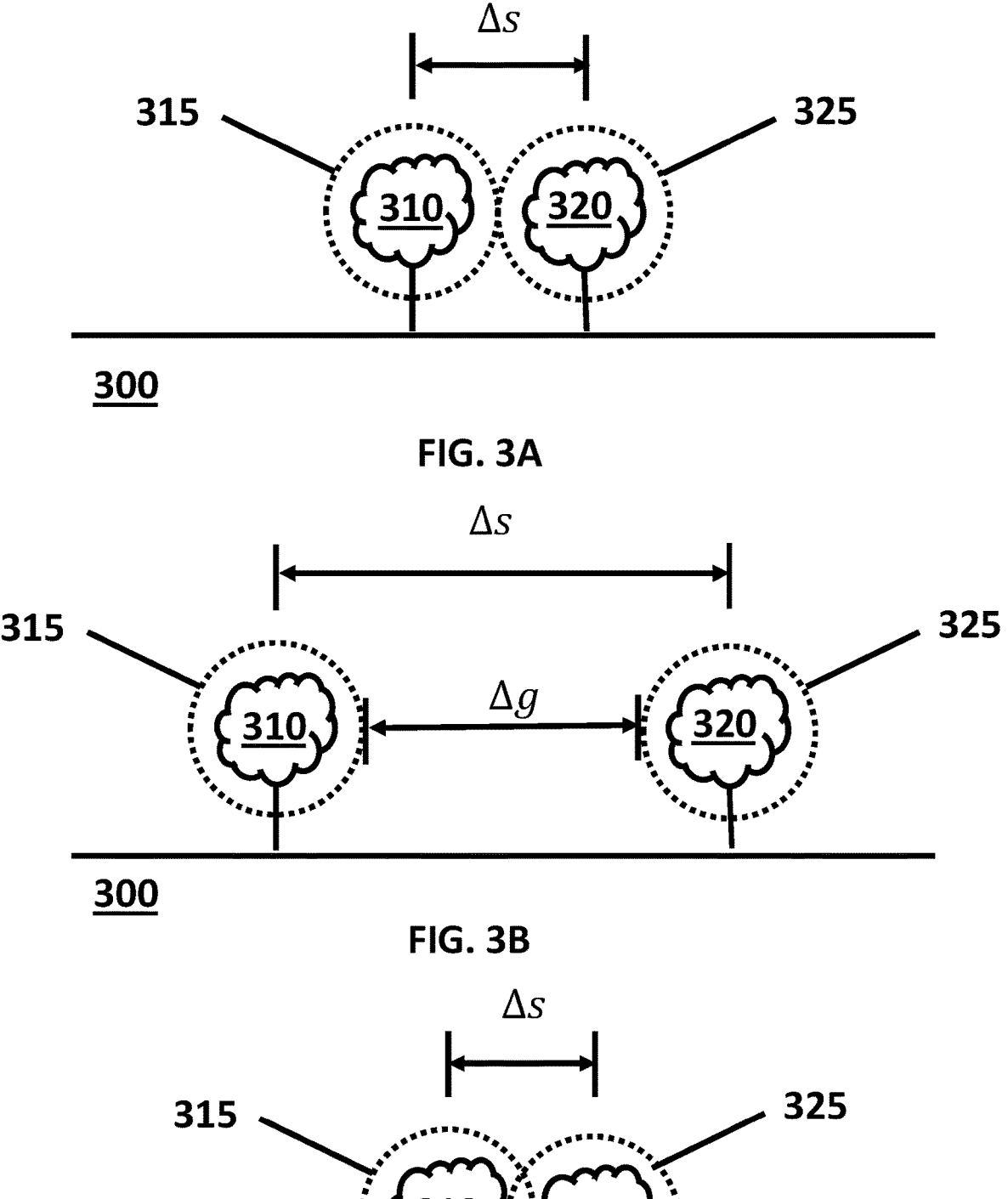
FIG. 3A shows relative separation between two binding components.
FIG. 3B shows relative separation between two binding components.
FIG. 3C shows relative separation between two binding components.

Binding components may be positioned on a retaining component with sufficient separation relative to other binding components such that affinity reagents do not have overlapping effective occupied volumes. FIG. 3A depicts a schematic of a first binding component 310 and a second binding component 320 that are attached to a retaining component 300. The first binding component 310 has an effective occupied volume 315 and the second binding component 320 has an effective occupied volume 325. The first binding component 310 and the second binding component 320 are attached to the retaining component 300 at a separation distance $\Delta s$ that is the minimum distance necessary to ensure that the effective occupied volumes 315 and 325 do not overlap.

In some configurations, binding components may be positioned on a retaining component with sufficient separation relative to other binding components such that binding components have a separation gap. FIG. 3B depicts a schematic of a first binding component 310 and a second binding component 320 that are attached to a retaining component 300 with a separation gap $\Delta s$. The first binding component 310 has an effective occupied volume 315 and the second binding component 320 has an effective occupied volume 325. The first binding component 310 and the second binding component 320 are attached to the retaining component 300 at a separation distance $\Delta s$ that is the minimum distance necessary to ensure that the effective occupied volumes 315 and 325 have a separation gap of length $\Delta g$.

In some configurations, binding components may be positioned on a retaining component with a separation relative to other binding components such that binding components have overlapping effective occupied volumes. FIG. 3C depicts a schematic of a first binding component 310 and a second binding component 320 that are attached to a retaining component 300. The first binding component 310 has an effective occupied volume 315 and the second binding component 320 has an effective occupied volume 325. The first binding component 310 and the second binding component 320 are attached to the retaining component 300 at a separation distance $\Delta s$ that causes the effective occupied volumes 315 and 325 to overlap, thereby creating an overlap volume $\Delta V$.

Positioning of binding components on a detectable probe or affinity reagent may be determined, in whole or in part, by the structural properties of optional linkers that connect a binding component to a retaining component. Linkers may be used for various purposes, such as providing separation between a retaining component and a binding component, positioning a binding component, providing attachment sites for other chemical entities, minimizing the likelihood of unwanted retaining component—binding component interactions, or generating desired chemical properties between a retaining component and binding component (e.g., hydrophobicity). A linker may include rigid or conformationally-constrained chemical groups (e.g., alkenes, alkynes, cyclic compounds). A linker may include flexible, dynamic, or moveable chemical groups (e.g., polyethylene glycol (PEG), polyethylene oxide (PEO), or alkane chains). A linker may include a polynucleotide that is not configured to bind to other nucleic acids present in a method or apparatus where it is present. A linker including nucleic acids (e.g., RNA, DNA, PNA) may include a polynucleotide that forms regions of secondary structure with itself (e.g., a hairpin, stem and/or loop structure). A linker may provide additionally degrees of freedom for movement of a binding component attached to a retaining component.

Figures 4A, 4B:
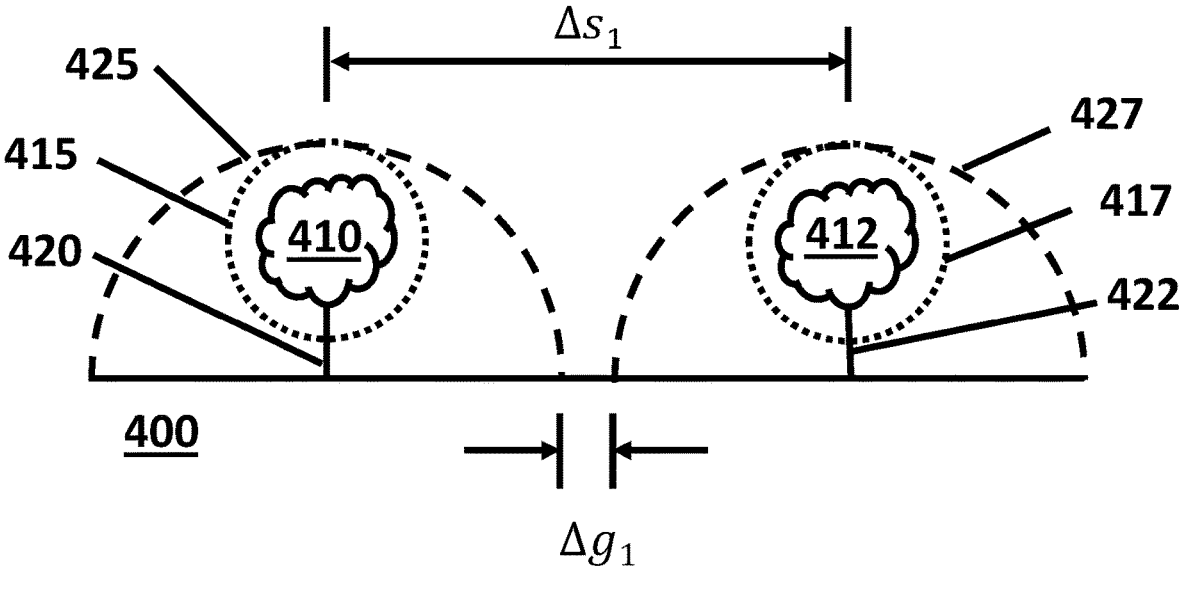
FIG. 4A shows configurations for separating two binding components.
FIG. 4B shows configurations for separating two binding components.

FIGS. 4A-4D depict exemplary methods of controlling the volume that a binding component may occupy when attached to a retaining component by a linker. FIG. 4A depicts a schematic of a first binding component 410 and a second binding component 412 that are attached to a substantially flat retaining component surface 400 by linkers 420 and 422, respectively. The first binding component 410 and the second binding component 412 have, respectively, static effective occupied volumes 415 and 417 (where the static effective occupied volumes are the maximum volumes occupied by the binding components absent motion caused by the linker). The linkers 420 and 422 provide additional degrees of freedom for the first binding component 410 and the second binding component 412 to move, thereby creating dynamic effective occupied volumes 425 and 427, respectively. The first binding component 410 and the second binding component 412 are attached by linkers 420 and 422 at positions on the flat retaining component surface 400 that are separated by a distance $\Delta s_1$ that creates a separation gap $\Delta g_1$ between the dynamic effective occupied volumes 425 and 427, ensuring that the binding component cannot contact or interact with each other. Alternatively, FIG. 4B depicts the use of an intermediate chemical moiety to interrupt interactions between two adjacent binding components. FIG. 4B depicts a schematic of a first binding component 410 and a second binding component 412, and an intermediate chemical moiety or blocking group 430 (e.g., PEG, PEO, alkane chains, dextran) that are attached to a substantially flat retaining component surface 400 by linkers 420, and 422, respectively. The first binding component 410, the second binding component 412, and the blocking group 430 have, respectively, static effective occupied volumes 415, 417, and 435 (where the static effective occupied volumes are the maximum volumes occupied by the binding components absent motion caused by the linker). The linkers 420 and 422 provide additional degrees of freedom for the first binding component 410 and the second binding component 412 to move, thereby creating dynamic effective occupied volumes 425 and 427, respectively. The first binding component 410 and the second binding component 412 are attached by linkers 420 and 422 at positions on the flat retaining component surface 400 that are separated by a distance $\Delta s_2$ and an effective separation gap $\Delta g_2$ is created between the dynamic effective occupied volumes 425 and 427 due to hindrance by intermediate chemical moiety or blocking group 430 (e.g., by steric repulsion). The use of an intermediate chemical moiety or blocking group 430 may decrease the necessary distance $\Delta s_2$ between binding component on the substantially flat surface due to the blocking of inter-binding component interactions.

Figure 4C:
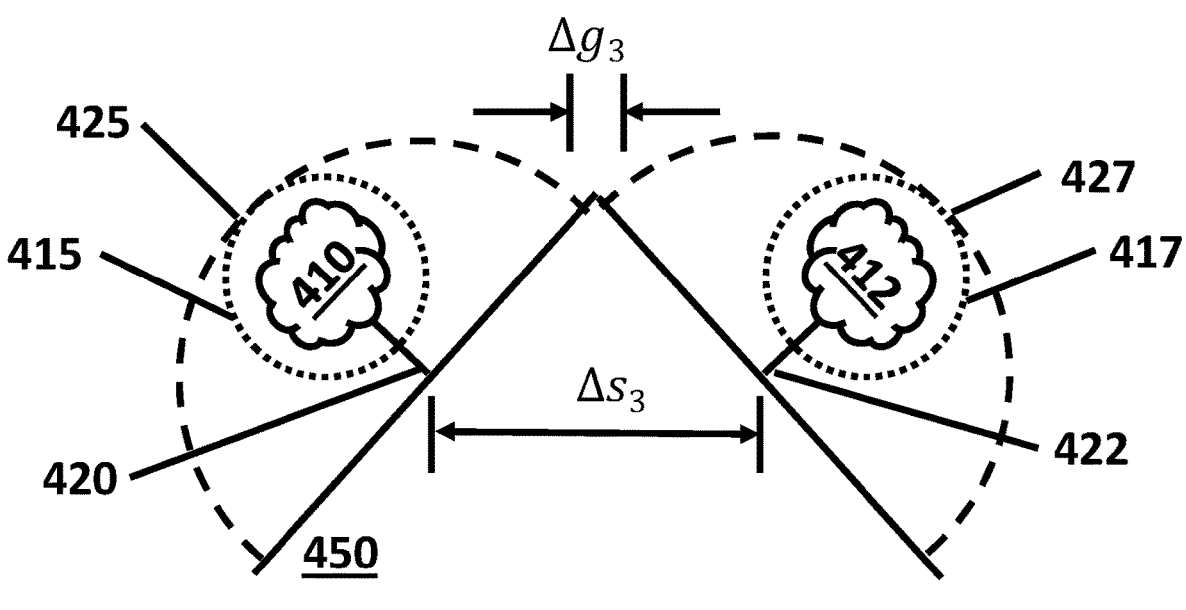
FIG. 4C shows configurations for separating two binding components.
Figure 4D:
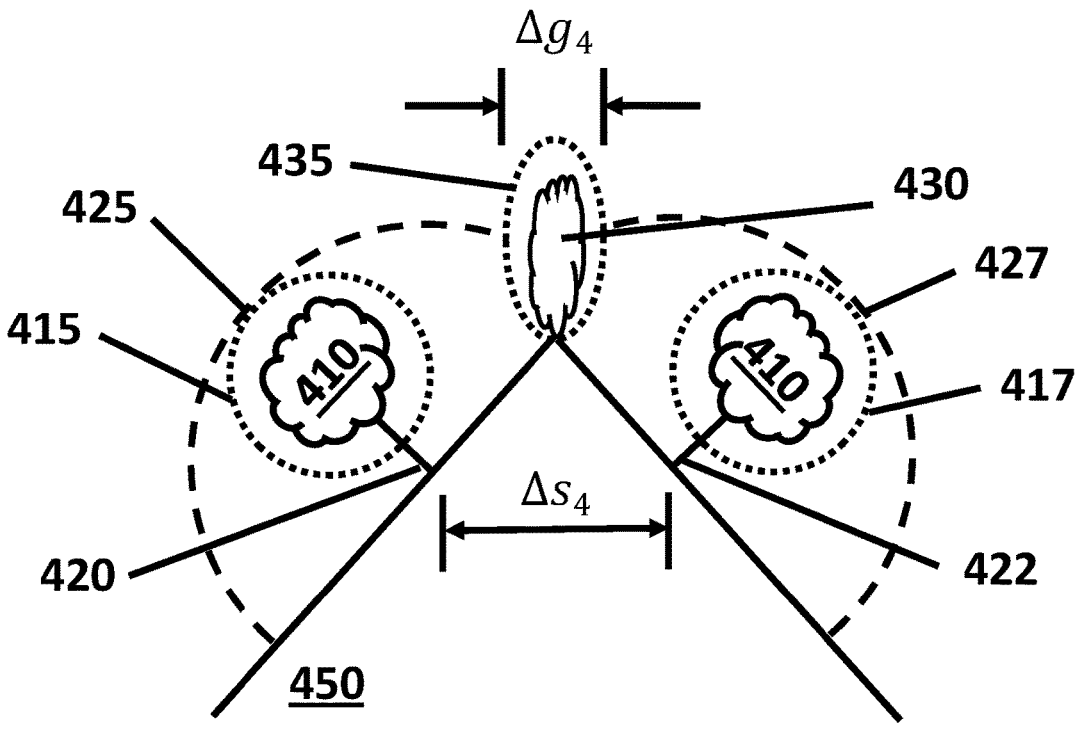
FIG. 4D shows configurations for separating two binding components.

FIG. 4C depicts a schematic of minimizing binding component interactions by altering the conformation of a retaining component. FIG. 4C depicts a schematic of a first binding component 410 and a second binding component 412 that are attached to a non-flat retaining component surface 450 by linkers 420 and 422, respectively. The first binding component 410 and the second binding component 412 have, respectively, static effective occupied volumes 415 and 417 (where the static effective occupied volumes are the maximum volumes occupied by the binding components absent motion caused by the linker). The linkers 420 and 422 provide additional degrees of freedom for the first binding component 410 and the second binding component 412 to move, thereby creating dynamic effective occupied volumes 425 and 427, respectively. The first binding component 410 and the second binding component 412 are attached by linkers 420 and 422 at positions on the non-flat retaining component surface 450 that are separated by a distance $\Delta s_3$ that creates a separation gap $\Delta g_3$ between the dynamic effective occupied volumes 425 and 427, ensuring that the binding components cannot contact or interact with each other. Alternatively, FIG. 4D depicts the use of an intermediate chemical moiety to interrupt interactions between two adjacent binding components. FIG. 4D depicts a schematic of a first binding component 410 and a second binding component 412, and an intermediate chemical moiety or blocking group 430 (e.g., PEG) that are attached to a non-flat retaining component surface 450 by linkers 420 and 422, respectively. The first binding component 410, the second binding component 412, and the intermediate chemical moiety or blocking group 430 have, respectively, static effective occupied volumes 415, 417, and 435 (where the static effective occupied volumes are the maximum volumes occupied by the binding components absent motion caused by the linker). The linkers 420 and 422 provide additional degrees of freedom for the first binding component 410 and the second binding component 412 to move, thereby creating dynamic effective occupied volumes 425 and 427, respectively. The first binding component 410 and the second binding component 412 are attached by linkers 420 and 422 at positions on the flat retaining component surface 450 that are separated by a distance $\Delta s_4$ and an effective separation gap $\Delta g_4$ is created between the dynamic effective occupied volumes 425 and 427 due to hindrance by intermediate chemical moiety 430 (e.g., by steric repulsion). The use of an intermediate chemical moiety or blocking group 430 may decrease the necessary distance $\Delta s$ between binding components on the non-flat surface due to the blocking of inter-binding component interactions.

FIGS. 5A and 5B display alternative configurations for controlling the relative position and/or orientation of label components on a retaining component including nucleic acids. FIG. 5A shows a short region of helical nucleic acids formed by hybridization between a continuous scaffold strand 510 and shorter staple oligonucleotides (e.g., oligonucleotides 520 and 522). The oligonucleotides are occasionally interrupted by short strand breaks 525. The staple oligonucleotides 520 and 522 further include fluorophores 530 and 532, respectively. Due to the positions on oligonucleotides 520 and 522 where fluorophores 530 and 532 are attached, the fluorophores 530 and 532 are positioned on the same side of the retaining component with a separation distance $\Delta s_{f1}$. The separation distance can be increased or decreased as necessary by changing the attachment positions of the fluorophores 530 and 532, or changing the oligonucle-otides on which the fluorophores are attached. Alternatively, FIG. 5B shows a short region of helical nucleic acids formed by hybridization between a continuous scaffold strand 510 and shorter staple oligonucleotides (e.g., oligonucleotides 520 and 522). The oligonucleotides are occasionally inter-rupted by short strand breaks 525. The staple oligonucle-otides 520 and 522 further include fluorophores 530 and 532, respectively. Due to the positions on oligonucleotides 520 and 522 where fluorophores 530 and 532 are attached, the fluorophores 530 and 532 are positioned on opposing sides of the retaining component with a separation distance $\Delta s_{f2}$. FIGS. 5A and 5B demonstrate how similar separation distances between label components can be achieved by differing label orientations.

The detectable probes or affinity reagents of the present disclosure can be configured to provide highly tunable platforms for displaying binding components and/or label components. The tunability of the detectable probes or affinity reagents may manifest as the ability to customize and/or optimize the avidity of the probe and/or the strength of the detectable signal generated. The tunability may arise from the customizable retaining components that can be attached to one or more binding components and/or attached to one or more label components at specific locations on the probe.

The detectable probes or affinity reagents of the present disclosure may be characterized as having a remarkably increased avidity. Without wishing to be bound by theory, the increased avidity of a detectable probe or affinity reagent may derive from the presence of a plurality of binding components that, collectively increase the on-rate (e.g., as indicated by increased dissociation rate constant, $k_{on}$), decrease the off-rate (e.g. as indicated by increased disso-ciation rate constant, $k_{off}$) of a detectable probe or affinity reagent from a binding partner, or decrease the likelihood that a probe will diffuse away from a binding partner before a binding component can re-bind to the binding partner. Surprisingly, it has been found that the detectable probe or affinity reagent compositions of the present disclosure can display an affinity for a binding partner that is at least an order of magnitude larger than the affinity of any single binding component from the plurality of binding compo-nents attached to the probe, as characterized by dissociation constants or binding on-rates or off-rates.

The tunable nature of detectable probes or affinity reagents may derive, in part, from the ability to customize the attachment of binding components to the retaining component of the probe. Several factors may influence the strength of the avidity effect, including: 1) the total number of binding components; 2) the location and/or orientation of the binding components; 3) the areal or volumetric density of the binding components; 4) the affinities of the plurality of binding components; 5) the structure of the retaining component; and 6) the overall size of the detectable probe or affinity reagent. Moreover, the design flexibility of the described probe structures permits the inclusion of addi-tional components that may increase avidity, such as pendant tails that may weakly interact with other adjacent entities to temporarily localize the detectable probe or affinity reagent near a binding partner.

The avidity and/or observability for a detectable probe or affinity reagent can be tuned by exploiting design flexibility of a retaining component therein. A retaining component may be chosen if it provides: 1) a 3-dimensional structure that provides a wide range of potential locations and orien-tations for binding component display; and 2) the ability to attach binding components to the 3-dimensional structure at desired locations with high specificity. Of particular interest are retaining components including nucleic acids that take advantage of the specificity of nucleic acid hybridization to create complex 3-dimensional structures with precisely located binding positions for binding components (and label components).

In some configurations, a nucleic acid structure (e.g., a DNA nanoball or a nucleic acid origami) may be utilized as a retaining component. A nucleic acid structure can yeild the advantage of providing a high degree of spatial control over the location and orientation of components that are added to the retaining component. Nucleic acid structures may typi-cally have about 10 to 11 base pairs per turn of the helical structure, meaning that each unique physical location within a double-stranded nucleic acid has an associated angle of orientation. This property of nucleic acids facilitates the tunability of a nucleic acid-based retaining component struc-ture by providing abundant variations in position and ori-entation to customize the amount of separation between probe components, such as binding components and/or label components.

In other configurations, retaining components may have controlled spatial and/or orientation control of probe com-ponents by rational control or modification of retaining component structure and/or chemistry. Non-nucleic acid retaining components may be manipulated or modified to produce retaining components with controlled or varied probe component location and/or orientation. In some cases, the location or orientation of probe components may be controlled by the shape or conformation of a non-nucleic acid particle, nanoparticle, or body. For example, shell-like structures or plate-like structures may provide multiple surfaces with varied properties that permit differential loca-tion of binding components relative to label components. Moreover, non-nucleic acid retaining components may be provided with coatings or formed into composites in spa-tially controlled fashions, thereby permitting increased con-trol over attachment locations and orientations.

Figure 6A:
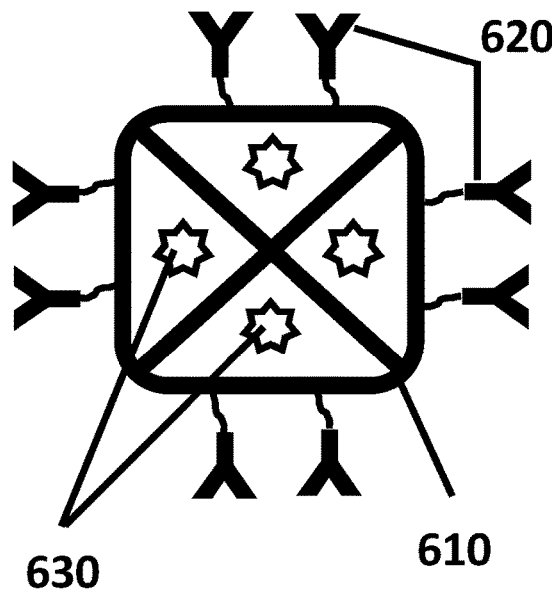
FIG. 6A shows a configuration of binding components and label components on a retaining component.
Figure 6B:
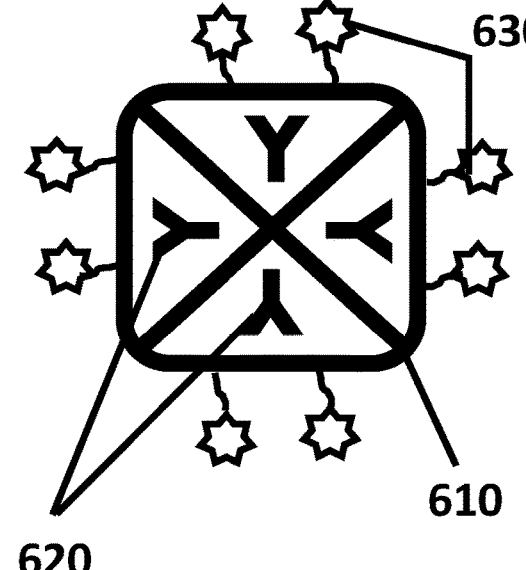
FIG. 6B shows a configuration of binding components and label components on a retaining component.

FIGS. 6A-6F depict various simplified configurations of detectable probe compositions to demonstrate the flexibility of arrangement created by 3-dimensional retaining compo-nent structures (e.g., DNA origami, carbon nanoparticles, silicon nanoparticles, etc.). FIG. 6A depicts top-down view of a rectangular or tile-shaped detectable probe. The probe contains a retaining component 610 that has a width and height as well as a depth (not shown), creating a top face (shown), plus sides and a bottom face (not shown). A plurality of binding components 620 is attached to the retaining component 610, the binding components being at specific locations along the sides of the retaining compo-nent. Label components 630 are located at specific positions on the top face (and optionally the bottom face) of the detectable probe. FIG. 6B depicts a top-down view of a rectangular or tile-shaped probe with a reversed attachment scheme from the probe shown in FIG. 6A. The probe contains a retaining component 610 that has a width and height as well as a depth (not shown), creating a top face (shown), plus sides and a bottom face (not shown). A plurality of binding components 620 are attached to the retaining component 610 at specific locations on the top face (and optionally the bottom face) of the detectable probe. Label components 630 are located at specific positions along the sides of the retaining component. The probe configura-tion depicted in FIG. 6A may be preferable for systems requiring a strong detection signal or a detection signal that is distributed over a larger area or volume, due to the increased locations for labeling on the high-area top face. The probe configuration depicted in FIG. 6B may be preferable for increasing probe avidity of detectable probes or affinity reagents due to the potential to increase the density of binding components on the high-area top surface.

Figure 6C:
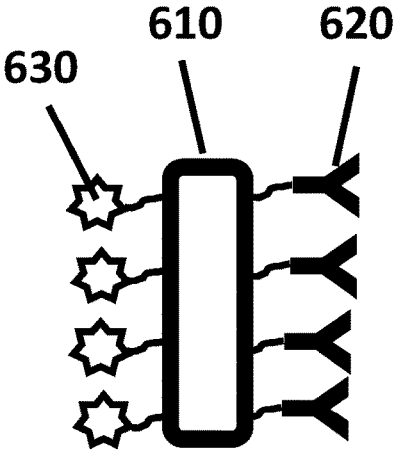
FIG. 6C shows a configuration of binding components and label components on a retaining component.
Figure 6D:
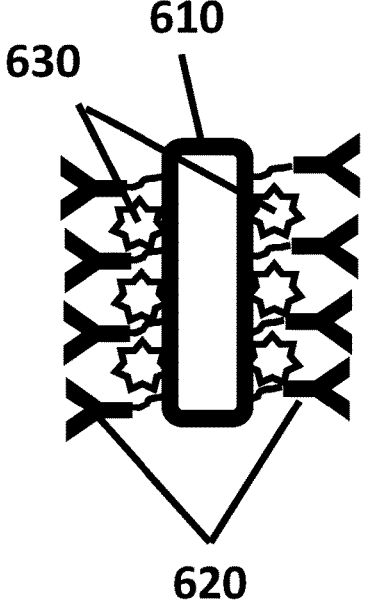
FIG. 6D shows a configuration of binding components and label components on a retaining component.

FIGS. 6C and 6D depict side-view configurations of rectangular or tile-shaped detectable probes, demonstrating the orientation of probe components relative to the thinner depth dimension of the probes. FIG. 6C shows a detectable probe containing a retaining component 610 that has a width and height (not shown) as well as a depth, creating sides, and a top and bottom face (not shown). A plurality of binding components 620 is attached to the retaining component 610, the binding components attached at specific locations on the top face of the detectable probe. Label components 630 are located at specific positions on the bottom face of the detectable probe. FIG. 6D shows a detectable probe containing a retaining component 610 that has a width and height (not shown) as well as a depth, creating sides, and a top and bottom face (not shown). A plurality of binding components 620 and label components 630 is attached to the retaining component 610, the binding components attached at specific locations on the top and bottom faces of the detectable probe. The probe configuration in FIG. 6C may be advantageous for fluorescent detection system as the large probe may shield some or all of the binding partner from interacting with label components, thereby possibly decreasing or mitigating any quenching of the label by the binding partner or its immediate environment. The probe configuration in FIG. 6D may be advantageous for maximizing the amount of binding component present for detectable probes or affinity reagents by increasing the likelihood of contacting a detectable probe with a binding partner.

Figure 6E:
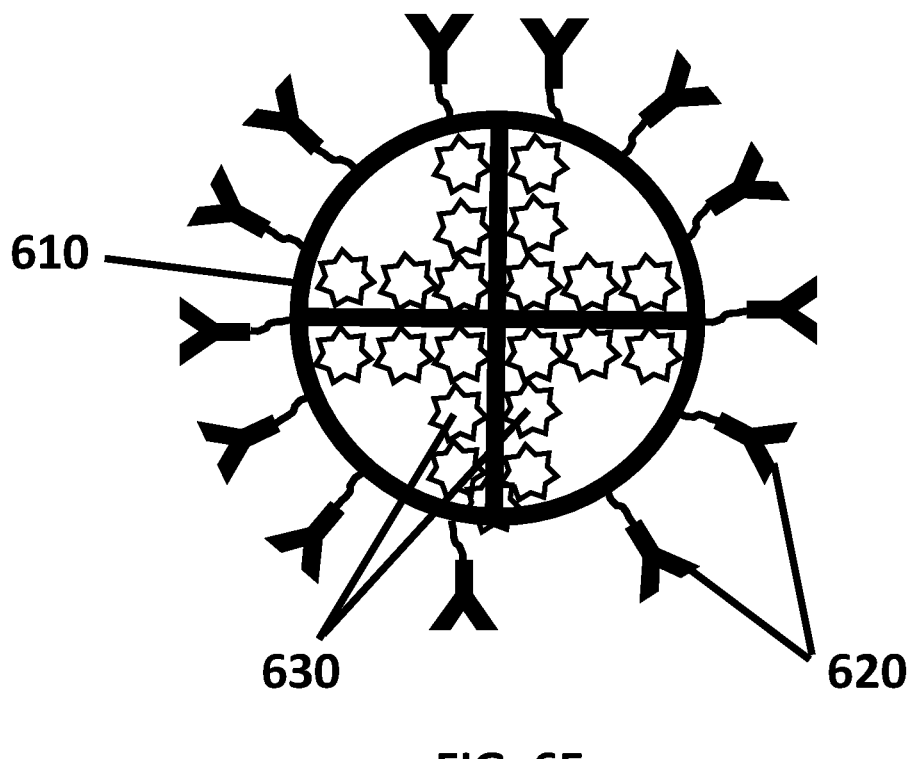
FIG. 6E shows a configuration of binding components and label components on a retaining component.
Figure 6F:
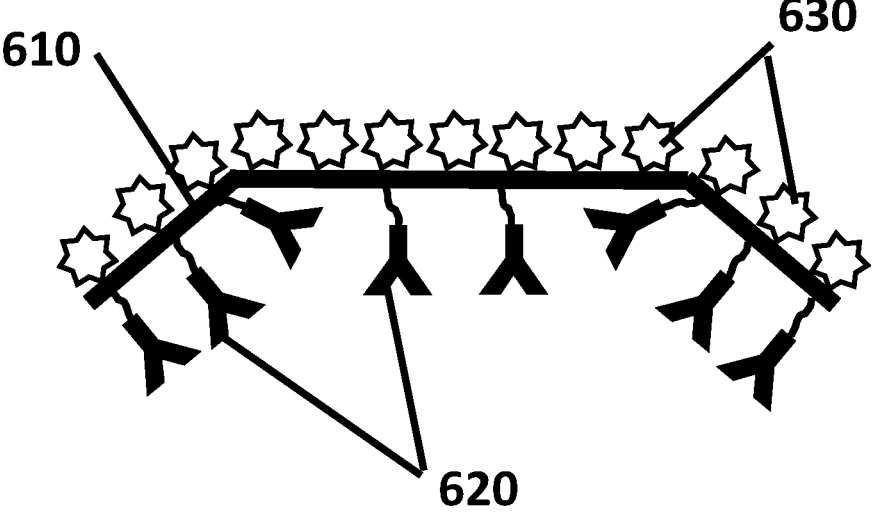
FIG. 6F shows a configuration of binding components and label components on a retaining component.

FIGS. 6E and 6F depict alternative retaining component geometries. FIG. 6E depicts a detectable probe including a circular or spherical configuration. The probe contains a retaining component 610 that optionally includes an internal structure that provides additional locations for attachment of probe components. A plurality of binding components 620 are attached to the outer perimeter or surface of the retaining component 610. The internal region of the retaining component 610 contains a plurality of label components 630. The configuration shown in FIG. 6E may increase the likelihood of the probe locating a binding partner due to the high coverage of binding components 620 on the retaining component 610, and may further provide high detectable signal due to the potential to concentrate a plurality of label components 630 in the internal space of the retaining component 610. FIG. 6F depicts a side view or cross-sectional view of a probe with a retaining component 610 that features angular offsets on one or more faces. One side of the retaining component 610 contains attached binding components 620. The opposite side of the retaining component 610 contains attached label components 630. The configuration shown in FIG. 6F may be advantageous for increasing avidity due to the increased volumetric density of binding components 620 attached to the bottom face of the retaining component 610. The more complex shape may increase contact of binding components 620 with a binding partner and increase resistance to diffusion of the probe away from a binding partner. The skilled person will recognize that innumerable variations of the geometries described in FIGS. 6A-6F may exist given the numerous potential designs of the retaining component.

A retaining component may include a body (e.g. particle, nanoparticle, or microparticle) that is not primarily composed of nucleic acids. A retaining component may be formed utilizing a retaining component that is a fabricated or synthesized body, such as a silicon or silica nanoparticle, a carbon nanoparticle, a cellulose nanobead, a PEG nanobead, a polymeric nanoparticle (e.g., polyacrylate particles, polystyrene-based particles, FluoSpheres™, etc.), or a quantum dot. A particle, nanoparticle, or body may include solid materials and shell-like materials (e.g., carbon nanospheres, silicon oxide nanoshells, iron oxide nanospheres, polymethylmethacrylate nanospheres, etc.). A retaining component including a particle, nanoparticle, or body may include distinct surfaces, such as plates or shells. In some configurations, distinct surfaces on a retaining component may be utilized to segregate components (e.g., binding components on a first surface, label components on a second surface). A retaining component may include a material that may be directly functionalized or modified to permit attachment of components (e.g., silanization of a silicon or silicon dioxide nanoparticle). A retaining component may include a commercially-available particle, nanoparticle, or body. A retaining component may be prepared by modifying a commercially-available particle, nanoparticle, or body. Methods and chemistries for modifying structures such as particles and nanoparticles are extensively described in the art.

FIGS. 31A-31D illustrate various configurations for fashioning retaining components from particles or nanoparticles. FIG. 31A depicts a solid spherical particle 3110 with a surface that is directly functionalized with a plurality of attachment sites 3120. The attachment sites may be configured to form covalent or non-covalent attachments to detectable probe components, such as binding components and/or label components. FIG. 31B depicts a solid spherical particle 3110 that includes a heterogeneous plurality of first attachment sites 3120 and second attachment sites 3125. In some configurations, there may be an equal number of first attachment sites 3120 and second attachment sites 3125. In other configurations, there may be differing numbers of first attachment sites 3120 and second attachment sites 3125. The first attachment sites 3120 and/or second attachment sites 3125 may be configured to form covalent or non-covalent attachments to detectable probe components, such as binding components and/or label components. The solid spherical particles of FIGS. 31A and 31B may readily be substituted with hollow particles. Hollow particles may be provided with attachment sites 3120 or 3125 on internal surfaces. In some configurations, a hollow particle may include a first plurality of attachment sites 3120 on an external surface and a second plurality of attachment sites 3125 on an internal surface to permit segregation of detectable probe components to differing surfaces.

FIGS. 31C and 31D illustrate retaining components formed from solid spherical particles including a surface coating, shell, or layer (e.g., a polymer, hydrogel coating, or monolayer of functional groups). FIG. 31C shows a solid spherical particle 3110 including a surface coating or layer 3130. The coating or layer 3130 is provided with a plurality of attachment sites 3120. The attachment sites may be configured to form covalent or non-covalent attachments to detectable probe components, such as binding components and/or label components. FIG. 31D shows a spherical detectable particle 3115 (e.g., a FluoSphere™, a quantum dot) including a surface coating 3130. The coating or layer 3130 is provided with a plurality of attachment sites 3120. The attachment sites may be configured to form covalent or non-covalent attachments to detectable probe components, such as binding components and/or label components. The coating or layer may function as a scaffold that permits the attachment of binding components or other components to the particle, nanoparticle, or body. The skilled person will readily recognize that the described retaining components can readily be adapted to non-spherical particles, nanoparticles, or bodies, such as nanotubes, plates, bowls, rods, and cones.

Figures 34A, 34B, 34C:
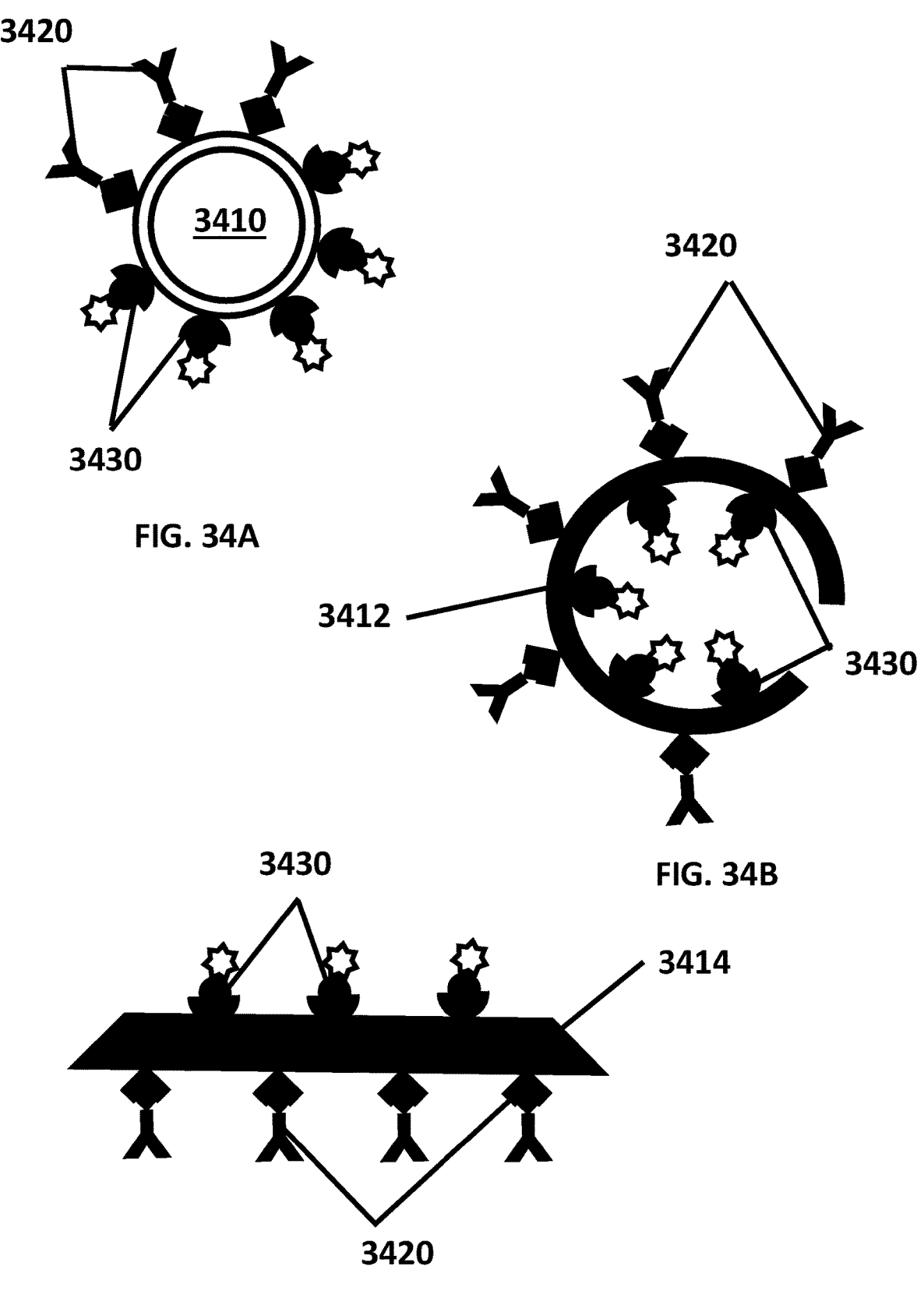
FIG. 34A shows a configuration of a detectable probe including a non-nucleic acid retaining component.
FIG. 34B shows a configuration of a detectable probe including a non-nucleic acid retaining component.
FIG. 34C shows a configuration of a detectable probe including a non-nucleic acid retaining component.

FIGS. 34A-34C illustrates various configurations of non-nucleic acid retaining components with spatially controlled or segregated probe components. FIG. 34A shows a spherical particle, nanoparticle, or body 3410 that has spatially-segregated binding components 3420 and label components 3430. FIG. 34B shows a hollow or shell-like particle or body 3412 that utilizes the hollow internal region of the particle or body 3412 to segregate label components 3430 from externally attached binding component 3420. FIG. 34C shows a plate-like particle or body 3414 that has two distinct surfaces with an approximately 180° angular offset. The upper surface may be used to attach a plurality of label components 3430 while the bottom surface may be used to attach a plurality of binding components 3420.

Two binding components may be attached to a retaining component in such a fashion that they have an angular offset in terms of their relative positions. For example, two binding components attached to a flat face of a retaining component would have about 0 degree (°) angular offset. In another example, two binding components attached to opposite sides of a cube-like retaining component would have about 180° angular offset. An angular offset may be utilized to constrain contact or other interactions between adjacent binding components. Two binding components may have a relative angular offset of at least about 0°, 5°, 10°, 15°, 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, 150°, 155°, 160°, 165°, 170°, 175°, or more. Alternatively or additionally, two binding components may have a relative angular offset of no more than about 180°, 175°, 170°, 165°, 160°, 155°, 150°, 145°, 140°, 135°, 130°, 125°, 120°, 115°, 110°, 105°, 100°, 95°, 90°, 85°, 80°, 75°, 70°, 65°, 60°, 55°, 50°, 45°, 40°, 35°, 30°, 25°, 20°, 15°, 10°, 5°, or less.

Figure 7A:
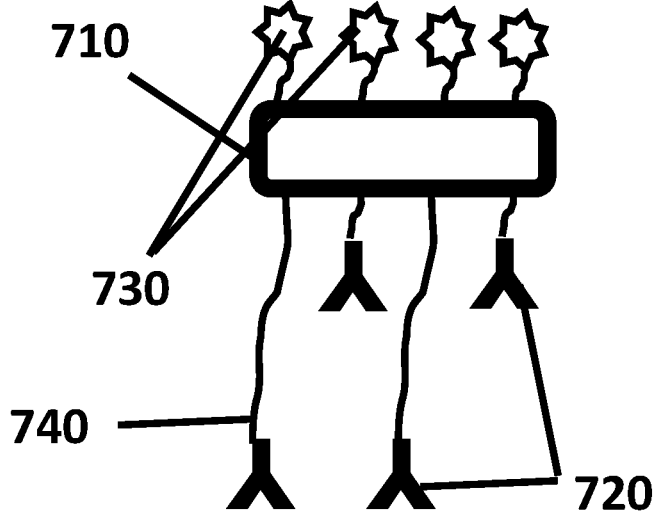
FIG. 7A shows a configuration of a detectable probe including linkers for binding components.
Figure 7B:
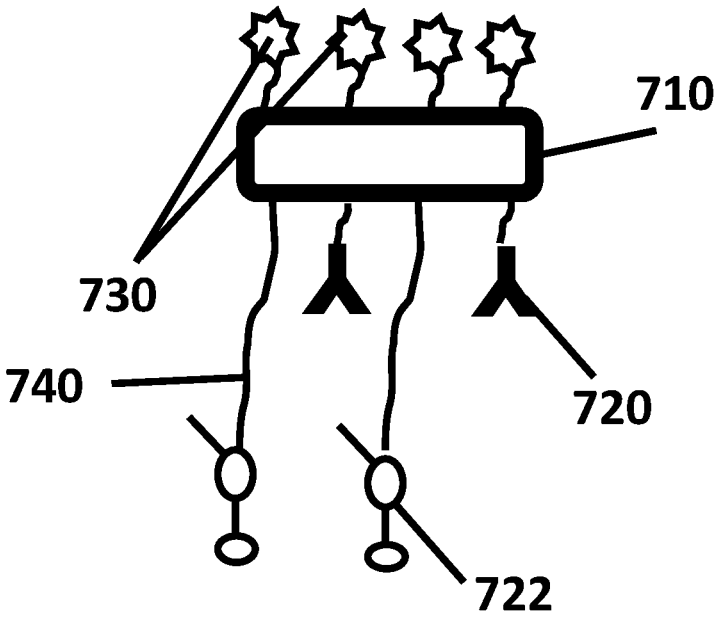
FIG. 7B shows a configuration of a detectable probe including linkers for binding components.

A detectable probe or affinity reagent may be further modified to increase the overall avidity of the probe. FIGS. 7A and 7B depict the use of linkers to increase the spatial degrees of freedom for display of binding components. FIG. 7A depicts a detectable probe including a retaining component 710 with a plurality of attached binding components 720 and a plurality of label components 730. A subset of the plurality of binding components 720 is attached to the retaining component 710 by linkers 740 (e.g., PEG, PEO, alkane chains, etc.) that permit the subset of binding components 720 to extend away from the retaining component 710. FIG. 7B depicts a similar probe configuration to FIG. 7A, however the probe includes two differing species of binding components. The probe contains a retaining component 710 with a plurality of attached label components 730. The probe further includes a first plurality of attached binding components 720 (e.g., antibodies or antibody fragments) and a second plurality of attached binding components 722 (e.g., aptamers) that are attached to the retaining component 710 by linkers 740. Linkers may be advantageous for increasing probe avidity by facilitating increased sensing of binding partners, epitopes, or target moieties over a larger volumetric region per unit of time. Moreover, linkers may provide flexibility or separation of components, and this may speed up the binding of a probe to a binding partner, epitope, or target moiety, and slow the possible diffusion of the probe away from the binding partner, epitope, or target moiety.

The size of a detectable probe or affinity reagent may be configured to suit an intended mode of use. The mode of use (e.g., polypeptide characterization, non-polypeptide characterization, therapeutics, diagnostics) may indicate the level of avidity and/or observability for a detectable probe or affinity reagent. A detectable probe or affinity reagent may be sized sufficiently to permit attachment of a sufficient number of binding components and/or label components for an intended mode of use. In some configurations, the size of a detectable probe or affinity reagent may refer to the approximate length, area, or volume of the retaining component. Components attached to retaining components (e.g., binding components, label components, linkers, blocking groups) may have increased degrees of spatial freedom that make characterization of their length, areal size, or volumetric size more difficult. Retaining components may be configured to have a more regular or less variable size, making the retaining component size a viable proxy for size of a detectable probe or affinity reagent.

A detectable probe, affinity reagent or retaining component thereof may have a characteristic length. A characteristic length may include a maximum, average or minimum length, for the width, height, radius, diameter, circumference, or other dimension. A detectable probe, affinity reagent or retaining component thereof may have a characteristic length of at least about 5 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 120 nm, 140 nm, 160 nm, 180 nm, 200 nm, 250 nm, 300 nm, 350 nm, 400 nm, 450 nm, 500 nm, 600 nm, 700 nm, 800 nm, 900 nm, 1000 nm, or more. Alternatively or additionally, a detectable probe, affinity reagent or retaining component thereof may have a characteristic length of no more than about 1000 nm, 900 nm, 800 nm, 700 nm, 600 nm, 500 nm, 450 nm, 400 nm, 350 nm, 300 nm, 250 nm, 200 nm, 180 nm, 160 nm, 140 nm, 120 nm, 100 nm, 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, 10 nm, 5 nm, or less.

A detectable probe, affinity reagent or retaining component thereof may have a characteristic footprint (e.g. occupied area on a surface). A footprint may constitute the area that a 2-dimensional projection of the detectable probe, affinity reagent or retaining component thereof would create on a planar surface. A 2-dimensional projection may have a regular shape or an approximately regular shape, such as triangular, square, rectangular, circular, pentagonal, hexagonal, octagonal, or elliptic. FIGS. 2A-2B display examples of 2-dimensional projections for retaining components 210 or 215 with approximate shapes, with ideal shapes shown as dashed lines (220 and 225, respectively). A detectable probe, affinity reagent or retaining component thereof may have an occupied area of at least about 25 nm$^2$, 100 nm$^2$, 500 nm$^2$, 1000 nm$^2$, 2000 nm$^2$, 3000 nm$^2$, 4000 nm$^2$, 5000 nm$^2$, 5500 nm$^2$, 6000 nm$^2$, 6500 nm$^2$, 7000 nm$^2$, 7500 nm$^2$, 8000 nm$^2$, 8500 nm$^2$, 9000 nm$^2$, 10000 nm$^2$, 15000 nm$^2$, 20000 nm$^2$, 25000 nm$^2$, 50000 nm$^2$, 100000 nm$^2$, 1000000 nm$^2$, or more. Alternatively or additionally, a detectable probe, affinity reagent or retaining component thereof may have an occupied area of no more than about 1000000 nm$^2$, 100000 nm$^2$, 50000 nm$^2$, 25000 nm$^2$, 20000 nm$^2$, 15000 nm$^2$, 10000 nm$^2$, 9000 nm$^2$, 8500 nm$^2$, 8000 nm$^2$, 7500 nm$^2$, 7000 nm$^2$, 6500 nm$^2$, 6000 nm$^2$, 5500 nm$^2$, 5000 nm$^2$, 4000 nm$^2$, 3000 nm$^2$, 2000 nm$^2$, 1000 nm$^2$, 500 nm$^2$, 100 nm$^2$, 25 nm$^2$, or less. The above ranges for occupied area can refer to an average for all faces of a detectable probe, affinity reagent or retaining component thereof; the smallest face of the detectable probe, affinity reagent or retaining component thereof; or the largest face of the detectable probe, affinity reagent or retaining component thereof, as desired.

A retaining component may be configured to have other components (e.g. binding components, label components or other retaining components) attached at a desired or optimal spacing. The spacing of binding components may be based on minimum spacing to reduce or eliminate unwanted or deleterious interactions (e.g., aptamer misfolding; fluorophore self-quenching). The spacing of binding components may be based on maximum spacing to achieve desired characteristics, such as avidity or detectable signal strength. For components joined to a retaining component by a linker or other flexible method of attachment (i.e., components having additional degrees of freedom for motion), the spacing of attached components may be measured as the spacing between attachment sites on the retaining component. Two adjacent attached components (e.g., binding components, label components, blocking groups) may have a characteristic spacing of at least about 0.1 nm, 0.2 nm, 0.3 nm, 0.4 nm, 0.5 nm, 0.6 nm, 0.7 nm, 0.8 nm, 0.9 nm, 1.0 nm, 1.1 nm, 1.2 nm, 1.3 nm, 1.4 nm, 1.5 nm, 1.6 nm, 1.7 nm, 1.8 nm, 1.9 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 35 nm, 40 nm, or more. Alternatively or additionally, two adjacent attached components may have a characteristic spacing of no more than about 40 nm, 35 nm, 30 nm, 29 nm, 28 nm, 27 nm, 26 nm, 25 nm, 24 nm, 23 nm, 22 nm, 21 nm, 20 nm, 19 nm, 18 nm, 17 nm, 16 nm, 15 nm, 14 nm, 13 nm, 12 nm, 11 nm, 10 nm, 9 nm, 8 nm, 7 nm, 6 nm, 5 nm, 4 nm, 3 nm, 2 nm, 1.9 nm, 1.8 nm, 1.7 nm, 1.6 nm, 1.5 nm, 1.4 nm, 1.3 nm, 1.2 nm, 1.1 nm, 1.0 nm, 0.9 nm, 0.8 nm, 0.7 nm, 0.6 nm, 0.5 nm, 0.4 nm, 0.3 nm, 0.2 nm, 0.1 nm, or less.

A detectable probe or affinity reagent may include a plurality of binding components that are attached to a surface or face of a retaining component. The number of binding components displayed on a surface of a detectable probe or affinity reagent may be configured to increase avidity or sufficiently space binding components to avoid unwanted interactions. The number of binding components on a surface of a detectable probe or affinity reagent may be characterized as an average number density (number per surface) or an area density (number per area). Two differing surfaces or faces of a detectable probe or affinity reagent may have differing number or area densities of binding components. A detectable probe or affinity reagent may have an average binding component number density of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more per surface. Alternatively or additionally, a detectable probe or affinity reagent may have an average binding component number density of no more than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or less. A detectable probe or affinity reagent may have an average binding component area density of at least about 0.00001, 0.0001, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, or more per $nm^2$. Alternatively or additionally, a detectable probe or affinity reagent may have an average binding component area density of no more than about 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0001, 0.00001, or less per $nm^2$.

A detectable probe or affinity reagent may include a plurality of label components that are attached to a surface or face of a retaining component. The number of label components displayed on a surface of a detectable probe or affinity reagent may be optimized to increase observability or sufficiently space label components to avoid unwanted interactions. The number of label components on a surface of a detectable probe or affinity reagent may be characterized as an average number density (number per surface) or an area density (number per area). Two differing surfaces or faces of a detectable probe or affinity reagent may have differing number or area densities of label components. A detectable probe or affinity reagent may have an average label components number density of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more per surface. Alternatively or additionally, a detectable probe or affinity reagent may have an average label components number density of no more than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or less than 2 per surface. A detectable probe or affinity reagent may have an average label components area density of at least about 0.00001, 0.0001, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, or more per $nm^2$. Alternatively or additionally, a detectable probe or affinity reagent may have an average label components area density of no more than about 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0001, 0.00001, or less per $nm^2$.

A detectable probe or affinity reagent may include a heterogeneous mixture of binding components. A heterogeneous mixture of binding components may include mixtures of differing types and/or species of binding components. For example, a detectable probe or affinity reagent may include a mixture of antibodies of differing affinity for a binding partner. In another example, a detectable probe or affinity reagent may include a mixture of antibodies and aptamers that possess affinity for the same binding partner. In another example, a detectable probe or affinity reagent may include a mixture of antibodies and antibody fragments with affinity for the same binding partner. A heterogeneous mixture of binding components may be advantageous for controlling the avidity of a detectable probe or affinity reagent. Mixtures of binding components with differing binding affinities may facilitate optimization of the binding on-rate and/or binding off-rate for a detectable probe or affinity reagent relative to a particular binding partner, epitope, or target moiety.

In some configurations, a detectable probe or affinity reagent may include a plurality of first binding components with affinity for a binding partner, epitope, or target moiety, and a second plurality of competitor binding components. Competitor binding components may be characterized as having a decreased affinity (e.g., having an increased binding promiscuity, for example, binding a plurality of different binding partners, epitopes, or target moieties) with an increased dissociation rate (e.g., a binding component that binds to many targets but easily dissociates from the targets). Without wishing to be bound by theory, competitor binding components may be identified as binding components whose displacement by another binding component is energetically and/or entropically favorable. For example, multiple small, low-affinity aptamers or mini-peptide binders may be easily displaced by a large, high-affinity antibody, thereby favoring antibody binding due to the entropic increase of displacing multiple binding components. Competitor binding components may further increase the avidity of a detectable probe or affinity reagent by forming brief, weak interactions with target moieties for which the first plurality of binding components lacks affinity. Such brief, weak interactions may facilitate increased duration of association between a detectable probe or affinity reagent and a binding partner, epitope, or target moiety.

A detectable probe or affinity reagent may be structurally stable under certain environmental conditions. Of particular interest are detectable probes or affinity reagents that are structurally stable under conditions that are intended to remove a bound probe from a binding partner. For example, a detectable probe or affinity reagent may be stable in the presence of heat or chemical compositions that interrupt intermolecular interactions, e.g., surfactants or denaturants. Structural stability may refer to a detectable probe or affinity reagent maintaining its full composition and, optionally, its shape or conformation, i.e., no loss of binding components, label components, or other components; no loss or degradation of components (e.g., dehybridization of nucleic acids from a DNA origami retaining component).

A detectable probe or affinity reagent may be structurally stable at a given temperature. Temperature may vary during a process that utilizes a detectable probe or affinity reagent. For example, each step of binding, observing, and removing a detectable probe or affinity reagent may occur at a unique and/or optimal temperature. Moreover, a detectable probe or affinity reagent may be structurally stable at a given storage temperature. A detectable probe or affinity reagent may be structurally stable at a temperature of at least about $-100°$ C., $-90°$ C., $-80°$ C., $-70°$ C., $-60°$ C., $-50°$ C., $-40°$ C., $-30°$ C., $-20°$ C., $-10°$ C., $-5°$ C., $0°$ C., $4°$ C., $10°$ C., $15°$ C., $20°$ C., $25°$ C., $30°$ C., $35°$ C., $40°$ C., $45°$ C., $50°$ C., $55°$ C., $60°$ C., $65°$ C., $70°$ C., $75°$ C., $80°$ C., $90°$ C., or higher. Alternatively or additionally, a detectable probe or affinity reagent may be structurally stable at a temperature of no more than about $90°$ C., $80°$ C., $75°$ C., $70°$ C., $65°$ C., $60°$ C., $55°$ C., $50°$ C., $45°$ C., $40°$ C., $35°$ C., $30°$ C., $25°$ C., $20°$ C., $15°$ C., $10°$ C., $4°$ C., $0°$ C., $-10°$ C., $-20°$ C., $-30°$ C., $-40°$ C., $-50°$ C., $-60°$ C., $-70°$ C., $-80°$ C., $-90°$ C., $100°$ C., or lower.

A detectable probe or affinity reagent may be structurally stable in the presence of a particular solution or solvent. A detectable probe or affinity reagent may be contacted with one or more solutions or solvents depending upon the mode of use for the detectable probe or affinity reagent. Solutions or solvents may have varying compositions depending upon the mode of use for a detectable probe or affinity reagent. Solutions or solvents may be used for processes such as probe formulation, probe storage, probe-partner binding, washing, rinsing, interaction detection, probe-partner separation, probe capture (e.g., recovery of probes after utilization), and probe analysis (e.g., post-process sequencing of nucleic acid barcodes). Solutions or solvents may be formulated to maintain the stability of detectable probe or affinity reagent structures. Solutions or solvents may be formulated with respect to chemical composition, pH, and ionic strength to ensure the stability of detectable probe or affinity reagents. Detectable probes or affinity reagents including nucleic acids may be present in solutions or solvents including magnesium salts to stabilize the nucleic acids.

A solution or solvent that is contacted with a detectable probe or affinity reagent may include one or more detectable probes or affinity reagents in solution or suspension. A solution or solvent that is contacted with a detectable probe or affinity reagent may be formulated to be a homogeneous liquid medium. A solution or solvent that is contacted with a detectable probe or affinity reagent may be formulated to be a single-phase liquid medium. A solution or solvent that is contacted with a detectable probe or affinity reagent may be formulated to be a multi-phase liquid medium, such as an oil-in-water emulsion or a water-in-oil emulsion.

A solution or solvent that is contacted with a detectable probe or affinity reagent may include a solvent species, pH buffering species, a cationic species, an anionic species, a surfactant species, a denaturing species, or a combination thereof. A solvent species may include water, acetic acid, methanol, ethanol, n-propanol, isopropyl alcohol, n-butanol, formic acid, ammonia, propylene carbonate, nitromethane, dimethyl sulfoxide, acetonitrile, dimethylformamide, acetone, ethyl acetate, tetrahydrofuran, dichloromethane, chloroform, carbon tetrachloride, dimethyl ether, diethyl ether, 1-4, dioxane, toluene, benzene, cyclohexane, hexane, cyclopentane, pentane, or combinations thereof. A solvent or solution may include a buffering species including, but not limited to, MES, Tris, Bis-tris, Bis-tris propane, ADA, ACES, PIPES, MOPSO, MOPS, BES, TES, HEPES, HEPBS, HEPPSO, DIPSO, MOBS, TAPSO, TAPS, TABS, POPSO, TEA, EPPS, Tricine, Gly-Gly, Bicine, AMPD, AMPSO, AMP, CHES, CAPSO, CAPS, and CABS. A solvent or solution may include cationic species such as $Na^+$, $K^+$, $Ag^+$, $Cu^+$, $NH_4^+$, $Mg^{2+}$, $Ca^{2+}$, $Cu^{2+}$, $Cd^{2+}$, $Zn^{2+}$, $Fe^{2+}$, $Co^{2+}$, $Ni^{2+}$, $Cr^{2+}$, $Mn^{2+}$, $Ge^{2+}$, $Sn^{2+}$, $Al^{3+}$, $Cr^{3+}$, $Fe^{3+}$, $Co^{3+}$, $Ni^{3+}$, $Ti^{3+}$, $Mn^{3+}$, $Si^{4+}$, $V^{4+}$, $Ti^{4+}$, $Mn^{4+}$, $Ge^{4+}$, $Se^{4+}$, $V^{5+}$, $Mn^{5+}$, $Mn^{6+}$, $Se^{6+}$, and combinations thereof. A solvent or solution may include anionic species such as $F^-$, $Cl^-$, $Br^-$, $ClO_3^-$, $H_2PO_4^-$, $HCO_3^-$, $HSO_4^-$, $OH^-$, $I^-$, $NO_3^-$, $NO_2^-$, $MnO_4^-$, $SCN^-$, $CO_3^{2-}$, $CrO_4^{2-}$, $Cr_2O_7^{2-}$, $HPO_4^{2-}$, $SO_4^{2-}$, $SO_3^{2-}$, $PO_4^{3-}$, and combinations thereof. A solvent or solution may include a surfactant species including, but not limited to, stearic acid, lauric acid, oleic acid, sodium dodecyl sulfate, sodium dodecyl benzene sulfonate, dodecylamine hydrochloride, hexadecyltrimethylammonium bromide, polyethylene oxide, nonylphenyl ethoxylates, Triton X, pentapropylene glycol monododecyl ether, octapropylene glycol monododecyl ether, pentaethylene glycol monododecyl ether, octaethylene glycol monododecyl ether, lauramide monoethylamine, lauramide diethylamine, octyl glucoside, decyl glucoside, lauryl glucoside, Tween 20, Tween 80, n-dodecyl-β-D-maltoside, nonoxynol 9, glycerol monolaurate, polyethoxylated tallow amine, poloxamer, digitonin, zonyl FSO, 2,5-dimethyl-3-hexyne-2,5-diol, Igepal CA630, Aerosol-OT, triethylamine hydrochloride, cetrimonium bromide, benzethonium chloride, octenidine dihydrochloride, cetylpyridinium chloride, adogen, dimethyldioctadecylammonium chloride, CHAPS, CHAPSO, cocamidopropyl betaine, amidosulfobetaine-16, lauryl-N,N-(dimethylammonio)butyrate, lauryl-N,N-(dimethyl)-glycinebetaine, hexadecyl phosphocholine, lauryldimethylamine N-oxide, lauryl-N,N-(dimethyl)-propanesulfonate, 3-(1-pyridinio)-1-propanesulfonate, 3-(4-tert-butyl-1-pyridinio)-1-propanesulfonate, N-laurylsarcosine, and combinations thereof. A solvent or solution may include a denaturing species including, but not limited to, acetic acid, trichloroacetic acid, sulfosalicylic acid, sodium bicarbonate, ethanol, ethylenediamine tetraacetic acid (EDTA), urea, guanidinium chloride, lithium perchlorate, sodium dodecyl sulfate, 2-mercaptoethanol, dithiothreitol, and tris(2-carboxyethyl) phosphine (TCEP).

A pH buffering species may be formulated in a solvent or solution in any quantity. A pH buffering species may be present in a detectable probe or affinity reagent solvent composition at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more. Alternatively or additionally, a pH buffering species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less.

A cationic species may be formulated in a solvent or solution in any quantity. A cationic species may be present in a detectable probe or affinity reagent solvent composition at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more. Alternatively or additionally, a cationic species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less.

An anionic species may be formulated in a solvent or solution in any quantity. An anionic species may be present in a solvent or solution at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more. Alternatively or additionally, an anionic species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less.

A surfactant species may be formulated in a solvent or solution in any quantity. A surfactant species may be present in a solvent or solution at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more. Alternatively or additionally, a surfactant species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less.

A denaturing species may be formulated in a solvent or solution in any quantity. A denaturing species may be present in a solvent or solution at a concentration of at least about 0.0001M, 0.001M, 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, 1M, 1.1M, 1.2M, 1.3M, 1.4M, 1.5M, 1.6M, 1.7M, 1.8M, 1.9M, 2M, 2.1M, 2.2M, 2.3M, 2.4M, 2.5M, 2.6M, 2.7M, 2.8M, 2.9M, 3M, 3.1M, 3.2M, 3.3M, 3.4M, 3.5M, 3.6M, 3.7M, 3.8M, 3.9M, 4M, 4.1M, 4.2M, 4.3M, 4.4M, 4.5M, 4.6M, 4.7M, 4.8M, 4.9M, 5M, 5.1M, 5.2M, 5.3M, 5.4M, 5.5M, 5.6M, 5.7M, 5.8M, 5.9M, 6M, 7M, 8M, 9M or more. A denaturing species may be present in a solvent or solution at a concentration of no more than about 10 M, 9M, 8M, 7M, 6M, 5.9M, 5.8M, 5.7M, 5.6M, 5.5M, 5.4M, 5.3M, 5.2M, 5.1M, 5.0M, 4.9M, 4.8M, 4.7M, 4.6M, 4.5M, 4.4M, 4.3M, 4.2M, 4.1M, 4.0M, 3.9M, 3.8M, 3.7M, 3.6M, 3.5M, 3.4M, 3.3M, 3.2M, 3.1M, 3.0M, 2.9M, 2.8M, 2.7M, 2.6M, 2.5M, 2.4M, 2.3M, 2.2M, 2.1M, 2.0M, 1.9M, 1.8M, 1.7M, 1.6M, 1.5M, 1.4M, 1.3M, 1.2M, 1.1M, 1.0M, 0.9M, 0.8M, 0.7M, 0.6M, 0.5M, 0.4M, 0.3M, 0.2M, 0.1M, 0.09M, 0.08M, 0.07M, 0.06M, 0.05M, 0.04M, 0.03M, 0.02M, 0.01M, 0.001M, 0.001M, or less.

A solvent or solution may be formulated to have a pH at a value or within a range of values. A solvent or solution may have a pH of at least about 0, 0.1, 0.2, 0.3, 0.4, 0.5, 0.6, 0.7, 0.8, 0.9, 1.0, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.1, 10.2, 10.3, 10.4, 10.5, 10.6, 10.7, 10.8, 10.9, 11.0, 11.1, 11.2, 11.3, 11.4, 11.5, 11.6, 11.7, 11.8, 11.9, 12.0, 12.1, 12.2, 12.3, 12.4, 12.5, 12.6, 12.7, 12.8, 12.9, 13.0, 13.1, 13.2, 13.3, 13.4, 13.5, 13.6, 13.7, 13.8, 13.9, 14.0 or more. Alternatively or additionally, a solvent or solution may have a pH of no more than about 14.0, 13.9, 13.8, 13.7, 13.6, 13.5, 13.4, 13.3, 13.2, 13.1, 13.0, 12.9, 12.8, 12.7, 12.6, 12.5, 12.4, 12.3, 12.2, 12.1, 12.0, 11.9, 11.8, 11.7, 11.6, 11.5, 11.4, 11.3, 11.2, 11.1, 11.0, 10.9, 10.8, 10.7, 10.6, 10.5, 10.4, 10.3, 10.2, 10.1, 10.0, 9.9, 9.8, 9.7, 9.6, 9.5, 9.4, 9.3, 9.2, 9.1, 9.0, 8.9, 8.8, 8.7, 8.6, 8.5, 8.4, 8.3, 8.2, 8.1, 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0, or less.

A detectable probe or affinity reagent may include one or more additional modifying groups. Modifying groups may be included to alter the chemical or physical properties of a detectable probe or affinity reagent. Modifying groups may be included on a detectable probe or affinity reagent to alter a property such as hydrophobicity, hydrophilicity, amphiphilicity, electrical charge, magnetic susceptibility, or any other physical property. In some cases, modifying groups may be used to increase, decrease, or alter the solubility or solution stability of a detectable probe or affinity reagent. In some cases, modifying groups may be used to maintain separation of detectable probes or affinity reagents by mechanisms such as electrical repulsion or steric occlusion. In some cases, modifying groups may be used to increase attraction between particles. For example, modifying groups may form brief attractive interactions between detectable probes and/or affinity reagents to create multi-probe complexes without causing aggregation or sedimentation of probes.

A surface of a retaining component may include one or more modifying groups. Modifying groups may be added to a surface to alter the characteristics of the surface while mediating an association between a detectable probe or affinity reagent and a surface or an interface. For example, hydrophobic modifying groups may be added to detectable probes or affinity reagents to cause probes to interact with oil droplets in an oil-in-water emulsion. Modifying groups may be attached covalently or non-covalently. Modifying groups may be coupled to a retaining component before, during, or after retaining component assembly. Surface modification groups may include electrically-charged moieties, magnetic moieties, steric moieties, amphipathic moieties, hydrophobic moieties, and hydrophilic moieties. Electrically-charged moieties may include functional groups that may carry an intrinsic positive or negative charge, or may carry a charge under dissociating conditions (e.g., carboxylic acids, nitrates, sulfones, phosphates, phosphonates, etc.). Magnetic moieties may include paramagnetic, diamagnetic, and ferromagnetic particles such as nanoparticles (e.g., gadolinium, manganese, iron oxide, bismuth, gold, silver, cobalt nanoparticles, etc.). Steric moieties may include polymers and biopolymers (e.g., PEG, PEO, alkane chains, dextran, sheared nucleic acids). Amphipathic moieties may include phospholipids (e.g., phosphatidic acid, phosphatidylethanolamine, phosphatidylcholine, phosphatidylserine, phosphatidylinositol, phosphatidylinositol phosphate, phosphatidylinositol biphosphate, phosphatidylinositol triphosphate, ceramide phosphorylcholine, ceramide phophoryletha- nolamine, ceramide phosphoryllipid), glycolipids (e.g., glyceroglycolipids, sphingoglycolipids, rhamnolipids, etc.), and sterols (e.g., cholesterol, campesterol, sitosterol, stigmasterol, ergosterol, etc.). Hydrophobic moieties may include steroids (e.g., cholesterol), saturated fatty acids (e.g., caprylic acid, capric acid, lauric acid, myristic acid, palmitic acid, stearic acid, arachidic acid, behenic acid, lignoceric acid, cerotic acid, etc.), and unsaturated fatty acids (e.g., myristoleic acid, palmitoleic acid, sapienic acid, oleic acid, elaidic acid, vaccenic acid, linoleic acid, arachidonic acid, eicosapentaenoic acid, erucic acid, docosahexanenoic acid, etc.). Hydrophilic compounds may include charged molecules and polar molecules (e.g., glycols, cyclodextrins, cellulose, polyacrylamides, etc.).

A surface of a detectable probe or affinity reagent may include one or more modifying groups. A surface of a detectable probe or affinity reagent may include at least about 10, 50, 100, 500, 1000, 5000, 10000, 50000, 100000, 50000, 1000000, or more modifying groups. Alternatively or additionally, a surface of a detectable probe or affinity reagent may include no more than about 1000000, 500000, 100000, 50000, 10000, 5000, 1000, 500, 100, 50, 10, or fewer modifying groups.

A plurality of detectable probes, affinity reagents or both may be assembled into multi-probe complexes. A multi-probe complex can include, for example, a plurality of detectable probes, a plurality of affinity reagents, an affinity reagent and a detectable probe, an affinity reagent and a plurality of detectable probes, or a plurality of affinity reagents and a detectable probe. Multi-probe complexes may be prepared to further enhance the desirable properties of detectable probes or affinity reagents, such as enhanced avidity and/or enhanced observability. In some configurations, a multi-probe complex may include multiple detectable probes, affinity reagents or both with similar or identical configurations that are formed into a single complex. A multi-probe complex including multiple similar or identical probes may be formed to increase the overall brightness of probes when interacting with a binding partner, or may provide an increased number of affinity reagents to increase the avidity over the avidity observed by a lone detectable probe or affinity reagent. In other configurations, a multi-probe complex may include multiple detectable probes, affinity reagents or both with differing or dissimilar configurations that are attached into a single complex. A multi-probe complex may include multiple detectable probes, affinity reagents or both with differing or dissimilar configurations may be formed to simultaneously bind to multiple binding partners, epitopes, or target moieties, or increase the likelihood of forming a binding interaction by increasing the number of binding partners, epitopes, or target moieties that the detectable probe or affinity reagent can recognize. A multi-probe complex may behave as a univalent complex (e.g., configured to only bind a single species of binding partner, epitope, or target moiety) or a plurivalent complex (e.g., configured to bind to a variety of different binding partners, epitopes, or target moieties). Multi-probe complexes may be attached by a covalent or non-covalent interaction. A covalent bond between two detectable probes, between two affinity reagents or between a probe and reagent may be formed by, for example a click reaction. A non-covalent interaction between probes and/or reagents may be formed by, for example, nucleic acid hybridization or a streptavidin-biotin coupling.

Figure 39A:
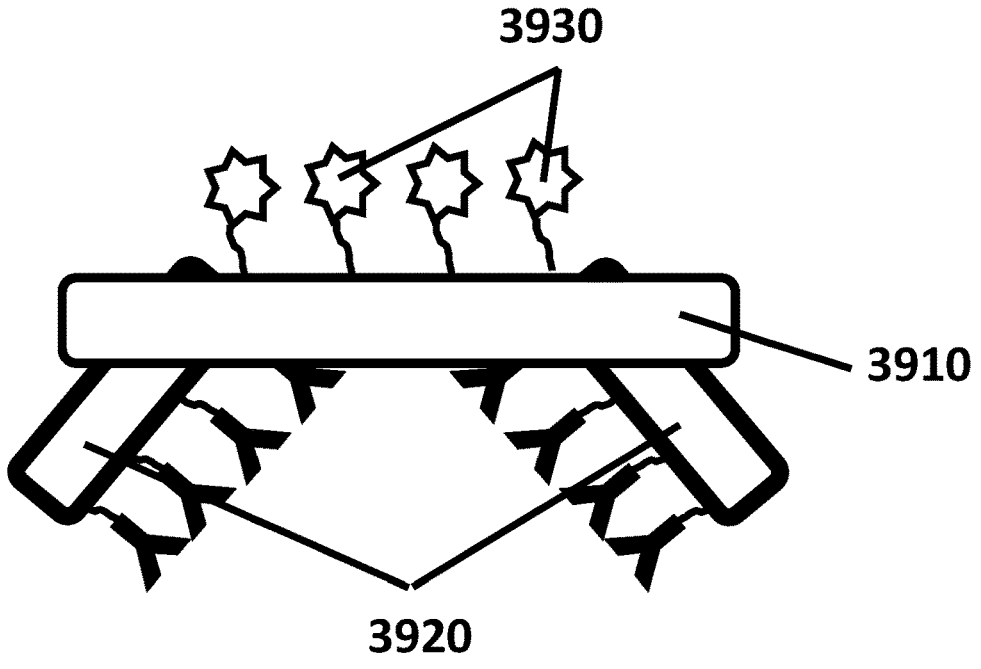
FIG. 39A shows multi-probe complexes formed with a secondary retaining component.
Figure 39B:
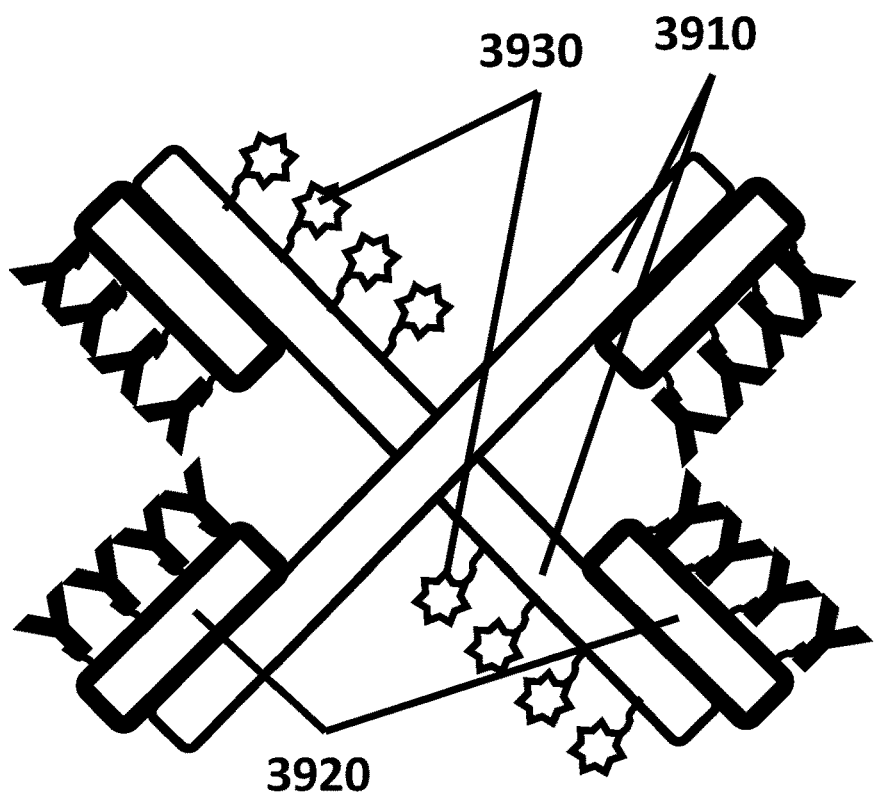
FIG. 39B shows multi-probe complexes formed with a secondary retaining component.

A multi-probe complex may be formed by coupling together two or more detectable probes, affinity reagents or both. Multi-probe complexes may be formed by direct attachment of detectable probe(s) and/or affinity reagent(s) (e.g., by nucleic acid hybridization, cross-linking, etc.). In some configurations, multi-probe complexes may be formed by attachment between one or more secondary retaining components, such as structured nucleic acid particles or nanoparticles. Secondary retaining components may be of particular interest if they provide tunable location and/or orientation of detectable probes or affinity reagents. In some configurations, a secondary retaining component may include additional components, such as modifying groups, binding components or label components. FIGS. 39A-39B show exemplary configurations of multi-probe complexes including a secondary retaining component. FIG. 39A shows a secondary retaining component 3910 (e.g., a structured nucleic acid particle, a nanoparticle) including two or more attached detectable probes 3920 that are attached with an inward orientation. The secondary retaining component 3910 further includes a plurality of attached label components 3930. FIG. 39B shows a secondary retaining component including two or more separate particles 3910 (e.g., SNAPs, nanoparticles) that includes a plurality of detectable probes 3920 that are coupled to form multiple pockets of inward oriented binding components. The secondary retaining component including the two or more particles 3910 further includes a plurality of label components 3930 that are attached to the secondary retaining component. In other configurations, a multi-probe complex may be formed by coupling or attaching multiple detectable probes or affinity reagents to an unstructured material or group, such as a polymer, metal, ceramic, semiconductor, glass, fiber, resin, or combination thereof. An unstructured material may be amorphous, globular, porous, or some combination thereof. An unstructured material may include a plurality of attachment sites that permit attachment of a plurality of detectable probes or affinity reagents.

Figure 35A:
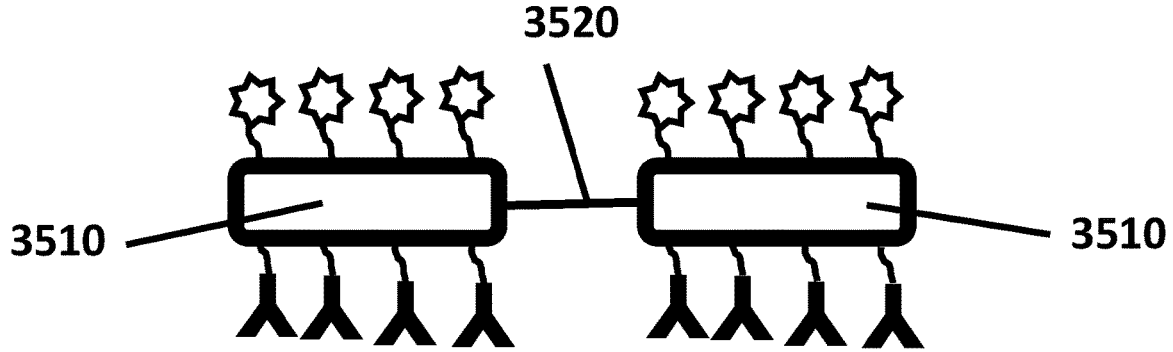
FIG. 35A shows a multi-probe complex formed from a plurality of detectable probes.
Figure 35B:
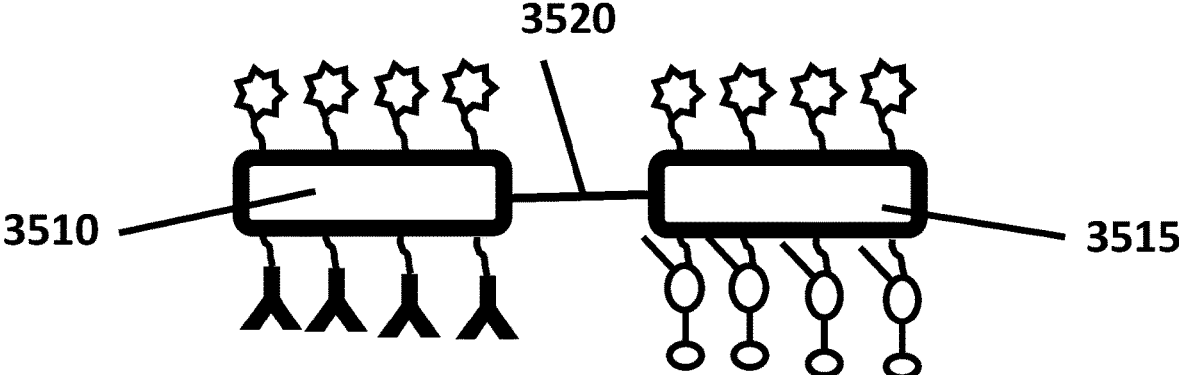
FIG. 35B shows a multi-probe complex formed from a plurality of detectable probes.
Figure 35C:
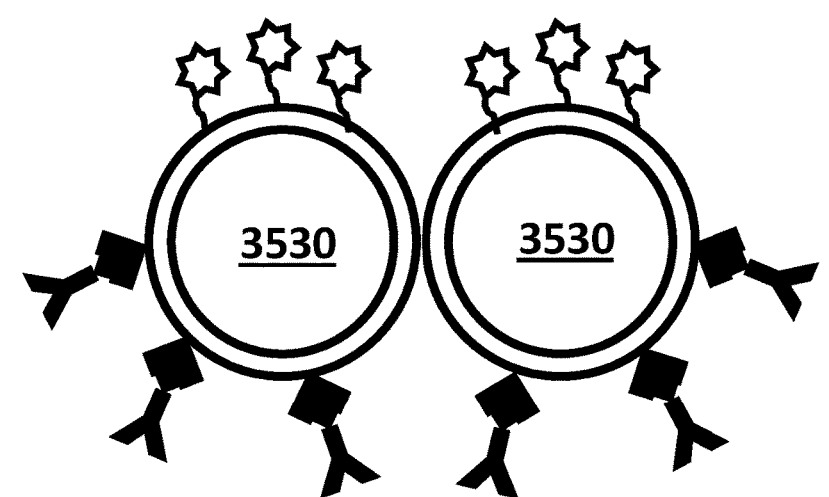
FIG. 35C shows a multi-probe complex formed from a plurality of detectable probes.

FIGS. 35A-35C depict various configurations of multi-probe complexes. FIG. 35A depicts two identical or similar tile-shaped nucleic acid detectable probes 3510 joined by a linking group 3520 (e.g., a covalent or non-covalent linking group). The detectable probes 3510 may have an affinity for a single target or group of targets (e.g, a binding partner, epitope, or target moiety). FIG. 35B depicts a first tile-shaped nucleic acid detectable probe with antibody binding components 3510 joined to a second tile-shaped detectable probe with aptamer binding components 3515 by a linking group 3520 (e.g., a covalent or non-covalent linking group). The detectable probes 3510 and 3515 may have differing affinities, thereby allowing the detectable probe to simultaneously bind more than one binding partner, epitope, or target moiety. FIG. 35C depicts a pair of non-nucleic acid-based detectable probes 3530 (e.g., particles, nanoparticles, etc.) that are joined by a non-covalent attractive interaction, such as an electrostatic or magnetic interaction. The non-nucleic acid-based detectable probes 3530 may include binding components with similar or dissimilar binding partners, epitopes, or target moieties.

Figure 36A:
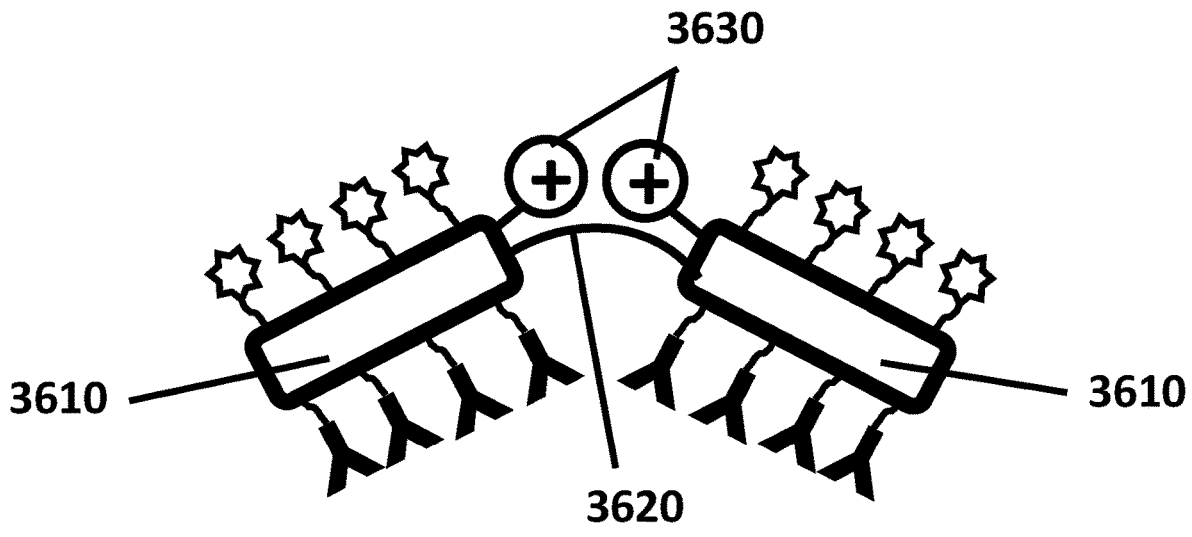
FIG. 36A shows a multi-probe complex with a controlled conformation.
Figure 36B:
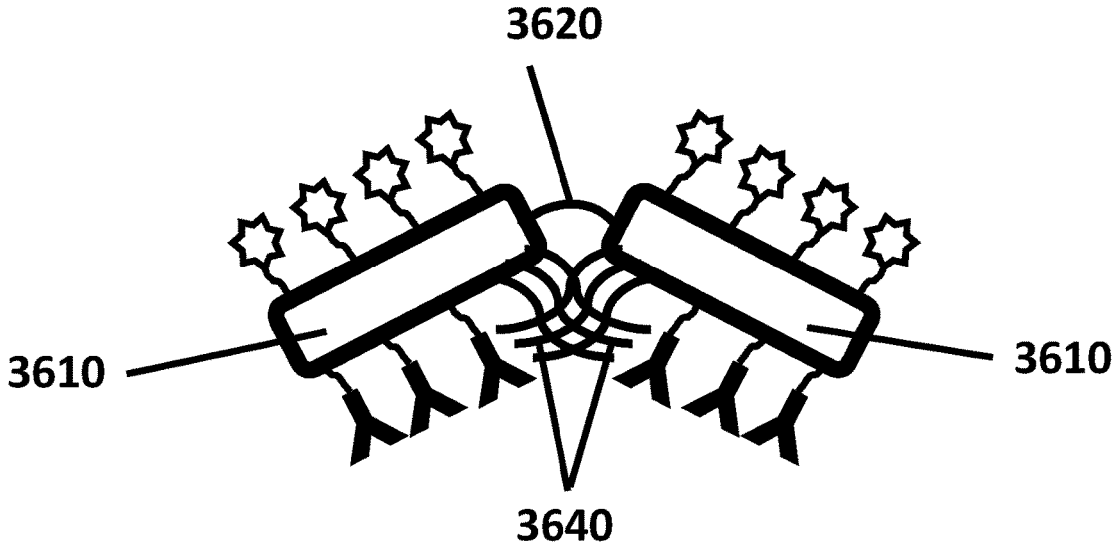
FIG. 36B shows a multi-probe complex with a controlled conformation.

In some configurations, multi-probe complexes may be configured to form complexes with controlled geometries. A controlled geometry may be employed to orient binding components more favorably for increased avidity. Multi-probe complexes may be configured to change shapes or conformations upon forming a binding interaction with a binding partner, epitope, or target moiety. Multi-probe complexes may be configured to resist changes to shape or conformation to increase contact or proximity of binding components to a binding partner, epitope, or target moiety. Individual probes or reagents included in a multi-probe complex may have modifying groups that form interactions with other probes or reagents in the multi-probe complex that affect the relative orientation of probes within the complex. FIG. 36A-36B depict configurations of detectable probes with designed or structured geometries. FIG. 36A depicts two tile-shaped nucleic acid detectable probes 3610 that are joined by a linker 3620. Each probe 3610 include one or more modifying groups 3630 (e.g., same electrical charge, same magnetic polarity, steric groups, etc.) that create a repulsion or hindrance to free motion of the linker 3620. The modifying groups 3630 cause an inward orientation of the probes, increasing the binding component density of the probe complex. FIG. 36B depicts two tile-shaped nucleic acid detectable probes 3610 that are joined by a linker 3620. Each probe 3610 include one or more modifying groups 3640 (e.g., hydrophobic groups, hydrophilic groups, etc.) that create an attraction between probes that creates an inward orientation of the probes 3610, increasing the binding component density of the probe complex. These configurations may resist deformation of the complex during a binding interaction with a binding partner.

A multi-complex may include two or more detectable probes and/or affinity reagents that are attached into a single complex. A multi-probe complex may include at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more detectable probes and/or affinity reagents. Alternatively or additionally, a multi-probe complex may include no more than about 100, 95, 90, 85, 80, 75, 70, 65, 60, 55, 50, 45, 40, 35, 30, 25, 20, 19, 18, 17, 16, 15, 14, 13, 12, 11, 10, 9, 8, 7, 6, 5, 4, 3, or fewer detectable probes and/or affinity reagents.

Affinity reagents or detectable probes described herein may include a binding component (also referred to as a binding component or probe component) that is capable of binding or associating with polypeptides, or other analytes, in a manner that allows one to interpret such binding in order to facilitate identification of the polypeptide or other analyte with which it associates (or does not associate). Affinity reagents or detectable probes may also include a label component that allows observation or detection of the binding or association of the affinity reagent or detectable probe with a target analyte such as a polypeptide or other analyte. A label component can be separable from a probe component, for example, when the label component is an exogenous label that is attached via a synthetic linker or attachment moiety. Alternatively, a label component can be an intrinsic characteristic of a probe, such as a detectable mass, charge, or optical characteristic. By identifying which affinity reagents or detectable probes bind to different polypeptides or other analytes within a sample, one can identify the presence, and potential quantity of such proteins or polypeptides within that sample.

In some embodiments, an affinity reagent or detectable probe that is directed towards identifying a target amino acid sequence may actually include a group of different components which are not differentiated or distinguishable from each other as used in methods described herein. In particular, the different components that may be used to identify the same target amino acid sequence may use the same label moiety to identify the same target amino acid sequence. For example, an affinity reagent or detectable probe which binds a trimer amino acid sequence (AAA) regardless of flanking sequences may include either a single binding component which binds the trimer AAA sequence without any effect from flanking sequences, or a group of binding components (e.g. 400 binding components), each of which binds to a different 5 amino acid epitope of the form $\alpha AAA\beta$, where $\alpha$ and $\beta$ may be any amino acid. In an example of the second case, the binding components may have a combined effect.

Binding and Avidity

For a single, monovalent affinity reagent, the strength of a binding interaction between the affinity reagent and a binding target (e.g., a binding partner, epitope, or target moiety) may be characterized by an affinity. Affinity may be expressed quantitatively in the form of a dissociation constant or an association constant. Without wishing to be bound by theory, a dissociation constant, $K_D$, may arise from an equilibrium analysis of binding between an affinity reagent, A, and a binding partner, B, to form a bound complex AB. The rates of association and disassociation between A and B depend upon the relative concentrations of A, B and AB, expressed as [A], [B], and [AB], respectively. The rate of association (or on-rate), $r_{on}$, may be expressed as:

$$r_{on}=k_{on}[A][B] \qquad (1)$$

where $k_{on}$ is the rate constant for binding. The rate of disassociation (or off-rate), $r_{off}$, may be expressed as:

$$r_{off}=k_{off}[AB] \qquad (2)$$

where $k_{off}$ is the rate constant for dissociation. Based upon an equilibrium between the on-rate (1) and the off-rate (2), a dissociation constant may be calculated as:

$$K_D = \frac{k_{off}}{k_{on}} \qquad (3)$$

For a given affinity reagent, smaller values of $K_D$ indicate stronger binding and higher values indicate weaker binding.

An apparent dissociation constant can be determined for a detectable probe or affinity reagent that has a plurality of binding components. The apparent dissociation constant may be calculated analogously to the dissociation constant for a monovalent affinity reagent. Without wishing to be bound by theory, an apparent dissociation constant, $K_{D,a}$, may arise from an equilibrium analysis of binding between detectable probe (or affinity reagent), P, and a binding partner, B, to form a bound complex PB. The apparent rates of association and disassociation between P and B may depend upon the relative concentrations of P, B and PB, expressed as [P], [B], and [PB], respectively. The apparent rate of association (or apparent on-rate), $r_{on,a}$, may be expressed as:

$$r_{on,a}=k_{on,a}[P][B] \qquad (4)$$

where $k_{on,a}$ is the apparent rate constant for binding. The apparent rate of disassociation (or apparent off-rate), $r_{off,a}$, may be expressed as:

$$r_{off,a}=k_{off,a}[PB] \qquad (5)$$

where $k_{off,a}$ is the apparent rate constant for dissociation. Based upon an equilibrium between the apparent on-rate (1) and the apparent off-rate (2), an apparent dissociation constant may be calculated as:

$$K_{D,a} = \frac{k_{off,a}}{k_{on,a}} \qquad (6)$$

For a multivalent detectable probe or multivalent affinity reagent, smaller values of $K_{D,a}$ indicate stronger binding and higher values indicate weaker binding.

Avidity of a detectable probe or affinity reagent may generally be described as a decrease in the apparent dissociation constant for the probe relative to the dissociation constants of its constitutive binding components. For example, for a probe including N binding components, each individual binding component may have an individual dissociation constant as described by equations 1-3 above, e.g., $\{K_{D,1}, K_{D,2}, \ldots K_{D,N}\}$. A detectable probe or affinity reagent having N binding components may be considered to have an increased avidity when the apparent dissociation constant for the detectable probe or affinity reagent as a whole, $K_{D,a}$, is less than the respective dissociation constants for each of the N binding components, e.g., $K_{D,a}<\{K_{D,1}, K_{D,2}, \ldots K_{D,N}\}$. In the case where a detectable probe or affinity reagent includes a plurality of N binding components of identical type and species whose dissociation constant is simply, $K_D$ (i.e., $K_{D,1}=K_{D,2}=\ldots=K_{D,N}=K_D$), then avidity may simply be defined as $K_{D,a}<K_D$. In the case where a detectable probe or affinity reagent includes a plurality of N binding components of differing types and/or species whose dissociation constants are $\{K_{D,1}, K_{D,2}, \ldots K_{D,N}\}$ and whose strongest binder is $K_{D,min}$, then avidity may simply be defined as $K_{D,a}<K_{D,min}$.

A detectable probe or affinity reagent of the present disclosure may be preferred if it displays a $K_{D,a}$ that is significantly smaller than $K_{D,min}$, for example $K_{D,a}$ ($K_{D,min}$ by about 1, 2, 3, 4, 5, 6, 7, 8, 9, 10, or more than 10 orders of magnitude. A detectable probe or affinity reagent may be selected for a particular binding target if $K_{D,a}<K_{D,min}$ by at least about 1, 2, 3, 4, 5, 6, 7, 8, 9, 10, or more than 10 orders of magnitude. Alternatively or additionally, a detectable probe or affinity reagent may be selected for a particular binding target if $K_{D,a}<K_{D,min}$ by no more than about 10, 9, 8, 7, 6, 5, 4, 3, 2, 1 or less than 1 order of magnitude. A detectable probe or affinity reagent may be less favorable if $K_{D,a}<K_{D,min}$ by too large an amount as it may indicate excessive binding as indicated by a very small off-rate.

The dissociation constant of a detectable probe, affinity reagent or a binding component thereof may be at least about 0.1 nM, 0.5 nM, 1 nM, 5 nM, 10 nM, 15 nM, 20 nM, 25 nM, 30 nM, 35 nM, 40 nM, 45 nM, 50 nM, 55 nM, 60 nM, 65 nM, 70 nM, 75 nM, 80 nM, 85 nM, 90 nM, 95 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM, 1 µM, 2 µM, 3 µM, 4 µM, 5 µM, 6 µM, 7 µM, 8 µM, 9 µM, 10 µM, or more. Alternatively or additionally, the dissociation constant of a detectable probe, affinity reagent or a binding component thereof may be no more than about 10 µM, 9 µM, 8 µM, 7 µM, 6 µM, 5 µM, 4 µM, 3 µM, 2 µM, 1 µM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 95 nM, 90 nM, 85 nM, 80 nM, 75 nM, 70 nM, 65 nM, 60 nM, 55 nM, 50 nM, 45 nM, 40 nM, 35 nM, 30 nM, 25 nM, 20 nM, 15 nM, 10 nM, 5 nM, 1 nM, 0.5 nM, 0.1 nM, or less.

A detectable probe or affinity reagent may have an apparent or measured dissociation constant that is less than the dissociation constant for a binding component that is attached to the detectable probe or affinity reagent. A lower dissociation constant for a detectable probe or affinity reagent may be attributed to an increased binding on-rate, increased $k_{on}$, decreased binding off-rate, decreased $k_{off}$, or a combination thereof. The decrease in an apparent or measured dissociation constant of a detectable probe or affinity reagent relative to any binding component of the plurality of binding components attached to the detectable probe or affinity reagent may be an N-fold decrease (i.e., $K_{D, probe}=(1/N)K_{D,binding component}$). The decrease in an apparent or measured dissociation rate constant of a detectable probe or affinity reagent relative to any binding component of the plurality of binding components attached to the detectable probe or affinity reagent may be at least about a 2-fold, 3-fold, 4-fold, 5-fold, 6-fold, 7-fold, 8-fold, 9-fold, 10-fold, 15-fold, 20-fold, 25-fold, 50-fold, 100-fold, 250- fold, 500-fold, 1000-fold, or more. Alternatively or additionally, the decrease in an apparent or measured dissociation constant of a detectable probe or affinity reagent relative to any binding component of the plurality of binding components attached to the detectable probe or affinity reagent may be no more than about a 1000-fold, 500-fold, 250-fold, 100-fold, 50-fold, 25-fold, 20-fold, 15-fold, 10-fold, 9-fold, 8-fold, 7-fold, 6-fold, 5-fold, 4-fold, 3-fold, 2-fold, or less.

In some cases, it may be useful to quantitatively describe avidity. For a set of N binding components whose strongest binder for a binding target has a dissociation constant $K_{D,min}$, an avidity, $A_N$, may be defined as:

$$A_N = \frac{K_{D,min}}{K_{D,a}} \tag{7}$$

Where $K_{D,a}$ is the apparent dissociation constant of a detectable probe or affinity reagent including the set of N binding components. In some configurations, a detectable probe or affinity reagent of the present disclosure may have an $A_N$ that is greater than 1. The $A_N$ of a detectable probe or affinity reagent may be at least about 2, 3, 4, 5, 6, 7, 8, 9, 10, 15, 20, 25, 30, 35, 40, 45, 50, 55, 60, 65, 70, 75, 80, 85, 90, 95, 100, 125, 150, 200, 250, 300, 400, 500, 600, 700, 800, 900, 1000, 2500, 5000, 10000, 25000, 50000, 100000, 1000000, 10000000, 100000000, 1000000000, 10000000000, or more. Alternatively or additionally, the $A_N$ of a detectable probe or affinity reagent may be no more than about 10000000000, 1000000000, 100000000, 10000000, 1000000, 100000, 50000, 25000, 10000, 5000, 2500, 1000, 900, 800, 700, 600, 500, 400, 300, 250, 200, 150, 125, 100, 95, 90, 85, 80, 75, 70, 65, 60, 55, 50, 45, 40, 35, 30, 25, 20, 15, 10, 9, 8, 7, 6, 5, 4, 3, 2, or less.

Avidity may refer to the ability of an affinity reagent or detectable probe to display an altered apparent affinity for a binding partner when the reagent or probe has multiple pathways for forming a binding interaction with the binding partner. For example, if a detectable probe or affinity reagent includes ten binding components, and each binding component has an affinity for a binding target X, the detectable probe or affinity reagent has ten possible pathways for forming a binding interaction with the target X. Avidity may be an amplified effect, in which the apparent affinity of a detectable probe or affinity reagent including a plurality of binding components for a binding partner, epitope, or target moiety may be stronger than the affinity of any binding component of the plurality of binding components. For example, a detectable probe or affinity reagent with 10 binding components may have a measured dissociation constant of 50 nanomolar (nM) when the strongest binding component attached to the detectable probe or affinity reagent has a dissociation constant of only 800 nM.

Avidity may occur due to the tendency of a new binding interaction to form soon after a prior binding interaction is disrupted in the presence of a plurality of binding components. Consequently, a binding interaction between a detectable probe (or affinity reagent) and a binding partner may be observed to occur over a longer time-scale than an observed binding interaction between a single binding component and the binding partner. Without wishing to be bound by theory, detectable probe or affinity reagent binding may be tunable by variation of probe design to alter the thermodynamic, kinetic, and/or mass transfer characteristics of a probe. Avidity of a detectable probe or affinity reagent may be affected by factors that alter the likelihood of binding interactions, including: 1) binding component density on the probe; 2) total number of binding components on the probe; 3) types and/or species of binding components; 4) binding component binding thermodynamics; 6) binding component binding kinetics; 5) probe size and/or weight; 6) probe shape and/or conformation; and 7) secondary binding interaction mediators.

Depending upon the thermodynamic and kinetic binding behaviors of a pool of detectable probes or affinity reagents, increased concentration of detectable probe or affinity reagent may encourage the binding of a detectable probe or affinity reagent to a binding partner, epitope, or target moiety. The effective or targeted concentration of detectable probes or affinity reagents utilized in a binding assay may be calculated with reference to the probes themselves, with reference to the total number of binding components on a probe, or, in the case of probes with heterogeneous binding component mixtures, the number of a specific species of binding component. For example, a solution provided at 0.1 mole/liter (M) of detectable probes or affinity reagents that are fabricated to contain 20 total binding components per probe at a 1:1 antibody/aptamer ratio would have a 2 M total concentration of binding components or a 1 M concentration of aptamers or antibodies. The effective or targeted concentration of detectable probes or affinity reagents may be determined on a mass or molar basis. A detectable probe, affinity reagent or a binding component thereof may be provided for an intended purpose at a preferred concentration (e.g., a concentration that optimizes avidity).

A detectable probe, affinity reagent or a binding component thereof may be provided at a concentration of at least about $1 \times 10^{-15}$ M, $5 \times 10^{-15}$ M, $1 \times 10^{-14}$ M, $5 \times 10^{-14}$ M, $1 \times 10^{-13}$ M, $5 \times 10^{-13}$ M, $1 \times 10^{-12}$ M, $5 \times 10^{-12}$ M, $1 \times 10^{-11}$ M, $5 \times 10^{-11}$ M, $1 \times 10^{-10}$ M, $5 \times 10^{-10}$ M, $1 \times 10^{-9}$ M, $5 \times 10^{-9}$ M, $1 \times 10^{-8}$ M, $5 \times 10^{-8}$ M, $1 \times 10^{-7}$ M, $5 \times 10^{-7}$ M, $1 \times 10^{-6}$ M, $5 \times 10^{-6}$ M, $1 \times 10^{-5}$ M, $5 \times 10^{-5}$ M, $1 \times 10^{-4}$ M, $5 \times 10^{-4}$ M, $1 \times 10^{-3}$ M, $5 \times 10^{-3}$ M, $1 \times 10^{-2}$ M, $5 \times 10^{-2}$ M, $1 \times 10^{-1}$ M, $5 \times 10^{-1}$ M, 1 M, or higher. Alternatively or additionally, a detectable probe, affinity reagent or a binding component thereof may be provided at a concentration of no more than about 1 M, $5 \times 10^{-1}$ M, $1 \times 10^{-1}$ M, $5 \times 10^{-2}$ M, $1 \times 10^{-2}$ M, $5 \times 10^{-3}$ M, $1 \times 10^{-3}$ M, $5 \times 10^{-4}$ M, $1 \times 10^{-4}$ M, $5 \times 10^{-5}$ M, $1 \times 10^{-5}$ M, $5 \times 10^{-6}$ M, $1 \times 10^{-6}$ M, $5 \times 10^{-7}$ M, $1 \times 10^{-7}$ M, $5 \times 10^{-8}$ M, $1 \times 10^{-8}$ M, $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$M, $5 \times 10^{-12}$ M, $1 \times 10^{-12}$ M, $5 \times 10^{-13}$ M, $1 \times 10^{-13}$ M, $5 \times 10^{-14}$ M, $1 \times 10^{-14}$ M, $5 \times 10^{-15}$ M, $1 \times 10^{-15}$ M, or lower.

The size of a probe may have an effect on the avidity properties of a detectable probe or affinity reagent. Without wishing to be bound by theory, the mass transfer properties of a detectable probe or affinity reagent may be affected by the size and/or weight of a probe. A mass transfer physical property (e.g., diffusion coefficient) of a detectable probe or affinity reagent may have a scaling relationship for a mass transfer physical property that depends upon the size and/or weight of the probe. For example, a detectable probe or affinity reagent may have a single-component diffusion coefficient in water that scales with a power law relationship to the probe molecular weight (i.e., $D \sim MW^{-2}$). A larger and/or heavier affinity reagent or detectable probe may experience a decrease in the diffusion rate in a solution or solvent. A decreased diffusion rate of a detectable probe or affinity reagent may be observed as a decrease in the apparent avidity of a detectable probe or affinity reagent due to an increased likelihood of a binding interaction occurring before a probe can diffuse away from a binding partner, epitope, or target moiety.

A probe may have a characterized molecular weight of at least about 1 kDa, 10 kDa, 50 kDa, 100 kDa, 500 kDa, 1000 kDa, 1500 kDa, 2000 kDa, 2500 kDa, 3000 kDa, 3500 kDa, 4000 kDa, 4500 kDa, 5000 kDa, 5500 kDa, 6000 kDa, 6500 kDa, 7000 kDa, 7500 kDa, 8000 kDa, 8500 kDa, 9000 kDa, 9500 kDa, 10000 kDa, or more. Alternatively or additionally, a probe may have a characterized molecular weight of no more than about 10000 kDa, 9500 kDa, 9000 kDa, 8500 kDa, 8000 kDa, 7500 kDa, 7000 kDa, 6500 kDa, 6000 kDa, 5500 kDa, 5000 kDa, 4500 kDa, 4000 kDa, 3500 kDa, 3000 kDa, 2500 kDa, 2000 kDa, 1500 kDa, 1000 kDa, 500 kDa, 100 kDa, 50 kDa, 10 kDa, 1 kDa, or less.

In some cases, the avidity of a detectable probe or affinity reagent may be affected by a secondary binding interaction. A secondary binding interaction may be a weak or short-term interaction involving a secondary molecule that a detectable probe or affinity reagent has been designed to have. A secondary binding interaction may include a weak or short-term interaction involving a secondary molecule that decreases the apparent rate of diffusion of the detectable probe or affinity reagent away from a binding partner, epitope, or target moiety. A secondary binding interaction may increase the likelihood of a detectable probe or affinity reagent being observed in association with a binding partner that the detectable probe or affinity reagent for which the detectable probe or affinity reagent has an affinity. In some configurations, a secondary molecule may include one or more ligands and/or moieties that may form a weak interaction with complementary ligands and/or moieties on a detectable probe or affinity reagent. For example, a secondary molecule may have a nucleic acid sequence that is at least partially complementary to a nucleic acid sequence in a detectable probe or affinity reagent. As such, the secondary molecule and probe can be configured to form a weak interaction via hybridization of the two sequences. For example, weak interaction may result from imperfect or discontinuous hybridization such as interactions resulting from use of hairpin or loop structures in the sequence of the detectable probe or affinity reagent or secondary molecule, mismatched nucleotides in otherwise complementary regions of the detectable probe (or affinity reagent) and secondary molecule, or modified or unnatural nucleotides in the detectable probe (or affinity reagent) or secondary molecule that create weaker base pair binding. In other configurations, a secondary molecule may include one or more ligands and/or moieties that may form a weak interaction with a binding partner. In some configurations, a detectable probe (or affinity reagent) or a secondary molecule may include a plurality of molecules that are configured to form a weak binding interaction.

In some configurations, a secondary molecule that interacts with a detectable probe or affinity reagent may be attached to a solid support. For example, the secondary molecule can be a SNAP, such as a nucleic acid origami or nucleic acid nanoball, that is attached to a solid support. The SNAP can optionally be attached to a binding partner for one or more binding components of a detectable probe or affinity reagent. Accordingly, a secondary molecule can mediate association of a detectable probe or affinity reagent with a solid support via binding of one or more binding components to the binding partner and the association can be enhanced by a weak interaction between the secondary molecule and the SNAP. In some configurations, a plurality of SNAPs is attached to a solid support in the form of an array. Each site in the array can have a SNAP that is attached to a spatially resolved binding partner, and each of the binding partners can be recognized by one or more detectable probes or affinity reagents. Exemplary SNAPs and solid supports that can be usefully applied in a composition or method of the present disclosure are set forth in U.S. patent application Ser. No. 17/062,405 (published as US Pat. App. Pub. No. 2021/0101930 A1) and WO 2019/195633 A1, each of which is incorporated herein by reference.

Figure 8:
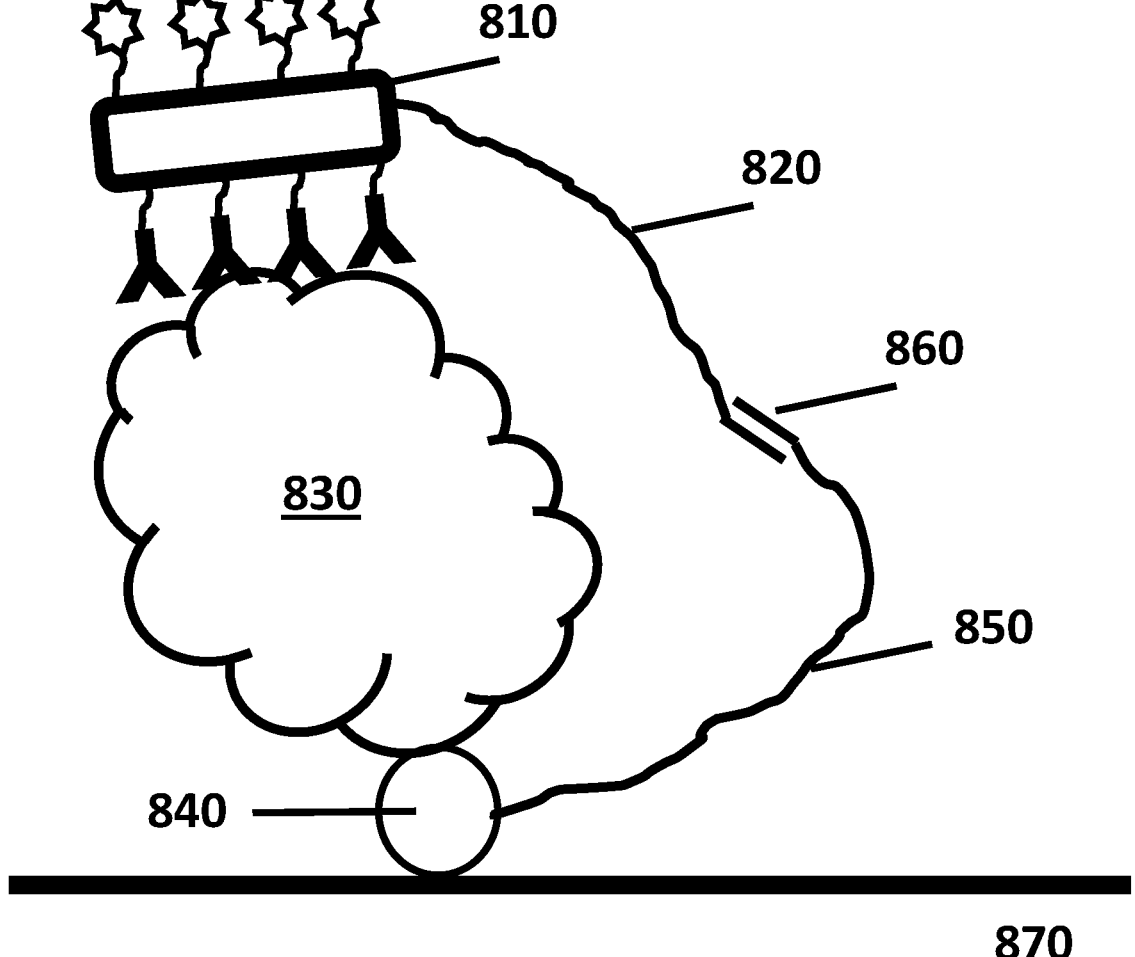
FIG. 8 shows a configuration of a detectable probe with an additional avidity component.

FIG. 8 depicts a detectable probe 810 that is configured to form an interaction with a binding partner 830 or an epitope or target moiety within the binding partner 830. The detectable probe further includes a pendant ligand 820 (e.g., a nucleic acid) that is configured to form a weak interaction with a complementary molecule 850 at an interaction region 860. In some configurations, the secondary molecule 850 may be bound or associated with an anchoring group 840, the binding partner 830, or a solid support 870. In some configurations, the interaction between the pendant ligand 820 and the complementary molecule 850 at the interaction region 860 may be naturally unstable, facilitating the eventual dissociation of the detectable probe 810 from the binding partner 830. In other configurations, the interaction between the pendant ligand 820 and the complementary molecule 850 at the interaction region 860 may be configured to be disrupted (e.g., in the presence of a denaturant).

Figure 9A:
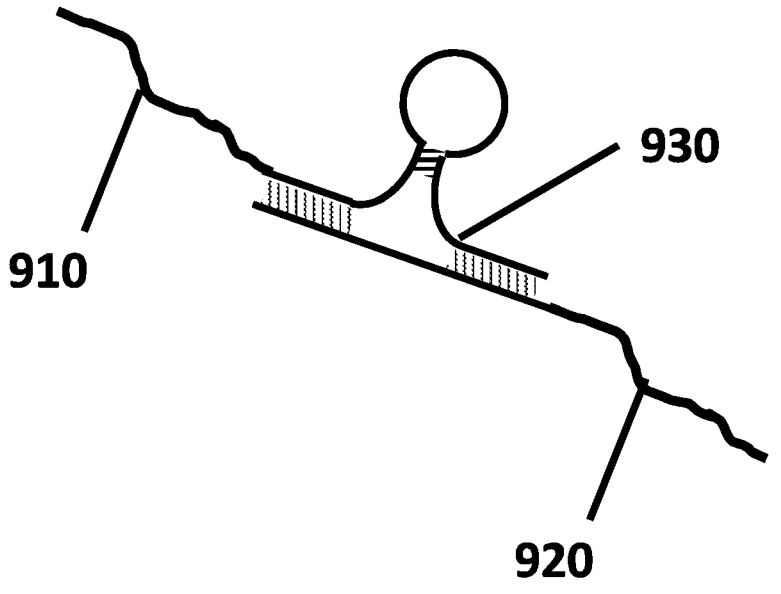
FIG. 9A shows a configuration of a system for creating a weak binding interaction for a detectable probe.
Figure 9B:
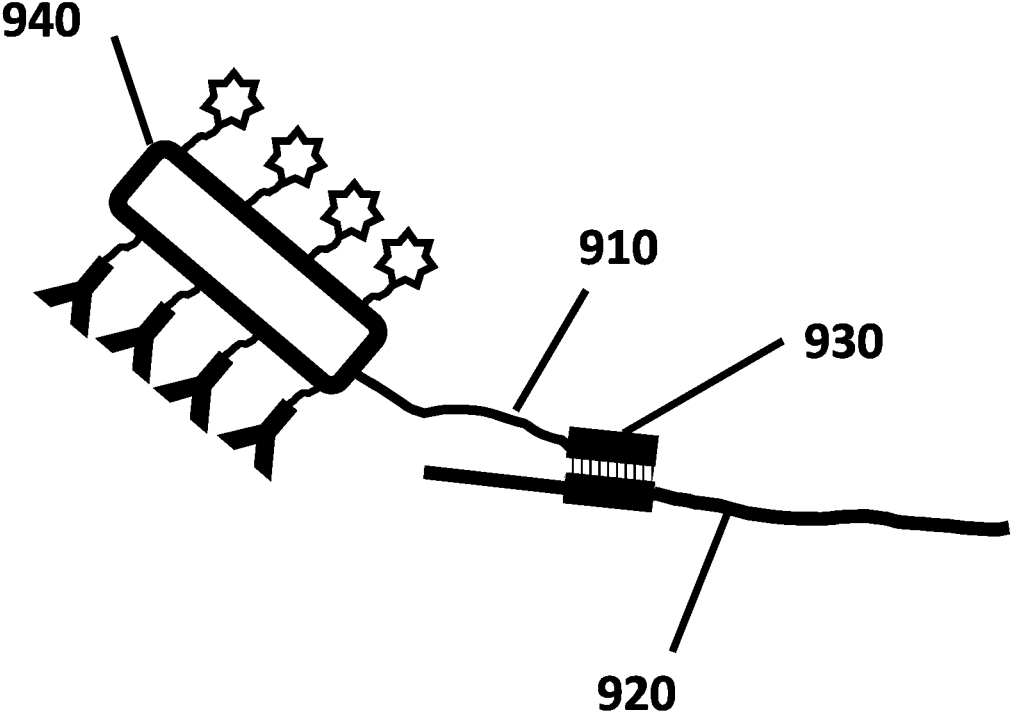
FIG. 9B shows a configuration of a system for creating a weak binding interaction for a detectable probe.

FIGS. 9A-9B depict possible configurations for forming weak interactions between a detectable probe and a secondary molecule utilizing a pair of complementary nucleic acids. FIG. 9A shows a first nucleic acid 910 which may be coupled to a detectable probe or a secondary molecule and a second nucleic acid 920 which may be coupled to the opposite molecule of the detectable probe-secondary molecule pair. The first nucleic acid 910 is configured to hybridize to the second nucleic acid 920 in an imperfect or discontinuous fashion, thereby forming a weak interaction region 930. In some configurations, the imperfect or discontinuous hybridization may include hairpin or loop structures, mismatched nucleotides, or modified or unnatural nucleotides that create weaker base pair binding. FIG. 9B shows a weak interaction between a detectable probe and a secondary molecule that is formed between two nucleic acids by a short hybridization region. A detectable probe 940 may include a first nucleic acid 910 that is configured to hybridize with a second nucleic acid 920. The first nucleic acid 910 and the second nucleic acid 920 hybridize at a weak interaction region 930 which contains a limited number of bonded base pairs such that the base pair bonding has a degree of reversibility or dissociation. The weak interaction region may include a limited number of nucleotides such as, for example, no more than about 15, 14, 13, 12, 11, 10, 9, 8, 7, 6, 5, 4, 3, 2, or less than about 2 nucleotides. A weak base pairing interaction region may be located at a terminal portion of a nucleic acid or in an internal portion of the nucleic acid sequence.

In some embodiments, the detectable probe further includes a partially non-hybridized nucleic acid having a single stranded region. In some embodiments, the single stranded region is bound to a complementary nucleic acid that is associated with a binding partner. In some embodiments, the single stranded region includes a primer sequence that is configured to bind to a complementary primer sequence. In some embodiments, the primer sequence is configured to cause a toehold displacement reaction. In some embodiments, the primer sequence is configured to form a hairpin or loop structure when binding to the complementary primer sequence.

Figure 10A:
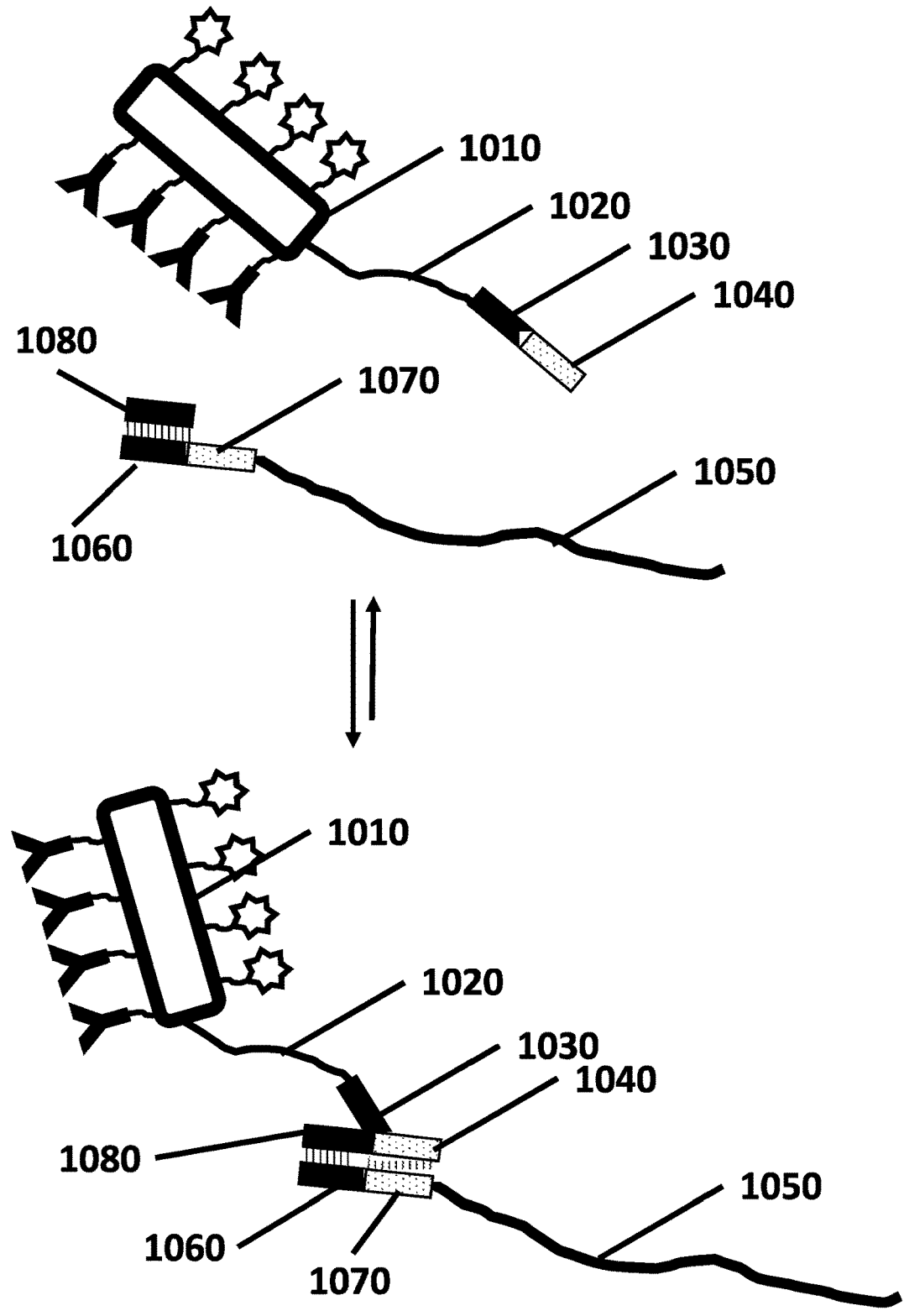
FIG. 10A shows a method for creating a weak binding interaction for a detectable probe.
Figure 10B:
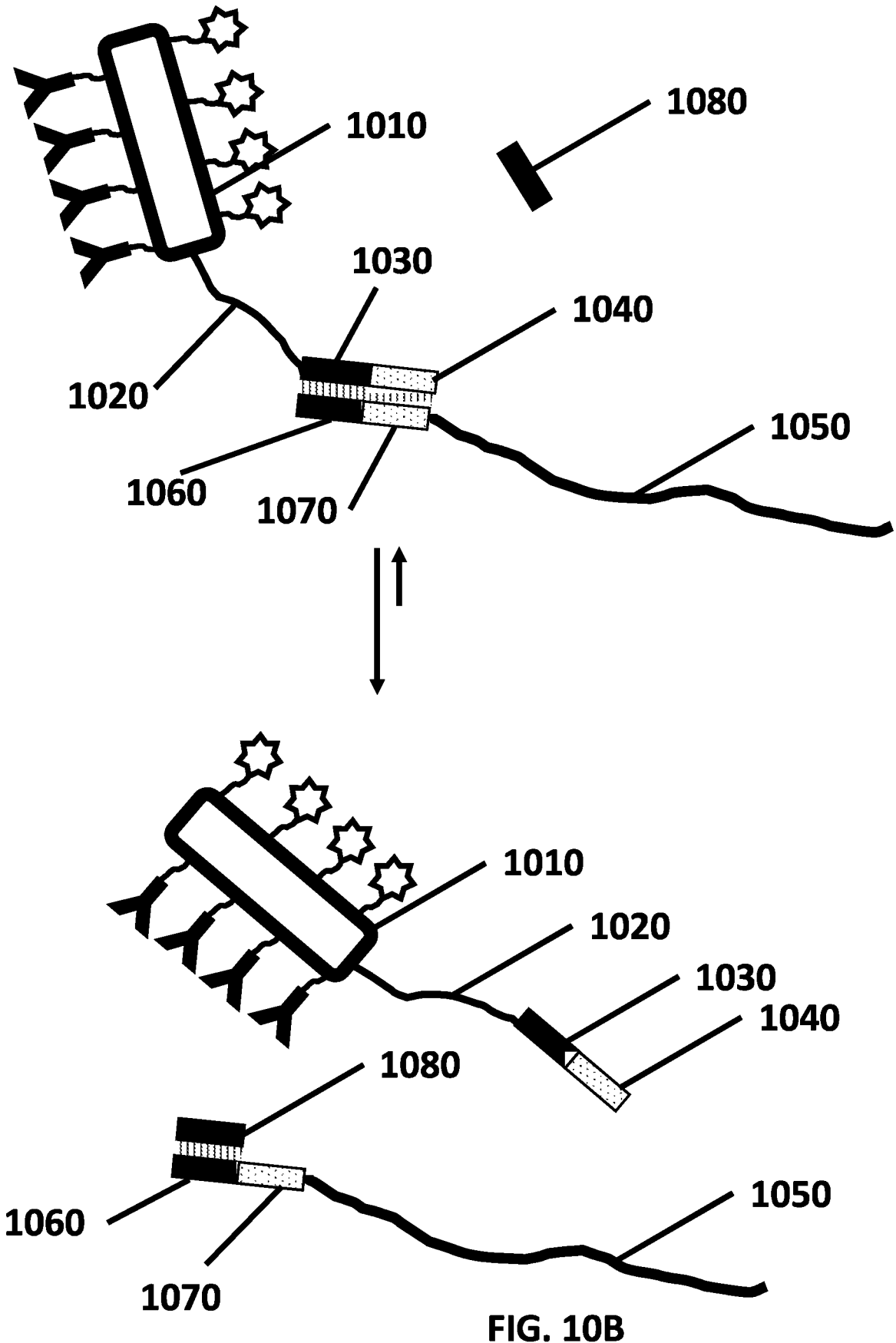
FIG. 10B shows a method for creating a weak binding interaction for a detectable probe.
Figure 10C:
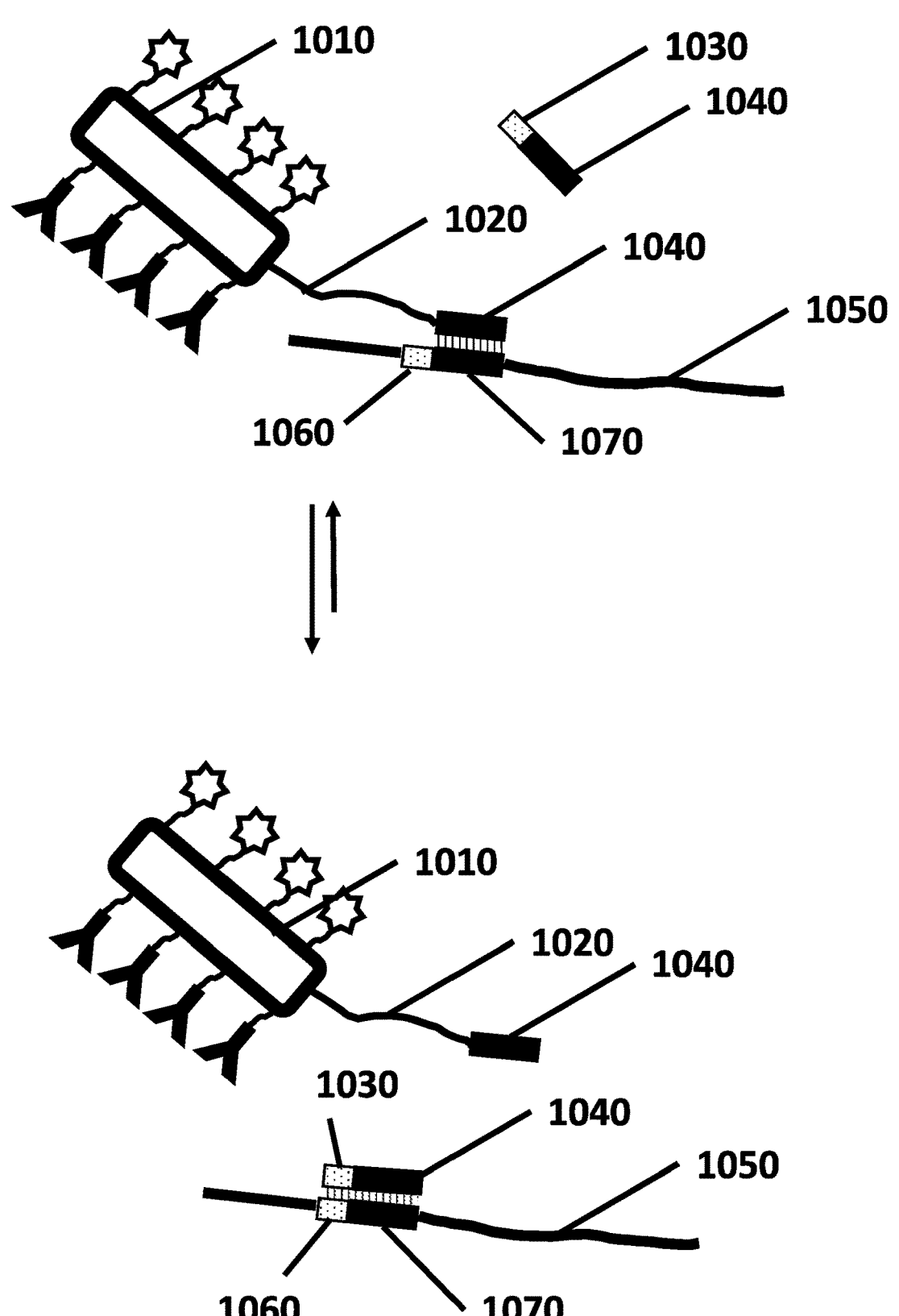
FIG. 10C shows a method for creating a weak binding interaction for a detectable probe.

FIG. 10A-10C depict a toehold displacement strategy for forming a weak binding interaction between a secondary molecule and a detectable probe. FIG. 10A shows the first step of a toehold displacement reaction. A detectable probe 1010 including a first nucleic acid 1020 approaches a second nucleic acid 1050 that is associated with a secondary molecule. The first nucleic molecule 1020 includes a hybridization sequence containing a toehold sequence 1030 and a priming sequence 1040. The second nucleic acid 1050 includes a complementary hybridization sequence including a complementary toehold sequence 1060 and a complementary priming sequence 1070. The second nucleic acid 1050 may be hybridized to a toehold primer 1080 that only hybridizes to the complementary toehold sequence 1060 of the hybridization sequence. The priming sequence 1040 of the first nucleic acid 1020 may hybridize to the complementary priming sequence 1070 of the second nucleic acid 1050, thereby forming an initial weak binding interaction between the detectable probe 1010 and the secondary molecule. The weak binding interaction between the detectable probe 1010 and the secondary molecule may have a degree of reversibility or dissociation. FIG. 10B shows the second step of a toehold displacement reaction. The toehold sequence 1030 of the first nucleic acid 1020 displaces the toehold primer 1080, allowing the toehold sequence to complete hybridization with the complementary toehold sequence 1060 of the second nucleic acid 1050. The continued presence of a toehold primer 1080 in the solution or solvent adjacent to the weak binding interaction may cause reversal of the toehold displacement reaction by displacement of the first nucleic acid 1020 from the second nucleic acid 1050 by the toehold primer 1080.

FIG. 10C depicts an alternative approach to forming a weak binding interaction between a detectable probe and a secondary molecule. A detectable probe 1010 includes a first nucleic acid strand 1020 that contains a priming sequence 1040 that binds to a complementary priming sequence 1070 on a second nucleic acid strand 1050. The second nucleic acid strand 1050 also contains a complementary toehold sequence 1060 that is not complementary to the sequence of the first nucleic acid 1020. The detectable probe—secondary molecule complex may be contacted with a solution or solvent that includes a toehold primer including a toehold sequence 1030 and a priming sequence 1040. The toehold primer may reversibly displace the first nucleic acid strand 1020 by disrupting the base pair binding of the priming sequence 1040 with the complementary priming sequence 1070. In some configurations, the equilibrium between binding and displacement of a detectable probe may be controlled by adjusting the concentration of one or more of the toehold displacement reactants (e.g., toehold primers, detectable probes).

The avidity of a detectable probe or affinity reagent may also be increased by utilizing another binding molecule with a differing affinity. In some configurations, an affinity reagent may include one or more binding components, e.g., a retaining component attached to a plurality of binding components. In some configurations, an affinity reagent has a single binding component. In some configurations, a binding molecule is a detectable probe or affinity reagent. A binding molecule may have the property of binding to a binding partner, epitope, or target moiety with a lower affinity and/or avidity than a detectable probe or affinity reagent. A binding molecule may be coupled to a detectable probe or affinity reagent such that the simultaneous binding of the detectable probe or affinity reagent to the binding molecule creates an apparent increase in the observed avidity or affinity of the detectable probe or affinity reagent.

Figure 11A:
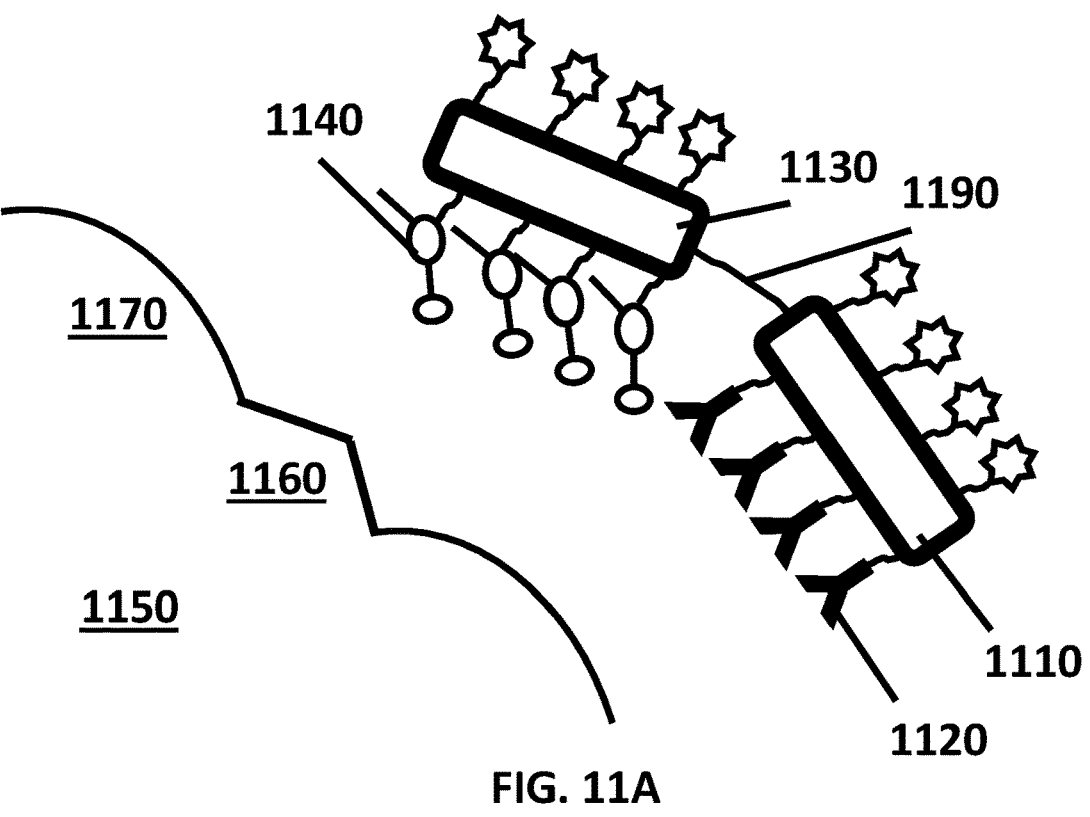
FIG. 11A shows a method for creating a weak binding interaction with two detectable probes.
Figure 11B:
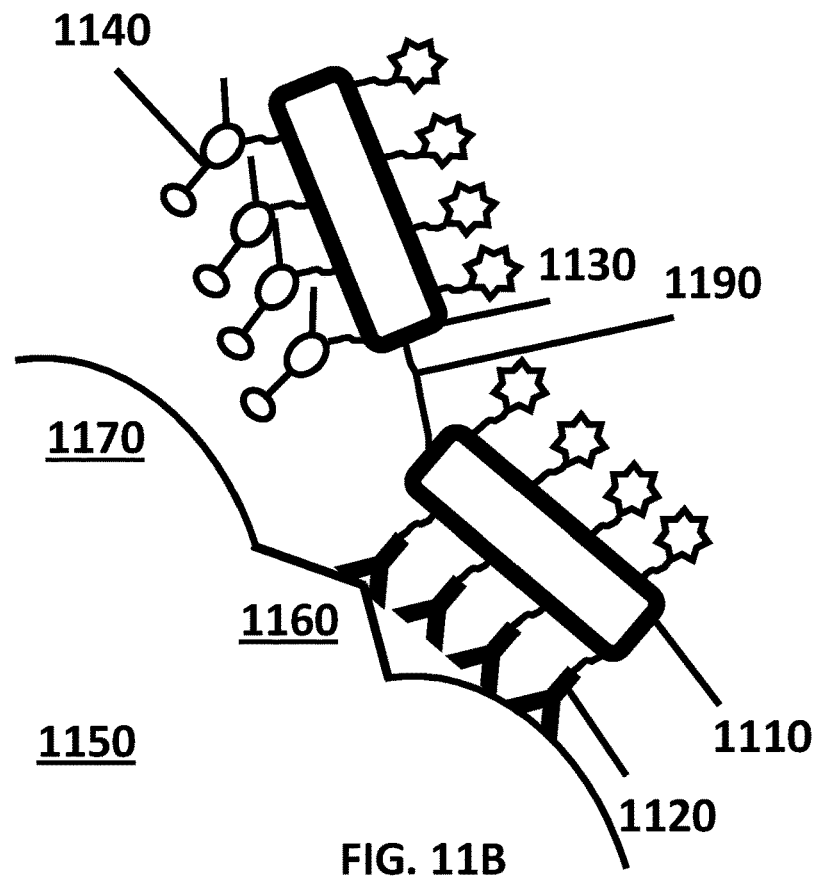
FIG. 11B shows a method for creating a weak binding interaction with two detectable probes.
Figure 11C:
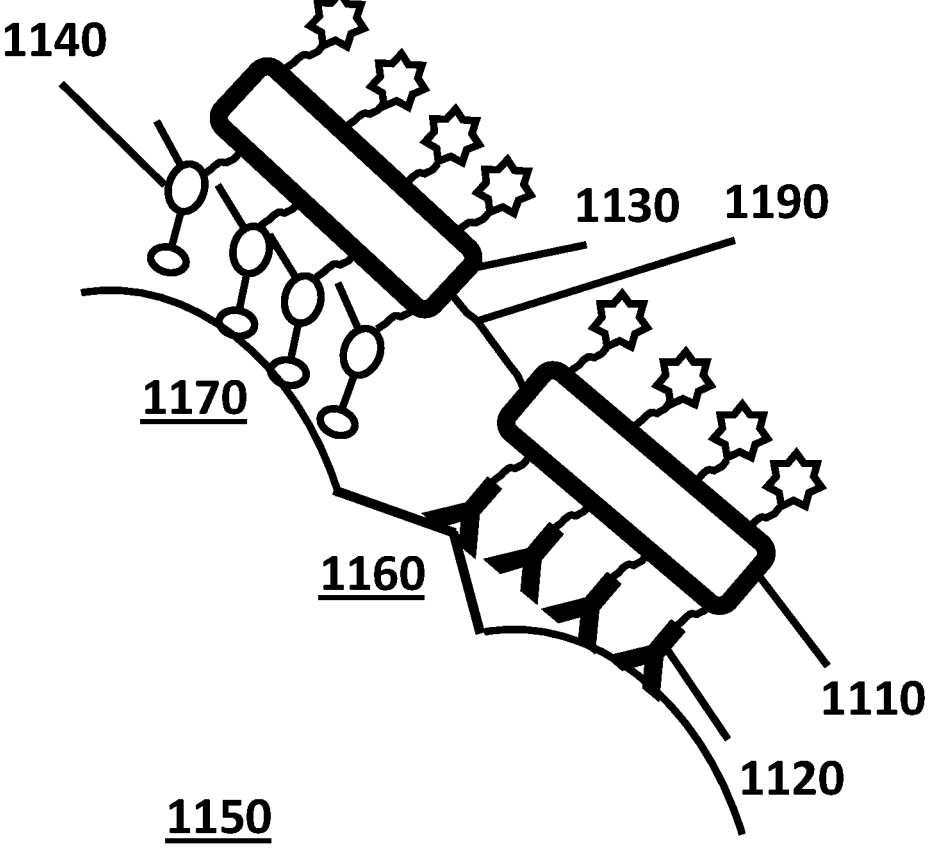
FIG. 11C shows a method for creating a weak binding interaction with two detectable probes.

FIG. 11A-11C depict a system for increasing the avidity of a detectable probe using a secondary binding interaction of a binding molecule. As shown in FIG. 11A, a detectable probe 1110 is joined to a binding molecule 1130 (e.g., a second detectable probe) by a linker 1190 (e.g., a covalent heterobifunctional linker, hybridized nucleic acids, etc.). The linker can be flexible, for example, allowing the detectable probe 1110 to interact directly with the binding molecule 1130. Alternatively, the linker can be relatively rigid, for example, constraining the detectable probe 1110 from directly interacting with the binding molecule 1130. The detectable probe 1110 includes a first plurality of binding components 1120, and the binding molecule 1130 includes a second plurality of binding components 1140. A composition including the complex formed by the joining of the detectable probe 1110 and the binding molecule 1130 is contacted with a binding partner 1150 that contains an epitope or target moiety 1160, and a secondary binding site 1170. As shown in FIG. 11B, a binding interaction may be initiated by the initial binding of a binding component of the first plurality of binding components 1120 with the epitope or target moiety 1160. At the time of initial binding, the binding molecule may not yet have formed a secondary interaction with the binding partner 1150. As shown in FIG. 11C, the binding process may be complete when a binding component of the second plurality of binding components 1140 forms a secondary binding interaction with the secondary binding site 1170, thereby binding the detectable probe 1110 and the binding molecule 1130 to the binding partner 1150. The weak secondary binding interaction between the binding molecule 1130 and the secondary binding target 1170 may increase the likelihood that the detectable probe 1110 will be observed as being bound to the binding partner 1150. The skilled person will readily recognize that the binding order of a binding complex may be reversed, e.g., a binding molecule 1130 binds a secondary binding site 1170 first, followed by binding of a detectable probe 1110 to the epitope or target moiety 1160.

Figure 11D:
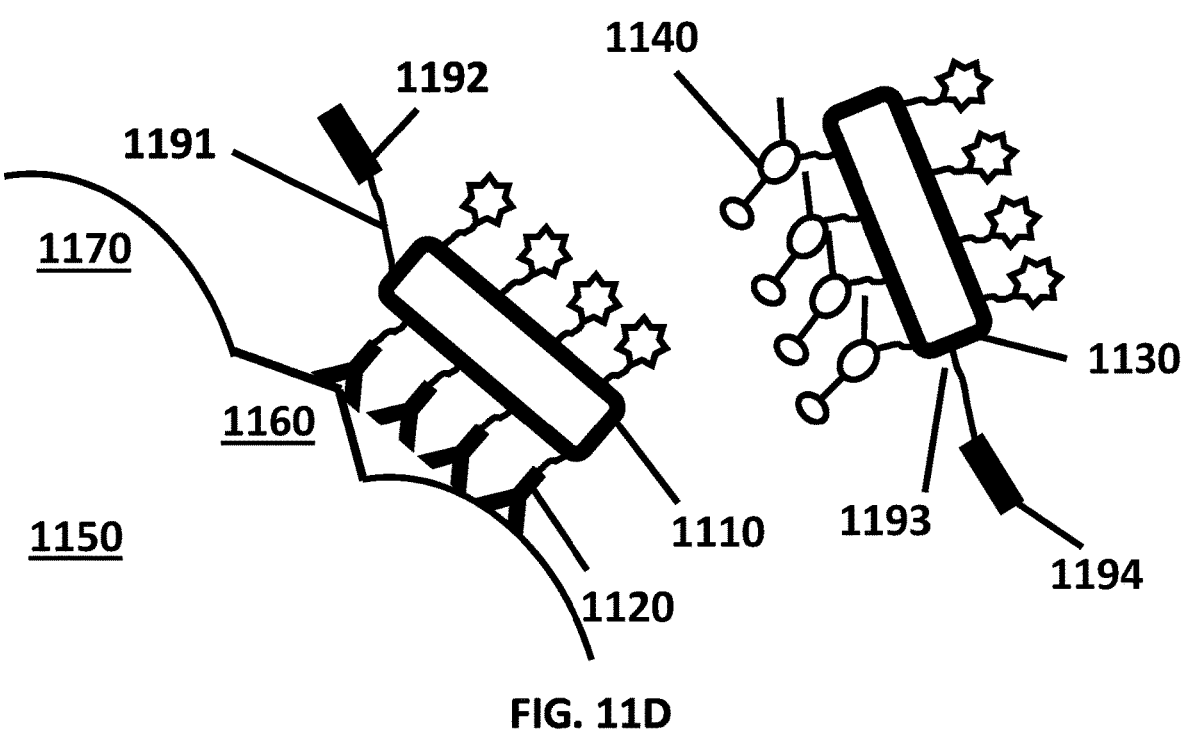
FIG. 11D shows a method for creating a weak binding interaction with two detectable probes.
Figure 11E:
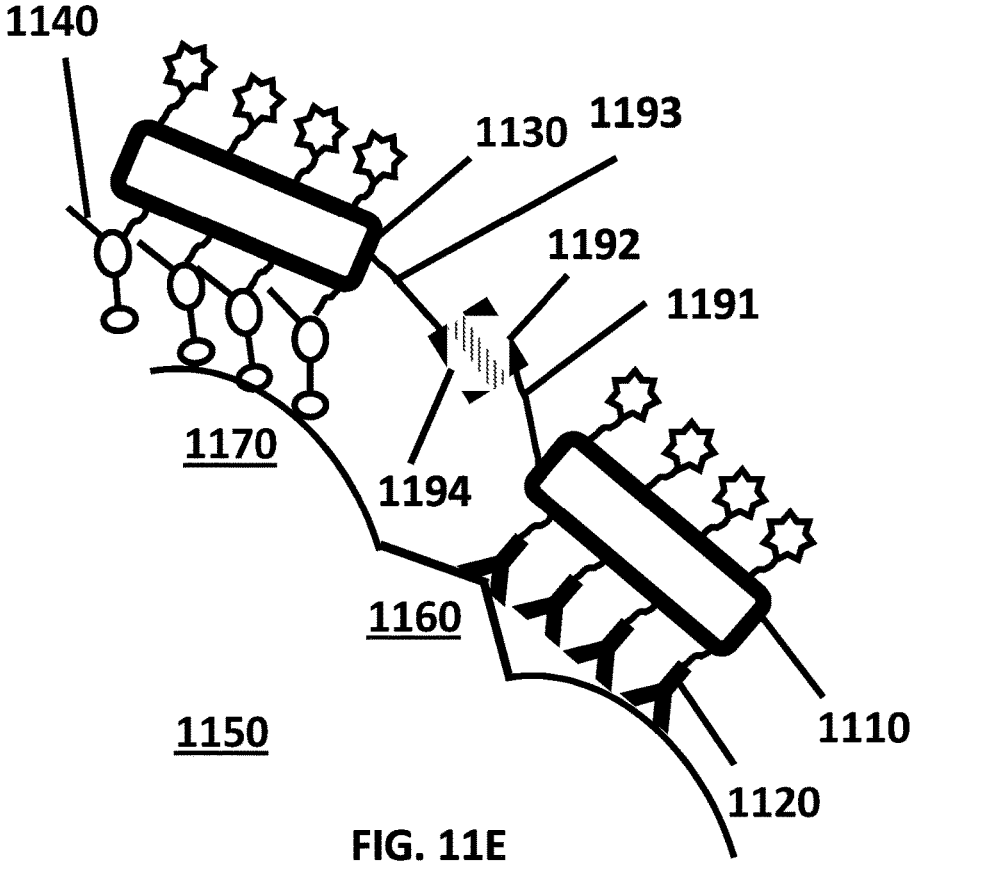
FIG. 11E shows a method for creating a weak binding interaction with two detectable probes.

FIGS. 11D-11E depict an alternative system for increasing the avidity of a detectable probe using a secondary binding interaction of a binding molecule. As shown in FIG. 11D, a detectable probe 1110 including a first plurality of binding components 1120 and a first linking group 1191 including a linking region 1192 is bound to an epitope or target moiety 1160 of a binding partner 1150. An unbound binding molecule 1130 including a second plurality of binding components 1140 and a second linking group 1193 including a complementary linking region 1194 is contacted with the binding partner 1150. As shown in FIG. 11E, a binding component of the plurality of binding components 1140 binds the binding molecule 1130 to a secondary binding site 1170 of the binding partner, thereby forming a weak secondary binding interaction. After the binding of the binding molecule 1130, the linking region 1192 and the complementary linking region 1194 can become joined, thereby forming a linker between the detectable probe 1110 and the binding molecule 1130. The weak secondary binding interaction between the binding molecule 1130 and the secondary binding target 1170 may increase the likelihood that the detectable probe 1110 will be observed as being bound to the binding partner 1150. The skilled person will readily recognize that the binding order of a binding complex may be reversed, e.g., a binding molecule 1130 binds a secondary binding site 1170 first, followed by binding of a detectable probe 1110 to the epitope or target moiety 1160. The first linking group 1191 and the second linking group 1193 may be configured to form a covalent or non-covalent interaction. For example, a first linking group 1191 may include a nucleic acid linking region 1192 and a second linking group 1193 may include a complementary nucleic acid linking region 1194 that is configured to hybridize to the nucleic acid linking region 1192. In another example, a linking region 1192 may include a functional group (e.g., a click reaction group) that is configured to chemically bond to a functional group in the complementary linking region 1194 (e.g., by a click reaction).

In many cases, an affinity reagent, detectable probe or binding component thereof may have a non-random probability of binding to selected binding partners (e.g. polypeptide molecules or amino acid epitopes within larger polypeptide structures), meaning that it displays some level of heightened affinity for a given epitope or set of epitopes over others, also termed "specificity". In many cases, specificity may not be binary, meaning that an affinity reagent or detectable probe may sometimes not appear to bind to a given epitope for which it has displayed heightened specificity, and sometimes it may appear to bind to an epitope for which it has no demonstrated specificity. In many cases, whether a given affinity reagent or detectable probe is specific for a given epitope or binding partner as described above, will be correlated with the probability of that affinity reagent or detectable probe binding to the given epitope or binding partner under the conditions of the binding assay. For example, an affinity reagent or detectable probe can be considered specific for a particular epitope or binding partner if the probability of binding is greater than a probability threshold. The probability threshold can be known prior to performing the binding assay (i.e. the threshold is predetermined) or it can determined from the binding assay itself (i.e. the threshold is empirically determined). In some cases, the probability threshold that is correlated with specific binding may be greater than 50%, 60%, 70%, 80%, 90%, 95%, 99% or more. In some cases, the probability threshold that is correlated with specific binding may be greater than 1%, 5%, 10%, 20%, 30%, or 40%. Conversely, the probability that a given affinity reagent or detectable probe does not bind a given epitope or binding partner under a given set of circumstances (e.g., providing a false negative binding result) may, in some cases, range from less than 1% to greater than 99%, meaning that there may be a significant likelihood of affinity reagent or detectable probes not binding to their complementary epitope or polypeptide. While in some cases, the probability threshold that is correlated with non-specificity or non-binding will be less than 50%, 40%, 30%, 20%, 10%, 5%, or less. In some cases, the probability threshold that is correlated with non-specificity or non-binding may be less than 60%, 70%, 80%, 90%, or 95%.

In some embodiments, a detectable probe or affinity reagent may have one of more of the following properties: may specifically bind to a particular amino acid species and may not bind to more than nineteen other amino acid species. For example, a detectable probe or affinity reagent may bind to one of the 20 essential amino acids but not the other 19 essential amino acids. A detectable probe or affinity reagent may bind at least 10% of sequences of the form $\alpha X\beta$, wherein X is the desired epitope and $\alpha$ and $\beta$ are any amino acid residues. In some cases, the detectable probe or affinity reagent may bind at least 0.25%, 0.5%, 0.75%, 1%, 2%, 3%, 4%, 5%, 6%, 7%, 8%, 9%, 10%, 11%, 12%, 13%, 14%, 15%, 20%, 30%, 40%, 50%, 75%, or 90% of sequences of the form $\alpha X\beta$. In some cases, a detectable probe or affinity reagent may bind to at least 10% of sequences of the form $\alpha X\beta$ with a $K_D$ value at least 10 fold lower than an average $K_D$ value of the detectable probe or affinity reagent for a pool of random sequences. In some cases, the detectable probe or affinity reagent may bind to at least 10% of sequences of the form $\alpha X\beta$ with a $K_D$ value at least 100 fold lower than an average $K_D$ value of the detectable probe or affinity reagent for a pool of random sequences. In some cases, the detectable probe or affinity reagent may bind to at least 10% of sequences of the form $\alpha X\beta$ with a $K_D$ value at least 1000 fold lower than an average $K_D$ value of the detectable probe or affinity reagent for a pool of random sequences.

In some embodiments, a detectable probe or affinity reagent may have one or more of the following properties: may specifically bind a desired epitope having a particular three amino acid sequence, may not bind any other three amino acid sequence, and may bind the desired epitope with substantially similar affinity regardless of flanking sequence surrounding the desired epitope. In some cases, the detectable probe or affinity reagent may have some, more, or all of these properties. In some cases, the detectable probe or affinity reagent may not bind a subset of the epitope. Another aspect of the present disclosure provides a detectable probe or affinity reagent which may preferentially bind a known set of three amino acid epitopes for which the preference for these epitopes relative to other epitopes, and subject to flanking amino acid residues, has been determined.

In some cases, a detectable probe or affinity reagent may include a switchable aptamer which binds to between 5% and 10% of all proteins in the human proteome. In some cases, the switchable aptamer may include two or more fluorescent moieties. A switchable aptamer may be a binding component of a detectable probe or affinity reagent of the present disclosure.

In some cases, a detectable probe or affinity reagent is configured to bind to a given sequence with a $K_D$ value for the detectable probe or affinity reagent and the given sequence that is at least 10, 100, or 1000 fold lower than an average $K_D$ value of the detectable probe or affinity reagent for a pool of proteins having random sequences.

In some cases, a detectable probe or affinity reagent may have an ability to bind a desired epitope that is in one or more structural context. In some embodiments, a detectable probe or affinity reagent may bind a desired epitope when a polypeptide having the epitope is in a denatured context, in a native context, or both. In some embodiments, a detectable probe or affinity reagent may have an ability to bind a desired epitope in a polypeptide within a folded or unfolded context. In some embodiments, polypeptides that have been denatured may contain or generate one or more microfold regions within the polypeptides. Detectable probes or affinity reagents may be designed to bind a desired epitope in a polypeptide that has been allowed to fold after having been denatured. The resulting polypeptide may be renatured to its active folded state, partially refolded, or folded into a different state. A detectable probe or affinity reagent may bind to an epitope in a folded or unfolded region of a polypeptide that has been denatured and/or allowed to fold from the denatured state.

In some embodiments, a detectable probe or affinity reagent that recognizes a desired epitope sequence (e.g. AAA) may bind equally well, or nearly equally well, to all polypeptides containing the epitope sequence. In some cases, detectable probes or affinity reagents may bind to a desired epitope with differing affinities according to differences in the sequence context of the epitope. In some cases, detectable probes or affinity reagents may bind several different epitopes regardless of sequence context. In some cases, detectable probes or affinity reagents of this disclosure may bind several different epitopes with different affinities depending on sequence context. Detectable probes or affinity reagents with such properties may be identified by a combination of screening methods to determine the binding characteristics of the detectable probe or affinity reagent. For example, a detectable probe or affinity reagent may be screened for the ability to bind to a set of polypeptide sequences that differ from one another except for a common core sequence (e.g. an amino acid epitope of the form αAAAβ, where AAA is the common core sequence and α and β may be any amino acid).

In some cases, the desired epitope of a detectable probe or affinity reagent may be a peptide sequence. In some cases, several different epitopes may be desired. In this case a detectable probe or affinity reagent may be selected which binds the plurality of desired epitopes. In some cases, the desired epitope or epitopes may be referred to as X. In some cases, the epitope includes a non-contiguous amino acid sequence. For example, an epitope may include a specified amino acid every second, third or fourth amino acid residue in a region of the primary sequence of a polypeptide. An epitope may include a sequence of 3 amino acids in which two specified amino acids are separated by a variable amino acid (e.g. AαA, where A is alanine and α is any amino acid), a sequence of 4 amino acids in which two specified amino acids are separated by two variable amino acids (e.g. AαβA where A is alanine and α and β are any amino acid), a sequence of 5 amino acids in which two specified amino acids are separated by three variable amino acids, etc. In some embodiments, an epitope can include a sequence of two or more of the non-contiguous epitopes. In another example, an epitope may include several amino acid residues that are located proximally to each other in a protein secondary or tertiary structure even though the residues are not proximal in the protein sequence (i.e. not proximal in the primary structure of the protein). In some cases, the epitope includes a contiguous sequence of specified amino acids. In some embodiments, the desired epitope, X, is a short amino acid sequence, of 2, 3, 4, 5, 6 or 7 amino acids. In some cases, X includes several different short amino acid sequences. In some embodiments, the desired epitope, X, is a three amino acid sequence, X1×2×3. Detectable probes or affinity reagents which bind this desired epitope in a variety of sequence contexts may be identified by screening for binding to target polypeptides including the desired epitope.

The target may include a plurality of polypeptides which include the desired sequence, X. The plurality may have any of a variety of configurations such as a pool of polypeptides in solution-phase, an array of polypeptides on a solid support, in a vessel, on a solid support, among a collection of vessels each containing one or more of the polypeptides in the plurality, etc. In some cases, the target is a plurality of polypeptides all of sequence X. In some embodiments the target may include a plurality of polypeptides of sequence αXβ, wherein X is the desired epitope and α and β may be any sequence of zero, one, or more than one amino acids. For example, if the desired epitope, X, is AAA, then examples of the sequences which may be found in the target polypeptides may include: AAAAA (SEQ ID NO: 1), AAAAC (SEQ ID NO: 2), CAAAA (SEQ ID NO: 3), CAAAC (SEQ ID NO: 4), and CAAAD (SEQ ID NO: 5). In some cases, α and β may each be any single amino acid. The amino acid for a may be the same as, or different from, the amino acid for β. In some cases, at least one of α and β may be 2, 3, 4, 5, 6, 7, 8, 9, 10, or more amino acids. The sequence for a may be the same as, or different from, the sequence for β. In some cases, at least one of α and β may include a linker or spacer. The linkers or spacers may be any linkers or spacers set forth herein or known in the art. In some cases, the linker has a peptide backbone, for example being an amino acid linker. In some cases, the linker is a polyethylene glycol (PEG) or a PEG polymer chain. The PEG chain may consist of 2, 3, 4, 5, 6, 7, 8, 9, 10, 12, 14, 16, 18, 20, 22, 24, 26, 28, 30, 34, 36, 38, 40, 42, 44, 46, 48, 50 or more ethylene glycol monomers. In some cases, the linker may be a carbon chain. The polypeptides may also include an N terminal or C terminal modification, for example, capping. In some cases, the polypeptides may be modified to remove a charge, for example, terminal amidation (C-terminus) or acetylation (N-terminus). In some cases, the αXβ peptide may contain non-naturally occurring amino acids. In some cases, the αXβ peptide may be modified with a linker and a functional group. For example, the molecule may be of the structure F-L-αXβ, where F is a functional group and L is a linker. In other cases, the molecule may be of the structure αXβ-L-F, where F is a functional group and L is a linker. Functional group F can optionally be capable of forming a covalent bond with a reactive moiety or binding to a receptor. In some cases, α and β may each be glycine, or may each be one or more glycine residues. In some embodiments, amino acid residues may be modified to alter their aptagenicity. For example, residues may be altered by adding a positive charge; adding a negative charge; adding a hydrophobic group; modified so as to add a sugar; or other modifications so as to increase chemical diversity.

Polypeptides may be synthesized using any method known in the art. Several commercial platforms exist for polypeptide synthesis, such as the MultiPep RSi synthesizer (Intavis, Germany). Polypeptides may be synthesized using liquid phase or solid phase methods. Synthesized polypeptides may be verified using any known method for polypeptide analysis. For example, polypeptides may be verified using Mass spectrometry, Matrix Assisted Laser Desorption/ Ionization Time of Flight Mass spectrometry (MALDI-TOF), Matrix Assisted Laser Desorption/Ionization, AMS (Accelerator Mass Spectrometry), Gas Chromatography-MS, Liquid Chromatography-MS, Inductively Coupled Plasma-Mass spectrometry (ICP-MS), Isotope Ratio Mass Spectrometry (IRMS), Ion Mobility Spectrometry-MS, Tandem MS, Thermal Ionization-Mass Spectrometry (TIMS), or Spark Source Mass Spectrometry (SSMS). Concentration of the synthesized peptides may also be assessed by spectroscopy.

Figure 48:
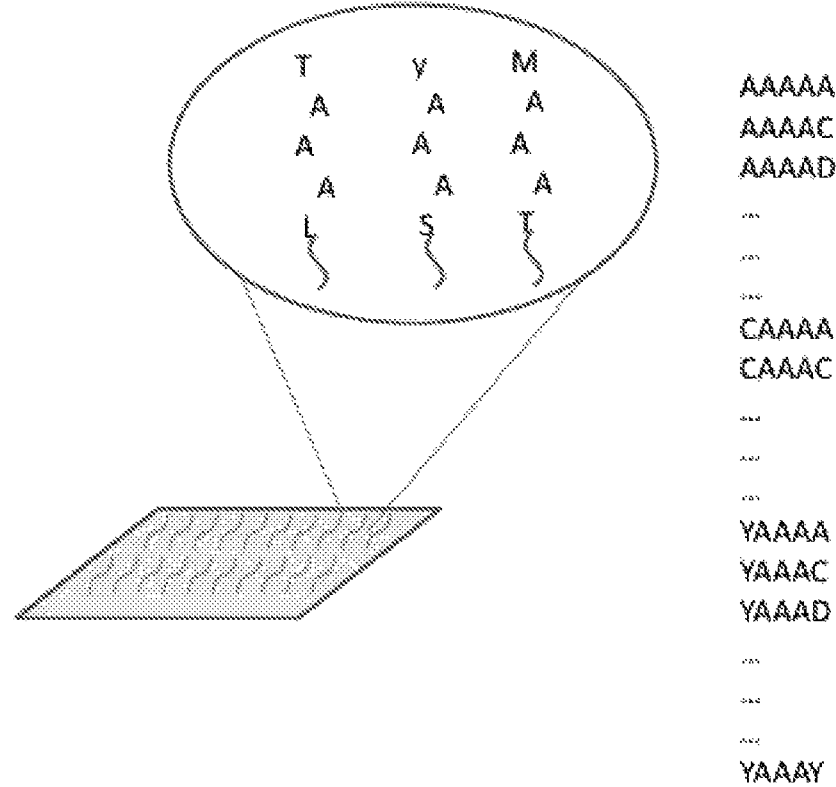

FIG. 48 illustrates an immobilized target for selection or characterization of detectable probes or affinity reagents, along with an exemplary list of polypeptides which include the target. In the example of FIG. 48 the desired epitope is AAA, and the polypeptides of the target include sequences αAAAβ, wherein α and β are each a single amino acid. In this example the target includes 400 different polypeptides, representing each possible sequence of αAAAβ, wherein α and β are each a single amino acid.

In this way, for any given 3-mer epitope a target including a pool of 5-mers may contain 400 different sequences (20 possibilities for α and 20 possibilities for β, where each of α and β are a single amino acid). In some cases, the target may include a pool of polypeptides longer than 5 amino acids in which each or both of α and β may include two or more amino acids. In some cases, one of α and β may include zero amino acids, and the other of a or R may include one or more amino acids. In some cases, the target may include a polypeptide of sequence X without additional amino acids.

In some cases, the target sequence X may be embedded in a longer sequence. For example the target sequence X may be a core sequence of fewer than 15 amino acids that is embedded in a 15-mer polypeptide molecule. The target sequence X may be embedded at any position within the 15-mer, for example in the case of a three amino acid target sequence X, the target sequence X may begin at position 1, 2, 3, 4, 5, 6, 7, 8, 9, 10, 11, 12, or 13 of the 15-mer. Polypeptides including embedded target sequences may be synthesized in solution, or may be synthesized on a chip, such as for example a PEPperPRINT chip or other peptide array. In some embodiments, polypeptides including embedded target sequences may be bound or synthesized onto a single molecule protein array. The longer sequence may be selected to form a secondary structure, or to lack secondary structure. Examples of such secondary structures include alpha helices, beta sheets, proline bends, turns, loops, and cysteine bridges. In some cases, the longer sequence may include non-naturally occurring amino acids, or other groups.

An initial selection step may include screening a library of affinity reagents or detectable probes against a target which includes a desired epitope. The affinity reagent or detectable probe or probe library may include DNA, RNA, or peptide aptamers with random sequences, or with sequences similar to those of known protein binding aptamers.

In some cases, the library may be an aptamer library. In some cases, an aptamer library may be a commercial library. In some cases, an aptamer library may be available from an institute, university, academic center, or research center. In some cases, a library may include a library of aptamers attached to beads or other particles. In some cases, an aptamer library may be generated from a library of known sequences, or from random sequences. In some cases, an aptamer library may include aptamers with particular structures, such as, for example, a stem loop library. In some cases, the aptamer library may include switchable aptamers—aptamers which can be switched between two conformations. For example, an aptamer may form a first conformation in the presence of a metal ion cofactor and a second conformation in the absence of the cofactor. Accordingly, adding a chelating agent such as EDTA, or EGTA, sequesters the metal ions and causes the aptamer to adapt a different conformation. Other factors that may be used to induce aptamer switching include light, pH, temperature, magnetic fields, and electrical current.

The screening of an aptamer library against the target may be performed by any method known in the art. In one aspect, the target may be immobilized on a solid support and the aptamers may be added under conditions that allow binding of aptamers with low specificity. Unbound aptamers may be washed from the target with a series of washes of increasing stringency. Aptamers that remain bound to the target through the wash steps may be sequenced and amplified for further rounds of selection or used for the design of additional aptamers with high sequence similarity. Several rounds of target binding, washing, sequencing and amplification, or design of new aptamers, may be repeated until aptamers of desired specificity and binding affinity are generated. An aptamer library may also be screened using a bead-based approach utilizing beads which each include multiple copies of an aptamer. An aptamer library may also be screened using an array-based approach, for example by spotting multiple copies of each aptamer of the library onto an array and then assessing the spots to which the target binds. An aptamer library may also be screened using a particle display approach. For example, beads or other particles that are attached to aptamers can be arrayed on a support to form an array. In some embodiments, an aptamer library may be screened using a single molecule protein array.

In some cases, the fraction or percentage of the targets to which an identified detectable probe or affinity reagent binds may be measured, for example by comparing the number of bound copies of the probe with the number of polypeptides available for binding. In some embodiments, a detectable probe or affinity reagent may bind to at least 10%, 20%, 30%, 40%, 50%, 60%, 70%, 80% or more of the polypeptides including the target. Additionally, once a particular detectable probe or affinity reagent is identified and selected, it may be validated. In some embodiments, a selected detectable probe or affinity reagent may be validated against a plurality of sequences containing epitopes to which the detectable probe or affinity reagent is characterized as binding. In some embodiments, a selected detectable probe or affinity reagent may be validated by assessing the selected detectable probe or affinity reagent against a plurality of protein sequences on a single molecule protein array.

The detectable probe or affinity reagent may be attached to detectable labels before or after the selection and characterization steps. In some cases, the detectable probe or affinity reagent may be attached to label(s) before the initial selection step. In some cases, the detectable probe or affinity reagent may be attached to label(s) after the initial selection step and before the characterization steps. In some cases, the detectable probe or affinity reagent may be attached to label(s) after the selection and characterization steps. In some cases, the detectable probe or affinity reagent may be attached to first labels for the selection step, and attached to second labels for the characterization steps. The second labels may be added with the first labels, or instead of the first labels. In some cases, a first label may be used for the selection and characterization steps, and a second label used to create a final affinity reagent or detectable probe.

Detection and Observability

A detectable probe of the present disclosure may be configured to provide a detectable signal that imparts observability to the probe. The observability may refer to the property of producing a physical signal that can be readily sensed by a detection device at a level that exceeds the background or noise of a detection system. For example, a fluorescent probe might be considered observable if it produces a fluorescent signal intensity that exceeds a background fluorescent signal intensity by a threshold amount, e.g., 10%, 50%, 100%, 2×, 3×, 4×, 5×, or more. In another example, a nucleic acid barcode signal might be considered observable if it produces a threshold number of sequence counts (e.g., by next-generation sequencing or array-based hybridization) with or without amplification, e.g., 1000 or more sequence counts after 10 rounds of signal amplification. In general, observability may be influenced by several factors, including: 1) likelihood of a detectable probe binding a target; 2) strength of background signal; and 3) signal-dampening mechanisms. Factors that may influence the likelihood of a detectable probe binding a target can include those set forth above.

A background signal may refer to a detectable signal that has the same or similar characteristics as compared to the desired signal. For example, in a fluorescent label system, a background signal may include detected radiation at the same wavelength or within a radiation wavelength range as the anticipated fluorescent signal from a fluorescent label, e.g., a background fluorescent signal may be detected between 485 nm and 495 nm when attempting to observe an Alexa-Fluor® 488 dye. For radiative signals, a background signal may arise due to natural fluorescence, natural luminescence, or autofluorescence of a material, transmission, reflection, or refraction of external radiation at a detected wavelength, or residual signal left by fluorescent probes from a prior detection process.

Background radiative signal may be spatially homogeneous or spatially heterogeneous. For some characterization assays, a radiative background signal may be measured before, during, or after an assay. For example, the spatial composition of a material may be characterized by multiple cycles of applying one or more detectable probes to the material. Over successive cycles, residual detectable probes may be randomly left on the material, creating a heterogeneous background signal during successive detection cycles. A residual detectable probe may eventually dissociate, meaning that the background signal may have spatial and temporal heterogeneity. In another example, the same above-described material characterization assay may occur in a detection system that is not optically sealed, permitting some external radiation to be detected in the system. The external radiation does not have a uniform distribution over the material, leading to detection of a non-homogenous gradient or distribution of radiation in the background signal. The external radiation may not vary over time, causing a spatially heterogeneous but temporally homogeneous background.

A detectable probe may be characterized as producing a detectable signal that exceeds a background signal threshold. A luminescently labeled, detectable probe may be characterized as having a fluorescent signal (or other type of luminescent signal) that exceeds a background fluorescent signal. A luminescent signal may be quantified, for example by total photon count over a fixed period of time, to obtain a background signal or a detected probe signal. A quantified luminescent signal may be measured at a point, location, or address, or over a region including a plurality of points, locations, or addresses. A detectable probe may be configured to have a detectable signal that exceeds a threshold background signal level, such as an average signal over an entire region or a maximum signal within a region. The overall strength of signal from a detectable probe may be controlled by the total number of signaling labels (e.g., fluorophores) attached to the detectable probe. The spatial strength of a probe (i.e., the signal strength at a specific location) may be controlled by the density of signaling labels (e.g., fluorophores) attached to the probe.

A detectable probe may be configured to produce a detectable signal that exceeds expected or observed background signal. For example, a detectable probe that is configured to bind to a material or to a binding partner on the material may produce a detectable signal that exceeds the measured background signal produced by the material. A detectable probe may produce a detectable signal that exceeds a background signal by a particular amount. Conversely, a detectable probe may produce a detectable signal that is less than a detectable limit depending upon the mode of signal sensing. A detectable probe may produce a detectable signal intensity that exceeds a background signal intensity by at least about 1.5×, 2×, 3×, 4×, 5×, 6×, 7×, 8×, 9×, 10×, 11×, 12×, 13×, 14×, 15×, 16×, 17×, 18×, 19×, 20×, 25×, 30×, 40×, 50×, 75×, 100×, or more. Alternatively or additionally, a detectable probe may have a detectable signal intensity that exceeds a background signal intensity by no more than about 100×, 75×, 50×, 40×, 30×, 25×, 20×, 19×, 18×, 17×, 16×, 15×, 14×, 13×, 12×, 11×, 10×, 9×, 8×, 7×, 6×, 5×, 4×, 3×, 2×, 1.5×, or less.

For radiative signals (e.g., fluorescence), signal-dampening may arise due to one or more mechanisms that remove or interfere with the radiative signal. Exemplary signal-dampening mechanisms may include quenching, self-quenching, photo-bleaching, and label loss. Quenching may occur due to the presence of chemical species that inhibit the emission of or that absorb emitted photons. Some species in a characterization system may inherently absorb emitted photons, leading to a reduction or quenching of radiative signal. In some configurations, particular species may be added to a detection system (e.g., oxygen scavengers such as ascorbate) that inhibit the formation of species that may quench a radiative signal. A specific form of quenching is self-quenching, where a luminescent signal from a luminophore may be quenched by a second luminophore of the same or similar species. Self-quenching may be related to inter-label configurations, such as the spacing between adjacent luminophores and the relative orientation of luminophores. In some configurations, luminescent signal may decrease as the spacing between adjacent luminophores decreases. In other configurations, luminescent signal may increase as the spacing between adjacent luminophores decreases (e.g., Forster resonant energy transfer).

Quenching, self-quenching, and related optical phenomena may be characterized by an effective quantum yield. Individual fluorophores may have a characteristic or measured quantum yield. The effective quantum yield of a detectable probe composition including a plurality of fluorophores may be a measured or characterized quantum yield under assay conditions. A detectable probe composition may have an effective quantum yield of at least about 0.1, 0.15, 0.2, 0.25, 0.3, 0.35, 0.4, 0.45, 0.5, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, or more. Alternatively or additionally, a detectable probe composition may have an effective quantum yield of no more than about 0.99, 0.98, 0.97, 0.96, 0.95, 0.94, 0.93, 0.92, 0.91, 0.90, 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, 0.69, 0.68, 0.67, 0.66, 0.65, 0.64, 0.63, 0.62, 0.61, 0.60, 0.59, 0.58, 0.57, 0.56, 0.55, 0.54, 0.53, 0.52, 0.51, 0.50, 0.45, 0.4, 0.35, 0.3, 0.25, 0.2, 0.15, 0.1, or less.

A radiative signal may also be dampened or otherwise diminished by a chemical mechanism such as photo-bleaching or label loss. Without wishing to be bound by theory, photo-bleaching may occur due to irreversible chemical changes to a label, such as a fluorescent label. Photo-bleaching may be due to any known mechanism, including interactions of photons with a fluorophore, interactions of photons with species that may damage a fluorophore (e.g., free radicals such as triplet oxygen), and interactions between chemical species and fluorophores that alter or damage a fluorophore. Photo-bleaching and other forms of signal-dampening may be transient or time-related phenomena. For example, photo-bleaching due to irradiation may increase in a proportion with total time or total time of irradiation. Likewise, total amount or concentration of disruptive chemically-modifying species may impact a rate of photo-bleaching. For example, photo-bleaching severity may increase with increased photon count or photon density. A rate of signal loss due to photo-bleaching or another chemical mechanism may be constant or variable (e.g., exponential, logarithmic) with time.

A detectable probe composition may experience a variable or increasing loss of signal over time due to quenching, self-quenching, photo-bleaching, label loss, or other mechanisms. A detectable probe composition may have a rate of signal loss of at least about 0.001%/min, 0.01%/min, 0.1%/min, 0.5%/min, 1%/min, 2%/min, 3%/min, 4%/min, 5%/min, 6%/min, 7%/min, 8%/min, 9%/min, 10%/min, 15%/min, 20%/min, 25%/min, 30%/min, 35%/min, 40%/min, 45%/min, 50%/min, 55%/min, 60%/min, 65%/min, 70%/min, 75%/min, 80%/min, 85%/min, 90%/min, 95%/min, or more. Alternatively or additionally, a detectable probe composition may have a rate of signal loss of no more than about 95%/min, 90%/min, 85%/min, 80%/min, 75%/min, 70%/min, 65%/min, 60%/min, 55%/min, 50%/min, 45%/min, 40%/min, 35%/min, 30%/min, 25%/min, 20%/min, 15%/min, 10%/min, 9%/min, 8%/min, 7%/min, 6%/min, 5%/min, 4%/min, 3%/min, 2%/min, 1%/min, 0.5%/min, 0.1%/min, 0.01%/min, 0.001%/min, or less.

A detectable probe may produce detectable signal that is distinguishable from background, for example, by having intensity that exceeds background signal or having a detectable characteristic that is resolved from background signal. A detectable probe may be characterized as producing signal intensity that exceeds background signal for a given amount of time despite signal degrading mechanisms such as photobleaching and label loss. For example, a fluorescent detectable probe may have a fluorescent signal that exceeds a background fluorescent signal for at least 10 minutes of continuous or non-continuous excitation. An observability time may be defined as the minimum length of time that a detectable probe produces a detectable signal that is distinguishable from a local or average background signal. In some configurations, observability time may be increased by increasing the total number of label components on a detectable probe. Observability time may scale proportionally with the number of label components attached to a detectable probe. The observability time of a detectable probe may be increased or even maximized to ensure detectability throughout an assay. The observability time of a detectable probe may be limited to within a certain value to enable intended signal removal, such as by photo-bleaching. A detectable probe may be observed for, or have an observability time of, at least about 1 s, 15 s, 30 s, 1 min, 2 min, 3 min, 4 min, 5 min, 6 min, 7 min, 8 min, 9 min, 10 min, 15 min, 20 min, 30 min, 45 min, 60 min, 90 min, 120 min, or more. Alternatively or additionally, a detectable probe may be observed for, or have an observability time of, no more than about 120 min, 90 min, 60 min, 45 min, 30 min, 20 min, 15 min, 10 min, 9 min, 8 min, 7 min, 6 min, 5 min, 4 min, 3 min, 2 min, 1 min, 30 s, 15 s, 1 s, or less.

Figures 12A, 12B:
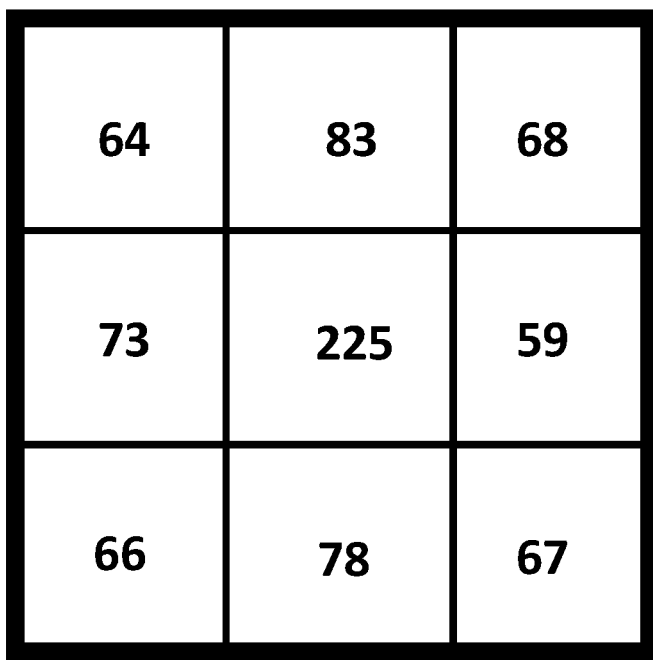
FIG. 12A shows fluorescence intensity measurements for a group of sensor pixels for a low-intensity fluorescent label.
FIG. 12B shows fluorescence intensity measurements for a group of sensor pixels for a high-intensity fluorescent label.

A detectable probe may improve the observability of a binding interaction by producing a detectable signal that is well in excess of a background signal. Moreover, a detectable probe may increase the observability of a binding interaction by improving spatial resolution of a detectable signal. A detectable probe may be configured to provide spatial resolution of a detectable signal in several ways, including: 1) concentration of labels within a small region of a retaining component to create an optically dense signal source; 2) distribution of labels over a large region of a retaining component to create an optically uniform signal source; or 3) concentration of labels over all or a large fraction of a retaining component to create an optically dense and uniform signal source. FIGS. 12A-12B depict an example of a luminescent signal (e.g. fluorescent signal) spatial resolution utilizing a detectable probe. FIG. 12A depicts fluorescent count data over a region (e.g., a surface of a material), including background fluorescent count, when a single binding component including a plurality of fluorophores is bound to a binding partner in the center of the region. The region may be uniformly divided into nine subregions where each subregion may be individually quantified for fluorescence (e.g., each subregion may correspond to a sensor pixel). The number of fluorophores attached to the affinity reagent may be limited due to the structure and affinity of the affinity reagent. The fluorescent counts in FIG. 12A show a modest increase in the fluorescence count of the center subregion, possibly due to a binding interaction between the affinity reagent and the binding partner, but the signal intensity may not be sufficiently above the background counts of the eight surrounding subregions to conclude that a binding interaction occurred. FIG. 12B depicts a similar situation to FIG. 12A, but with a detectable probe including a significantly larger number of fluorophores than the affinity reagent described for FIG. 12A. The significantly increased fluorescent signal observed in the central subregion, along with the increases in signal from the surrounding subregions (possibly due to signal cross-talk from the central subregion), increase the confidence that the observed signal is due to a binding interaction of the detectable probe with the binding partner.

A detectable probe may be sized to provide a detectable signal over a region of a solid support, surface or field of view. The size of a region over which a detectable probe provides a signal may be determined by the size of a feature within the region. For example, a detectable probe may be sized to provide a signal over an area that is larger than the area occupied by a binding partner (e.g., a polypeptide). A detectable probe may be designed to be larger than a binding partner to reduce a background signal, for example by reducing autofluorescence from the binding partner or a material adjacent to the binding partner. Alternatively, a detectable probe may be designed to be smaller than a binding partner to increase the spatial resolution of the detectable signal from the detectable probe.

Figure 13:
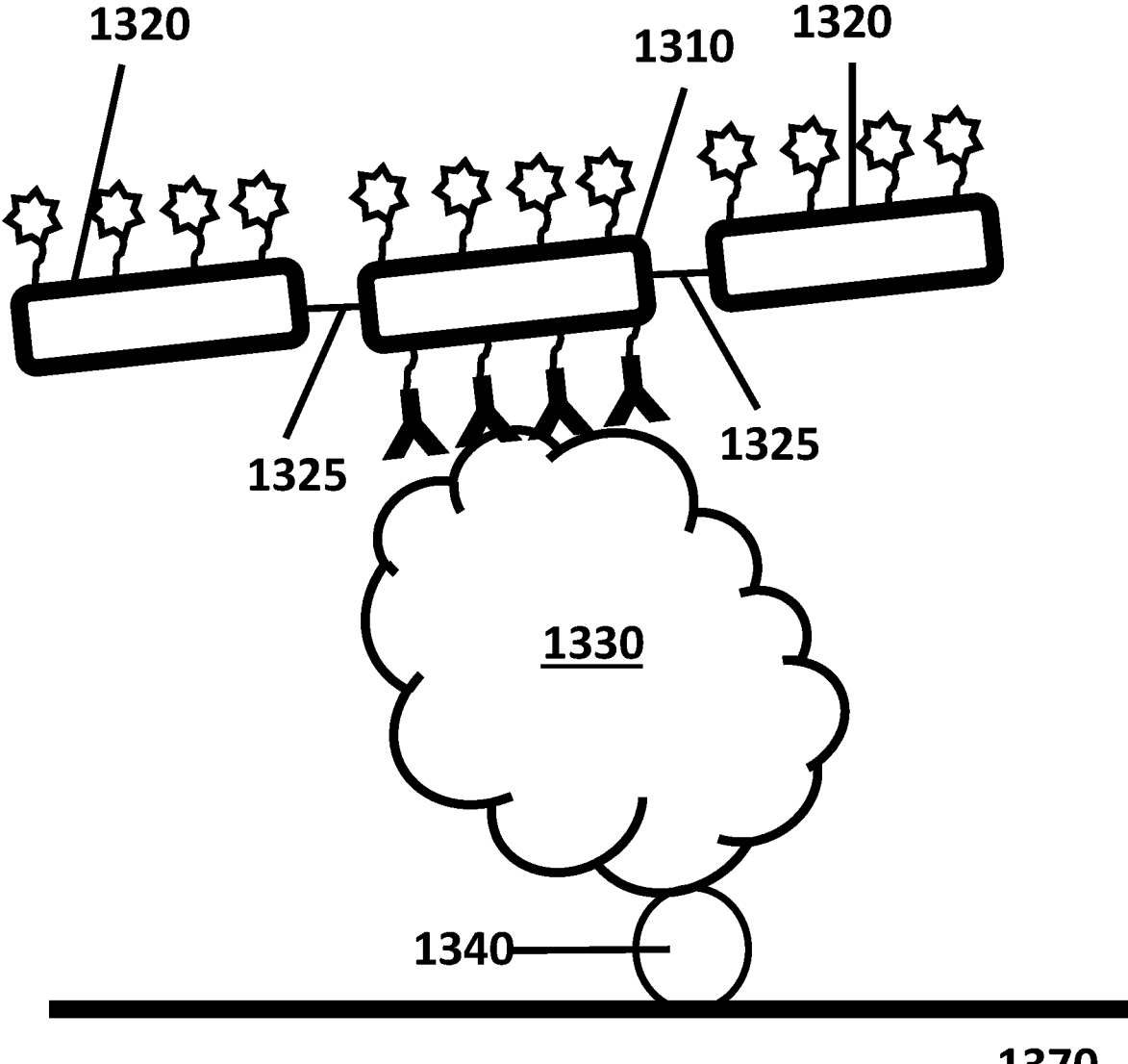
FIG. 13 shows a cross-sectional view of a highly observable detectable probe binding with a binding partner.

In some configurations, a detectable probe composition may be designed to produce a detectable signal over an area of a solid support, surface or field of view that is larger than the binding partner to which the detectable probe may bind or have affinity. Observability of the probe over a particular area may be improved by increasing the distribution and/or concentration of label components over a surface of the detectable probe. The probe may produce a detectable signal over a relatively large area by including additional detection molecules that enhance the detectable signal provided by the detectable probe. FIG. 13 illustrates a detectable probe composition for creating a detectable signal over a large area relative to the area occupied by the binding partner that it recognizes. A detectable probe 1310 binds to a binding partner 1330 (e.g., a polypeptide) that is anchored to a surface or solid support 1370, optionally by an anchoring group 1340 (e.g., a nucleic acid such as a structured nucleic acid particle or a functional group linkage). The area of detectable signal produced by the detectable probe 1310 is increased by joining the detectable probe 1310 with additional detection molecules 1320. The detection molecules 1320 may include a retaining component and a plurality of label components (e.g., fluorophores). The retaining components of the detection molecules 1320 need not be attached to binding components. However, the retaining components of the detection molecules 1320 can be attached to binding components other than those present in detectable probe 1310. The detection molecules 1320 are joined to the detectable probe 1310 by linkers 1325. The linkers 1325 may be permanent linkers (e.g., heterobifunctional linkers, click reaction products, streptavidin-biotin linkages) or may be non-permanent linkers (e.g., hybridized nucleic acids). The linkers can be flexible, for example, allowing direct interaction between the detection molecules 1320 and the detectable probe 1310; or the linkers can be rigid, for example, constraining the detection molecules 1320 from interacting with the detectable probe 1310. The complex formed by the detectable probe 1310 and the detection molecules 1320 may be formed prior to the binding of the detectable probe 1310 to the binding partner 1330, or may be formed by binding of the detectable probe, followed by contacting of detection molecules 1320 with the detectable probe 1310.

A detectable probe that is configured to bind with binding partner may be smaller or larger sized relative to the size of the polypeptides. Size can be measured as volume, molecular weight, longest dimension, effective diameter, radius of gyration, hydrodynamic radius, projection (e.g. footprint) or the like. Alternatively, a detectable probe that is configured to bind with a binding partner at a site (e.g. a site in an array of polypeptides) may be smaller or larger sized relative to the size of the site. A detectable probe or a complex including a detectable probe may be sized to be at least about 1%, 5%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 140%, 150%, 175%, 200%, 250%, 300%, 400%, 500%, 600%, 700%, 800%, 900%, 1000%, or more compared to the size of a binding partner or site. Alternatively or additionally, a detectable probe or a complex including a detectable probe may be sized to be no more than about 1000%, 900%, 800%, 700%, 600%, 500%, 400%, 300%, 250%, 200%, 175%, 150%, 140%, 130%, 120%, 110%, 100%, 95%, 90%, 85%, 80%, 75%, 70%, 65%, 60%, 55%, 50%, 45%, 40%, 35%, 30%, 25%, 20%, 15%, 10%, 5%, 1%, or less compared to the size of the binding partner or site.

The label components of a detectable probe may be configured for multiplex detection by the inclusion of more than one type or species of label component on the detectable probe. The ability to attach a plurality of binding components to a detectable probe adds to the dynamic flexibility of the detectable probe for multiplexing. A detectable probe can have a unique combination of label components that constitutes a unique fingerprint or signature for the detectable probe. Binding pools can be created from mixtures of detectable probes with differing binding specificities that are indicated by the specific probe signature or fingerprint such that an observed specific binding interaction can be determined through the observation of the signature or fingerprint. A signature or fingerprint may be created by altering the number of types or species of binding components as well as the ratios of label components attached to the detectable probe. A detectable probe may include at least about 2, 3, 4, 5, 6, 7, 8, 9, 10, or more different species of label component. Alternatively or additionally, a detectable probe for a multiplexing composition may include no more than about 10, 9, 8, 7, 6, 5, 4, 3, or fewer different species of label component. The ratio of a first species of label component to a second species of label component may be at least about 1.5:1, 2:1, 3:1, 4:1, 5:1, 6:1, 7:1, 8:1, 9:1, 10:1, or more. Alternatively or additionally, the ratio of a first species of label component to a second species of label component may be no more than about 10:1, 9:1, 8:1, 7:1, 6:1, 5:1, 4:1, 3:1, 2:1, 1.1:1, or less.

A multiplexed probe composition may include a plurality of detectable probes with differing binding affinities, where the binding affinity of any given detectable probe can be determined by the unique fingerprint or signature of label components on the detectable probe. The number of unique types of detectable probes in a multiplexed probe composition may be determined by the type of detection system used to observe binding interactions and the sensitivity of the detection system to distinguish differences in probe signatures or fingerprints. For fluorescent labels, a fluorescent detection system may have a limited number of detection channels based upon the fluorescence wavelengths of fluorophores on the detectable probes. The detection range within each detection channel may also constrain the amount of each fluorophore added to a detectable probe.

A multiplexed probe composition may include at least about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more unique types of detectable probes. Alternatively or additionally, a multiplexing probe composition may include no more than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, or fewer unique types of detectable probes. Uniqueness may be manifest in the number or diversity of components present in the detectable probes, such as the number or diversity of binding components present in the probes, the number or diversity of label components present in the probes, the number or diversity of retaining components present in the probes and/or the number or diversity of tags or barcodes present in the probes.

A detectable probe may be configured to be detected by Forster resonant energy transfer (FRET). In some configurations, a detectable probe may contain attached fluorophore pairs that are configured to be detected by a FRET mechanism. Without wishing to be bound by theory, efficient FRET detection can exploit an absorber fluorophore and an emitter fluorophore that are positioned within a sufficient distance to allow energy to be efficiently transferred between fluorophores. In some configurations, FRET can provide the advantage of increasing the number of probes that can be distinguished from each other using a given excitation source. For example, a first probe can include fluorophore component D that emits at a first wavelength when excited by the excitation source. A second probe can include fluorophore component D and fluorophore component A, in which excitation of fluorophore component D by the excitation source causes energy transfer to fluorophore component A which, in turn, emits at a second wavelength. The two emission wavelengths can be resolved using standard optics to distinguish the two probes from each other.

Figure 14A:
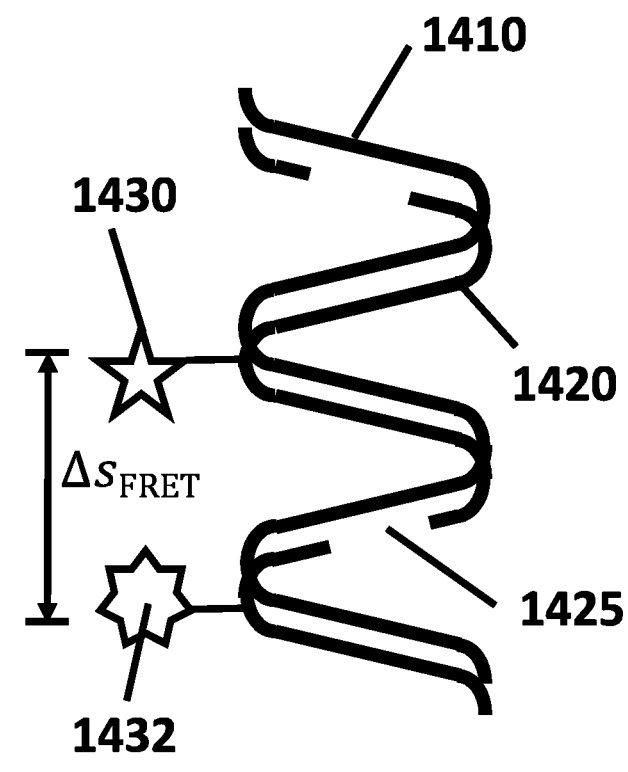
FIG. 14A shows a configuration for creating a Fluorescent resonance energy transfer (FRET) pair on a retaining component.
Figure 14B:
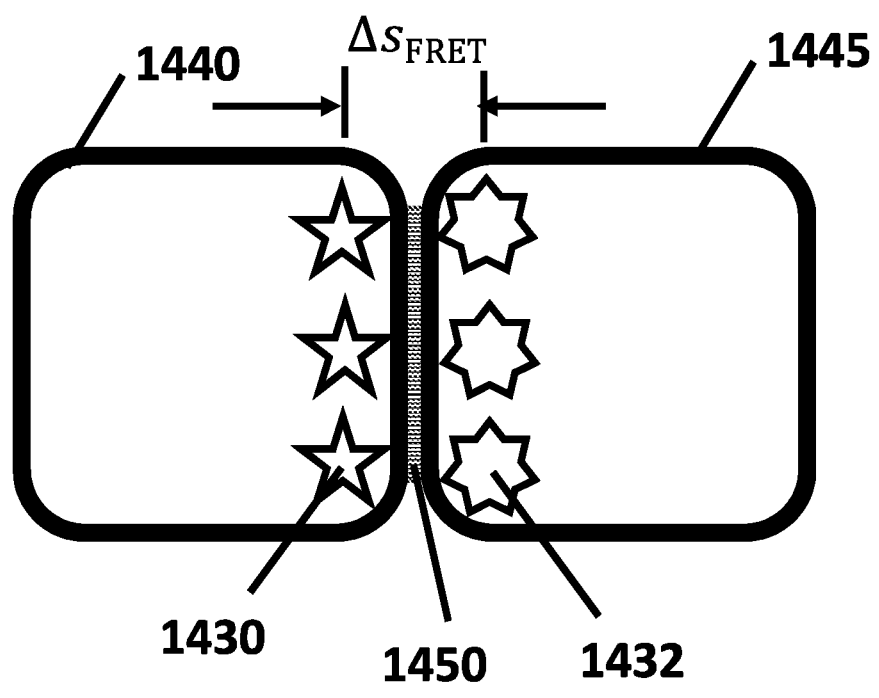
FIG. 14B shows a configuration for creating a Fluorescent resonance energy transfer (FRET) pair on a detectable probe.

FIGS. 14A-14B depict various configurations for detectable probes that can be detected by a FRET mechanism. FIG. 14A depicts a configuration for generating FRET fluorophore pairs utilizing the helical structure of a nucleic acid to position the donor fluorophore and the acceptor fluorophore at a critical pairing distance, $\Delta s_{FRET}$. A retaining component may include a continuous nucleic acid strand 1410. Oligonucleotides 1420 may be hybridized to the continuous nucleic acid strand 1410, creating regions of double-stranded nucleic acids and single-stranded nucleic acid 1425. Oligonucleotides may include donor fluorophores 1430 or acceptor fluorophores 1432 in alternating patterns to generate FRET fluorophore pairs at a proper spacing of $\Delta s_{FRET}$. FIG. 14B depicts an alternative method of generating FRET fluorophore pairs utilizing a binding molecule that is configured to hybridize to a detectable probe. A detectable probe 1440 may include a plurality of donor fluorophores 1430 along a portion of the detectable probe 1440 that is configured to bind with a binding molecule 1445. The binding molecule 1445 includes a plurality of acceptor fluorophores 1432 that are aligned along the edge of the binding molecule 1445 that binds with the detectable probe 1440. The contacting of a detectable probe 1440 with a binding molecule 1445 may cause a binding region 1450 to form, aligning the donor fluorophores 1430 and the acceptor fluorophores 1432 to form FRET fluorophore pairs that are within the proper FRET spacing of $\Delta s_{FRET}$. In some configurations, the binding molecule 1445 may be coupled to a binding partner or a location where a binding partner is located, thereby permitting the FRET interaction to occur when the detectable probe 1440 binds to the binding partner and the binding molecule 1445 then binds the detectable probe 1440. In some configurations the binding molecule 1445 may be a SNAP or other substance that is attached to a binding partner for one or more binding components attached to detectable probe 1440. Accordingly, binding of the probe to the binding partner can be determined based on the observation of FRET between the donor fluorophores 1430 and acceptor fluorophores 1432.

A detectable probe composition may include a coupled pair of donor and acceptor luminophores. Acceptable donor/acceptor pairs may include Cy2/Cy3, Cy3/Cy5, FITC/TRITC, PE/APC, Alexa-Fluor® 488/Alexa-Fluor® 514, Alexa-Fluor® 488/Alexa-Fluor® 532, Alexa-Fluor® 488/Alexa-Fluor® 546, Alexa-Fluor® 488/Alexa-Fluor® 610, Alexa-Fluor® 647/Alexa-Fluor® 680, Alexa-Fluor® 647/Alexa-Fluor® 700, Alexa-Fluor® 647/Alexa-Fluor® 750, Cyan FP/YFP, Cerulean FP/YFP, GFP/YFP, GFP/mRFP, or combinations thereof.

FRET dye pairs may be coupled to a nucleic acid, such as an oligonucleotide or a scaffold strand that forms a portion of a structured nucleic acid particle. An nucleic acid containing a FRET dye pair may have modified nucleotides to which the dyes are attached spaced sufficiently to allow a FRET interaction to occur. The proper spacing may be determined by the naturally arising helical structure that arises when an oligonucleotide hybridizes to a scaffold strand. Two adjacent dyes in a FRET pair may be spaced at least about 2, 3, 4, 5, 6, 7, 8, 9, 10, 11, 12, 13, 14, 15, 16, 17, 18, 19, 20, or more nucleotides apart. Alternatively or additionally, two adjacent dyes in a FRET pair may be spaced no more than about 20, 19, 18, 17, 16, 15, 14, 13, 12, 11, 10, 9, 8, 7, 6, 5, 4, 3, or fewer nucleotides apart.

Binding interactions involving detectable probes may be observed using label components other than fluorophores. A detectable probe may include a barcode label component (e.g., a nucleic acid barcode). A barcode label component may include a unique sequence (e.g., DNA, RNA, amino acids) that, when decoded, provides information identifying a detectable probe species. For example, a plurality of identical detectable probes may each be labeled with the same species of barcode (i.e. the barcodes having the same sequence), thereby providing a uniform and singular signal of binding interaction for that particular detectable probe. A barcode signal may be detected and decoded by a method such as next-generation sequencing to obtain an observation of an interaction between a detectable probe and a binding partner, epitope, or target moiety.

Figure 15A:
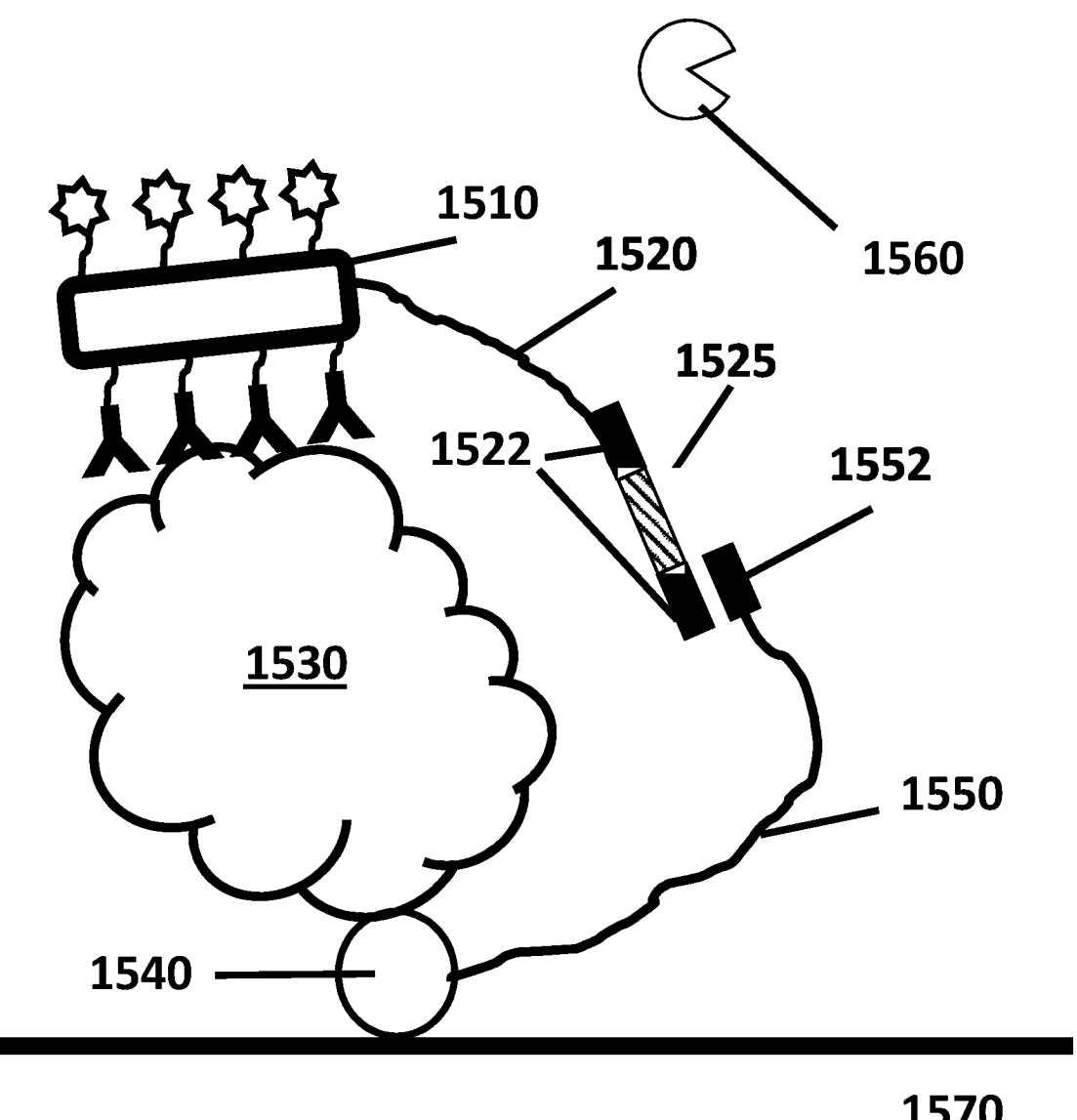
FIG. 15A shows a first step of a method for detecting a binding interaction utilizing a nucleic acid barcode and a weak secondary interaction.
Figure 15B:
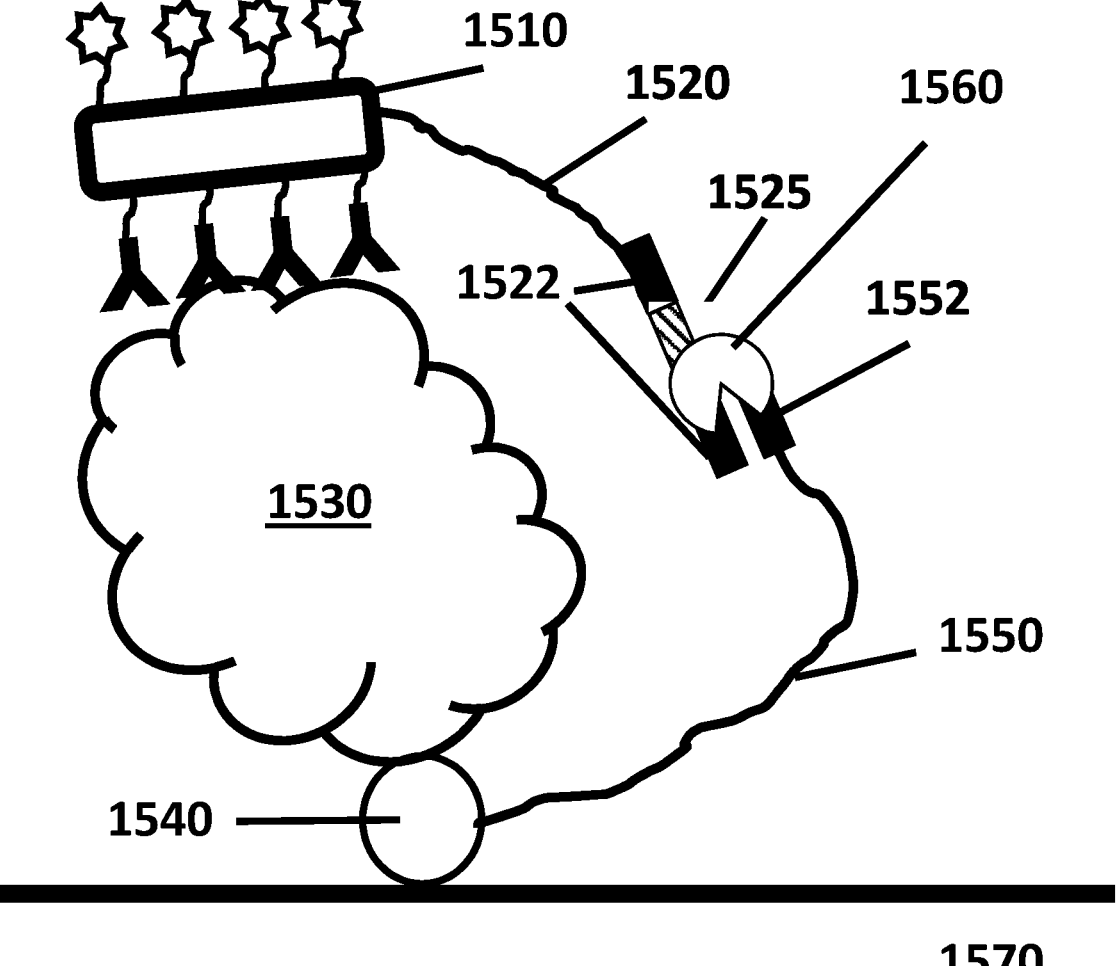
FIG. 15B shows a second step of a method for detecting a binding interaction utilizing a nucleic acid barcode and a weak secondary interaction.
Figure 15C:
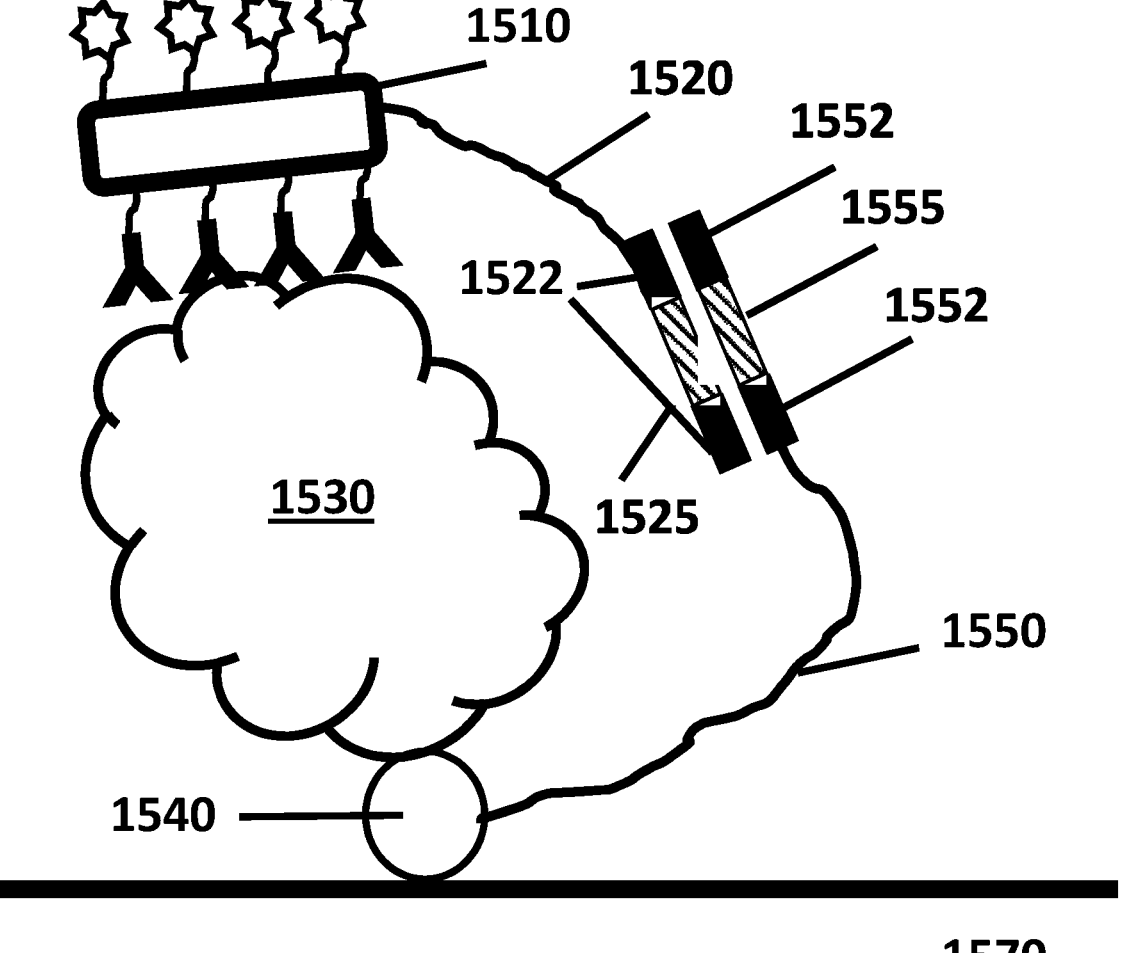
FIG. 15C shows a third step of a method for detecting a binding interaction utilizing a nucleic acid barcode and a weak secondary interaction.
Figure 15D:
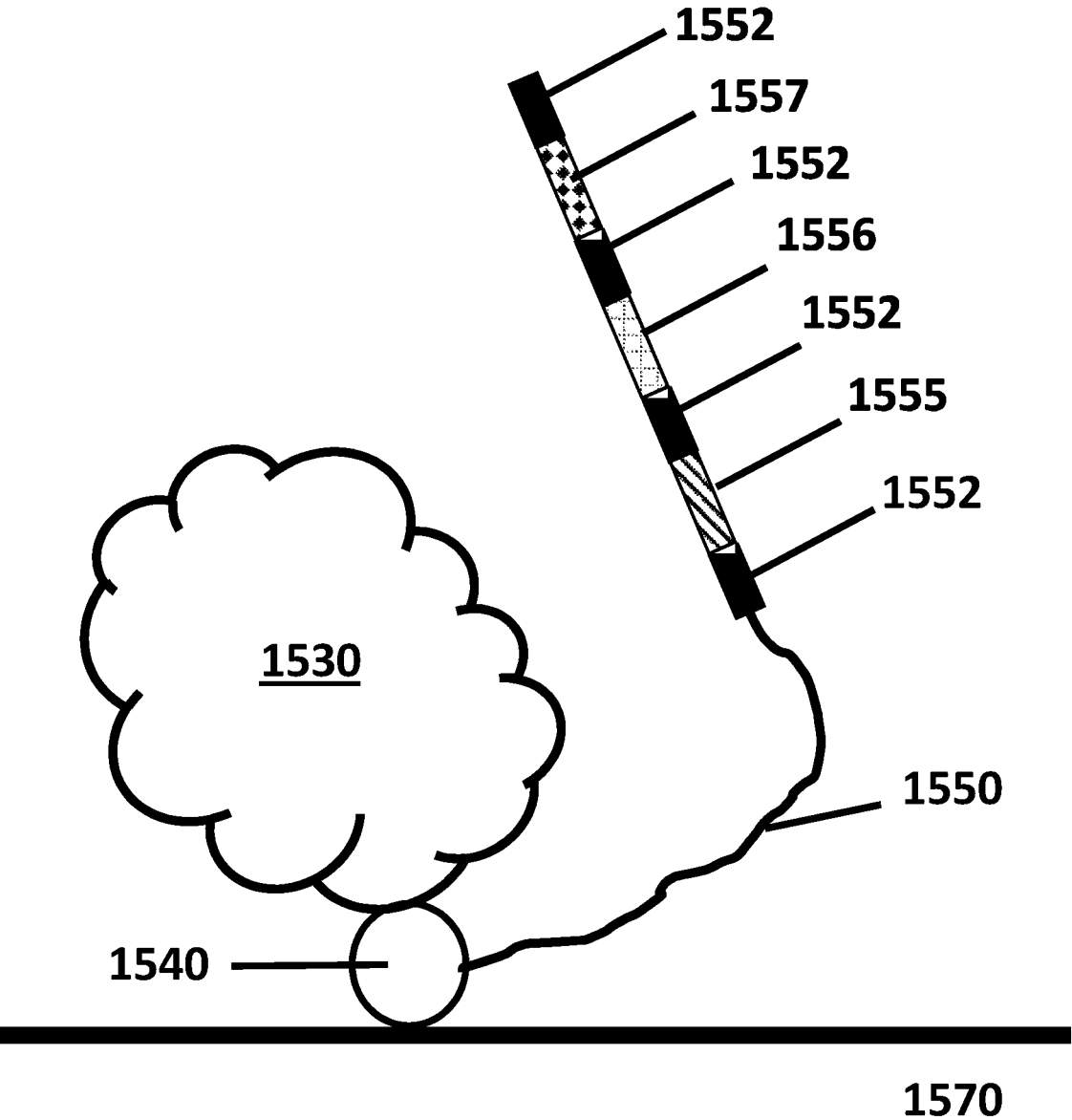
FIG. 15D shows a fourth step of a method for detecting a binding interaction utilizing a nucleic acid barcode and a weak secondary interaction.

FIGS. 15A-15D depict a system for utilizing nucleic acid barcodes to record binding interactions between a detectable probe and a binding partner, epitope, or target moiety. FIG. 15A depicts a system containing a detectable probe 1510 including a nucleic acid barcode sequence that is joined to the detectable probe 1510 by a linker 1520. The nucleic acid barcode sequence includes two priming sequences 1522 and an identifying sequence 1525 between the two priming sequences 1522. The detectable probe 1510 binds a binding partner, epitope, or target moiety 1530 that is optionally bound to a solid support 1570. The binding partner, epitope, or target moiety 1530 may be bound to the solid support 1570 by an anchoring group 1540 (e.g. a SNAP or chemical linker). The binding partner, epitope, or target moiety 1530 may have an associated linker 1550 (e.g., attached to the solid support 1570, anchoring group 1540, or binding partner, epitope, or target moiety 1530). The associated linker 1550 may be terminated with a complementary priming sequence 1552 that forms a hybridized bond with a priming sequence 1522 of the detectable probe 1510 nucleic acid barcode. The complex formed by the detectable probe 1510 and the binding partner, epitope, or target moiety 1530 is contacted with polymerase enzyme 1560 that is configured to bind a nucleic acid. FIG. 15B shows the binding of the polymerase 1560 to the hybridized nucleic acid sequence formed by the joining of the priming sequence 1522 and the complementary priming sequence 1552 to initiate an extension reaction. FIG. 15C depicts a final step of the extension reaction. The identifying sequence 1525 and the priming sequence 1522 have been added by extension onto the terminal sequence of the associated linker 1550 to add a complementary identifying sequence 1555 and an additional complementary priming sequence 1552. FIG. 15D depicts the binding partner, epitope, or target moiety 1530 after multiple cycles of detectable probe 1510 binding and primer extension. Each probe adds a unique identifying sequence (e.g., 1555, 1556, 1557) to the sequence at the end of the linker 1550. The addition of a complementary priming sequence 1552 at the end of each identifying sequence (1555, 1556, 1557) permits subsequent binding of the linker 1550 to a detectable probe. Detectable probe 1510 is shown with an optional plurality of label components (shown as 6 pointed stars). It will be understood that the detectable probe need not include labels, for example, in configurations where identifying sequences are decoded to determine the biding history for target moiety 1530. Accordingly, an affinity reagent can be configured or used as exemplified in FIGS. 15A-15D.

Other examples of tags that can be attached to an affinity reagent of the present disclosure and methods for using and detecting the tags, for example, in assays for detecting, sequencing or quantifying polypeptides are set forth in US Pat App. Pub. Nos. 2020/0348308 A1, 2020/0348307 A1, or 2019/0145982 A1, each of which is incorporated herein by reference.

Methods of Fabricating Detectable Probes and Affinity Reagents

Detectable probes or affinity reagents as described in the present disclosure may be fabricated by a suitable method. Fabrication of a detectable probe or affinity reagent may include one or more of the following steps: 1) creating a retaining component that is configured to attach a plurality of binding components and/or a plurality of label components; 2) attaching one or more binding components to the retaining component; 3) attaching one or more label components to the retaining component; and 4) attaching additional components to the retaining component.

Retaining components may be obtained through a fabrication process. Non-nucleic acid retaining components (e.g., polymers, metal, ceramic, carbon, or semiconductor nanoparticles) may be fabricated through a bulk fabrication and/or purification process. Following the production of non-nucleic acid retaining components, one or more processing steps may occur to add one or more surface functionalities to the retaining components. The functionalities may be added for the purposes of improving retaining component solvent solubility properties or providing attachment sites for binding components and/or label components. Surface functionalities may include functional groups (e.g., functional groups configured to undergo a click reaction) that are configured to attach binding components and/or label components, or nucleic acids that are configured to hybridize with a complementary nucleic acids containing an attached binding component and/or label component. For example, retaining components including silicon or silicon dioxide nanoparticles may be functionalized with silanized compounds to covalently add a plurality of functionalities to the silicon-containing surface of the particle. After functionalization of non-nucleic acid retaining components, affinity groups may be joined to the retaining components by any suitable technique, such as click reactions or nucleic acid hybridization.

Fabrication of nucleic acid retaining components (e.g., nucleic acid origami, nucleic acid nanoballs) may be formed by conventional techniques. Nucleic acid nanoballs may be fabricated by a method such as rolling circle amplification to generate a scaffold strand that may be further modified to attach a plurality of binding components and/or label components. Exemplary methods for making nucleic acid nanoballs are described, for example, in U.S. Pat. No. 8,445,194, which is incorporated herein by reference. Nucleic acid retaining components including nucleic acid origami may be fabricated, for example, using techniques described in Rothemund, *Nature* 440:297-302 (2006) and U.S. Pat. Nos. 8,501,923 and 9,340,416, each of which is incorporated herein by reference.

Figure 21A:
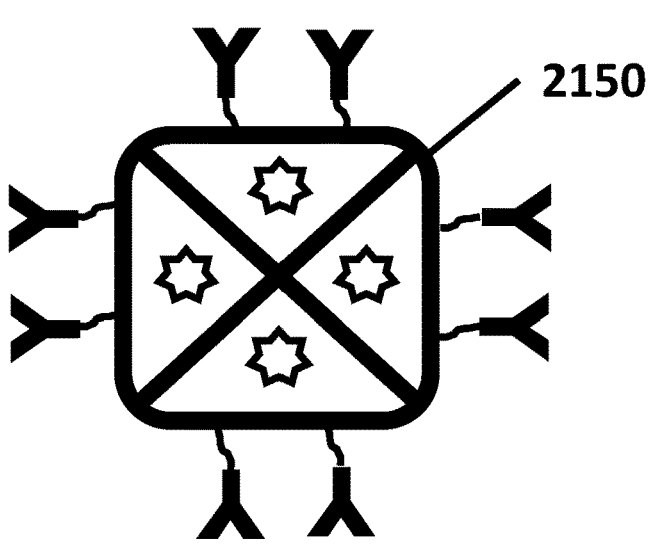
FIG. 21A shows a method of fabricating a detectable probe.

FIG. 21A shows a first pathway to forming a detectable probe with a nucleic acid retaining component. Oligonucleotides with attached binding components 2120 and oligonucleotides with attached label components 2130 are prepared before the retaining component is assembled. The oligonucleotides with attached binding components 2120 and oligonucleotides with attached label components 2130 are contacted with a single-stranded scaffold 2110 (e.g., M13 phage DNA, plasmid DNA) and additional structural nucleic acids 2140. The nucleic acids are contacted in a suitable DNA buffer at an elevated temperature (e.g., at least about 50° C., 60° C., 70° C., 80° C., or 90° C.), then cooled. Oligonucleotides will hybridize to the scaffold strand 2110 at the appropriate sequence-dependent positions to form a detectable probe 2150.

Figure 21B:
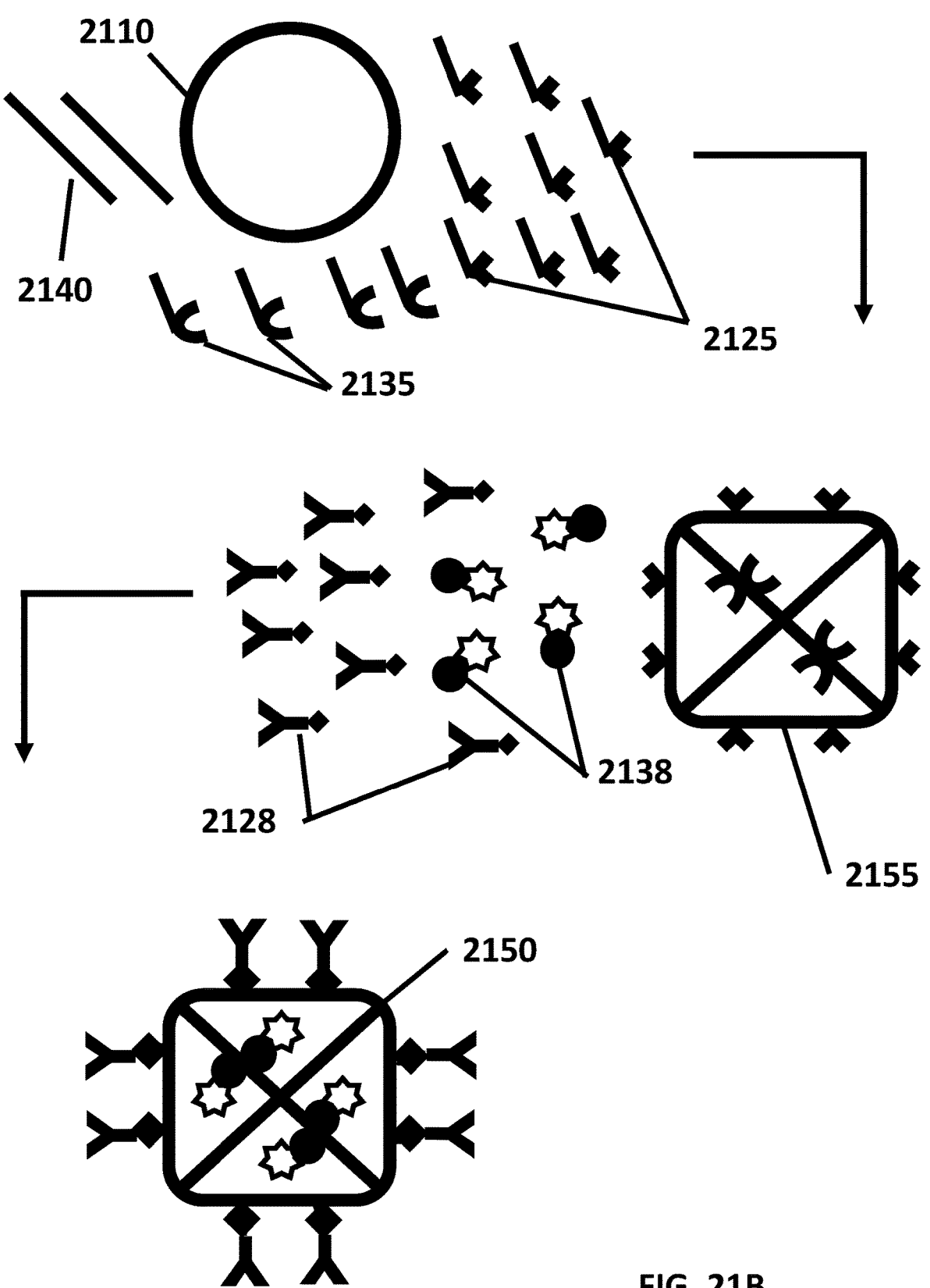
FIG. 21B shows a method of fabricating a detectable probe.

FIG. 21B shows an alternative pathway to forming a detectable probe with a nucleic acid retaining component. Oligonucleotides with handles that are configured to attach binding components 2125 and oligonucleotides with handles that are configured to attach label components 2135 are prepared before the retaining component is assembled. The oligonucleotides with handles that are configured to attach binding components 2125 and oligonucleotides with handles that are configured to attach label components 2135 are contacted with a single-stranded scaffold 2110 (e.g., M13 phage DNA, or plasmid DNA) and additional structural nucleic acids 2140. The nucleic acids are contacted in a suitable buffer at an elevated temperature (e.g., at least about 50° C., 60° C., 70° C., 80° C., or 90° C.), then cooled. After cooling, a retaining component 2155 that is configured to bind a plurality of binding components and/or label components is formed. The retaining component 2155 is contacted with a plurality of binding components 2128 and/or label components 2138 that have complementary handles to the handles on the retaining component 2155 in a suitable attachment buffer. After attachment of the plurality of binding components 2128 and/or the plurality of label components 2138, detectable probe 2150 is formed.

In some configurations, a detectable probe or affinity reagent may be formed by the attachment of a binding component and/or a label component by the reaction of a functional group configured to form a bond with another molecule or group, e.g., a bioorthogonal reaction or click chemistry (see, for example, U.S. Pat. Nos. 6,737,236 and 7,427,678, each incorporated herein by reference in its entirety); azide alkyne Huisgen cycloaddition reactions, which use a copper catalyst (see, for example, U.S. Pat. Nos. 7,375,234 and 7,763,736, each incorporated herein by reference in its entirety); Copper-free Huisgen reactions ("metal-free click") using strained alkynes or triazine-hydrazine moieties which can link to aldehyde moieties (see, for example, U.S. Pat. No. 7,259,258, which is incorporated by reference); triazine chloride moieties which can link to amine moieties; carboxylic acid moieties which can link to amine moieties using a coupling reagent, such as EDC; thiol moieties which can link to thiol moieties; alkene moieties which can link to dialkene moieties that are coupled through Diels-Alder reactions; and acetyl bromide moieties which can link to thiophosphate moieties (see, for example, WO 2005/065814, which is incorporated by reference). A functional group may be configured to react via a click reaction (e.g., metal-catalyzed azide-alkyne cycloaddition, strain-promoted azide-alkyne cycloaddition, strain-promoted azide-nitrone cycloaddition, strained alkene reactions, thiol-ene reaction, Diels-Alder reaction, inverse electron demand Diels-Alder reaction, [3+2] cycloaddition, [4+1] cycloaddition, nucleophilic substitution, dihydroxylation, thiol-yne reaction, photoclick, nitrone dipole cycloaddition, norbornene cycloaddition, oxanorbornadiene cycloaddition, tetrazine ligation, tetrazole photoclick reactions). Exemplary silane-derivative CLICK reactants may include alkenes, alkynes, azides, epoxides, amines, thiols, nitrones, isonitriles, isocyanides, aziridines, activated esters, and tetrazines (e.g., dibenzocyclooctyne—azide, methyltetrazine—transcyclooctylene, epoxide—thiol, etc.). A click reaction may provide an advantageous method of rapidly forming a bond under benign conditions (e.g., room temperature, aqueous solvents).

In some configurations, a retaining component or other component of a detectable probe or affinity reagent may include different species of functional groups. The use of different functional groups can provide a level of control over the number and location of different components that will be attached to the detectable probe or affinity reagent. In particular configurations the different functional groups demonstrate orthogonal reactivity, whereby a first component has a moiety that is reactive for a first functional group on the probe but not substantially reactive with a second functional group on the probe, and whereby a second component has a moiety that is reactive for the second functional group but not the first functional group. Accordingly, the number of different binding components and their locations can be adjusted by appropriate use of orthogonal functional groups on a detectable probe or affinity reagent, or the number of different label components and their locations can be adjusted by appropriate use of orthogonal functional groups on a detectable probe or affinity reagent. Moreover, binding components can be located differently from label components on a detectable probe or affinity reagent by appropriate use of orthogonal functional groups, respectively, on the detectable probe or affinity reagent.

Retaining components including non-nucleic acids may be formed by appropriate methods. Of particular interest are methods that permit a degree of spatial control in attaching binding components, label components, or other components to the retaining component during probe assembly. Spatial control may include the ability to separate or segregate probe components, or vary the orientation of probe components. For example, spatial control may include separating binding components and/or label components from adjacent or neighboring binding components and/or label components. In another example, spatial control may include segregating regions of attached binding components from regions of attached label components. In yet another example, spatial control may include controlling the relative dispersion or distribution of binding components and/or labeling components, e.g., providing binding components and labeling components in a region of a retaining component at a 10:1 ratio.

Figures 32A, 32B:
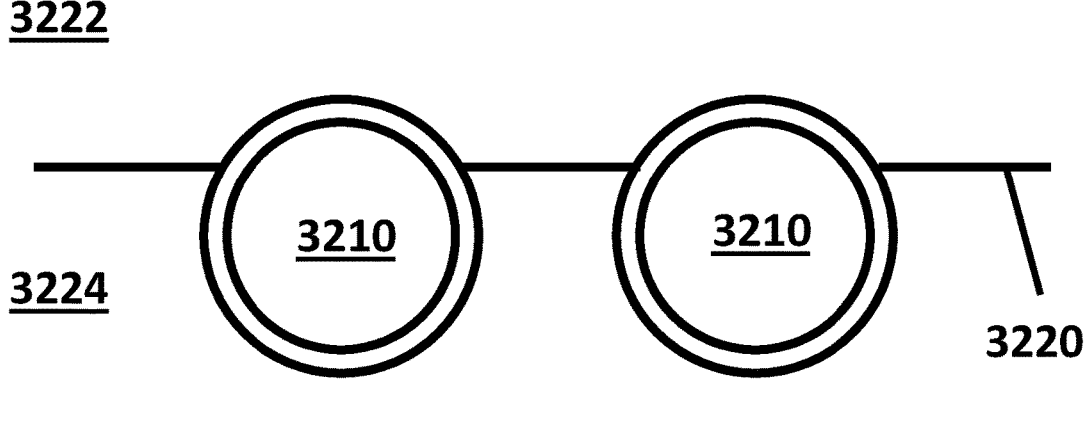
FIG. 32A shows a first step of a method for forming a non-nucleic acid retaining component.
FIG. 32B shows a second step of a method for forming a non-nucleic acid retaining component.

FIGS. 32A-32B depict a scheme for controlling probe component location during the assembly of a detectable probe or affinity reagent including a non-nucleic acid retaining component. FIG. 32A depicts a plurality of particles 3210 (e.g., nanoparticles, nanobeads, nanospheres, etc.) that are configured to associate with an interface 3220, such as a multiphase boundary (e.g., air/liquid interface, oil/water interface). The interface 3220 is formed between a first fluid medium 3222 and a second fluid medium 3224. The portions of each particle of the plurality of particles 3210 are exposed to different modification chemistries depending upon exposure to the first liquid medium 3222 or second liquid medium 3224. The portions of each particle of the plurality of particles 3210 that are exposed to the first liquid medium 3222 form a first plurality of functional groups 3235 on the surface of the particles. The portions of each particle of the plurality of particles 3210 that are exposed to the second liquid medium 3224 form a second plurality of functional groups 3230 on the surface of the particles. The first plurality of functional groups 3235 may provide an attachment site for a first type of probe component (e.g., binding components) and the second plurality of functional groups 3230 may provide an attachment site for a second type of probe component (e.g., label components).

Figure 32C:
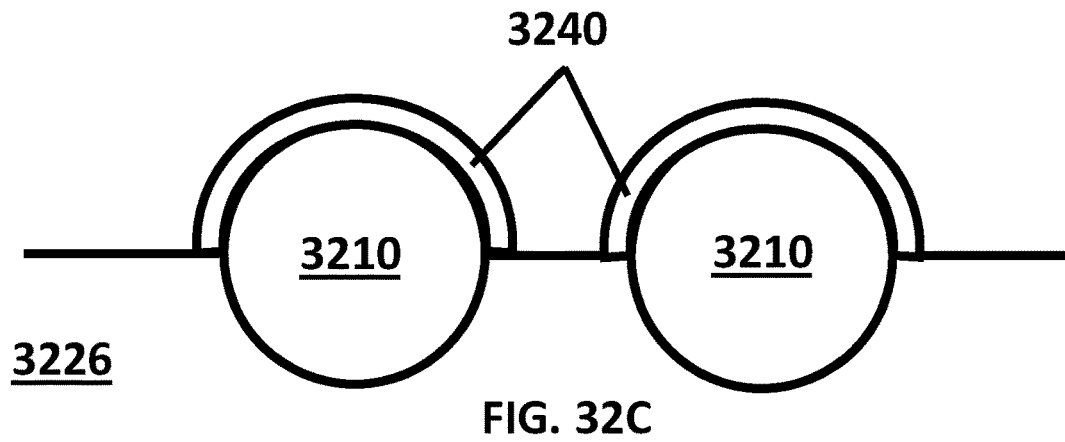
FIG. 32C shows a first step of a method for forming a non-nucleic acid retaining component.
Figure 32D:
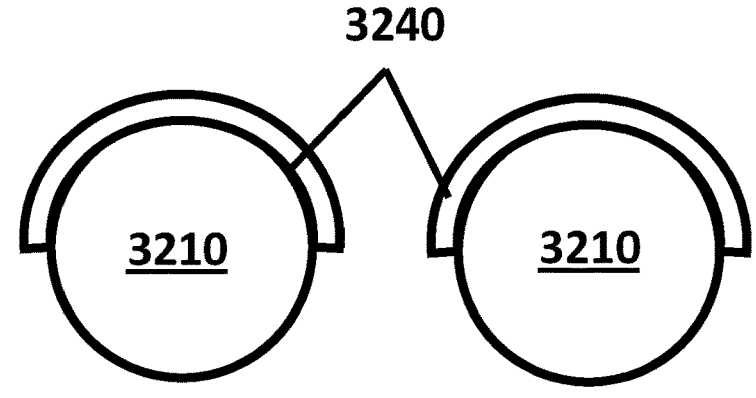
FIG. 32D shows a second step of a method for forming a non-nucleic acid retaining component.
Figure 32E:
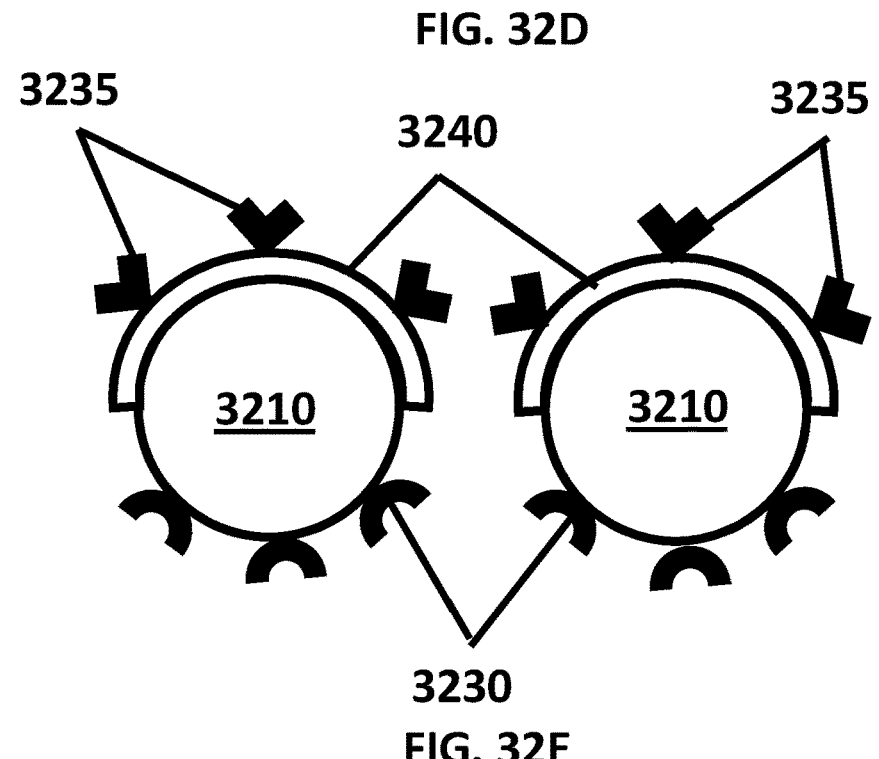
FIG. 32E shows a third step of a method for forming a non-nucleic acid retaining component.

FIGS. 32C-32E depict a scheme for controlling probe component location during the assembly of a detectable probe or affinity reagent including a non-nucleic acid retaining component. FIG. 32C depicts a plurality of particles 3210 (e.g., nanoparticles, nanobeads, nanospheres, etc.) that are partially embedded or fixed within a medium 3226. A coating or layer 3240 (e.g., a metal, metal oxide, polymer, or hydrogel) is applied to the exposed portions of each particle of the plurality of particles 3210. As shown in FIG. 32D, after a coating or layer 3240 has been applied to the plurality of particles 3210, the medium 3226 may be removed, thereby providing a plurality of particles 3210 with a partial coating or layer 3240. As shown in FIG. 32E, the differing surface chemistries of the uncoated and coated portions of the plurality of particles 3210 may be used to differentially functionalize the plurality of particles 3210 with a partial coating or layer 3240. The coating or layer 3240 may be provided with a first plurality of functional groups 3235 that can provide an attachment site for a first type of probe component (e.g., binding components). The uncoated portions of each particle may be provided with a second plurality of functional groups 3230 that can provide an attachment site for a second type of probe component (e.g., binding components).

Figure 33:
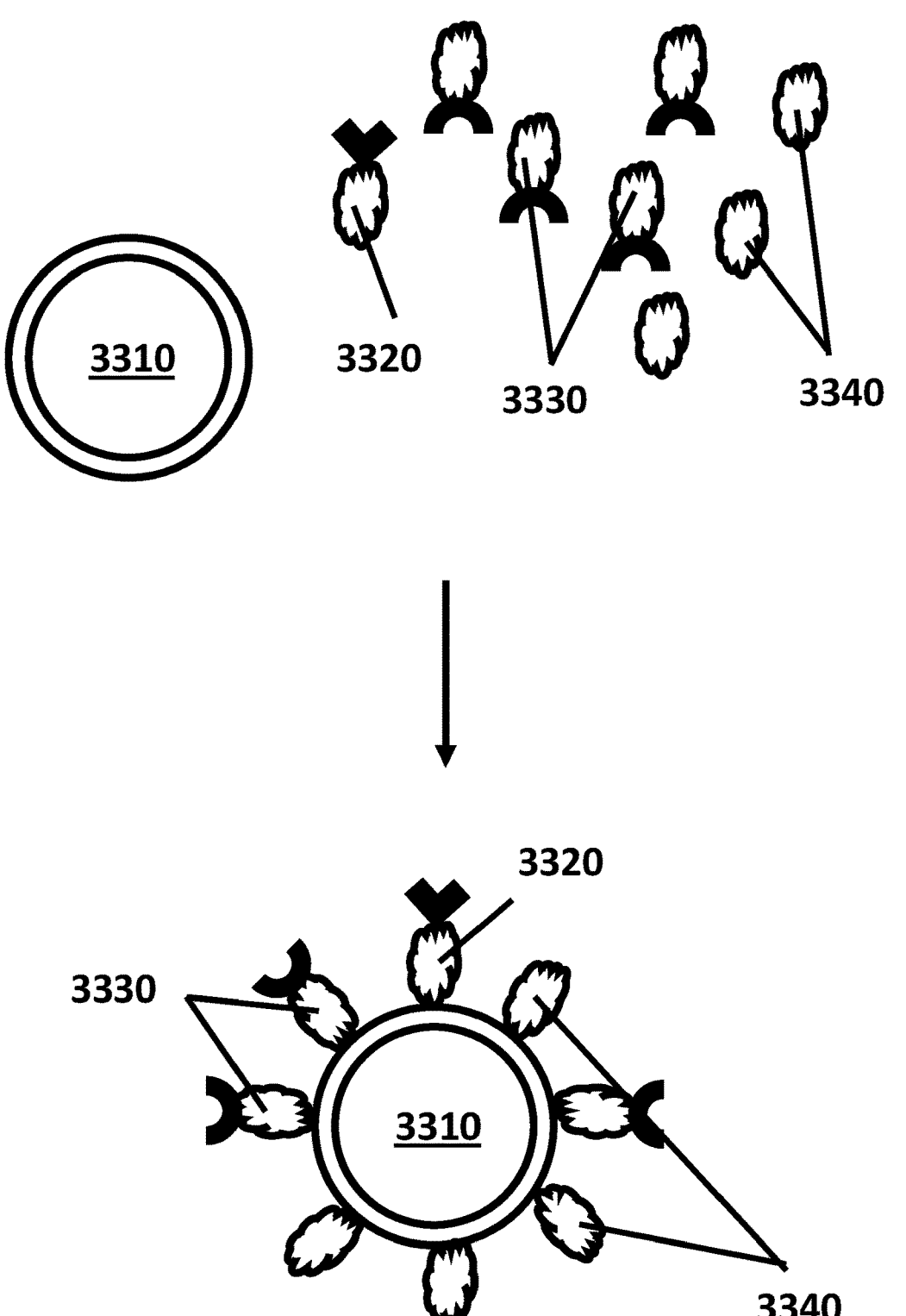
FIG. 33 shows a method of forming a non-nucleic acid retaining component.

The location or positioning of binding components and/or label components on a non-nucleic acid retaining component may also be controlled by controlling the spatial or surface density of attachment sites on the surface of the non-nucleic acid retaining component. FIG. 33 depicts a preparation process for a particle or nanoparticle retaining group. A particle or nanoparticle 3310 is combined with a mixture of moieties that are to be attached to the particle or nanoparticle 3310 surface, such as binding component attachment sites 3320, label component attachment sites 3330, or modifying groups 3340. The ratios of components within the mixture of moieties is balanced to ensure proportional modification of the particle or nanoparticle 3310 surface. The final result is a retaining component with homogeneous or near-homogeneous distribution of each component over the particle or nanoparticle 3310 surface based upon the component concentration in the mixture of moieties. Alternatively, components can be added sequentially by initially adding a two-component mixture consisting of a first type of attachment site and blocking groups. After surface functionalization, the blocking groups can be completely or partially removed to provide surface sites for attaching other types of attachment sites.

A plurality of affinity reagents, a plurality of detectable probes, or a combination of at least one affinity reagent and at least one detectable probe may be conjugated to form a multi-probe complex. Similarly, detectable probes or affinity reagents may be configured with one or more coupling groups that permit attachment of a reagent or probe to one or more other reagents or probes. The coupling groups may be configured to form a covalent interaction, a non-covalent interaction, an electrostatic interaction, a magnetic interaction, or any other interaction that forms an association between detectable probes affinity reagents or both. An association between two or more probes in a multi-probe complex may be weak, temporary, or reversible. An association between two or more probes in a multi-probe complex may be strong, permanent, or irreversible. In some cases, detectable probes or affinity reagents may be coupled by hybridization of complementary nucleic acid strands or streptavidin-biotin coupling groups. In other cases, detectable probes or affinity reagents may be covalently coupled by, for example a click reaction or cross-linking (e.g., chemical or photo-initiated cross-linking).

Figure 37A:
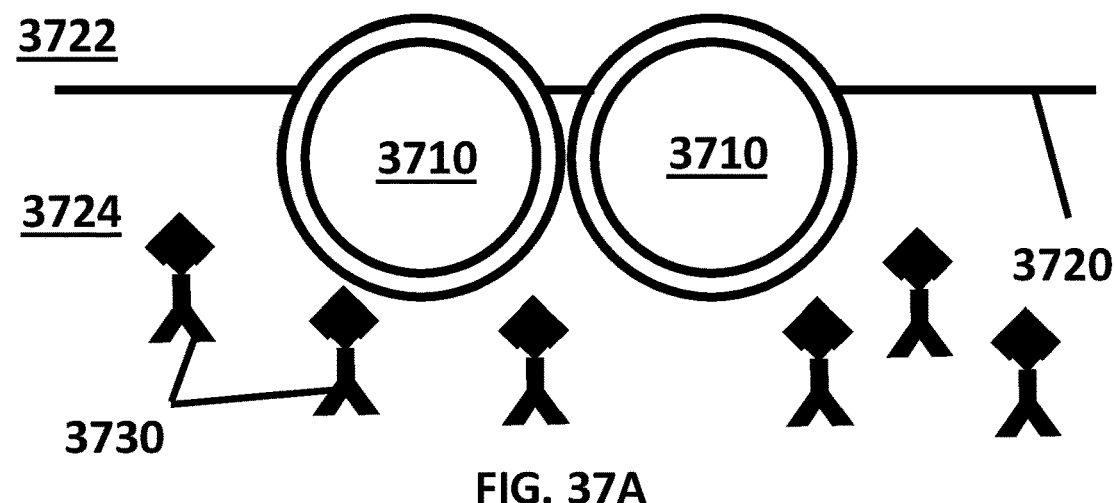
FIG. 37A shows a first step of a method for forming a detectable probe from a non-nucleic acid retaining component.
Figure 37B:
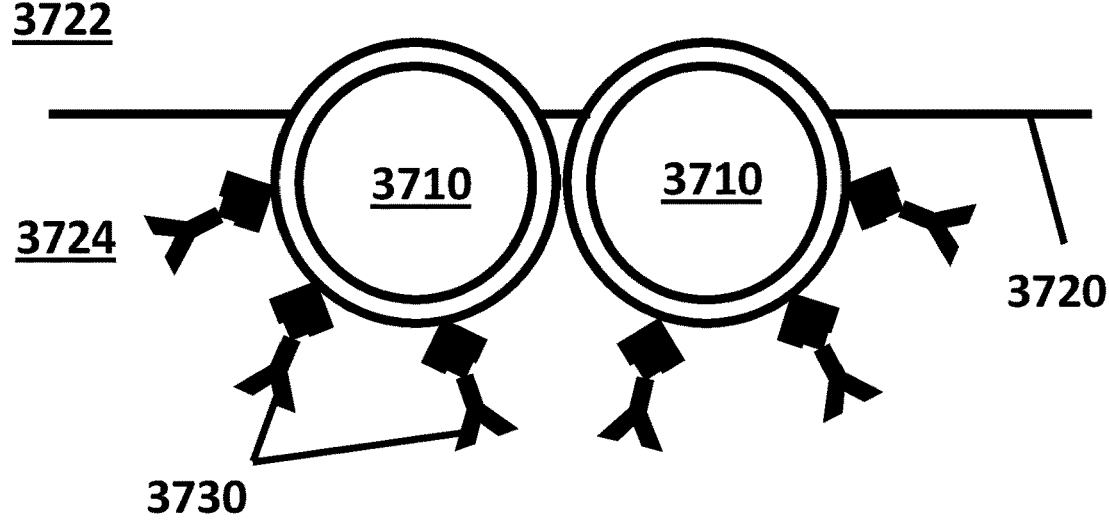
FIG. 37B shows a second step of a method for forming a detectable probe from a non-nucleic acid retaining component.
Figure 37C:
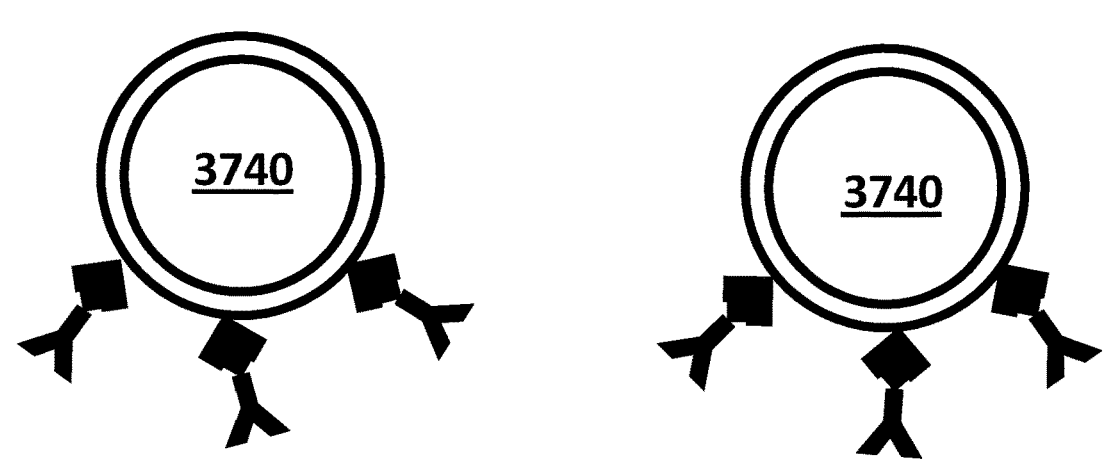
FIG. 37C shows a third step of a method for forming a detectable probe from a non-nucleic acid retaining component.

A multi-probe complex may be formed as a portion of a probe synthesis process. Formation of probes or retaining components may facilitate the location, orientation, and attachment of probe components, such as binding components and/or label components. FIG. 37A-37C depicts a process for utilizing a complex to tune the location of binding components on non-nucleic acid retaining components. FIG. 37A depicts two particle retaining components 3710 (e.g., nanoparticles) that form an association with a phase boundary 3720 formed between a first medium 3722 and a second medium 3724. The retaining components 3710 are configured to form a complex by an attractive interaction between particles (e.g., an electrostatic or magnetic attraction, miscible surface functionalities, etc.). The retaining components 3710 are contacted with a plurality of binding components 3730 within the second medium 3724 that are configured to attach to attachment sites on the particles 3710. FIG. 37B depicts the complexed particles 3710 after the plurality of binding components 3730 have attached to the particle surface within the second medium 3724. The binding components 3730 have been limited to certain regions of the particle 3710 surfaces due to exclusion of surface area within the first medium 3722 and exclusion of surface near the inter-particle association region. FIG. 37C shows an optional process in which the interaction between the particles is broken, releasing individual detectable probes 3740. In other configurations, the particles may be retained as a multi-probe complex.

Nucleic acid-based retaining components (e.g. a scaffold as set forth in U.S. Provisional Application No. 63/112,607) may be synthesized through standard nucleic acid synthesis chemistries, and be provided with specific label groups, e.g., through incorporation of prelabeled nucleotides, or by providing attachment sites for label groups to be added subsequently, e.g., providing functional side groups, as well as one or more sites for coupling to the binding component. Likewise, a PEG scaffold may be synthesized and functionalized with functional groups which will allow the attachment of either, or both of, binding components or label components. In another example, a polypeptide scaffold may be synthesized including groups which will allow for the attachment of either, or both of, probe components or label components. In some cases, a retaining component may be considerably larger than the label to which it is attached. In other cases, the retaining component may be of a similar size as the label component to which it is attached. In other cases, the label component may be larger than the retaining component to which it is attached.

In some cases a retaining component, such as a nucleic acid scaffold, may be synthesized directly upon a binding component. For example, a reagent used for synthesis of the retaining component can include the binding component. In some cases a retaining component, such as a nucleic acid scaffold, may be synthesized directly upon a linker molecule that is to be attached to the binding component. For example, a reagent used for synthesis of the retaining component can include the linker. In some embodiments, a retaining component may be produced by a template mediated polymerase extension reaction using a nucleotide mix in which some or all of the nucleotides that are to be incorporated have a label or a functional moiety for attaching a label component. For example, three nucleotide species used by the polymerase during extension can be unlabeled (and/or can lack a functional group), and the fourth nucleotide species can be labeled with a fluorescent moiety or other label moiety (or the fourth nucleotide can have the functional group). In this example, the complementary base of the fourth nucleotide can occur in a predetermined pattern in the template. For example, the complementary base of the fourth nucleotide may occur in at a nucleotide spacing set forth elsewhere herein.

As shown in FIG. 49A, a binding component, illustrated here as a nucleic acid aptamer, may include a primer sequence at one terminus, e.g., the 3' terminus. A template nucleic acid, e.g., as described above, that includes a sequence segment complementary to the primer sequence may then be hybridized to the primer segment of the binding component (see FIG. 49B, Step 1). Polymerase mediated template based extension of the primer sequence on the binding component in the presence of the unlabeled and labeled nucleotides, e.g. as described above, then results in an affinity probe that includes the binding component (e.g., the aptamer), along with the label component that includes the nucleic acid of the retaining component with the incorporated labels (the extension product of the polymerase reaction with labeled nucleotides (See FIG. 49B, Step 2). In some cases, the template may include a specific nucleotide species, e.g., a guanosine nucleotide at desired intervals or in desired locations, while the extension reaction is carried out in the presence of unlabeled adenosine, thymidine and guanosine triphosphates, and labeled cytosine triphosphate. This results in periodic incorporation of the labeled cytosine nucleotides into the extension product scaffold. For example, by including a template with a guanosine nucleotide at every 3rd, $4^{th}$, $5^{th}$ etc. position in the template, one can allow for incorporation of a labeled cytosine at every $3^{rd}$, $4^{th}$, $5^{th}$, etc. position of the retaining component. As will be appreciated, the specific labeled nucleotide or the periodicity of the incorporated label may be selected depending upon particular needs of the analysis. In some cases, following this synthesis, the template nucleic acid may remain in place to provide a double stranded label portion of the affinity probe, for example, as set forth elsewhere herein.

In some cases, the template for the scaffold may include a circular nucleic acid, where extension of a primer sequence produces an extended concatemer having duplicated sequence segments, e.g., through rolling circle amplification. In an optional format, a template sequence may be provided coupled to the binding component. A primer may be hybridized to the template and extended by polymerization in the presence of labeled and unlabeled nucleotides, in order to create a second, associated strand that includes label groups as described above.

In some cases, affinity reagents or detectable probes may be constructed using a modular format that allows more targeted tailoring of the end-product labeled probe. For example, in some cases, binding components, e.g., aptamers or antibodies, may be produced and maintained as unlabeled libraries. In such cases, these binding components may be maintained with attachment regions for coupling label components to the binding components in accordance with a desired labeling protocol for a given experiment. Such attachment regions may include chemical coupling moieties, e.g., NHS esters, "click" chemistry components (see, e.g., H. C. Kolb; M. G. Finn; K. B. Sharpless (2001), "Click Chemistry: Diverse Chemical Function from a Few Good Reactions" Angewandte Chemie International Edition. 40 (11): 2004-2021), and other routine chemical coupling approaches, where the labeling component includes any necessary complementary coupling moieties. An advantage of this modularity is that a variety of different detectable probes or affinity reagents can be readily formed using the same or similar retaining component. Accordingly, a plurality of different detectable probes or affinity reagents can differ with regard to one or more of the number label components, variety of label components, number of binding components, and variety of binding components, while having retaining components that share a common structural characteristic. The common structural characteristic can be, for example, size of the retaining component, shape of the retaining component, chemical composition of the retaining component, nucleic acid sequence of the retaining component, three-dimensional structure of an origami in the retaining component, three-dimensional structure of a scaffold in an origami in the retaining component or the like. In some configurations, a plurality of different detectable probes can differ with regard to the number of staple oligonucleotides annealed in an origami structure, the location where one or more staple oligonucleotides are annealed to a scaffold strand in an origami structure, the length of one or more staple oligonucleotides annealed to a scaffold strand in an origami structure, the sequence of one or more staple oligonucleotides annealed to a scaffold strand in an origami structure, or the number, type or location of functional groups in an origami structure.

In some cases, binding components may include one member of a binding or coupling pair (e.g. a receptor), while the label components include a complementary member of the binding or coupling pair (e.g. a ligand for the receptor). For example, in some cases, a binding component may be coupled to a single strand nucleic acid sequence while the label component is coupled to a second strand having a sequence that is complementary to the single strand. In such cases, coupling can be carried out through hybridization of the label bound nucleic acid strand to the binding component bound nucleic acid strand. As will be appreciated, in the case of aptamer binding components, production of the aptamer and the label coupling component may be produced using, e.g., PCR amplification of the single stranded probe and label coupling component, followed by removal of the complementary strand prior to hybridization of the label component.

In any of the above contexts, label components and retaining components may be synthesized separately from the binding component, either with labeling groups attached, or as a functionalized retaining component to which label components may be subsequently attached either before or after coupling to the binding component. In the case of nucleic acid-based retaining components, such structures may generally be synthesized through well known solid phase nucleic acid synthesis techniques, where known nucleotides are added in succession to build polynucleotide structures, or through polymerase chain reaction amplification of a scaffold sequence. As noted, such processes may employ periodic introduction of labeled nucleotides during synthesis in order to build a multi-labeled probe in the form desired. Alternatively, modified nucleotides may be incorporated during synthesis that allow easy addition of label components post synthesis.

Covalent attachment of a separately synthesized retaining component to another component (e.g. binding component, label component or another retaining component) may be accomplished via chemical or biochemical approaches, e.g., through chemical coupling of a nucleic acid scaffold to the binding component, e.g., using known chemical coupling techniques such as click chemistry, or through biochemical methods such as ligation of a nucleic acid scaffold to a nucleic acid component of a binding component. Alternatively, a retaining component may be non-covalently attached to the binding component through hybridization to a complementary nucleic acid component that is already coupled to the binding component. An example of such attachment is schematically illustrated in FIG. 51. As shown, the binding component 400 includes a nucleic acid probe sequence 400b attached to it. A separately synthesized labeled nucleic acid retaining component 401 having a sequence complementary to the probe sequence 400b is then hybridized to the binding component to provide a labeled affinity probe.

Any of a variety of covalent or non-covalent chemistries can be used to attach or join components of a detectable probe or affinity reagent set forth herein. Chemistries and methods set forth herein in the context of attaching retaining components to other components can also be used to attach detectable probes or affinity reagents to other substances such as binding partners (e.g. polypeptides), surfaces, solid supports, sites of an array, or particles. Moreover, the chemistries and methods can be used to synthesize retaining components, binding components or label components, or to add functional groups or linkers to such components.

In some configurations that employ polypeptide-based binding components, e.g., antibodies or antibody fragments, a coupling approach may be employed for coupling of only a single label component to a single binding component through incorporation of a single coupling group to a given polypeptide. In particular, a binding component, such as an antibody or antibody fragment may be provided with a first coupling handle or functional group, while a separate label component (or component that may be readily labeled) is provided with a second coupling handle or functional group that reacts with or binds to the first coupling moiety to achieve label attachment between the binding component and the label component.

One example of such an approach is a SpyTag/Spy-Catcher approach to labeling (See, e.g., Zakeri B, Fierer J O, Celik E, Chittock E C, Schwarz-Linek U, Moy V T, Howarth M (March 2012). "Peptide tag forming a rapid covalent bond to a protein, through engineering a bacterial adhesin". *Proceedings of the National Academy of Sciences of the United States of America.* 109 (12): E690-7). In this approach, a 13 amino acid tag polypeptide (SpyCatcher) forms a first coupling handle, with a 12.3 kDa protein (Spy Tag) forming the other coupling handle. By way of example, the Spy Catcher may be integrated into a first component (e.g. a binding component or label component) as a recombinant fusion protein. The Spy Catcher component irreversibly binds to the Spy Tag through an isopeptide bond, which may be fluorescently or otherwise labeled for detection. As will be appreciated either the Tag or the Catcher may be integrated with the first component.

In some cases, different components may be attached to each other using click chemistry. In cases of components having nucleic acid moieties these may be attached using ligation and or hybridization. In some cases, a linker is used for attachment. Examples of linkers include double stranded DNA, single stranded DNA, or different molecular weight polyethylene glycol. Linkers may also include functional groups that allow for bioconjugation.

In some cases, attachment can employ chemical conjugation, bioconjugation, enzymatic conjugation, photo-conjugation, thermal-conjugation, or a combination thereof. (Spicer, C. D., Pashuck, E. T., & Stevens, M. M., Achieving Controlled Biomolecule-Biomaterial Conjugation. Chemical Reviews., 2018, 118, Pgs. 7702-7743, and Greg T. Hermanson, "Bioconjugate Techniques", Academic Press; 3$^{rd}$ Edition, 2013, herein incorporated by reference for this disclosure). For example, bioconjugation may be used to form a covalent bond between two molecules, at least one of which is a biomolecule. In some cases, two components of a detectable probe or affinity reagent that are to be attached to each other may be functionalized. Functionalizing both partners may improve the efficiency or speed of an attachment (e.g. conjugation) reaction. For example, a sulfhydryl group (—SH) or amine (—NH$_2$) of a chemically active site of an aptamer, biological, or chemical entity may be functionalized to allow for greater reactivity or efficiency of an attachment reaction. Any of a variety of sulfhydryl-reactive (or thiol-reactive) or amine conjugation chemistries may be used to couple chemical moieties to sulfhydryl or amine groups. Examples include, but are not limited to, use of haloacetyls, maleimides, aziridines, acryloyls, arylating agents, vinylsulfones, pyridyl disulfides, TNB-thiols and/or other sulfhydryl-reactive/amine-reactive/thiol-reactive agents. Many of these groups attach to sulfhydryl groups through either alkylation (e.g., by formation of a thioether or amine bond) or disulfide exchange (e.g., by formation of a disulfide bond). More strategies and detail regarding reactions for bioconjugation are described down below and may be extended to other appropriate molecules.

Attachment can be accomplished in part by a chemical reaction of a chemical moiety or linker molecule with a chemically active site on a biomolecule or other substance. The chemical conjugation may proceed via an amide formation reaction, reductive amination reaction, N-terminal modification, thiol Michael addition reaction, disulfide formation reaction, copper(I)-catalyzed alkyne-azide cycloaddition (CuAAC) reaction, strain-promoted alkyne-azide cyc-loadddtion reaction (SPAAC), Strain-promoted alkyne-nitrone cycloaddition (SPANC), inverse electron-demand Diels-Alder (IEDDA) reaction, oxime/hydrazone formation reaction, free-radical polymerization reaction, or a combi-nation thereof. Enzyme-mediated conjugation may proceed via transglutaminases, peroxidases, sortase, SpyTag-Spy-Catcher, or a combination thereof. Photo conjugation and activation may proceed via photoacrylate cross-linking reac-tion, photo thiol-ene reaction, photo thiol-yne reaction, or a combination thereof. In some cases, attachment or conjuga-tion may proceed via noncovalent interactions, these may be through self-assembling peptides, binding sequences, host-guest chemistry, nucleic acids, or a combination thereof.

In some cases, site-selectivity methods may be employed to modify reaction moieties of detectable probes, affinity reagents or components thereof to increase attachment effi-ciency, ease of use, and/or reproducibility. Three common strategies can be employed for site-selective attachment. (i) Modification strategies that can select a single motif among many, rather than targeting a generic functional group or moiety. This may be determined by surrounding sequence, local environment, or subtle differences in reactivity. The ability of enzymes to modify a specific amino acid within a protein sequence or a glycan at a single position are par-ticularly prominent. Reactions that display exquisite chemo-selectivity also fall within this category, such as those that target the unique reactivity of the protein N-terminus or the anomeric position of glycans. (ii) The site-specific incorpo-ration of unnatural functionalities, by hijacking native bio-synthetic pathways may be utilized. (iii) The installation of unique reactivity via chemical synthesis may be utilized. The complete or partial synthesis of polypeptides and oli-gonucleotides is widespread, particularly using solid-phase approaches. These techniques allow access to sequences of up to 100 amino acids or 200 nucleotides, with the ability to install a wide variety of functionalized monomers with precise positional control.

In some cases, chemical conjugation techniques may be applied for creating attached species such as biomaterial-biomolecule conjugates. Functional groups used for attach-ment may be native to a substance that is to be modified (e.g. a biomolecule that is to be modified) or may be incorporated synthetically. In the illustrations below, R and R' may be a biomolecule (for example, but not limited to: SNAP, pro-teins, nucleic acids such as nucleic acid origami or nucleic acid nanoballs, carbohydrates, lipids, metabolites, small molecules, monomers, oligomers, polymers), affinity reagent, detectable probe, binding component, label com-ponent, retaining component, and/or a solid support.

In some cases, reductive amination may be utilized for attachment such as attachment via bioconjugation. Amines can react reversibly with aldehydes to form a transient imine moiety, with accompanying elimination of water. This reac-tion takes place in rapid equilibrium, with the unconjugated starting materials being strongly favored in aqueous condi-tions due to the high concentration of water. However, in a second step the unstable imine can be irreversibly reduced to the corresponding amine via treatment with sodium cyano-borohydride. This mild reducing reagent enables the selec-tive reduction of imines even in the presence of unreacted aldehydes. As a result, irreversible conjugation of a biomo-lecule or other substance can gradually occur to a second substance such as a biomaterial of interest. In contrast, stronger reducing agents such as sodium borohydride are also able to reduce aldehydes. This two-step reductive amination process can also be utilized for the modification of ketones. For example, reductive amination has therefore been primarily used for the modification of sodium perio-date-treated alginate and chitosan scaffolds. The order of reactivity may also be reversed for the attachment of reduc-ing sugars, by exploiting the terminal aldehyde/ketone gen-erated in the open-chain form. This strategy, for example, may be exploited to mimic the glucosylation and galacto-sylation patterns of native collagen in ECM, via reductive amination of maltose and lactose respectively.

In some cases, isothiocyanates may be used to attach substances to each other. For example, isothiocyanates of a biomolecule or solid support may be utilized for bioconju-gation. An isothiocyanate moiety may react with nucleo-philes such as amines, sulfhydryls, the phenolate ion of tyrosine side chains or other molecules to form a stable bond between two molecules.

In some cases, an isocyanate may be utilized for attach-ment of two substances. For example, an isocyanate of a biomolecule or solid support may be utilized for bioconju-gation. For example, isocyanates can react with amine-containing molecules to form stable isourea linkages.

In some cases, an acyl azide may be utilized for attach-ment of two substances. For example, an acyl azide of a biomolecule or solid support may be utilized for bioconju-gation. For example, acyl azide are activated carboxylate groups that can react with primary amines to form amide bonds.

In some cases, an amide may be utilized for attachment of two substances. For example, an amide of a biomolecule or solid support may be utilized for bioconjugation. For example, the use of reactive N-hydroxysuccinimide (NHS) esters is particularly widespread. While NHS-esters can be preformed, often they are instead generated in situ through the use of N-(3-(dimethylamino)propyl)-N'-ethylcarbodiim-ide (EDC) coupling chemistry and coupled directly to the species of interest. Although formation of the activated NHS-ester is favored under mildly acidic conditions (pH ~5), subsequent amide coupling is accelerated at higher pH wherein the amine coupling partner is not protonated. One-step modification at an intermediate pH of ~6.5 is possible. Attachment is typically undertaken by first forming the active NHS-ester at pH 5, before raising the pH to ~8 and adding the amine coupling partner in a two-step procedure. In some cases, water-soluble derivative sulfo-NHS may be utilized as an alternative. In some cases, NHS esters of a biomolecule or other substance can react and couple with tyrosine, serine, and threonine —OH groups as opposed to N-terminal ca-amines and lysine side-chain ε-amines.

In some cases, a sulfonyl chloride may be utilized for attachment of two substances. For example, a sulfonyl chloride of a biomolecule or solid support may be utilized for bioconjugation. For example, reaction of a sulfonyl chloride compound with a primary amine-containing mol-ecule proceeds with loss of the chlorine atom and formation of a sulfonamide linkage.

In some cases, a tosylate ester may be utilized for attach-ment of two substances. For example, a tosylate ester of a biomolecule or solid support may be utilized for bioconju-gation. For example, functional groups including tosylate esters can be formed from the reaction of 4-toluenesulfonyl chloride (also called tosyl chloride or TsCl) with a hydroxyl group to yield the sulfonyl ester derivative. The sulfonyl ester may couple with nucleophiles to produce a covalent bond and may result in a secondary amine linkage with primary amines, a thioether linkage with sulf-hydryl groups, or an ether bond with hydroxyls.

In some cases, a carbonyl may be utilized for attachment of two substances. For example, a carbonyl of a biomolecule or solid support may be utilized for bioconjugation. For example, carbonyl groups such as aldehydes, ketones, and glyoxals can react with amines to form Schiff base intermediates which are in equilibrium with their free forms. In some cases, the addition of sodium borohydride or sodium cyanoborohydride to a reaction medium containing an aldehyde compound and an amine-containing molecule will result in reduction of the Schiff base intermediate and covalent bond formation, creating a secondary amine linkage between the two molecules.

In some cases, an epoxide or oxirane may be utilized for attachment of two substances. For example, an epoxide or oxirane of a biomolecule or solid support may be utilized for bioconjugation. For example, an epoxide or oxirane group may react with nucleo-philes in a ring-opening process. The reaction can take place with primary amines, sulfhydryls, or hydroxyl groups to create secondary amine, thioether, or ether bonds, respectively.

In some cases, a carbonate may be utilized for attachment of two substances. For example, a carbonate of a biomolecule or solid support may be utilized for bioconjugation. For example, carbonates may react with nucleophiles to form carbamate linkages, disuccinimidyl carbonate, can be used to activate hydroxyl-containing molecules to form amine-reactive succinimidyl carbonate intermediates. In some cases, this carbonate activation procedure can be used in coupling polyethylene glycol (PEG) to proteins and other amine-containing molecules. In some cases, nucleophiles, such as the primary amino groups of proteins, can react with the succinimidyl carbonate functional groups to give stable carbamate (aliphatic urethane) bonds In some cases, an aryl halide may be utilized for attachment of two substances. For example, an aryl halide of a biomolecule or solid support may be utilized for bioconjugation. For example, aryl halide compounds such as fluorobenzene derivatives can be used to form covalent bonds with amine-containing molecules like proteins. Other nucleophiles such as thiol, imidazolyl, and phenolate groups can also react to form stable bonds. In some cases, fluorobenzene-type compounds have been used as functional groups in homobifunctional crosslinking agents. For example, their reaction with amines involves nucleophilic displacement of the fluorine atom with the amine derivative, creating a substituted aryl amine bond.

In some cases, an imidoester may be utilized for attachment of two substances. For example, an imidoester of a biomolecule or solid support may be utilized for bioconjugation. For example, the α-amines and ε-amines of proteins may be targeted and crosslinked by reacting with homobifunctional imidoesters. In some cases, after conjugating two proteins with a bifunctional imidoester crosslinker, excess imidoester functional groups may be blocked with ethanolamine.

In some cases, a carbodiimide may be utilized for attachment of two substances. For example, carbodiimides may be utilized for bioconjugation. Generally, carbodiimides are zero-length crosslinking agents that may be used to mediate the formation of an amide or phosphoramidate linkage between a carboxylate group and an amine or a phosphate and an amine, respectively. Carbodiimides are zero-length reagents because in forming these bonds no additional chemical structure is introduced between the conjugating molecules. In some cases, N-substituted carbodiimides can react with carboxylic acids to form highly reactive, O-acyli-sourea derivatives. This active species may then react with a nucleophile such as a primary amine to form an amide bond. In some cases, sulfhydryl groups may attack the active species and form thioester linkages. In some cases, hydrazide-containing compounds can also be coupled to carboxylate groups using a carbodiimide-mediated reaction. Using bifunctional hydrazide reagents, carboxylates may be modified to possess terminal hydra-zide groups able to conjugate with other carbonyl compounds.

In some cases, a phosphate may be utilized for attachment of two substances. For example, a biomolecule containing phosphate groups, such as the 5' phosphate of oligonucleotides or a phosphorylated amino acid of a polypeptide, may also be conjugated to amine-containing molecules by using a carbodiimide-mediated reaction. For example, the carbodiimide of a biomolecule may activate the phosphate to an intermediate phosphate ester similar to its reaction with carboxylates. In the presence of an amine, the ester reacts to form a stable phosphoramidate bond.

In some cases, an acid anhydride may be utilized for attachment of two substances. For example, an acid anhydride of a biomolecule or solid support may be utilized for bioconjugation. Anhydrides are highly reactive toward nucleophiles and are able to acylate a number of the important functional groups of proteins and other molecules. For example, protein functional groups able to react with anhydrides include but not limited to the α-amines at the N-terminals, the ε-amine of lysine side chains, cysteine sulfhydryl groups, the phenolate ion of tyrosine residues, and the imid-azolyl ring of histidines. In some cases, the site of reactivity for anhydrides in protein molecules is modification of any attached carbohydrate chains. In some cases, in addition to amino group modification in a polypeptide chain, glycoproteins may be modified at their polysaccharide hydroxyl groups to form esterified derivatives.

In some cases, a fluorophenyl ester may be utilized for attachment of two substances. For example, a fluorophenyl ester of a biomolecule or solid support may be utilized for bioconjugation. Flurophenyl esters can be another type of carboxylic acid derivative that may react with amines consists of the ester of a fluorophenol compound, which creates a group capable of forming amide bonds with proteins and other molecules. In some cases, fluorophenyl esters may be: a pentafluorophenyl (PFP) ester, a tetrafluorophenyl (TFP) ester, or a sulfo-tetrafluoro-phenyl (STP) ester. In some cases, fluorophenyl esters react with amine-containing molecules at slightly alkaline pH values to give the same amide bond linkages as NHS esters.

In some cases, a hydroxymethyl phosphine may be utilized for attachment of two substances. For example, a hydroxymethyl phosphine of a biomolecule or solid support may be utilized for bioconjugation. Phosphine derivatives with hydroxymethyl group substitutions may act as attachment agents for coupling or crosslinking purposes. For example, tris(hydroxymethyl) phosphine (THP) and β-[tris (hydroxymethyl)phos-phino] propionic acid (THPP) are small trifunctional compounds that spontaneously react with nucleophiles, such as amines, to form covalent linkages.

In some cases, a thiol may be utilized for attachment of two substances. For example, the thiol reactivity of a biomolecule or solid support may be utilized for bioconjugation. For example, the thiol group of cysteine is the most nucleophilic functional group found among the 20 proteinogenic amino acids. Through careful control of pH, selective modification over other nucleophilic amino acid residues such as lysine can be readily achieved. Another example, thiol modification of oligonucleotides may be used to enable derivatization, though the ease with which alternative functional groups with enhanced chemical orthogonality can be installed has limited use for biomaterial-conjugation. Further, the conjugate addition of thiols to α,β-unsaturated carbonyls, also known as Michael addition, may be used to form polypeptide conjugates in the fields of tissue engineering, functional materials, and protein modification. In general, reaction rates and conjugation efficiencies are primarily controlled by three factors and may be modified as needed: (i) the $pK_a$ of the thiol; (ii) the electrophilicity of the Michael-acceptor; (iii) the choice of catalyst. Regarding (i): the thiolate anion is the active nucleophile during Michael addition, and the propensity of the thiol to undergo deprotonation may determine thiolate concentration and thus reaction rates. For example, the lower $pK_a$ of aromatic thiols, when compared to their aliphatic counterparts, leads to a higher rate of reaction rate a weak base is used to catalyze the. As a result, local structure can significantly alter conjugation efficiency, particularly for polypeptide substrates. The $pK_a$ and reactivity of cysteine containing peptides can be altered significantly through rational choice of surrounding amino acids, the presence of positively charged amino acids, such as lysine and arginine, acts to lower the thiol $pK_a$ and thus enhance reactivity. Regarding (ii): the Michael-acceptor becomes more electron deficient it becomes more activated toward nucleophilic attack, and thus reaction rates increase. Within the most widely utilized acceptors in the biomaterial field, a trend of reactivity can be generalized as maleimides>vinyl sulfones>acrylates>acrylamides>methacrylates. Regarding (iii) Michael additions can be accelerated by either basic or nucleophilic catalysis (although both act by increasing the concentration of the active thiolate).

In some cases, the unique nucleophilicity of thiols can be exploited for selective reaction with a number of alternative electrophiles, which allow efficient and selective attachment to be achieved. For example, one such group includes α-halocarbonyls, with iodoacetamide based reagents finding particular utility. Higher thiol selectivity may be achieved using less electrophilic bromo- and even chloro-derivatives, though reactivity is also drastically reduced. More recently, methylsulfonyl heteroaromatic derivatives have emerged as promising reagents for thiol-specific conjugation. In other cases, alternative thiol-functional groups, such as disulfide-bridging pyridazinediones, carbonylacrylic reagents, and cyclopropenyl ketones may be utilized for bioconjugation.

In some cases, a sulfhydryl may be utilized for attachment of two substances. For example, sulfhydryl of a biomolecule or solid support may be utilized for bioconjugation. In some cases, three forms of activated halogen derivatives can be used to create sulfhydryl-reactive compounds: haloacetyl, benzyl halides, and alkyl halides. In each of these compounds, the halogen group may be easily displaced by an attacking nucleophilic substance to form an alkylated derivative with loss of HX (where X is the halogen and the hydrogen comes from the nucleophile). Haloacetyl compounds and benzyl halides typically are iodine or bromine derivatives, whereas the halo-mustards mainly employ chlorine and bromine forms. Iodoacetyl groups have also been used successfully to couple affinity ligands to chromatography supports.

In some cases, a maleimide may be utilized for attachment of two substances. For example, a maleimide of a biomolecule or solid support may be utilized for bioconjugation. The double bond of maleimides may undergo an alkylation reaction with sulfhydryl groups to form stable thioether bonds.

In some cases, an aziridine may be utilized for attachment of two substances. For example, an aziridine of a biomolecule or solid support may be utilized for bioconjugation. The highly hindered nature of this heterocyclic ring gives it strong reactivity toward nucleophiles. For example, sulfhydryls will react with aziridine-containing reagents in a ring-opening process, forming thioether bonds. The simplest aziridine compound, ethylenimine, can be used to transform available sulfhydryl groups into amines. In some cases, substituted aziridines may be used to form homobifunctional and trifunctional crosslinking agents.

In some cases, thiol-maleimide reactions are particularly useful for undertaking conjugation at low concentrations or when requiring extremely high efficiencies due to the value of the biomolecule substrate. The use of maleimides for attachment is further enhanced by the ease with which they may be introduced into a wide range of materials, through the modification of amines with the difunctional reagent succinimidyl 4-(N-maleimidomethyl) cyclohexane-1-carboxylate, commonly referred to by its abbreviation SMCC. For example, this reagent has been widely used to first introduce a maleimide functional group on a biomaterial of choice and then to enable the attachment of both peptides and growth factors to produce bioactive scaffolds.

In some cases, an acryloyl may be utilized for attachment of two substances. For example, an acryloyl of a biomolecule or solid support may be utilized for bioconjugation. The reactive double bonds are capable of undergoing additional reactions with sulfhydryl groups. In some cases, the reaction of an acryloyl compound with a sulfhydryl group occurs with the creation of a stable thioether bond. In some cases, the acryloyl has found use in the design of the sulfhydryl-reactive fluorescent probe, 6-acryloyl-2-dimethylaminonaphthalene.

In some cases, an aryl group may be utilized for attachment of two substances. For example, an aryl group of a biomolecule or solid support may be utilized for bioconjugation with a sulfhydryl group. Although aryl halides are commonly used to modify amine-containing molecules to form aryl amine derivatives, they also may react quite readily with sulfhydryl groups. For example, fluorobenzene-type compounds have been used as functional groups in homobifunctional crosslinking agents. Their reaction with nucleophiles involves bimolecular nucleophilic substitution, causing the replacement of the fluorine atom with the sulfhydryl derivative and creating a substituted aryl bond. Conjugates formed with sulfhydryl groups are reversible by cleaving with an excess of thiol (such as DTT).

In some cases, a disulfide may be utilized for attachment of two substances. For example, the disulfide group of a biomolecule or solid support may be utilized for bioconjugation. In some cases, compounds containing a disulfide group are able to participate in disulfide exchange reactions with another thiol. The disulfide exchange (also called interchange) process involves attack of the thiol at the disulfide, breaking the —S—S— bond, with subsequent formation of a new mixed disulfide including a portion of the original disulfide compound. The reduction of disulfide groups to sulfhydryls in proteins using thiol-containing reductants proceeds through the intermediate formation of a mixed disulfide. In some cases, crosslinking or modification reactions may use disulfide exchange processes to form disulfide linkages with sulfhydryl-containing molecules.

In some cases, disulfide bonds may be utilized for attachment such as bioconjugation. For example, the use of disulfide exchange reactions may be favored for modifying polypeptides of interest. The most commonly used reagents in tissue engineering are based upon reactive pyridylthio-disulfides, which undergo rapid thiol-exchange to release the poorly nucleophilic and spectroscopically active 2-mercaptopyridine. Additionally, due to the reversible nature of disulfide bond formation, cleavage can be controlled with temporal precision by the addition of reducing agents such as dithiothreitol (DTT) or glutathione.

In some cases, an pyridyl dithiol may be utilized for attachment of two substances. For example, a pyridyl dithiol functional group may be used in the construction of cross-linkers or modification reagents for bioconjugation. Pyridyl disulfides may be created from available primary amines on molecules through the reaction of 2-iminothiolane in tandem with 4,4'-dipyridyl disulfide. For instance, the simultaneous reaction among a protein or other molecule, 2-iminothiolane, and 4,4'-dipyri-dyl disulfide yields a modification containing reactive pyridyl disulfide groups in a single step. A pyridyl disulfide will readily undergo an interchange reaction with a free sulfhydryl to yield a single mixed disulfide product.

In some cases, sulfhydryl groups activated with the leaving group 5-thio-2-nitrobenzoic acid can be used to couple free thiols by disulfide interchange similar to pyridyl disulfides, as described herein. The disulfide of Ellman's reagent readily undergoes disulfide exchange with a free sulfhydryl to form a mixed disulfide with concomitant release of one molecule of the chromogenic substance 5-sulfido-2-nitro-ben-zoate, also called 5-thio-2-nitrobenzoic acid (TNB). The TNB-thiol group can again undergo interchange with a sulfhydryl-containing target molecule to yield a disulfide crosslink. Upon coupling with a sulfhydryl compound, the TNB group is released.

In some cases, disulfide reduction may be performed using thiol-containing compounds such as TCEP, DTT, 2-mercaptoethanol, or 2-mercaptoethylamine.

In some cases, an vinyl sulfone may be utilized for attachment of two substances. For example, a vinyl sulfone group of a biomolecule or solid support may be utilized for bioconjugation. For example, the Michael addition of thiols to activated vinyl sulfones to form biomolecule-material conjugates have been used to demonstrate that cysteine capped peptides could cross-link vinyl-sulfone functionalized multiarm PEGs to form protease responsive hydrogels, enabling cell invasion during tissue growth. In some cases, in addition to thiols, vinyl sulfone groups can react with amines and hydroxyls under higher pH conditions. The product of the reaction of a thiol with a vinyl sulfone gives a single stereoisomer structure. In addition, crosslinkers and modification reagents containing a vinyl sulfone can be used to activate surfaces or molecules to contain thiol-reactive groups.

In some cases, thiol-containing molecules can interact with metal ions and metal surfaces to form dative bonds for bioconjugation. In some cases, oxygen- and nitrogen-containing organic or biomolecules may be used to chelate metal ions, such as in various lanthanide chelates, bifunctional metal chelating compounds, and FeBABE. In addition, amino acid side chains and prosthetic groups in proteins frequently form bioinorganic motifs by coordinating a metal ion as part of an active center.

In some cases, thiol organic compounds may be used routinely to coat metallic surfaces or particles to form biocompatible layers or create functional groups for further conjugation of substances such as biomolecules. For instance, thiol-containing aliphatic/PEG linkers have been used to form self-assembled monolayers (SAMs) on planar gold surfaces and particles.

In some cases, a number of alternative coupling systems may be used for attachment between substances or biomolecule functionalization. These include the use of O-nitrophenyl esters (which possess reduced stability in aqueous conditions) or 1,1'-carbonyldiimidazole (CDI) to form amine-bridging carbamate linkages rather than amides. Hydrazines can also be used in place of amines during EDC/NHS mediated couplings. Hydrazine-functionalized peptides can be coupled to biomaterials in a single step at pH 5-6. In doing so, a degree of site-selectivity can be achieved over lysine residues present.

In some cases, N-terminal modification of a biomolecule may be utilized for bioconjugation. For example, 2-pyridinecarboxaldehyde modified acrylamide hydrogels may react specifically with the N-terminus of ECM proteins, forming a cyclic imidazolidinone product with the adjacent amide bond and enabling the orientated display of these key bioinstructive motifs.

In some cases, acrylates, acrylamides, and methacrylates of a substance such as a biomolecule or solid support may be utilized for attachment. In some cases, thiolynes of a substance such as a biomolecule or solid support may be utilized for bioconjugation.

In some cases, thiol-reactive conjugation such as native chemical ligation (NCL) can be utilized to attach substances via peptide bond formation, for example, to attach peptides and proteins to biomaterial scaffolds. For example, a peptide having a C-terminal thioester reacts with an N-terminal cysteine residue in another peptide to undergo a trans-thioesterification reaction, which results in the formation of an intermediate thioester with the cysteine thiol.

In some cases, strong binding of (strept)avidin to the small molecule biotin may be used for attachment. In some cases, (strept)avidin may be attached to a first substance and biotin may be attached to a second substance such that the substances can become attached via binding of the (strept) avidin to the biotin. In some cases, modification reagents can add a functional biotin group to proteins, nucleic acids, and other molecules. In some cases, depending on the functionality present on the biotinylation compound, specific functional groups on antibodies or other proteins may be modified to create a (strept)avidin binding site. Amines, carboxylates, sulfhydryls, and carbohydrate groups can be specifically targeted for biotinylation through the appropriate choice of biotin derivative. In some cases, photoreactive biotinylation reagents are used to add nonselectively a biotin group to molecules containing no convenient functional groups for modification. In some cases, biotin-binding proteins can be immobilized onto surfaces, chromatography supports, microparticles, and nanoparticles for use in coupling biotinylated molecules. In some cases, a series of (strept)avidin-biotin interactions can be built upon each other to utilize the multivalent nature of each tetrameric (strept)avidin molecule and enhance the detection capability for the target. In some cases, amine-reactive biotinylation reagents that may contain functional groups off biotin's valeric acid side chain are able to form covalent bonds with primary amines in proteins and other molecules. In some cases, NHS esters spontaneously react with amines to form amide linkages whereas carboxylate-containing biotin compounds can be coupled to amines via a carbodiimide-mediated reaction using EDC. In some cases, NHS-imino-biotin can be used to label amine-containing molecules with an iminobiotin tag, providing reversible binding potential with avidin or streptavidin. In some cases, Sulfo-NHS-SS-biotin (also known as NHS-SS-biotin) is sulfosuccinimidyl-2-(biotinamido)ethyl-1,3-dithiopropionate, a long-chain cleavable bio-tinylation reagent that can be used to modify amine-containing proteins and other molecules. In some cases, 1-biotinamido-4-[4'-(maleimidomethyl) cyclohexane-carboxamido]butane, a biotinylation reagent containing a maleimide group at the end of an extended spacer arm reacts with sulfhydryl groups in proteins and other molecules to form stable thioether linkages. In some cases, N-[6-(bioti-namido)hexyl]-3'-(2'-pyridyldithio)propionamide where the reagent contains a 1,6-diaminohexane spacer group which is attached to biotin's valeric acid side chain, the terminal amino group of the spacer may be further modified via an amide linkage with the acid precursor of SPDP to create a terminal, sulfhydryl-reactive group. The pyridyl disulfide end of biotin—HPDP may react with free thiol groups in proteins and other molecules to form a disulfide bond with loss of pyridine-2-thione.

In some cases, a carboxylate may be utilized for attachment of two substances. For example, a carboxylate of a biomolecule or solid support may be utilized for bioconjugation. In some cases, diazomethane and other diazoalkyl derivatives may be used to label carboxylate groups. In some cases, N,N'-Carbonyl diimidazole (CDI) may be used to react with carboxylic acids under nonaqueous conditions to form N-acylimidazoles of high reactivity. An active carboxylate can then react with amines to form amide bonds or with hydroxyl groups to form ester linkages. In addition, activation of a styrene/4-vinylbenzoic acid copolymer with CDI may be used to immobilize an enzyme lysozyme or other molecule through its available amino groups to the carboxyl groups on to a matrix.

In some cases, carbodiimides function as zero-length crosslinking agents capable of activating a carboxylate group for coupling with an amine-containing compound for attachment. In some cases, carbodiimides are used to mediate the formation of amide or phosphoramidate linkages between a carboxylate and an amine or a phosphate and an amine.

In some cases, N,N'-disuccinimidyl carbonate or N-hydroxysuccinimidyl chloroformate may be utilized to attach species, for example, via bioconjugation. N,N'-Disuccinimidyl carbonate (DSC) consists of a carbonyl group containing, in essence, two NHS esters. The compound is highly reactive toward nucleophiles. In aqueous solutions, DSC will hydrolyze to form two molecules of N-hydroxysuccinimide (NHS) with release of one molecule of $CO_2$. In nonaqueous environments, the reagent can be used to activate a hydroxyl group to a succinimidyl carbonate derivative. DSC-activated hydroxylic compounds can be used to conjugate with amine-containing molecules to form stable crosslinked products.

In some cases, sodium periodate can be used to oxidize hydroxyl groups on adjacent carbon atoms, forming reactive aldehyde moieties suitable for coupling with amine- or hydrazide-containing molecules for attachment, for example, via bioconjugation. For example, these reactions can be used to generate crosslinking sites in carbohydrates or glycoproteins for subsequent conjugation of amine-containing molecules by reductive amination.

In some cases, enzymes may be used to oxidize hydroxyl-containing carbohydrates to create aldehyde groups for bioconjugation. For example, the reaction of galactose oxidase on terminal galactose or N-acetyl-d-galactose moieties proceeds to form C-6 aldehyde groups on polysaccharide chains. These groups can then be used for conjugation reactions with amine- or hydrazide-containing molecules.

In some cases, reactive alkyl halogen compounds can be used to specifically modify hydroxyl groups in carbohydrates, polymers, and other substances for attachment.

In some cases, an aldehyde or ketone may be utilized for attachment of two substances. For example, an aldehyde or ketone of a biomolecule or solid support may be used for bioconjugation. For example, derivatives of hydrazine, especially the hydrazide compounds formed from carboxylate groups, can react specifically with aldehyde or ketone functional groups in target molecules. To further stabilize the bond between a hydrazide and an aldehyde, the hydrazone may be reacted with sodium cyanoborohydride to reduce the double bond and form a secure covalent linkage.

In some cases, an aminooxy may be utilized for attachment of two substances. For example, an aminooxy group of a biomolecule or solid support may be used for bioconjugation. For example, the chemoselective ligation reaction that occurs between an aldehyde group and an aminooxy group yields an oxime linkage (aldoxime) that has been used in many bioconjugation reactions, as well as in the coupling of ligands to insoluble supports including surfaces. This reaction is also quite efficient with ketones to form an oxime called a ketoxime.

In some cases, cycloaddition reactions may be utilized for attachment, such as attachment via bioconjugation. In cycloaddition reactions, two or more unsaturated molecules are brought together to form a cyclic product with a reduction in the degree of unsaturation, these reaction partners are typically absent from natural systems, and so the use of cycloadditions for conjugation utilizes the introduction of unnatural functionality within a coupling partner.

In some cases, Copper-Catalyzed Azide-Alkyne Cycloadditions (CuAAC) may be utilized for attachment of two substances. For example, CuAAC may be utilized for bioconjugation. In some cases, the (3+2) cycloaddition between an azide and alkyne proceeds spontaneously at high temperatures (>90° C.), producing a mixture of two triazole isomers. In some cases, this reaction proceeds at room temperature, ambient, oxygenated, and/or aqueous environments. In some cases, for example, the formation of peptide-material conjugates by CuAAC, using alkyne-capped peptides to form hydrogels with azide-functionalized PEG. In some cases, to achieve conjugation via CuAAC, the copper (I) catalyst can either be added directly, or generated in situ by reduction of an initial copper(II) complex, most commonly using ascorbic acid. The addition of a reducing agent further reduces the sensitivity of the CuAAC ligation to oxygen. Although no additional ligand is necessary for triazole formation, the addition of tertiary amine based ligands may be used.

In some cases, Strain-Promoted Azide-Alkyne Cycloadditions (SPAAC) may be utilized for attachment of two substances. SPAAC may be utilized for bioconjugation. In some cases, highly strained cyclooctynes react readily with azides to form triazoles under physiological conditions, without the need for any added catalyst. In some cases, in addition to the use of SPAAC for peptide conjugation, a number of prominent reports have used SPAAC to attach protein substrates to cyclooctyne functionalized biomaterials via the introduction of an unnatural azide motif into the protein coupling partner. In some cases, for example, this is achieved by including maleimide functionalization of native cysteines present in bone morphogenetic protein-2 (BMP-2), via enzyme-mediated N-terminal modification of IFN-γ, or via codon reassignment with the unnatural amino acid 4-azidophenylalanine in a number of protein substrates. In some cases, supramolecular host-guest interactions can also be used to promote azide-alkyne cycloaddition. For example, by bringing two reactive partners into close proximity within the cavity of a cucurbit[6]uril host, efficient cycloaddition could be achieved on the surface of proteins, this strategy may be extended to other appropriate molecules.

In some cases, inverse-electron demand Diels-Alder reactions (IEDDA) may be utilized for attachment, such as attachment via bioconjugation. For example, the IEDDA reaction between 1,2,4,5-tetrazines and strained alkenes or alkynes may be employed. A wide range of suitable derivatives for undertaking molecule conjugation have been reported, for example, a series of increasingly strained (and thus reactive) trans-cyclooctenes may be utilized. In some cases, functionalized norbornene derivatives may be utilized for undertaking IEDDA reactions. In some cases, triazines may be utilized. In some cases, spirohexene may be utilized. These strategies may be extended to other appropriate molecules. In some cases, hetero-Diels-Alder cycloaddition of maleimides and furans may be utilized for attachment. For example, the coupling of furan-functionalized RGDS peptides (SEQ ID NO: 6) to maleimide-functionalized PEG-hydrogels may be utilized, this strategy may be extended to other appropriate molecules. In some cases, furan-functionalized hyraluronic acid hydrogels can be cross-linked with a dimaleimide-functionalized peptide via Diels-Alder cycloaddition.

In some cases, oxime and hydrazone may be utilized for attachment of two substances. For example, oxime and hydrazone formation may be utilized for bioconjugation. In some cases, the stable attachment of peptides and DNA to biomaterials via hydrazone formation can be achieved via difunctional cross-linking, this strategy may be extended to other appropriate molecules. For example, protein cross-linked hydrogels can be produced through oxime modification at both the protein N- and C-termini.

In some cases, the Diels-Alder reaction consists of the covalent coupling of a diene with an alkene to form a six-membered ring complex for attachment.

In some cases, transition metal complexes may be utilized for attachment, such as attachment via bioconjugation. The nature of late transition metals may make a transition metal complex well suited to the manipulation of unsaturated and polarizable functional groups (olefins, alkynes, aryl iodides, arylboronic acids, etc.). For example, Pd(0)-functionalized solid supports may mediate allyl carbamate deprotections and Suzuki-Miyaura cross-coupling in the cytoplasm. In other examples, a ruthenium catalyst may be used to mediate allyl carbamate deprotection of a caged fluorophore inside living cells. In some cases, applications of palladium-based applications in cell culture include copper-free Sonagashira coupling, extracellular Suzuki coupling on the surface of *E. coli* cells, and conjugation of thiol groups with allyl selenosulfate salts. In some cases, olefin metathesis may be utilized for bioconjugation. For example, with ruthenium complexes, S-allylcysteine can be easily introduced into proteins by a variety of methods, including conjugate addition of allyl thiol to dehydroalanine, direct allylation of cysteine, desulfurization of allyl disulfide, or metabolic incorporation as a methionine surrogate in methionine auxotrophic *E. coli*.

In some cases, complex formation with boronic acid derivatives may be used for attachment of substances, for example, via bioconjugation. For example, boronic acid derivatives are able to form ring structures with other molecules having neighboring functional groups consisting of 1,2- or 1,3-diols, 1,2- or 1,3-hydroxy acids, 1,2- or 1,3-hydroxylamines, 1-2- or 1,3-hydroxyamides, 1,2- or 1,3-hydroxyoximes, as well as various sugars or biomolecules containing these species.

In some cases, enzyme-mediated conjugation may be utilized to attach substances. For example, the transglutaminase enzyme family catalyzes the formation of isopeptide bonds between the primary amine of lysine side chains and the amide bonds of a complementary glutamine residue, this strategy may be extended to other appropriate molecules. In other cases, peroxidase-mediated conjugation may be utilized for conjugation. For example, horse radish peroxidase (HRP) may be utilized to oxidize a wide range of organic substrates such as phenol group of tyrosine to generate a highly reactive radical or quinone intermediate that undergoes spontaneous dimerization, resulting in the formation of an ortho carbon-carbon bond between two tyrosine residues, this strategy may be extended to other appropriate molecules. In some cases short peptide tags may be utilized for bioconjugation. These peptide tags may be as short as 5 amino acids long and may be appended to a polypeptide which allows for their subsequent modification.

In some cases, polymerization of low molecular weight monomers may be utilized for attachment of substances, for example, via bioconjugation. Polymerization may be classified as proceeding via one of two mechanisms, either chain-growth or step-growth. During chain-growth polymerization, monomers are added at the "active" end of a growing polymer chain, resulting in the formation of high molecular weight materials even at low conversions. During step-growth polymerizations short oligomer chains couple to form polymeric species, requiring high conversions in order to reach high molecular weights. Both techniques can be used to form conjugates such as biomolecule-polymer conjugates. The polymerization of acrylate and methacrylate monomers has proven particularly fruitful. For example, acrylate and methacrylate modified proteins can be readily polymerized. Similarly, availability of the synthetic oligonucleotide phosphoramidite building block "Acrydite", free-radical polymerization remains one of the most common methods through which to form DNA and RNA functionalized substances. By undertaking polymerization in the presence of a comonomer, the density of molecule presentation can be easily tuned, allowing potential difficulties from steric hindrance to be overcome. Initiation of polymerization can be triggered by a number of means, including heat, UV and visible light, redox reactions, and electrochemistry. Acrylate modified proteins can also undergo polymerization to produce functional materials, while retaining biological activity. In some cases living radical polymerizations (LRPs) may be utilized for bioconjugation. For example, the most commonly used LRPs for the formation of bioconjugates include atom-transfer radical polymerization (ATRP), reversible addition-fragmentation chain transfer (RAFT) polymerization, and nitroxide-mediated polymerization (NMP).

In some cases, photoconjugation may be utilized for attachment of substances, for example, via bioconjugation. In some cases, polymerization is initiated by the production of a radical species, which then propagates through bond formation to create an active polymer chain. The initiation step can be induced via a number of stimuli, with thermal decomposition, redox activation, and electrochemical ionization of an initiating species being among the most common. Alternatively, many initiators can be activated via light-induced photolytic bond breakage (type I) or photoactivated abstraction of protons from a co-initiator (type II). Photoinitiation offers the benefits of being applicable across a wide temperature range, using narrow and tunable activation wavelengths dependent on the initiator used, rapidly generating radicals, and the ability to control polymerization by removing the light source. Importantly, the tolerance of polymerizations to oxygen is greatly enhanced, enabling polymerization in the presence of cells and tissues. The incorporation of acrylate-functionalized peptides and proteins during photopolymerization may be used as a method for producing biomaterial conjugates. Alternatively, the photoinitiated attachment of polypeptides to pendant vinyl groups on preformed materials has also been widely reported and more recently used for 3D patterning via two-photon excitation. A wide range of photoinitiators may be used in photoconjugation conjugations. For example, but not limited to, Eosin Y, 2,2-dimethoxy-2-phenyl-acetophenone, Igracure D2959, lithium phenyl-2,4,6-trimethylbenzoylphosphinate, and riboflavin may be used as photoinitiators. Photoinitiators generally absorb light to initiate the photoreaction processes. In some cases, photoconjugation may utilize a photo thiol-ene reaction. Thiols can also react with alkenes via a free-radical mechanism. A thiol radical first reacts with an alkene to generate a carbon-centered radical, which can then abstract a proton from another thiol and thus propagate the reaction. Photo thiol-ene reactions may be accelerated by electron-rich alkenes, which generate unstable carbon-radical intermediates able to rapidly abstract thiol-hydrogens. Exceptions to this rule are norbornene derivatives, in which reactivity is driven instead by the release of ring strain upon thiol addition. This leads to a general trend in reactivity of norbornene>vinyl ether>propenyl>allyl ether>acrylate>maleimide. Norbornenes and allyloxycarbonyls (alloc groups) have been particularly widely used for peptide/protein-biomaterial functionalization, due to the almost negligible contribution of chain transfer and their ease of introduction during peptide synthesis, respectively. For example, an alloc group, typically used as an orthogonal lysine protecting group during solid-phase peptide synthesis, is an efficient photo thiol-ene functional group. In other examples, norbornene photo thiol-ene reactions may be used for the tethering and spatial patterning of bioactive peptides and growth factor proteins. In addition to the most commonly used alloc and norbornene functional groups, other alkenes have also been used for biomaterial functionalization. For example, codon reassignment has been used to site-specifically incorporate allyl-cysteine residues into proteins, which can subsequently undergo conjugation through the use of photo thiol-ene reactions. Alternatively, acrylates can undergo mixed-mode photopolymerizations in the presence of cysteine capped peptides, while allyl disulfide structures have recently been shown to undergo reversible and controlled exchange of conjugated thiols.

In some cases, aryl azide or halogenate aryl azides can be used to attach substances.

In some cases, a photoreactive group such as benzophenone may be utilized for attachment of substances.

In some cases, photoreactive group anthraquinone may be utilized for attachment of substances, such as attachment via bioconjugation. In some cases, photo thiol-yne reactions may be utilized for attachment of substances, such as attachment via bioconjugation. Most examples of photo thiol-yne reactions have exploited simple propargyl-ether or -amine functional groups.

In some cases, photocaging and activation of reactive functionalities may be utilized for attachment of substances, such as attachment via bioconjugation. Generally, a transient reactive species is formed whether it be an acrylate or thiol derived radical. In some cases, photocaging may be used to mask or protect a functional group until it is desirable for it to be exposed. In some cases, the most widely utilized cages are based around o-nitrobenzyl and coumarin chromophores. For example, nitrobenzyl-capped cysteine residues may be decaged by irradiation with 325 nm UV light, the released thiol may then react with maleimide-functionalized peptides via Michael addition, to generate a patterned hydrogel able to guide cell migration. In some cases, 6-bromo-hydroxycoumarins may be used for thiol-caging. In some cases, photoaffinitiy probes may be utilized for bioconjugation where a highly reactive intermediate upon irradiation, which then reacts rapidly with the nearest accessible functional group with high spatial precision. In some cases, the most commonly used are phenylazides, benzophenones, and phenyl-diazirines. In some cases, photocaged cycloadditions may be used. For example, the UV irradiation of tetrazoles has been shown to generate a reactive nitrile-imine intermediate which can undergo rapid cycloaddition with electron-deficient alkenes such as acrylates or acrylamides. In some cases, the nitrile-imine side-reactivity with thiols may be utilized for site-specifically conjugation of cysteine containing proteins to tetrazole functionalized surfaces.

In some cases, noncovalent interactions may be utilized for attachment of substances, such as attachment via bioconjugation. In some cases, noncovalent sequences which display a binding affinity for the biomolecule of interest, allow for postfabrication modification or for native biomolecules to be simply sequestered from the surroundings within biological samples. Useful binding sequences are short peptides between 7 and 20 amino acids in length, derived from a variety of sources, including known protein binding domains present in vivo or determined through techniques such as phage display. In some cases, aptamers can also be used to bind a variety of protein substrates, including the cytokines vascular endothelial growth factor (VEGF) and platelet derived growth factor (PDGF), as well as cell surface proteins such as epidermal growth factor receptor (EGFR). In some cases, binding sequences can also be introduced into a biomaterial with affinity for native biopolymers, such as heparin. In some cases, by first inducing biopolymer binding, the adsorption of an added or endogenous growth factor or signaling protein to a biomaterial scaffold can then be controlled. In some cases, binding affinity at the amino acid level can also be exploited to enable peptide and protein conjugation to certain biomaterial substrates. For example, the binding of unnatural catechol-based amino acids can be used to induce binding to metal oxide containing bioglasses and metallic implants, enabling the bioactivity of these important technologies to be enhanced.

In some cases, self-assembling peptides may be utilized for attachment of substances, such as attachment via bioconjugation. For example, native peptides and proteins adopt a series of secondary structures, including β-sheets and α-helices, which can both stabilize individual sequences and control interprotein aggregation. In some cases, self-assembling peptides have been used extensively to assemble hydrogels and fibrous materials. In many of these structures, biological epitopes or functional groups can be appended to some or all of the peptide building blocks during peptide synthesis, to add the desired bioactivity into the system. Peptide-ligands ranging from simple adhesion motifs, to laminin derived epitopes, and growth factor mimetics have all been displayed on the surface of self-assembled fibrils. Alternatively, glycopeptides can be assembled in order to recruit extracellular signaling proteins and growth factors, mimic glycosylation patterns within hyaluronic acid, or investigate optimal sulfonation ratios in glycosaminoglycan scaffolds. In some cases, self-assembling domains can also be added to full-length proteins, leading to the incorporation of pendant functionality during hydrogel formation. In some cases, the propensity of peptides to form secondary structures has also been exploited within nonself-assembling scaffolds. This may be achieved by mixing a self-assembling peptide into a covalent hydrogel, composed of either a noninteracting polymer such as interpenetrating networks of PEG or systems where additional charge interactions further stabilize the final construct, for example between positively charged peptides and negatively charged alginate gels. As an alternative, pendant helical groups can be attached to a covalent material and used to drive the noncovalent attachment of bioactive groups such as growth factors via self-assembly into coiled-coil triple helices.

In some cases, host-guest chemistry may be utilized for attachment of substances, such as attachment via bioconjugation. For example, the adhesive properties of a β-cyclodextrin modified alginate scaffold could be controlled in situ through the addition of a guest naphthyl-functionalized RGDS peptide (SEQ ID NO: 6) and by subsequently introducing a non-cell adhesive adamantane-RGES peptide (SEQ ID NO: 7) with a higher host binding constant, dynamic modulation of fibroblast cell attachment was enabled. Host-guest interactions between cyclodextrin and naphthyl- or adamantane-functionalized peptides allow alginate functionalization, this may be applied to other appropriate molecules.

In some cases, nucleic acids may be utilized for attachment of substances, such as attachment via bioconjugation. In some cases, in an analogous fashion to self-assembling peptides, nucleic acids can also form assembled materials themselves, to generate tunable platforms for the display of molecules. In some cases, DNA-tagged polypeptides can be conjugated to a suitably functionalized substance.

Generally, incorporating functional groups may be utilized for attachment of substances. For example, introducing uniquely reactive motifs into molecules provides a chemical "tag" which allows single-site selectivity or specificity to be achieved. In some cases, polypeptides or nucleic acids can be produced via solid phase synthesis (SPS). The versatility of organic synthesis allows difficulties in functional group incorporation to be overcome, with a wide range of suitably functionalized amino acids and nucleotides available as described herein. In some cases, an alternative approach is to introduce unnatural amino acids (UAAs) bearing the desired functional groups. This may be achieved via the modification of lysine residues with amine-reactive derivatives. In some cases, the use of auxotrophic bacterial strains, which are unable to biosynthesize a particular amino acid and thus require uptake from the growth media. By starving the bacteria of the native amino acid and supplementing it with a structurally related unnatural analogue, the bacterial cells can be induced to incorporate the UAA during translation. This technique may be used to install azide- and alkyne-based mimics of methionine, leading to the introduction of functional groups for undertaking CuAAC and SPAAC reactions. In some cases, the use of codon reassignment using orthogonal tRNA and tRNA synthetase pairs that selectively recognize and charge an UAA during translation. In some cases, this may be achieved by reassigning the amber stop-codon, UAG, by incorporating a tRNA$_{CUA}$/ tRNA synthetase pair from an alternative kingdom into the host cell. This pair may be able to install the desired UAA, while being effectively invisible to the endogenous cell machinery. As a result, site-directed mutagenesis can be used to introduce a single TAG codon at the desired position of the coding DNA, leading to the singular introduction of the UAA with high specificity and selectivity.

Compositions and Kits

Compositions or kits may be formed including detectable probes or affinity reagents as described in the present disclosure. Several configurations are set forth below in the context of compositions. It will be understood that kits can be similarly configured. A composition may include one or more detectable probes or affinity reagents along with a solution or solvent, and other constitutive components. The specific formulation of a detectable probe or affinity reagent composition may depend upon the intended use of the detectable probe or affinity reagent and the specific composition of a detectable probe or affinity reagent in the composition. Compositions may be formulated based upon several factors, including: 1) stability and storage requirements for a detectable probe or affinity reagent; 2) properties and/or characteristics of the detectable probe or affinity reagent; and 3) mode of use for the detectable probe or affinity reagent. Stability and/or storage considerations may include conditions to maintain retaining component, binding component, and or label component stability. Property or characteristic considerations may include affinity and/or avidity characteristics, probe dissociation, and label component characteristics. Mode of use considerations may include detection methods, multiplexing, and secondary binding interactions.

In general, a composition may include one or more detectable probes or affinity reagents in a liquid medium. In some configurations, the liquid medium may be aqueous or otherwise include water. In some configurations, the liquid medium may include a non-aqueous solvent, such as a polar solvent or a non-polar solvent. A liquid medium may include a pH buffered solution. A pH buffered solution may be formulated to maintain solution pH within a desired range, for example to maintain stability of a retaining component or a binding component, or to mediate the strength of a binding component binding interaction. A liquid medium may further include one or more salts. Salts in a liquid medium may be added to alter the ionic strength of the liquid medium. Ionic strength may be adjusted to, for example, maintain stability of a retaining component or a binding component, or to mediate the strength of a binding component binding interaction. A probe composition may include an emulsion or colloidal suspension, e.g., a water-in-oil emulsion or an oil-in-water emulsion.

Detectable probes or affinity reagents including nucleic acids (e.g., DNA origami, DNA nanoballs, aptamers) may be provided in compositions that are specifically formulated to maintain nucleic acid stability. In some configurations, detectable probes or affinity reagents that include nucleic acids may be provided in a liquid medium including a magnesium salt (e.g., MgCl$_2$). The magnesium salt may be provided at a sufficient concentration to maintain nucleic acid stability (e.g., base-pair binding, helical structures, etc.). The magnesium salt may have a concentration of at least about 10 mM, 50 mM, 100 mM, 120 mM, 140 mM, 160 mM, 180 mM, 200 mM, 220 mM, 240 mM, 260 mM, 280 mM, 300 mM, 350 mM, 400 mM, 500 mM, or more. Alternatively or additionally, the magnesium salt may have a concentration of no more than about 500 mM, 400 mM, 350 mM, 300 mM, 280 mM, 260 mM, 240 mM, 220 mM, 200 mM, 180 mM, 160 mM, 140 mM, 120 mM, 100 mM, 50 mM, 10 mM, or less.

A liquid medium including a detectable probe or affinity reagent may further include a scavenger species. Scavengers may include any chemical species that is intended to remove a chemically detrimental or damaging species, such as free-radical scavengers, oxygen scavengers, and metal-chelating agents. Possible scavengers in a detectable probe or affinity reagent composition may include species such as hydrazine, ascorbic acid, tocopherol, naringenin, gluta-thione, stannenes, and EDTA. Scavengers may be included in liquid media that are intended for storage of detectable probe or affinity reagent compositions prior to an assay or other mode of use.

In some configurations, a detectable probe or affinity reagent composition that includes a liquid medium may be formulated as a multiphase liquid, such as a water-in-oil emulsion or an oil-in-water emulsion. A multiphase liquid medium may permit localization and/or confinement of detectable probes or affinity reagents before or during a mode of use. For example, the release of detectable probes or affinity reagents may be controlled by the breaking of an emulsion, thereby releasing probes confined within the emulsion. Additionally, multiphase formulations may increase the stability of detectable probes or affinity reagents with mixed chemical characteristics (e.g., hydrophobic and hydrophilic components) or sensitivity to aqueous chemistry (e.g., susceptibility to hydrolysis).

In some configurations, a detectable probe or affinity reagent composition may be formulated to include a competitor species. A competitor species may include an affinity reagent or other molecule that is configured to bind to a binding partner, epitope, or target moiety. A competitor species may be characterized by low affinity for a binding partner, epitope, or target moiety. In some configurations, a competitor species may be characterized by a low affinity for a binding partner, epitope or target moiety that is identical to a binding partner, epitope, or target moiety for a detectable probe or affinity reagent. In other configurations, a competitor species may be characterized by a low affinity for a plurality of binding partners, epitopes, or target moieties (e.g., reduced binding specificity). Without wishing to be bound by theory, a competitor species may include a binding species whose displacement from a binding partner, epitope, or target moiety is driven by an increase in the Gibbs free energy of binding. For example, a competitor species may have a larger binding enthalpy for a binding partner than a detectable probe or affinity reagent, so it is energetically favorable to displace the competitor and bind the probe. Likewise, a competitor species may increase the entropy of a system by dissociating from a binding partner in favor of a detectable probe or affinity reagent. A competitor species may be advantageous for creating tunable avidity in detectable probe or affinity reagent compositions because: 1) a competitor species may thermodynamically encourage the binding of a detectable probe or affinity reagent to a binding partner, epitope, or target moiety, and 2) a competitor species may affect the kinetics of probe binding by offering concentration-dependent competition for a binding partner, epitope, or target moiety. FIGS. 20A-20B depict the use of detectable probe or affinity reagent competition including a binding competitor to encourage binding. FIG. 20A shows the contacting of a binding partner 2010 including an epitope or target moiety 2020 with a detectable probe 2040. The surface of the binding partner 2010 may be bound with a plurality of competitor affinity reagents 2030 that bind non-specifically to the surface. FIG. 20B shows free competitor affinity reagents 2035 that are displaced by the binding of the detectable probe 2040 to the epitope or target moiety 2020. The displacement of the competitor affinity reagents may energetically or entropically encourage the binding of the detectable probe to the binding partner 2010.

Figure 16A:
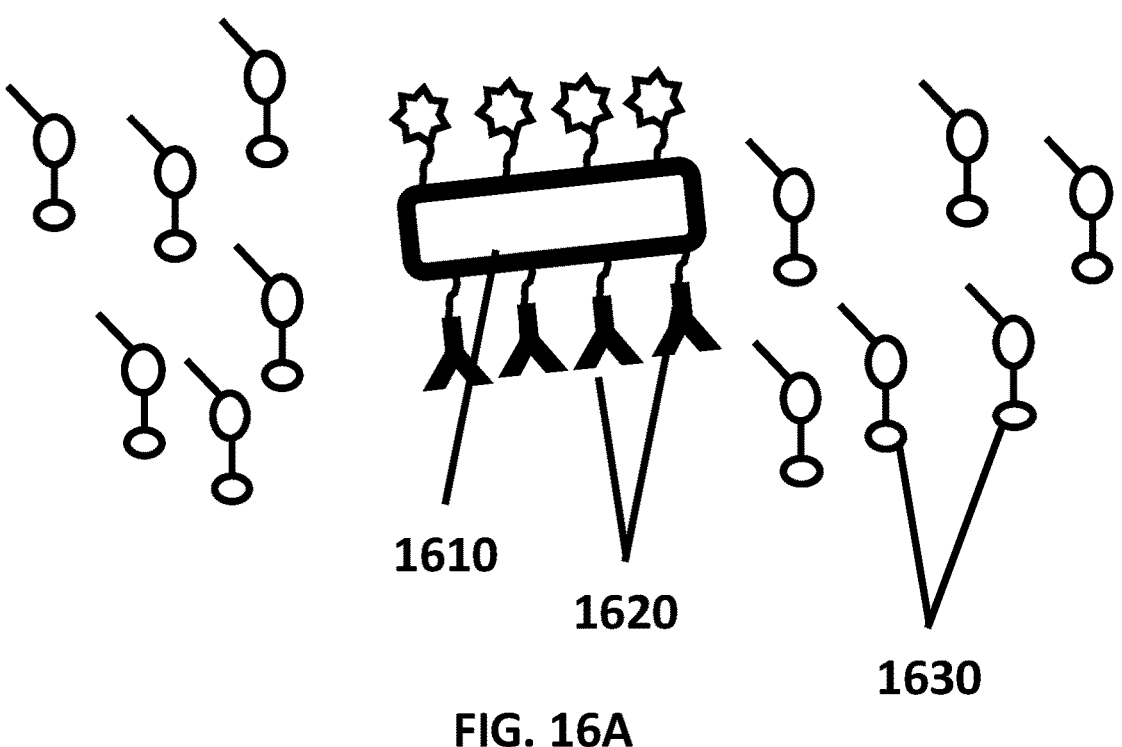
FIG. 16A shows a detectable probe composition including a binding competitor.
Figure 16B:
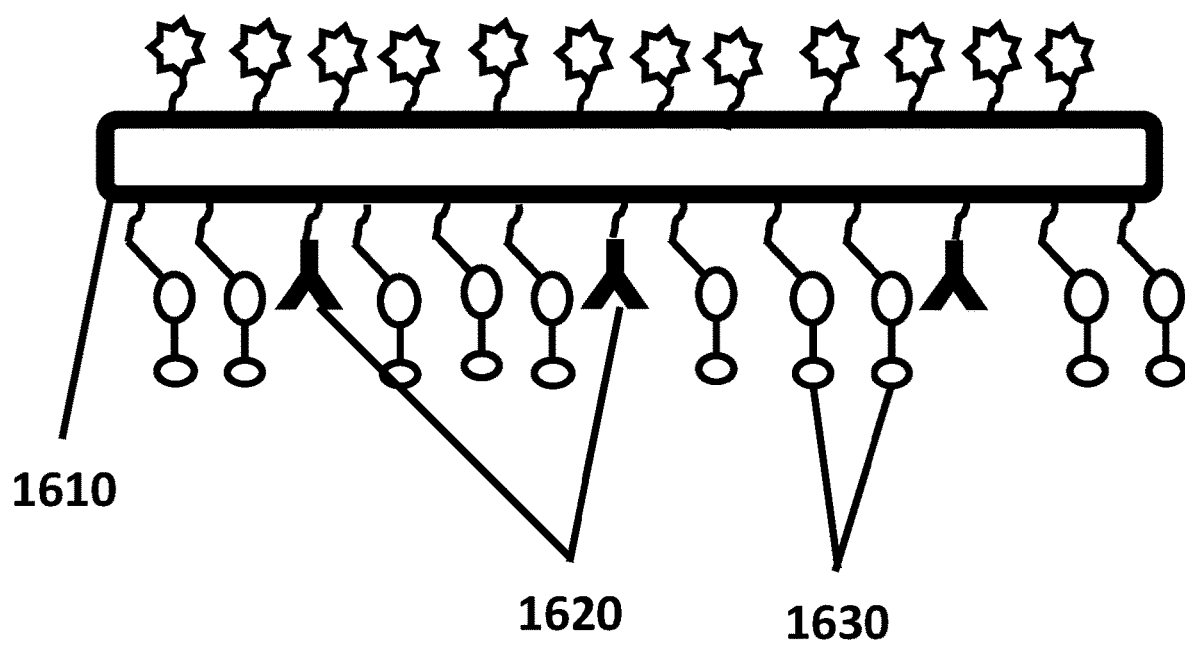
FIG. 16B shows a detectable probe composition including a binding competitor.

A competitor species may include an affinity reagent such as an aptamer, peptamer, designed ankyrin repeat protein (DARPin), antibody, or antibody fragment. A competitor species may be provided as a component of a detectable probe or affinity reagent or as a species that is separate from any detectable probe or affinity reagent. FIG. 16A-16B illustrate detectable probe compositions including a competitor species. FIG. 16A illustrates a detectable probe composition including a competitor species in free solution. The composition includes a detectable probe 1610 that contains a plurality of attached binding components 1620 (e.g., antibodies or antibody fragments). The composition further includes a competitor affinity reagent 1630 (e.g., aptamers) that is free in solution due to being separate from the probe 1610. The competitor species 1630 are able to freely associate with a binding partner, epitope or target moiety, but the competitor species are separable and can dissociate from the binding partner, epitope, or target moiety. FIG. 16B illustrates a detectable probe composition including a competitor component that is attached to the detectable probe. The detectable probe 1610 includes a plurality of attached binding components 1620 (e.g., antibodies or antibody fragments) and a plurality of attached competitor components 1630 (e.g., aptamers). A detectable probe or affinity reagent composition including an attached competitor component may be advantageous for facilitating dissociation of a bound affinity reagent with a slow off-rate due to a net decrease in likelihood of the strongest binder being bonded to a target at any given time.

Alternatively, a competitor species may include a species that competes with a binding partner, epitope, or target moiety to bind the detectable probe or affinity reagent. For example, a competitor species may be a short peptide sequence (e.g., 2-15 amino acid residues) containing a target sequence that is free in solution. The free peptide may be able to competitively bind with a detectable probe or affinity reagent, thereby altering the apparent avidity of a detectable probe or affinity reagent in an analogous fashion to a competitor for binding interactions with a binding partner, epitope, or target moiety.

A competitor species may be present when a detectable probe or affinity reagent is contacted with a binding partner, epitope, or target moiety. A competitor species may be introduced before or after a detectable probe or affinity reagent is contacted with a binding partner, epitope, or target moiety. The ratio of detectable probe or affinity reagent to competitor species in a composition may be adjusted to tailor the avidity characteristics of the composition. A detectable probe or affinity reagent composition may be adjusted to tailor a binding characteristic, such as probe on-rate or off-rate, to achieve a desired level of avidity. A competitor species may be present in a ratio of at least about 1:1000000, 1:100000, 1:10000, 1:1000, 1:100, 1:10, 1:5, 1:2, 1:1, 2:1, 5:1, 10:1, 100:1, 1000:1, 10000:1, 100000:1, 1000000:1 or more relative to the detectable probe or affinity reagent, on a mass or molar basis. Alternatively or additionally, a competitor species may be present in a ratio of no more than about 1000000:1, 100000:1, 10000:1, 1000:1, 100:1, 10:1, 5:1, 2:1, 1:1, 1:2, 1:5, 1:10, 1:100, 1:1000, 1:10000, 1:100000, 1:1000000 or less relative to the detectable probe or affinity reagent, on a mass or molar basis.

The presence of a competitor species, for example, in the form of a competitor component, in a detectable probe or affinity reagent composition, may affect a binding or affinity characteristic of the detectable probe or affinity reagent. The presence of a competitor species, for example, in the form of a competitor component, in a detectable probe or affinity reagent composition may affect an off-rate, on-rate, dissociation constant, or avidity, of the detectable probe or affinity reagent. The presence of a competitor species, for example, in the form of a competitor component, in a detectable probe or affinity reagent composition may increase an off-rate, on-rate, dissociation constant, or avidity, of the detectable probe or affinity reagent. The presence of a competitor species, for example, in the form of a competitor component, in a detectable probe or affinity reagent composition may decrease an off-rate, on-rate, dissociation constant, or avidity, of the detectable probe or affinity reagent. The presence of a competitor species, for example, in the form of a competitor component, may increase or decrease an off-rate, on-rate, dissociation constant, or avidity of the detectable probe or affinity reagent by a factor of at least about 2, 5, 10, 25, 50, 100, 250, 500, 1000, 5000, 10000, 50000, 100000, 500000, 1000000, or more. Alternatively or additionally, the presence of a competitor species, for example, in the form of a competitor component, may increase or decrease an off-rate, on-rate, dissociation constant, or avidity of a detectable probe or affinity reagent by a factor of no more than about 1000000, 500000, 100000, 50000, 10000, 5000, 1000, 500, 250, 100, 50, 25, 10, 5, 2, or less.

A detectable probe or affinity reagent composition may include one or more components that are configured to alter the binding characteristics of the detectable probe or affinity reagent. A component may be added to a detectable probe or affinity reagent composition to increase the on-rate, off-rate, dissociation constant, and/or avidity of the detectable probe or affinity reagent composition. A component may be added to a detectable probe or affinity reagent composition to decrease the on-rate, off-rate, dissociation constant, and/or avidity of the detectable probe or affinity reagent composition. A component may affect the affinity or avidity of a detectable probe or affinity reagent by chemically altering a binding interaction between the detectable probe or affinity reagent and a binding partner, epitope, or target moiety (e.g., altering the conformation of a binding component, weakening the electrostatic interaction between a binding component and a binding partner). A component may affect the affinity or avidity of a detectable probe or affinity reagent by creating a weak secondary binding interaction with the detectable probe or affinity reagent.

A component may be added to a detectable probe or affinity reagent composition to alter the binding interaction between the detectable probe or affinity reagent composition and a binding partner, epitope, or target moiety. The added component may alter a binding interaction by altering the binding partner, epitope, or target moiety, altering the detectable probe or affinity reagent, or by altering the binding interaction between the detectable probe or affinity reagent composition and the binding partner, epitope, or target moiety. An added component may cause a conformational change in a detectable probe or affinity reagent, binding component, and/or binding partner, epitope, or target moiety that increases or decreases the likelihood and/or strength of a binding interaction. An added component may alter a binding interaction, for example by electrostatically screening a binding interaction or competing to form a binding interaction.

A denaturant, surfactant, or chaotropic agent may be added to a detectable probe or affinity reagent composition to alter a binding interaction between the detectable probe or affinity reagent and a binding partner, epitope, or target moiety. A denaturant, surfactant, or chaotropic agent may be added to a detectable probe or affinity reagent composition to alter a binding characteristic of the detectable probe or affinity reagent, such as an on-rate, off-rate, dissociation constant, or avidity. Denaturants, surfactants, or chaotropic agents may facilitate the removal of a detectable probe or affinity reagent from a binding partner, epitope, or target moiety. Denaturants, surfactants, or chaotropic agents may be introduced to a detectable probe or affinity reagent composition after probe binding to facilitate the removal of the detectable probe or affinity reagent from a binding partner, epitope, or target moiety. Binding of a detectable probe or affinity reagent in the presence of a denaturant, surfactant, or chaotropic agent may reduce the on-rate of the detectable probe or affinity reagent when binding to a binding partner, epitope, or target moiety. The concentration of a denaturant, surfactant, or chaotropic agent in a detectable probe or affinity reagent composition may be adjusted to tune an affinity characteristic of the detectable probe or affinity reagent. The concentration of a denaturant, surfactant, or chaotropic agent in a detectable probe or affinity reagent composition may be limited to avoid destabilizing the detectable probe or affinity reagent or a component of the detectable probe or affinity reagent (e.g., a DNA origami component). A denaturant, surfactant, or chaotropic agent in a detectable probe or affinity reagent composition may be combined with heat to facilitate the removal of the detectable probe or affinity reagent from a binding partner, epitope, or target moiety.

A salt, such as a metal salt, may be added to a detectable probe or affinity reagent composition to alter a binding interaction between the detectable probe or affinity reagent and a binding partner, epitope, or target moiety. A salt, or the ionic species including a salt, may form interactions with a detectable probe or affinity reagent or a binding partner, epitope, or target moiety that alter the chemistry of the binding interaction between the detectable probe or affinity reagent and a binding partner, epitope, or target moiety. A salt, or an ionic species including a salt, may disrupt the chemistry of the binding interaction between a detectable probe or affinity reagent and a binding partner, epitope, or target moiety. A salt, or an ionic species including a salt, may facilitate a binding interaction between a detectable probe or affinity reagent and a binding partner, epitope, or target moiety. In some configurations, a salt may be added to a detectable probe or affinity reagent composition to facilitate the removal of the detectable probe or affinity reagent from a binding partner, epitope, or target moiety. A salt in a detectable probe or affinity reagent composition may be combined with heat to facilitate the removal of the detectable probe or affinity reagent from a binding partner, epitope, or target moiety. A salt may be introduced to a detectable probe or affinity reagent composition after probe binding to alter a binding interaction of the detectable probe or affinity reagent with a binding partner, epitope, or target moiety (e.g., to remove a detectable probe or affinity reagent).

A detectable probe or affinity reagent composition may further include a binding molecule that alters the avidity and/or observability of the detectable probe or affinity reagent. A binding molecule may include a molecule that is configured to form a reversible or irreversible binding interaction with a detectable probe or affinity reagent. A binding molecule may form a weak binding interaction with a binding partner, epitope, target moiety, or a detectable probe or affinity reagent to keep the detectable probe or affinity reagent near a possible target, thereby increasing the likelihood that a binding interaction may occur. A binding molecule may include additional label components that increase the signal produced when a binding interaction occurs. Exemplary binding molecules are described elsewhere herein. A binding molecule may be provided to a detectable probe or affinity reagent composition before, during, or after the detectable probe or affinity reagent has been contacted with a binding partner, epitope, or target moiety.

A detectable probe or affinity reagent composition of the present disclosure can be provided in kit form including, if desired, a suitable packaging material. In one embodiment, for example, a detectable probe or affinity reagent composition can include a plurality of detectable probes or affinity reagents, for example, provided in a solution or suspension. In another embodiment, for example, a detectable probe or affinity reagent composition can include a plurality of detectable probes or affinity reagents, for example, provided as a solid, such as crystals or a lyophilized solid. Accordingly, any combination of reagents or components that is useful in a method of the disclosure, such as those set forth herein previously in regard to particular methods, can be included in a kit provided by the disclosure. Without limitation, those reagents or components may include buffers, salts, stabilizers, retaining components, binding components, label components, and competitor affinity reagents. For example, a kit can include a plurality of detectable probes or affinity reagents provided in a storage buffer containing a stabilizing surfactant and an oxygen scavenger.

As used herein, the phrase "packaging material" refers to one or more physical structures used to house the contents of the kit, such as detectable probes, affinity reagents or the like. The packaging material can be constructed by well-known methods, preferably to provide a sterile, contaminant-free environment. The packaging materials employed herein can include, for example, those customarily utilized in affinity reagent systems. Exemplary packaging materials include, without limitation, glass, plastic, paper, foil, and the like, capable of holding within fixed limits a component useful in the methods of the disclosure such as a detectable probe or affinity reagent composition.

The packaging material can include a label which indicates that the detectable probes or affinity reagents can be used for a particular method. For example, a label can indicate that the kit is useful for detecting a particular binding partner, epitope, or target moiety, thereby providing a characterization during a polypeptide assay. In another example, a label can indicate that the kit is useful for a therapeutic or diagnostic purpose.

Instructions for use of the packaged reagents or components are also typically included in a kit of the disclosure. "Instructions for use" typically include a tangible expression describing the reagent or component concentration or at least one assay method parameter, such as the relative amounts of kit components and sample to be admixed, maintenance time periods for reagent/sample admixtures, temperature, buffer conditions, and the like.

A kit or composition can include a plurality of different detectable probes and/or different affinity reagents that differ with respect to the number or type of binding component(s) attached thereto. Alternatively or additionally, a kit or composition can include a plurality of different detectable probes and/or different affinity reagents that are attached to different label components, respectively. The detectable probes or affinity reagents, although differing with respect to the number or type of binding components or with respect to the number or type of label components, can nonetheless have substantially the same type of retaining component. For example, a plurality of different detectable probes and/or different affinity reagents can contain nucleic acid origami-based retaining components wherein the structure of the origami or the structure of a scaffold in the origami is the same for all the different probes and/or agents. A plurality of different detectable probes and/or different affinity reagents can include at least about 2, 3, 4, 5, 10, 25, 50, 100, 250, 500, 1000 or more different detectable probes and/or different affinity reagents. Alternatively or additionally, a plurality of different detectable probes and/or different affinity reagents can include at most about 1000, 500, 250, 100, 50, 25, 10, 5, 4, 3, 2 or fewer detectable probes and/or different affinity reagents.

Methods of Use

Detectable probes or affinity reagents of the present disclosure may be utilized for a broad range of uses, including binding assays. In general, utilization of detectable probes or affinity reagent compositions may involve one or more of the steps of: 1) contacting a detectable probe or affinity reagent with a solution and/or solid support having a binding partner for the detectable probe or affinity reagent; 2) permitting the detectable probe or affinity reagent to bind with the binding partner in the solution or on the solid support; 3) rinsing unbound probes from the solution and/or solid support; 4) observing the solution and/or solid support to detect a signal from one or more detectable probes or affinity reagents; 5) removing one or more bound probes or reagents from the binding partner; 6) optionally repeating one or more of steps 1)-5); and 7) using the presence and/or absence of a signal from one or more probes or reagents to predict the presence and/or absence of the binding partner in the solution and/or on the solid support.

A method of observing binding interactions between detectable probes or affinity reagents and binding partners may be utilized for any of a variety of characterizations. In some cases, a detectable probe or affinity reagent may be utilized to facilitate a polypeptide characterization assay. The assay may be configured to determine or predict one or more characteristics (e.g., size, identity, isotype, etc.) for one or more polypeptides. Alternatively or additionally, the assay may be an assay configured to determine or predict the amount of one or more polypeptides in a sample. A polypeptide characterization assay or quantification assay may be configured for single-molecule detection where one or more polypeptide molecules are individually resolved. For example, in a multiplex format one or more characteristic and/or quantity can be predicted or determined for each polypeptide of a plurality of polypeptides based on detection of the polypeptides individually. In some configurations, a polypeptide assay may include single-molecule characterization or quantification of polypeptides to determine the presence of one or more epitopes (e.g., dimer, trimer, or tetramer amino acid sequences; post-translational modifications, etc.) in a plurality of polypeptides. Detectable probes or affinity reagents may be advantageous for polypeptide characterization assays due to their strong avidity for binding targets and their strong signal output, thereby giving high-confidence binding interaction data.

A polypeptide or other analyte can be attached to a structured nucleic acid particle (SNAP) when bound to an affinity reagent or detectable probe. FIG. 58A shows polypeptide 5840 attached to SNAP 5850. Polypeptide 5840 is an exemplary analyte and can be replaced with other analytes of interest. SNAP 5850 functions as a retaining component for polypeptide 5840 and can be replaced or modified with a retaining component set forth herein in the context of affinity reagents and detectable probes. For example, SNAP 5850 can be a nucleic acid origami or can be replaced with a fluorescent particle. Polypeptide 5840 can be covalently or non-covalently attached to SNAP 5850. Polypeptide 5840 can be contacted with a detectable probe having a SNAP-based retaining component 5810, one or more label components 5820 and one or more binding components 5830. Optionally, SNAP 5810 can be replaced or modified with a retaining component set forth herein in the context of affinity reagents and detectable probes. For example, SNAP 5810 can be a nucleic acid origami or can be replaced with a fluorescent particle. Because polypeptide 5840 is a binding partner for the one or more binding components 5830, a complex is formed. The complex includes SNAP 5850 which is attached to polypeptide 5840 and SNAP 5810 which is attached to one or more binding components 5830, at least one of which is bound to polypeptide 5840, SNAP 5810 also being attached to at least one label component 5820. Optionally, SNAP 5850 can be attached to a solid support such as a site on an array. A SNAP can be attached to a solid support using any of a variety of covalent or non-covalent chemistries including, but not limited to those set forth herein in the context of attaching components of affinity reagents or detectable probes to each other.

In some configurations, a polypeptide assay may include contacting a detectable probe or affinity reagent with a plurality of polypeptides, wherein each polypeptide of the plurality of polypeptides is bound to a solid support at a unique, optically observable spatial location, such as a site in an array of polypeptides. The detection of a signal at a given spatial location may be evidence that a detectable probe or affinity reagent has bound to a polypeptide at the spatial location, thereby suggesting the presence of a particular epitope or target moiety in the polypeptide at the spatial location. The predicted or determined presence or absence of one or more epitopes or target moieties may predict or determine a characteristic for a polypeptide bound at a given spatial location. Moreover, the quantity of a particular polypeptide in a sample can be predicted or determined based on the intensity of signal from a given spatial location and/or based on the number of sites in an array that produce a signal indicating that a particular probe (or series of probes) has bound.

A multiplex binding reaction is shown in FIG. 58B. The reaction is exemplified for polypeptide analytes but can be performed with other analytes known in the art or set forth herein. Polypeptide array 5800 includes four different polypeptides 5841 through 5844. Each of the polypeptides is attached to a SNAP 5851. Attachment can be covalent or non-covalent. Array 5800 is contacted with a plurality of detectable probes. Each of the probes includes a SNAP-based retaining component 5811 attached to at least one label component and at least one binding component. Three different detectable probes are shown including a first probe having SNAP 5811 attached to at least one label moiety 5821 and at least one binding moiety 5831, a second probe having SNAP 5811 attached to at least one label moiety 5822 and at least one binding moiety 5832, and a third probe having SNAP 5811 attached to at least one label moiety 5823 and at least one binding moiety 5833. The product of the binding reaction is binding of the first probe and third probe to respective polypeptides on array 5800. Because polypeptide 5841 is a binding partner for the one or more binding components 5831, a first complex is formed. The first complex includes SNAP 5851 which is attached to polypeptide 5841 and SNAP 5811 which is attached to one or more binding components 5831, at least one of which is bound to polypeptide 5841, SNAP 5811 also being attached to at least one label component 5821. Because polypeptide 5843 is a binding partner for the one or more binding components 5833, a second complex is formed on array 5800. The first complex includes SNAP 5851 which is attached to polypeptide 5843 and SNAP 5811 which is attached to one or more binding components 5833, at least one of which is bound to polypeptide 5843, SNAP 5811 also being attached to at least one label component 5823. In this example, polypeptides 5842 and 5844 remain unbound since they are not binding partners with any of the detectable probes. Also the third detectable probe, which includes SNAP 5811 attached to at least one binding component 5832 and at least one label component 5822, does not have a binding partner on array 5800 and remains unbound. The first and second detectable probes can be detected on the array where they are spatially resolved and where they can be further distinguished and identified based on their different label types. Accordingly, signals detected from the array sites can be used to identify the polypeptides based on knowledge of the binding properties for each detectable probe and the label type associated with each detectable probe.

In the example of FIG. 58B, the polypeptides although separated into individual sites on array 5800, are attached to SNAPs having a common structure. For example, SNAP 5851 can be a nucleic acid origami and the polypeptides can be attached to origami having the same scaffold fold as each other. A subset of one or more staples in the origami can differ between the origamis, for example, to accommodate attachment of the different polypeptides. The use of a common SNAP structure, or other retaining component for that matter, can provide convenient loading of the polypeptides on the array. For example, the array can be configured to have uniform sites that interact with uniform structural elements of the SNAPs to achieve attachment of the polypeptides to the array. A common retaining component structure can also be used for a plurality of different detectable probes or a plurality of different affinity reagents. As exemplified in FIG. 58B, the three detectable probes differ with respect to the label components and binding components that are attached to SNAP 5811. However, the three affinity probes have substantially the same SNAP structure. For example, SNAP 5811 can be a nucleic acid origami having the same scaffold fold for each of the three detectable probes. A subset of one or more staples in the origami can differ between the different detectable probes, for example, to accommodate attachment of different label components or different binding components. Although FIG. 58B is exemplified with common SNAPs attached to different analytes and common SNAPs attached to different detectable probes, it will be understood that the SNAPs can differ in structure instead. Moreover, the SNAPs can include sequence tags that differ from one detectable probe to another or that differ from one polypeptide to another. The tags can be used to identify individual probes in a mixture or to identify individual polypeptides in an array.

Arrays can be used for multiplex processing of analytes, whereby the multiple different types of analytes are manipulated or detected in parallel. Particularly useful analytes include, but are not limited to, binding partners for affinity reagents set forth herein, such as polypeptides, nucleic acids, or the like. Although it is also possible to serially process different types of analytes using one or more steps of the methods set forth herein, parallel processing can provide cost savings, time savings and uniformity of conditions. An array can include at least 2, 10, 100, 1000, $1 \times 10^4$, $1 \times 10^5$, $1 \times 10^6$, $1 \times 10^7$, $1 \times 10^8$, $1 \times 10^9$, or more different analyte sites. Alternatively or additionally, an array can include at most $1 \times 10^9$, $1 \times 10^8$, $1 \times 10^7$, $1 \times 10^6$, $1 \times 10^5$, $1 \times 10^4$, 1000, 100, 10, 2 or fewer, different analyte sites. The different analytes may optionally be attached to the sites via structured nucleic acid particles or retaining components that have common structures. As such, sites of an array can be attached to structured nucleic acid particles or retaining components having substantially the same structure as each other, and each of the structured nucleic acid particles or retaining components in the array can be attached to a different analyte.

An array can be attached to an inner surface of a flow cell wall or to a solid support inside of a flow cell. The flow cell or solid support can be made from any of a variety of materials used for analytical biochemistry. Suitable materials may include glass, polymeric materials, silicon, quartz (fused silica), borofloat glass, silica, silica-based materials, carbon, metals, an optical fiber or bundle of optical fibers, sapphire, or plastic materials. The material can be selected based on properties desired for a particular use. For example, materials that are transparent to a desired wavelength of radiation are useful for analytical techniques that will utilize radiation at that wavelength. Conversely, it may be desirable to select a material that does not pass radiation of a certain wavelength (e.g. being opaque, absorptive or reflective). Other properties of a material that can be exploited are inertness or reactivity to certain reagents used in a downstream process, such as those set forth herein, or ease of manipulation, or low cost of manufacture.

A polypeptide or other analyte can be attached to a support in a way that provides detection at a single molecule level. For example, a plurality of different polypeptides can be attached to a solid support in a way that an individual detectable probe or affinity reagent that binds to an individual polypeptide site on the support can be distinguished from all neighboring sites on the array even if the neighboring sites bind to detectable probes or affinity reagents. As such, one or more different polypeptides (or other binding partners for detectable probes or affinity reagents set forth herein) can be attached to a solid support in a format where each single polypeptide molecule is physically isolated and detected in a way that the single molecule is resolved from all other molecules on the solid support. Alternatively, a method of the present disclosure can be carried out for one or more ensembles, an ensemble being a population of analytes of substantially the same type such as a population of nucleic acids or polypeptides having a common sequence.

Figure 22:
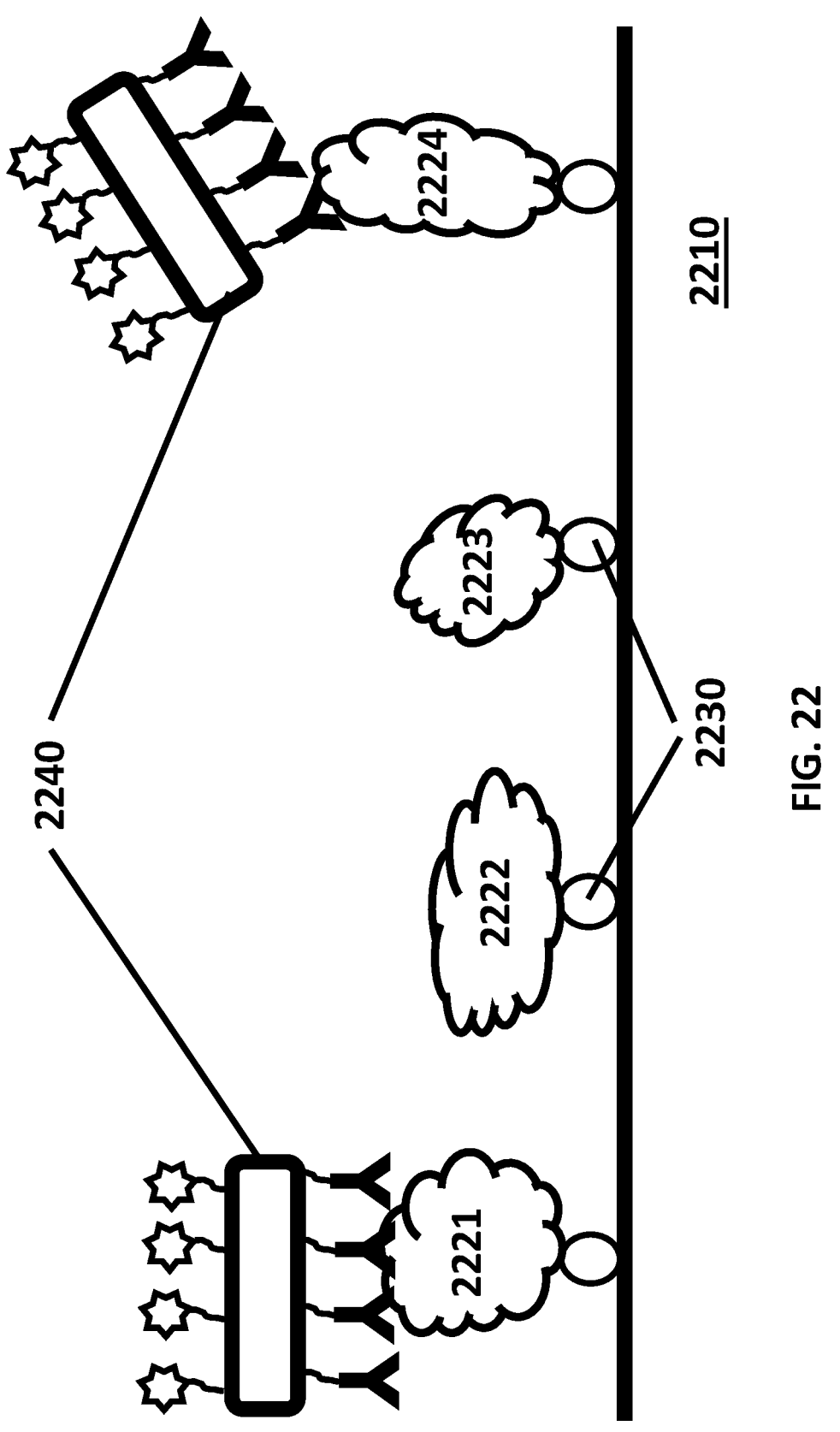
FIG. 22 shows the use of detectable probes for characterization of a plurality of binding partners.

FIG. 22 illustrates a configuration of a polypeptide assay. A plurality of polypeptides is bound to a solid support 2210, optionally by anchoring groups 2230 (e.g. SNAP or chemical linker). Detectable probes 2240 are contacted with the plurality of polypeptides, permitting detectable probes 2240 to bind with available binding targets. After the contacting, detectable probes 2240 have bound to the first polypeptide 2221 and the fourth polypeptide 2224, and have not bound to the second polypeptide 2222 or the third polypeptide 2223. If observed by an appropriate detection system, such as a fluorescent microscope, a detectable signal may be observed at spatial locations on the solid support 2210 corresponding to the location of the first polypeptide 2221 and the fourth polypeptide 2224.

Polypeptides may be of natural or synthetic origin. Polypeptides may contain one or more post-translational modifications. Alternatively or additionally, one or more post-translational modifications can be absent from a polypeptide. In some cases, polypeptides may be treated to remove, reverse or alter post-translational modifications. For example, a polypeptide assay set forth herein can be performed to detect one or more polypeptides before and after removing, reversing or altering post-translational modifications. Comparing the before and after results can provide benefits such as increased confidence in identifying the number or type of post-translational modifications for a polypeptide. In some cases, polypeptides may be treated to produce post-translationally modified. For example, a polypeptide assay set forth herein can be performed to detect one or more polypeptides before and after making post-translational modifications. Conversely, a polypeptide assay set forth herein can be performed to detect one or more polypeptides before and after removing post-translational modifications. Comparing the before and after results can provide benefits such as identifying the number or type of post-translational modifications or post-synthesis modifications to which a polypeptide is susceptible. In some cases, polypeptides may be proteolyzed to remove at least a portion of the polypeptide. For example, a polypeptide assay set forth herein can be performed to detect one or more polypeptides before and after proteolysis. Comparing the before and after results can provide benefits such as locating an epitope or target moiety in a polypeptide relative to the location of proteolytic site in the polypeptide. A further benefit of comparing the before and after results can be easier identification of the number or type of post-translational modifications in a polypeptide that is susceptible to proteolysis.

Post-translational modifications may include myristoylation, palmitoylation, isoprenylation, prenylation, farnesylation, geranylgeranylation, lipoylation, flavin moiety attachment, Heme C attachment, phosphopantetheinylation, retinylidene Schiff base formation, dipthamide formation, ethanolamine phosphoglycerol attachment, hypusine, beta-Lysine addition, acylation, acetylation, deacetylation, formylation, alkylation, methylation, C-terminus amidation, arginylation, polyglutamylation, polyglyclyation, butyrylation, gamma-carboxylation, glycosylation, glycation, polysialylation, malonylation, hydroxylation, iodination, nucleotide addition, phosphoate ester formation, phosphoramidate formation, phosphorylation, adenylylation, uridylylation, propionylation, pyrolglutamate formation, S-glutathionylation, S-nitrosylation, S-sulfenylation, S-sulfinylation, S-sulfonylation, succinylation, sulfation, glycation, carbamylation, carbonylation, isopeptide bond formation, biotinylation, carbamylation, oxidation, reduction, pegylation, ISGylation, SUMOylation, ubiquitination, neddylation, pupylation, citrullination, deamidation, elminylation, disulfide bridge formation, proteolytic cleavage, isoaspartate formation, racemization, and protein splicing. A particularly interesting and useful post-translational modification is proteolysis which may be site-specific (i.e. occurring at particular amino acid residues or amino acid sequences) or non-site specific. Post-translational modifications can be reversed or removed from a polypeptide using biological enzymes, chemical agents, or physical manipulations such as those known to those skilled in the art. Polypeptides can be modified post-translationally using biological enzymes, chemical agents, or physical manipulations such as those known to those skilled in the art.

Characterized polypeptides may be of a particular size. A polypeptide may be at least about 0.1 Daltons (Da), 0.5 Da, 1 Da, 5 Da, 10 Da, 50 Da, 100 Da, 200 Da, 300 Da, 400 Da, 500 Da, 600 Da, 700 Da, 800 Da, 900 Da, 1 kiloDalton (kDa), 1.5 kDa, 2 kDa, 2.5 kDa, 3 kDa, 3.5 kDa, 4 kDa, 4.5 kDa, 5 kDa, 6 kDa, 7 kDa, 8 kDa, 9 kDa, 10 kDa, 15 kDa, 20 kDa, 25 kDa, 30 kDa, 40 kDa, 50 kDa, 60 kDa, 70 kDa, 80 kDa, 90 kDa, 100 kDa, 200 kDa, 300 kDa, 400 kDa, 500 kDa, 600 kDa, 700 kDa, 800 kDa, 900 kDa, 1000 kDa, 1200 kDa, 1400 kDa, 1600 kDa, 1800 kDa, 2000 kDa, 2500 kDa, 3000 kDa, 3500 kDa, 4000 kDa, or more. Alternatively or additionally, a polypeptide may be no more than about 4000 kDa, 3500 kDa, 3000 kDa, 2500 kDa, 2000 kDa, 1800 kDa, 1600 kDa, 1400 kDa, 1200 kDa, 1000 kDa, 900 kDa, 800 kDa, 700 kDa, 600 kDa, 500 kDa, 400 kDa, 300 kDa, 200 kDa, 100 kDa, 90 kDa, 80 kDa, 70 kDa, 60 kDa, 50 kDa, 40 kDa, 30 kDa, 25 kDa, 20 kDa, 15 kDa, 10 kDa, 9 kDa, 8 kDa, 7 kDa, 6 kDa, 5 kDa, 4.5 kDa, 4 kDa, 3.5 kDa, 3 kDa, 2.5 kDa, 2 kDa, 1.5 kDa, 1 kDa, 900 Da, 800 Da, 700 Da, 600 Da, 500 Da, 400 Da, 300 Da, 200 Da, 100 Da, 50 Da, 10 Da, 5 Da, 1 Da, 0.5 Da, or less. A polypeptide may contain a minimum or maximum number of amino acid residues. A polypeptide may contain at least about 2, 3, 4, 5, 6, 7, 8, 9, 10, 15, 20, 25, 30, 35, 40, 45, 50, 60, 70, 80, 90, 100, 125, 150, 200, 250, 300, 400, 500, 600, 700, 800, 900, 1000, 1500, 2000, 3000, 4000, 5000, 6000, 7000, 8000, 9000, 10000, 15000, 20000, 30000, 40000 or more amino acid residues. Alternatively or additionally, a polypeptide may contain no more than about 40000, 30000, 20000, 15000, 10000, 9000, 8000, 7000, 6000, 5000, 4000, 3000, 2000, 1500, 1000, 900, 800, 700, 600, 500, 400, 300, 200, 250, 200, 150, 125, 100, 90, 80, 70, 60, 50, 45, 40, 35, 30, 25, 20, 15, 10, 9, 8, 7, 6, 5, 4, 3, or less amino acid residues.

A polypeptide assay may involve one or more fluid transfer operations, including fluids containing detectable probes or affinity reagents, and fluids that mediate binding interactions involving detectable probe or affinity reagents (e.g., rinse fluids, removal reagents). A fluid transfer operation may occur when a fluid is transferred into or transferred out of a fluidic device, such as a flow cell or chip. A polypeptide characterization assay may require that a plurality of polypeptides bound to a solid support be in contact with a fluid medium at all time. Fluid transfer operations may utilize a second fluid medium to displace a first fluid medium from a flow cell to ensure the presence of fluid in contact with the solid support including a plurality of polypeptides at all times.

A sample may be provided to a polypeptide detection system or method. A sample may be provided as a fraction, for example, including a plurality of polypeptides or other analytes. A sample may be provided as a fraction including a plurality of polypeptide conjugates or other analyte conjugates. An analyte conjugate may include the analyte (e.g. a polypeptide analyte) attached to a solid support directly or via a linker moiety such as a structured nucleic acid particle, polymer, or protein moiety. A sample may be provided to a detection system or method in a liquid medium (e.g., an aqueous, pH buffering medium). A sample may be provided to a detection system or method as a solid (e.g., a lyophilized, precipitated, or crystallized sample). A solid may be dissolved or suspended in a liquid medium before, during or after being added to a detection system or method. A sample may be stored in a detection system after being provided to the system.

A sample including polypeptides or other analytes may be bound to a solid support in a fluidic device. A fluid including the sample may be pumped or flowed through a fluidics system to a detection chamber, such as a flow cell or well, including a solid support within a fluidics device. The fluid including the sample may be contacted to the solid support for a sufficient amount of time to attach the analytes to the solid support. Optionally the analytes can be conjugated to a substance, such as a structured nucleic acid particle, that mediates attachment of the analyte to the solid support. In some cases, additional fluids may be mixed with sample fluid to facilitate the binding of the analytes to the solid support. If a sample includes polypeptides, a solid support may first be contacted with a fluid including polypeptide linking groups (e.g., structured nucleic acid particles, polymers, proteins) for a sufficient amount of time to deposit the polypeptide linking groups on the surface of the solid support. After the solid support has been deposited with polypeptide linking groups, a fluid medium including the sample may be pumped or flowed into the detection chamber containing the solid support in the fluidic device. An attachment reaction between the polypeptides and the polypeptide linking groups may be allowed to occur for a sufficient amount of time to attach the polypeptides to the linking groups. One or more reagents may be added to the fluidic device to facilitate a polypeptide attachment reaction, such as reactants and/or catalysts. In some cases, polypeptides and polypeptide linking groups may be configured to react via a spontaneous attachment reaction, such as a "click" reaction. In some cases, polypeptides may be directly attached to a solid support, for example by a bond between a functional group on the polypeptide and a functional group on the solid support. After an attachment reaction, the solid support will include one or more polypeptides bound to the solid support.

After analytes (e.g. polypeptides) have been attached to a solid support, for example within a fluidic device, the detection chamber of the fluidic device may be rinsed one or more times. A rinsing process may utilize one or more washing or rinsing reagents that are pumped or flowed into the fluidic device, either together or in succession. A volume of rinsing fluid provided to the fluidic device may exceed the total volume of the detection chamber including the solid support. The rinsing step may remove some or all unbound polypeptides, polypeptide conjugates, or other reagents. The flow rate of rinsing fluid to the fluidic device may be limited to prevent the dislodging of attached analytes from the solid support.

Optionally, attached analytes (e.g. conjugated polypeptides) may be subjected to one or more processes that alter the structure of the analytes. For example polypeptide analytes may be partially or fully denatured, for example, by the addition of a denaturing fluid to the fluidic device. A denaturing fluid may be contacted to the solid support for a sufficient time to promote full denaturation of a polypeptide, or may be briefly contacted to the solid support to cause partial denaturation of a polypeptide. Polypeptides may also be altered by the application of altering reagents to the solid support, for example enzymes (ligases, kinases, glycosylases, phosphatases, proteases, etc.), oxidants, or reductants. A fluidic device may undergo a rinsing process after the addition of a structure-altering reagent, thereby removing residual reagent from the fluidic device. In some cases, the solid support may be held in contact with an altering agent (e.g., a denaturant) until an affinity reagent is introduced to the fluidic device. In some cases, a polypeptide may partially or fully re-fold after a structure-altering processes.

An affinity reagent may be contacted with a solid support including a plurality of polypeptides (e.g. an array of polypeptides) or other analytes, for example, in a fluidic device. In some configurations, an affinity reagent may be provided as a detectable probe or affinity reagent. Affinity reagents such as detectable probes may be provided in a fluidic medium that is pumped or flowed into a fluidic device. A fluidic medium may include a single species of affinity reagent or detectable probe, or may include a mixture of differing species of affinity reagents or detectable probes. For example, a fluidic medium may include at least two detectable probes or affinity reagents with differing epitope-binding specificities. Or, a fluidic medium may include at least two detectable probes or affinity reagents that are different types of detectable probes or affinity reagents, e.g., 1 aptamer probe and 1 antibody probe. Affinity reagents or detectable probes may be contacted to a solid support in a fluidic device for a sufficient amount of time to promote binding of an affinity reagent or a detectable probe to an epitope or target moiety that is present in at least one analyte (e.g. an amino acid sequence epitope in a polypeptide).

Affinity reagents or binding components that are utilized in a binding assay may be distinguished by the nature of their binding specificity. In particular, an affinity reagent may have an epitope binding specificity that has been characterized in a probabilistic fashion. Rather than being characterized in a binary fashion (e.g., affinity reagent A binds to epitope X, does not bind to epitope Y), an affinity reagent of the present disclosure may be characterized by a plurality of binding probabilities. For example, over the 8000 possible trimer amino acid sequences (20×20×20), a non-zero binding probability for an affinity reagent may be known, measured, or estimated for some or all of the 8000 sequences. In some cases, an affinity reagent may be useful to the present disclosure if it has a high known, measured, or estimated binding probability for a first epitope (e.g., greater than 50%, 55%, 60%, 65%, 70%, 75%, 80%, 85%, 90%, 95%, 99%, 99.9%, 99.99%, 99.999% or higher probability of binding), and a low known, measured, or estimated binding probability for a second epitope (e.g., less than 1%, 0.1%, 0.01%, 0.001%, 0.0001%, 0.00001%, 0.000001% or lower probability of binding). In some cases, an affinity reagent may include high known, measured, or estimated binding probabilities for a family of epitopes (e.g., greater than 50%, 55%, 60%, 65%, 70%, 75%, 80%, 85%, 90%, 95%, 99%, 99.9%, 99.99%, 99.999% or higher probability of binding), and low known, measured, or estimated binding probabilities for other epitopes (e.g., less than 1%, 0.1%, 0.01%, 0.001%, 0.0001%, 0.00001%, 0.000001% or lower probability of binding). Families of epitopes may include epitopes related by amino acid sequence (e.g., amino acid sequences AXA, where A is alanine and X may be any amino acid; amino acid sequences αAAAβ, where α and β are independently any possible amino acid flanking sequences) or may be related by chemical properties (e.g., non-polar, polar, positively charged, negatively charged, post-translational modifications, etc.).

After an affinity reagent, such as a detectable probe, has been given sufficient time to bind to an analyte (e.g. a polypeptide analyte) in a fluidic device, a detection chamber of the device may undergo one or more washes or rinses to remove any unbound affinity reagents. A polypeptide characterization assay may only utilize a single rinse step after affinity reagent binding to minimize the likelihood of an analyte-affinity reagent interaction becoming disrupted. An affinity reagent rinse fluid may be displaced from a fluidic device after a rinsing process by a medium that is configured for performing physical measurement, such as an optical imaging buffer.

An analyte:affinity reagent or analyte:probe interaction may be measured after affinity reagents or detectable probes have been contacted with a plurality of analytes bound to a solid support. Physical measurements, such as detection of label components of detectable probes, may occur under quiescent fluid conditions. A fluid may be held static in a fluid by isolating all inlet and outlet ports, for example by the closing of valves. A fluid may be held in the fluidic device for a sufficient amount of time to permit imaging of one, some or all unique, optically observable spatial locations.

After binding and/or physical measurements of analyte:affinity reagent or analyte:probe interactions have occurred, bound affinity reagents or detectable probes may be stripped from the analytes by the addition of a disrupting medium to the fluidic device. The disrupting medium may include a denaturant, chaotrope, or other chemical entity that is likely to disrupt an analyte:affinity reagent or analyte:probe interaction. The disrupting medium may be contacted with the analytes under quiescent or flowing conditions. After a disrupting medium has been contacted with the analytes, the fluidic device may be rinsed or washed with a rinsing medium one or more times to remove any unbound affinity reagents or unbound detectable probes from the fluidic device.

In some cases, analytes (e.g. polypeptide analytes) may be removed from the surface of a solid support during or after a binding measurement. For example, a plurality of polypeptides may be characterized to determine which polypeptides are glycosylated, followed by the release from the solid support of all non-glycosylated polypeptides. In some cases, all analytes may be released from the solid support after a characterization assay is complete to permit reuse of the fluidic device. An analyte or analyte-conjugate may be released from a solid support by the addition of a stripping fluid. The stripping fluid may provide a more stringent wash than other rinse mediums utilized during the characterization assay such that it causes displacement of analytes from the solid support. Displacement of analytes from a solid support may also utilize physical conditions such as heat or light, for example, by severing a photoactivatable linker between an analyte and solid support.

During or following the displacement of analytes from a solid support, a rinsing medium may flow through the fluidic device to remove displaced analytes. A solid support may be subsequently observed by a physical measurement method to determine or confirm the displacement of analytes from the surface.

Regardless of the specificities described above, in some cases, one may identify a particular polypeptide analyte based upon a series of observations of different probes that either bind or don't bind to that protein. Such series may be evaluated using software algorithms that utilize probabilistic modeling to evaluate probabilities of given series being identifying of given proteins or polypeptides. In a multiplexed configuration, a plurality of different polypeptides can be observed for a pattern of binding and non-binding. For example, the proteins can be displayed in an array, the array composed of individually resolvable sites, each site having one of the polypeptides. A series of observations can be made for each site as to whether different probes either bind or don't bind. The identity of the polypeptide at each site can be determined from the series of observations at each site. The overall pattern for the series of observations at each site can be useful for identifying multiple polypeptides across the array. Examples of software algorithms, methods and compositions that are useful for identifying proteins are described, for example, in published International Patent Application No. WO 2019/133892, U.S. Pat. No. 10,473,654, or US Pat. App. Pub. No. 2020/0286584 A1, each of which is incorporated herein by reference.

In some cases, detection, identification or characterization of polypeptides may utilize affinity reagents set forth herein. Affinity reagents of the present disclosure may be promiscuous or broad-spectrum affinity reagents that possess a likelihood to interact with (e.g., bind to) more than one polypeptide in a sample. In some cases, the affinity reagents may possess a likelihood to interact with two or more unique, structurally dissimilar proteins in a sample. For example, an affinity reagent may bind with near-equal probability to a particular membrane protein and a particular cytoplasmic protein based upon a region of structural similarity within otherwise dissimilar proteins. In some cases, a binding affinity reagent may possess a likelihood of binding to a particular amino acid epitope or family of epitopes regardless of the sequence context (e.g., amino acid sequence upchain and/or downchain from the epitope).

An affinity reagent of the present disclosure may be characterized such that it has an identified, determined, or assessed probability-based binding profile. An affinity reagent may have the property of binding to a first polypeptide with an identified, determined, or assessed binding probability of greater than about 50% (e.g., at least about 50%, 60%, 70%, 80%, 90%, 95%, 99%, 99.9%, 99.99%, 99.999% or greater than about 99.999%) and binding to a second structurally non-identical polypeptide with an identified, determined, or assessed binding probability of less than about 50% (e.g., no more than about 50%, 40%, 30%, 20%, 10%, 5%, 1%, 0.1%, 0.01%, 0.001% or less than about 0.001%). In a particular case, the difference in observed binding probabilities of the affinity reagent to the first and second polypeptides may be due to the presence, absence, or inaccessibility of a particular epitope or family of epitopes in either the first or second polypeptide. Probabilistic affinity reagent binding profiles may be determined or identified by in vitro measurements or in silico predictions.

Alternative and Additional Embodiments and Examples

The skilled person will readily recognize the usefulness of the detectable probes and affinity reagents of the present disclosure, including for example, their tunable avidity and observability characteristics. The detectable probe or affinity reagent compositions of the present disclosure may be useful for providing high-resolution spatial characterizations in micro-scale and single-molecule systems and contexts. The described detectable probes or affinity reagents may also provide useful characteristics for biological contexts, such as diagnostic and therapeutic applications.

A detectable probe or affinity reagent of the present disclosure may facilitate immunohistochemistry for purposes such as the elucidation of cellular and tissue structures. Detectable probes or affinity reagents may be attached to a plurality of binding components with high specificity for particular cellular components (e.g., surface biomarkers, polysaccharides, structural proteins, organelle proteins, etc.). Detectable probes or affinity reagents may be directly contacted to cellular (e.g., microorganisms) or tissue samples (e.g., tissue sections, frozen tissue samples, formalin-fixed paraffin-embedded samples) and incubated for a sufficient time to permit binding interactions between detectable probes or affinity reagents and cellular or tissue-related targets to form treated cellular or tissue samples. The treated cellular or tissue samples may be directly observed by any suitable method (probe dependent—e.g., fluorescence microscopy, scintillation counting, etc.). The detectable probes or affinity reagents may be advantageous for immunohistochemistry applications due to the high binding avidity and high observability of the detectable probes or affinity reagents. Analysis of binding data may provide high-resolution, spatial data on biomarker or biomolecule quantity and distribution in cellular and/or tissue samples.

A detectable probe or affinity reagent may be utilized as a pull-down or capture reagent. The high binding avidity may facilitate the capture and retention of targeted species from a heterogeneous mixture of species. An affinity reagent may be free in solution or may be attached to a solid support (e.g., a bead, chip or chromatography resin) during or after binding to a binding partner. Contacting of an affinity reagent with a heterogeneous mixture that may include a binding partner may permit separation of the binding partner from at least one other component of the mixture. For example, an affinity reagent that is attached to a solid support can be contacted with a sample to allow a binding partner to be bound to the solid support via the affinity reagent, the solid support can be separated from the sample, and the solid support can optionally be washed to remove residual sample components from the solid support. In another example, an affinity reagent can be contacted with a sample to allow a binding partner to be bound to the affinity reagent, the resulting affinity reagent-binding partner complex can be attached to a solid support, the solid support can be separated from the sample, and the solid support can optionally be washed to remove residual sample components from the solid support. In either example, subsequent collection and isolation of the affinity reagent or release of the binding partner can effect a separation of the binding partner from the sample (e.g. heterogeneous mixture). Optionally, one or more binding partners that are captured by an above method can then be detected in a detection assay set forth elsewhere herein. For example, a subset of different polypeptides can be captured from a sample such that other polypeptides from the sample are removed and then the subfraction of polypeptides can be quantified or characterized using a polypeptide assay set forth herein.

A detectable probe or affinity reagent may be utilized as a component within a separation system, such as an affinity chromatography column. An affinity chromatography system may be formulated to attach a plurality of detectable probes or affinity reagents with a particular affinity for one or more binding partners, epitopes, or target moieties within a porous matrix or resin. Taking polypeptides as an exemplary analyte, a mixture including polypeptides (e.g., a cellular lysate, a sample of synthetic proteins or peptides, a non-biological sample containing possible biological contamination, etc.) may be applied to a column including detectable probes or affinity reagents to affect a separation between the targeted polypeptides (e.g., those including a binding partner, epitope, or target moiety) and non-targeted polypeptides. A detectable probe or affinity reagent affinity chromatography system may include a resin or matrix that permanently or irreversibly conjugates the detectable probes or affinity reagents to the resin or matrix, thereby permitting reuse of the system. Captured polypeptides may be eluted from a column after the non-targeted fraction of the mixture has passed out of the column. A detectable probe or affinity reagent affinity chromatography system may include a resin or matrix that reversibly attaches the detectable probes or affinity reagents to the resin or matrix, thereby permitting release of detectable probes or affinity reagents including captured targets from the system. In some cases, an affinity chromatography system may include a detection system (e.g., fluorescence measurement, IR, UV) that permits detection of a signal from a detectable probe or affinity reagent as the probe elutes from the system. The detection system may permit measurement of background or unintended release of detectable probes or affinity reagents from a resin or matrix, as well as monitoring intended release of detectable probes or affinity reagents from a matrix or resin. After capture of target polypeptides from a mixture, polypeptides may be eluted from the system by release of the detectable probes or affinity reagents. In some cases, released detectable probe-polypeptide complexes (or affinity reagent-polypeptide complexes) may be collected then deposited on a solid support for a polypeptide assay, such as a polypeptide characterization assay or a binding ligand assay.

Figure 17A:
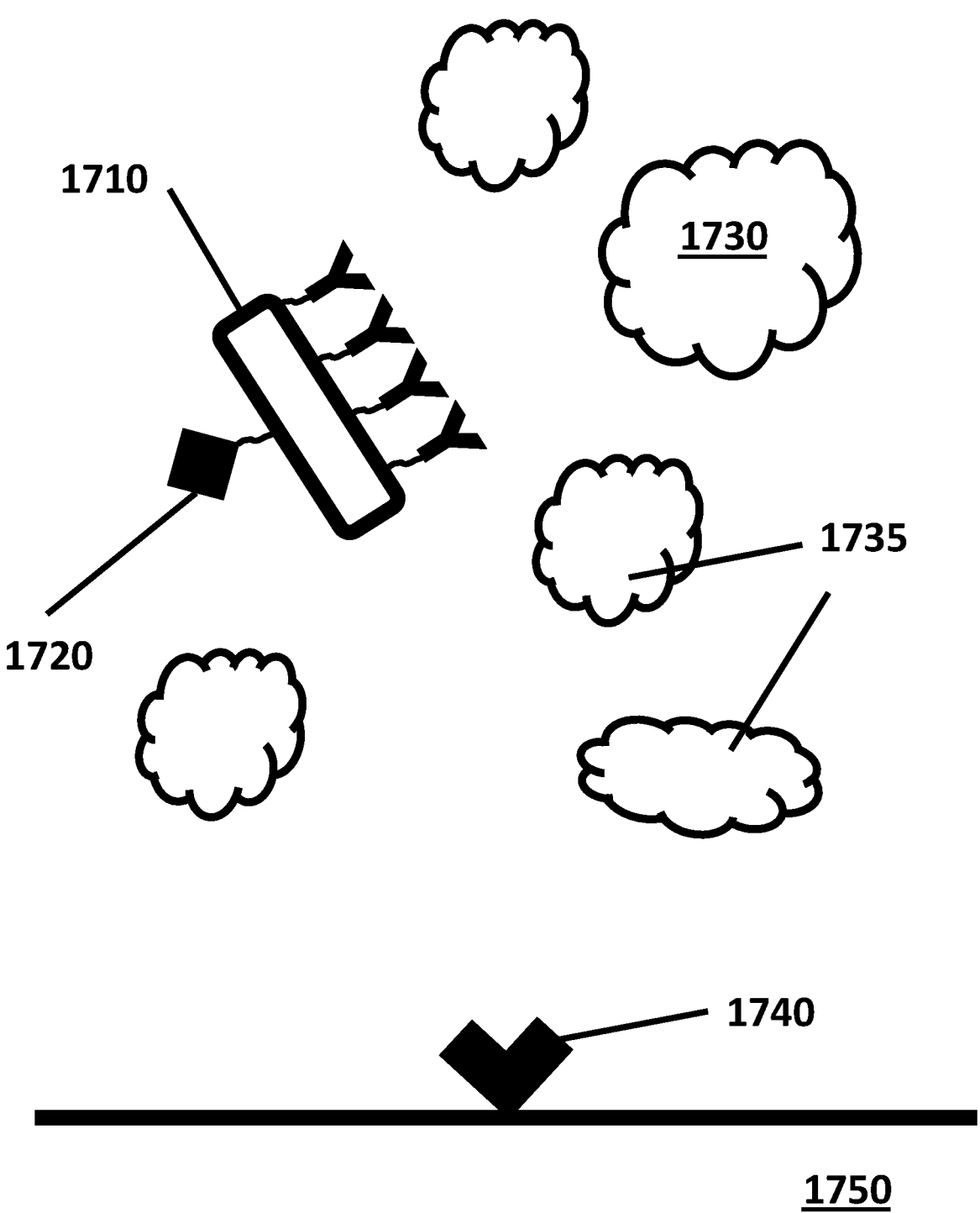
FIG. 17A shows a method of utilizing a detectable probe or affinity reagent as a capture agent.
Figure 17B:
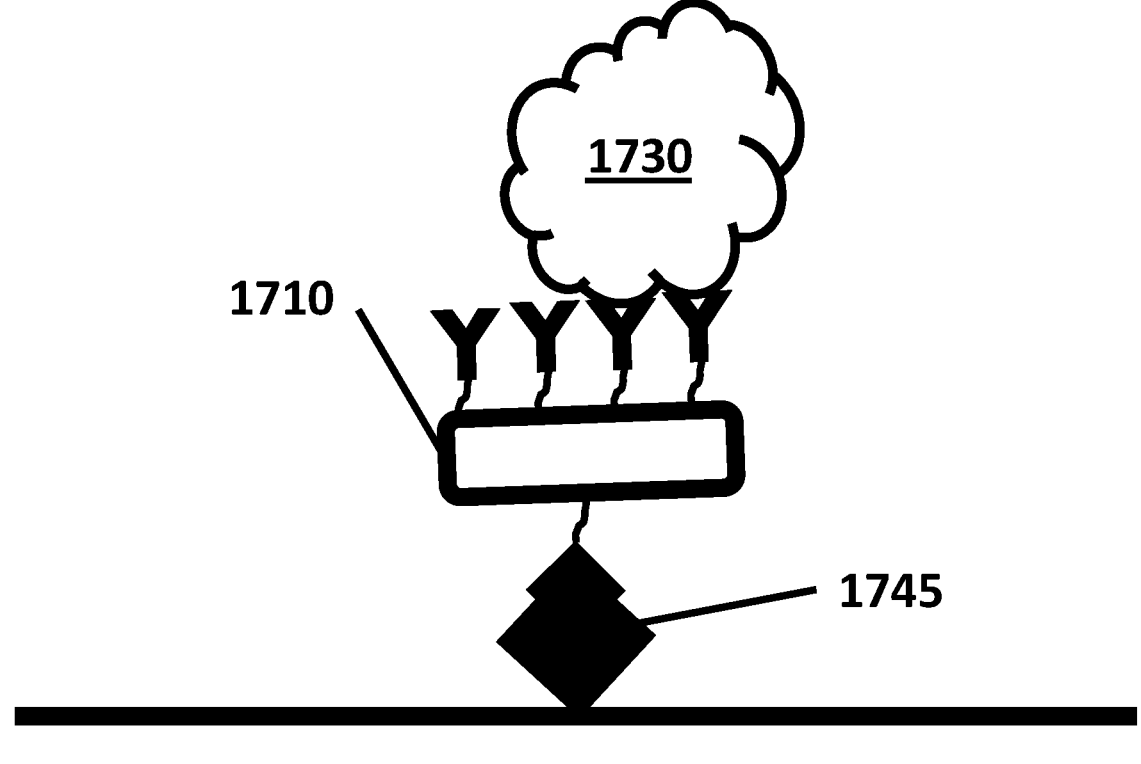
FIG. 17B shows a method of utilizing a detectable probe or affinity reagent as a capture agent.
Figure 17C:
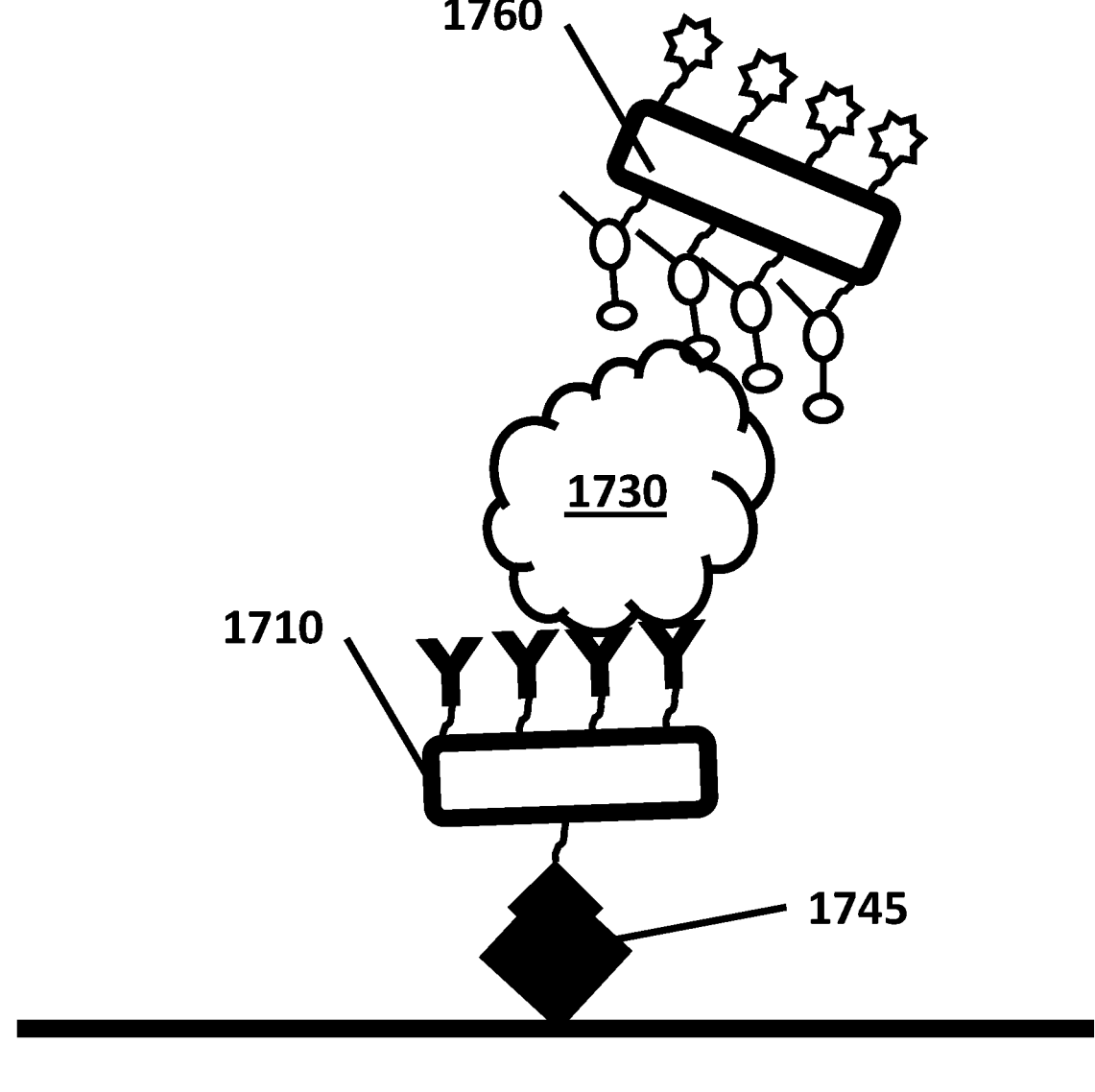
FIG. 17C shows a method of utilizing a detectable probe or affinity reagent as a capture agent for a polypeptide assay.

FIG. 17A-17C depict a scheme for utilizing an affinity reagent as a capture agent. As shown in FIG. 17A, an affinity reagent 1710 is provided, where the affinity reagent includes a capture handle 1720 and a plurality of binding components with a high binding specificity for a target binding partner 1730. The capture handle may include any suitable handle, such as a capture tag (e.g., biotin), a nucleic acid, or a functional group (e.g., a click functional group). The affinity reagent 1710 is contacted with a heterogeneous mixture including the target binding partner 1730 and a plurality of non-target species 1735, thereby facilitating the binding of the affinity reagent 1710 to the target binding partner 1730. Optionally, a solid support 1750 including a capture site 1740 that is configured to bind with a capture handle 1720 may be present. Capture sites may be generated on the solid support, for example, as a patterned array or random array. As shown in FIG. 17B, the heterogeneous mixture is separated from affinity reagent 1710—target binding partner 1730 complex. If a solid support 1750 is present, the affinity reagent 1710 and the target binding partner 1730 may become bound to the solid support at an anchor point 1745 created by the binding of the capture handle 1720 at the capture site 1740. Deposition of affinity reagents 1710 and target binding partners 1730 on the solid support 1750 may generate a random or patterned array of captured target binding partners (e.g., target polypeptides). Alternatively, an affinity reagent 1710—target binding partner 1730 complex may be separated from a free solution by a separation method such as affinity chromatography, size exclusion chromatography, gravity sedimentation, filtration, magnetic capture (of a magnetic or paramagnetic solid support) or centrifugation.

FIG. 17C depicts an optional final step. A captured target binding partner 1730 may be subjected to a characterization or quantification assay utilizing detectable probes 1760 as assay reagents. One or more detectable probes 1760 may be contacted with the captured target binding partners 1760 to characterize presence or absence of a binding interaction between the target binding partners 1730 and the detectable probe 1760. Observation of presence or absence of a detectable signal from the detectable probe 1760 may indicate a probability that a binding partner, epitope, or target moiety is present at the observed location on the solid support 1750.

Detectable probes or affinity reagents may be utilized for co-binding assays. Co-binding assays may refer to any assay where multiple affinity reagents and/or detectable probes are simultaneously contacted with a binding partner, epitope, or target moiety to simultaneously determine the presence of two or more characteristics (e.g., epitopes) in a binding target. Co-binding assays may be utilized, for example, to determine the simultaneous presence of two distinct epitopes in a polypeptide, thereby yielding a high-confidence prediction of polypeptide identity.

A detectable probe or affinity reagent may be formulated for co-binding assays by combining two or more unique species of detectable probes or affinity reagents, each distinguished by a unique detection signature or fingerprint (e.g., first probe uses Alexa-Fluor® 488, second probe uses Alexa-Fluor® 647 fluorescent dyes). Simultaneous detection of unique signatures or fingerprints (or lack thereof) at a spatial location can provide evidence whether one or more detectable probes or affinity reagents has bound a binding partner, epitope, or target moiety at the spatial location.

Figure 18A:
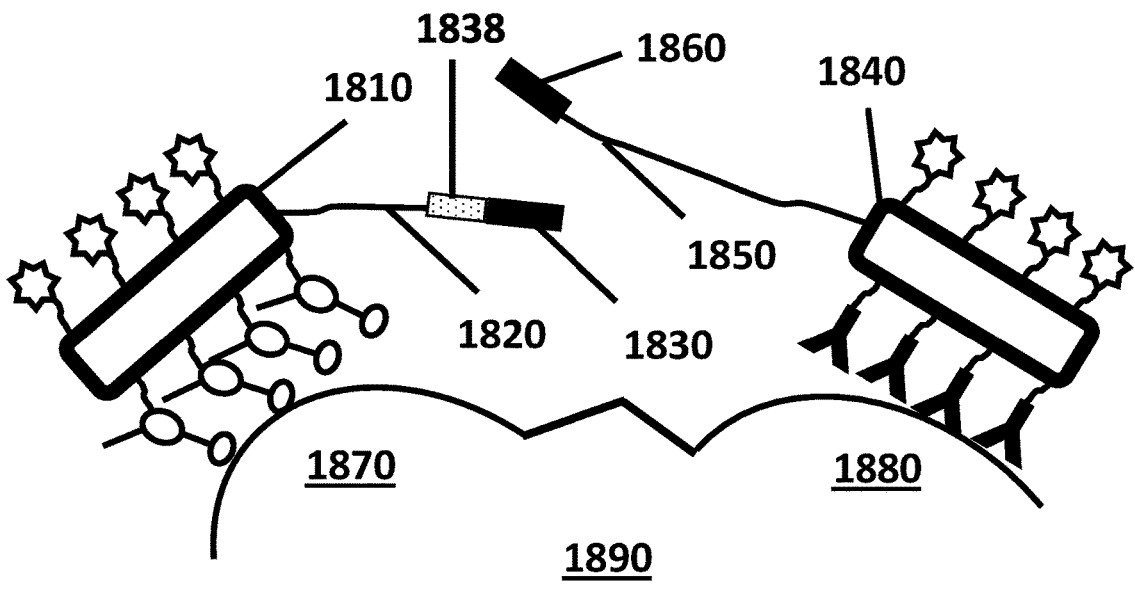
FIG. 18A shows a first step of a method of detecting the binding of more than one detectable probe to a binding partner.
Figure 18B:
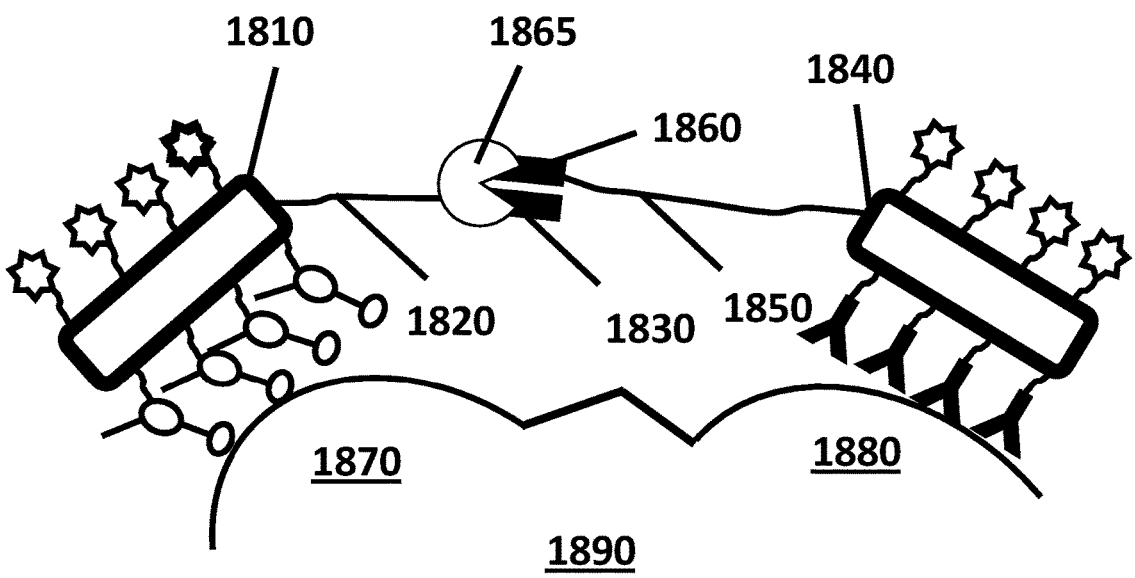
FIG. 18B shows a second step of a method of detecting the binding of more than one detectable probe to a binding partner.
Figure 18C:
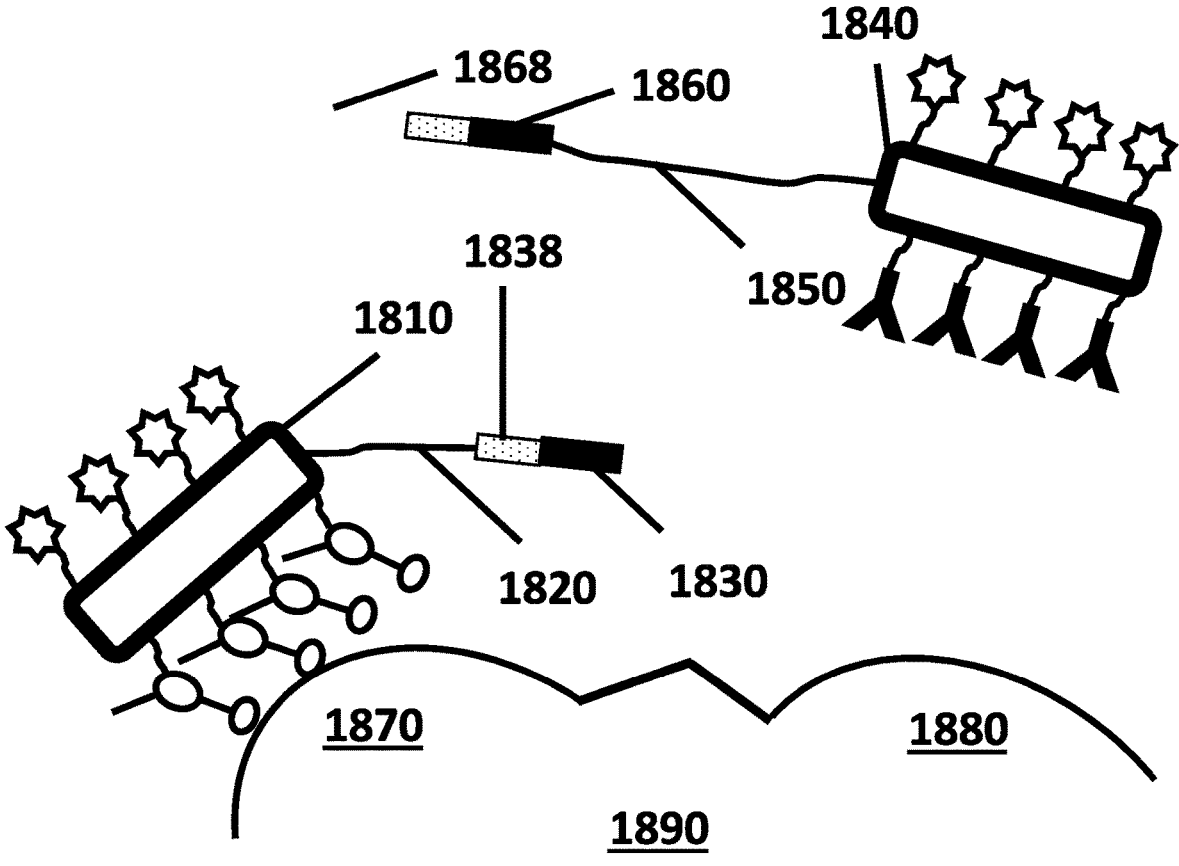
FIG. 18C shows a third step of a method of detecting the binding of more than one detectable probe to a binding partner.

Alternatively, co-binding assays utilizing detectable probes or affinity reagents may be performed with detectable probes or affinity reagents including nucleic acid barcodes. FIGS. 18A-18C depict a scheme for performing a co-binding assay utilizing a barcode detection signal. FIG. 18A depicts a binding partner 1890 that is contacted with a first detectable probe 1810 and a second detectable probe 1840. The first detectable probe 1810 is configured to bind with a first epitope or target moiety 1870, and includes a first linker 1820 with a barcode sequence 1838 and a terminal priming sequence 1830. The second detectable probe 1840 is configured to bind with a second epitope or target moiety 1880, and includes a second linker 1850 with a terminal complementary priming sequence 1860. If a binding interaction occurs between the first detectable probe 1810 and the first epitope or target moiety 1870, and a binding interaction occurs between the second detectable probe 1840 and the second epitope or target moiety 1880, the terminal priming sequence 1830 and the complementary priming sequence 1860 may be in sufficient proximity to hybridize by nucleic acid base pairing. As shown in FIG. 18B, a contacted polymerase enzyme 1865 may bind to the hybridized nucleic acids at the priming sequences, permitting an extension reaction to take place. As shown in FIG. 18C, after the extension reaction, the second detectable probe 1840 may be dissociated from the binding partner 1890 after a complementary barcode sequence 1868 has been added to the complementary priming sequence 1860. Subsequent analysis of detectable probe barcodes will detect the transcribed barcode, thereby indicating that the two detectable probes simultaneously bound a binding partner 1890.

Detectable probes or affinity reagents of the present disclosure may be useful for medical diagnostic purposes, such as diagnostic assays. Detectable probes or affinity reagents may be applicable in both in vitro and in vivo systems. Detectable probes or affinity reagents may be adapted to common in vitro assays such as western blotting and ELISA with the detectable probes or affinity reagents substituting for antibodies normally used in such assays. Detectable probes or affinity reagents may also be utilized as capture or pull-down reagents for locating proteins or other biomarkers from fluid or other biological samples. For example, detectable probes or affinity reagents may be contacted with blood or blood plasma to isolate blood-borne biomarkers. Detectable probes or affinity reagents may be utilized for in vivo assays such as PET scanning. In some configurations, in vivo detectable probes or affinity reagents may be attached to radiolabels (e.g., $^{15}$O, $^{18}$F, $^{68}$Ga, $^{89}$Zr, $^{82}$Rb) to enable the detectable probes or affinity reagents as radiotracers. The detectable probes or affinity reagents may provide high-resolution, high signal data for observation of tissues displaying biomarkers for which the detectable probes or affinity reagents are configured to have a high avidity. Likewise, detectable probes or affinity reagents may be applied as real-time prognostics or diagnostics for medical procedures. For example, detectable probes or affinity reagents with a high avidity for a tumor surface biomarker may be utilized to monitor radiation or surgical treatments in real-time. High-resolution fluorescent data regarding the presence of the surface biomarker can provide feedback to surgeons on the clearance of cancer markers from surgical margins and the progression of the radiation or surgical treatment (fluorescence extinction would correlate to destruction of residual tumor tissue).

Affinity reagents or detectable probes may be utilized as therapeutic agents for medical applications. High avidity affinity reagents or probes may constitute logical disruptors or promoters of in vivo signaling and/or binding processes. Affinity reagents or detectable probes may be attached to a plurality of binding ligands (e.g., hormones, cytokines, etc.) or binding targets (e.g., surface receptors) to promote an interaction with an in vivo signaling or binding system. A high-avidity affinity reagent or detectable probe may be provided to an in vivo system in sufficient quantity to partially or fully block a signaling or binding receptor system, thereby reducing or increasing a cellular response. A high-avidity affinity reagent or detectable probe may be provided to an in vivo system in sufficient quantity to partially or fully capture one or more signaling or binding ligands, thereby reducing or increasing a biological response. A high-avidity affinity reagent or detectable probe may be useful as an anti-microbial or anti-viral composition. For example, an affinity reagent or detectable probe may be configured to bind a receptor system utilized by a microbe or virus to initiate its reproductive cycle. Or, an affinity reagent or detectable probe may be configured to bind a microbe or virus (e.g., by a viral spike protein), thereby inhibiting the microbe or virus' ability to bind with a cellular target.

Detectable probes or affinity reagents including alternative binding components may be useful for therapeutics, diagnostics, or drug discovery. Detectable probes or affinity reagents including a plurality of attached affinity reagent chimeras may be useful for therapeutic or drug discovery purposes. Affinity reagent chimeras may include any complex including an affinity reagent coupled to a secondary molecule, such as a small molecule, nucleic acid, peptide, or protein. Chimeras may include secondary molecules with specific biological functions, such as antisense nucleic acids, exons, introns, transcriptional repressors, transcriptional promoters, receptor-binding ligands, enzyme-binding ligands, enzymatic substrates, etc. Affinity reagent chimeras may include aptamer-siRNA chimeras, antibody-siRNA chimeras, aptamer-ligand chimeras, or antibody-ligand chimeras. Detectable probes or affinity reagents including affinity reagent chimeras may be utilized to locate a target for a secondary molecule, such as binding a target molecule to deliver an anti-sense RNA to the target molecule. In some configurations, a detectable probe or affinity reagent may include a plurality of affinity reagents coupled to the probe, and an additional plurality of secondary molecules that are coupled to the detectable probe or affinity reagent.

Figure 38A:
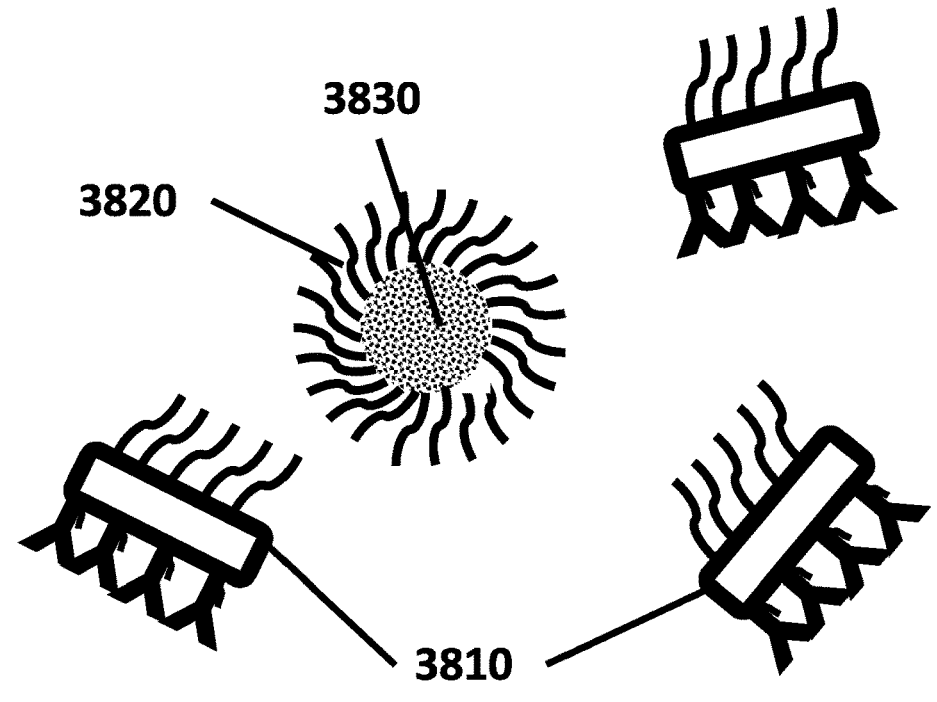
FIG. 38A shows the first step of utilizing a detectable probe or affinity reagent complex for drug delivery.
Figure 38B:
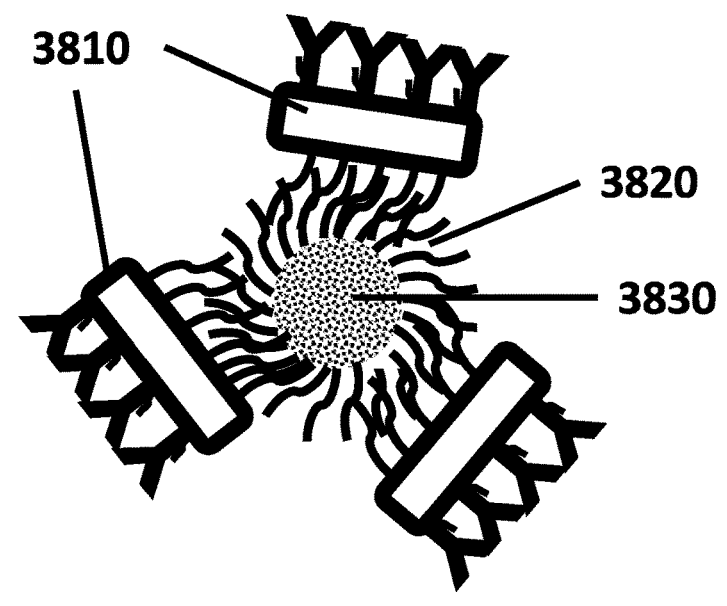
FIG. 38B shows the second step of utilizing a detectable probe or affinity reagent complex for drug delivery.
Figure 38C:
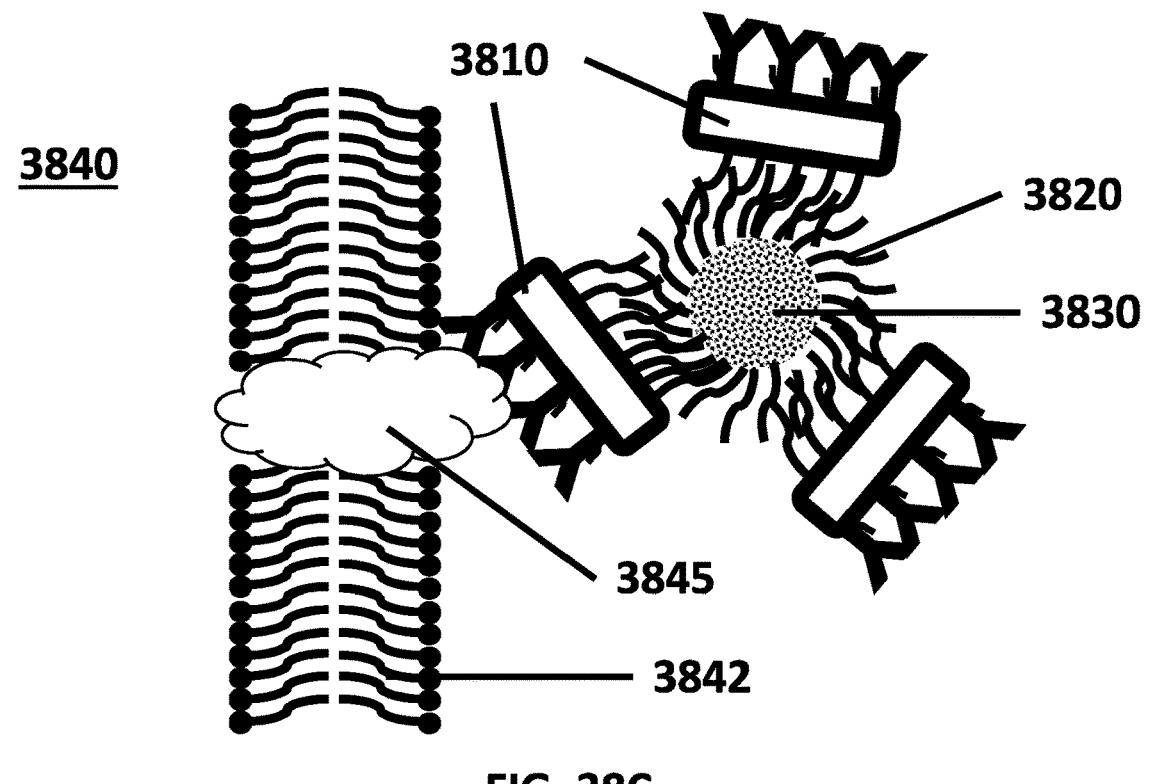
FIG. 38C shows the third step of utilizing a detectable probe or affinity reagent complex for drug delivery.
Figure 38D:
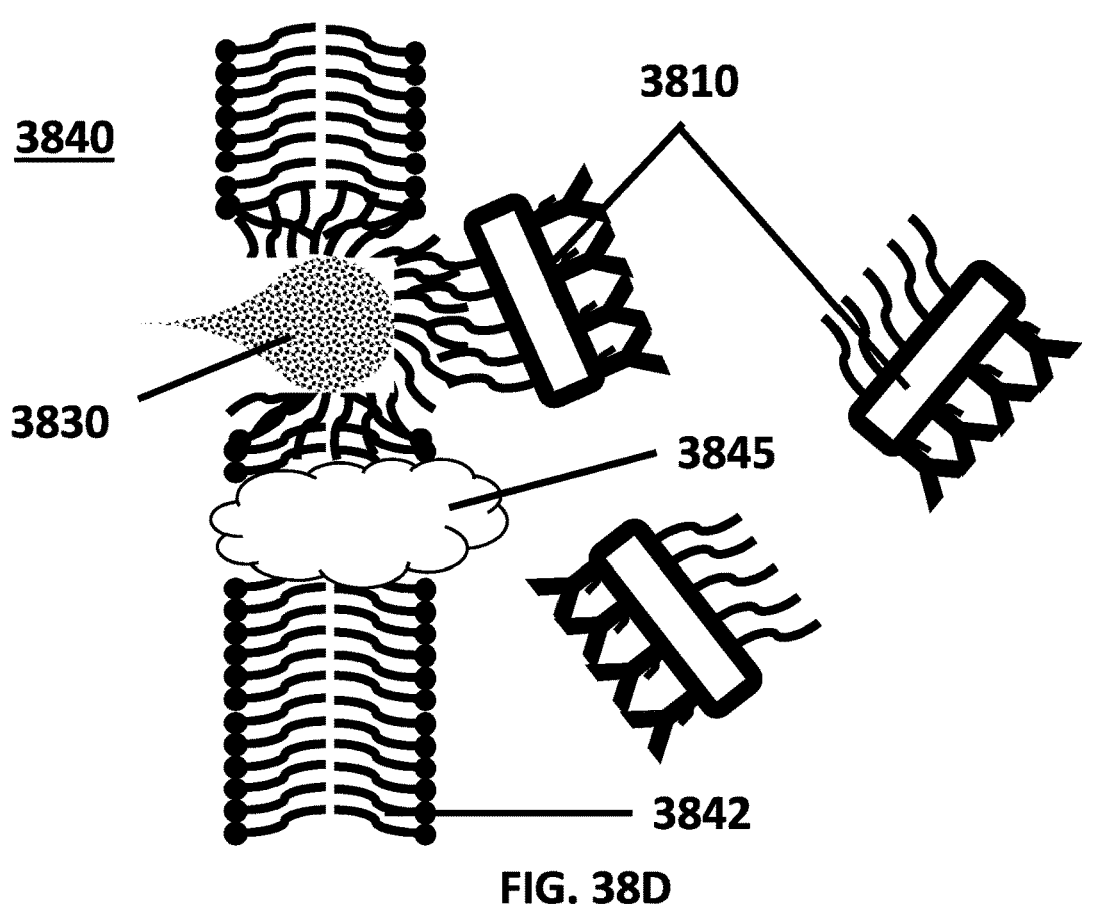
FIG. 38D shows the fourth step of utilizing a detectable probe or affinity reagent complex for drug delivery.

A detectable probe or affinity reagent may be utilized as a drug delivery platform. The increased binding avidity of the detectable probes or affinity reagents provided herein would permit a high degree of binding to membrane receptors or other targetable systems for cellular uptake. A detectable probes or affinity reagent may be associated with a drug delivery formulation, such as a colloidal particle or a coated pharmaceutical formulation. FIGS. 38A-38D depict the use of detectable probes or affinity reagents for cellular drug delivery. FIG. 38A shows the combining of detectable probes or affinity reagents including hydrophobic surface modifying groups 3810 with a colloidal drug particle 3820 including a drug formulation 3830. As shown in FIG. 38B, the hydrophobic interactions between the colloidal particle 3820 and the hydrophobic modifying groups of the detectable probes or affinity reagents 3810 form a targeted drug delivery complex. FIG. 38C depicts an interaction between a membrane-associated protein 3845 (e.g., a cellular receptor) embedded within a cell membrane 3842 of a cell 3840 and the targeted drug delivery complex due to a binding interaction between the membrane-associated protein 3845 and the targeted drug delivery complex. FIG. 38D depicts the uptake of the drug formulation 3830 into the cell 3840 after the targeted drug delivery complex has interacted with the targeted membrane-associated protein 3845, thereby releasing the drug formulation 3830 into the cell 3840. The detectable probes or affinity reagents 3810 may be released or absorbed into the cell during uptake of the colloidal particle 3820.

Detectable probes or affinity reagents may be useful for characterizing non-biological materials. High-avidity reagents or probes may be configured to bind with non-biological targets (e.g., nanoparticles, polymer structures, etc.). Detectable probes or affinity reagents may enable high-resolution imaging of structures in non-biological materials. For example, detectable probes or affinity reagents with avidity for certain nanoparticle structures could be utilized to study the structure, degradation, and poisoning processes of composite catalyst materials. Likewise, detectable probes or affinity reagents with avidity for certain charged surface active sites could be used to provide high-resolution data on the distribution and availability of reactive sites on a material surface. Detectable probes or affinity reagents could be utilized to target and locate micro-scale degradation and/or damage in polymer systems, such as synthetic and natural textiles. The resolution provided by high-avidity probes may permit identification of features not apparent to normal optical inspection processes in a wide variety of materials.

Figure 19A:
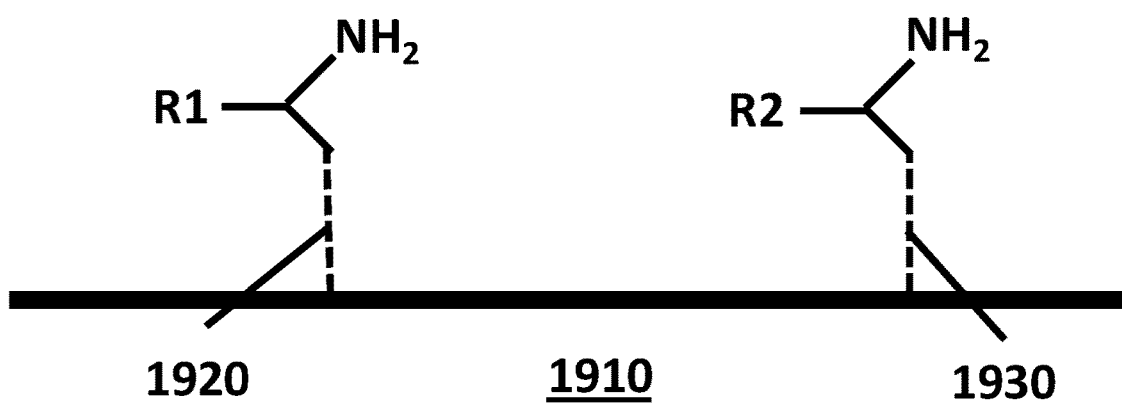
FIG. 19A shows a method of utilizing a detectable probe to determine a peptide sequence.
Figure 19B:
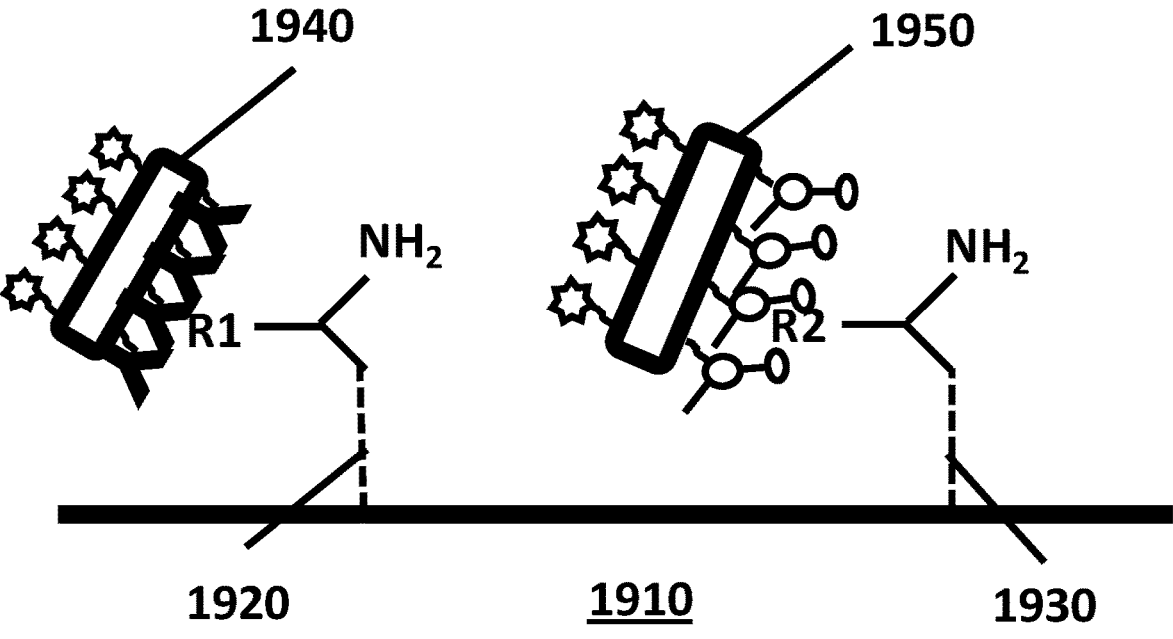
FIG. 19B shows a method of utilizing a detectable probe to determine a peptide sequence.
Figure 19C:
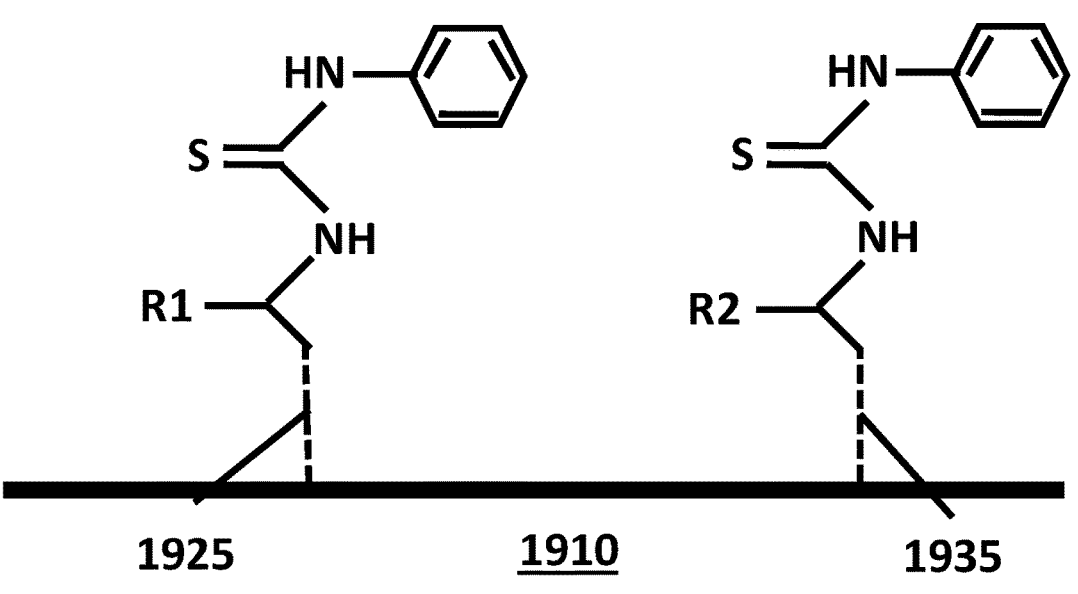
FIG. 19C shows a method of utilizing a detectable probe to determine a peptide sequence.
Figure 19D:
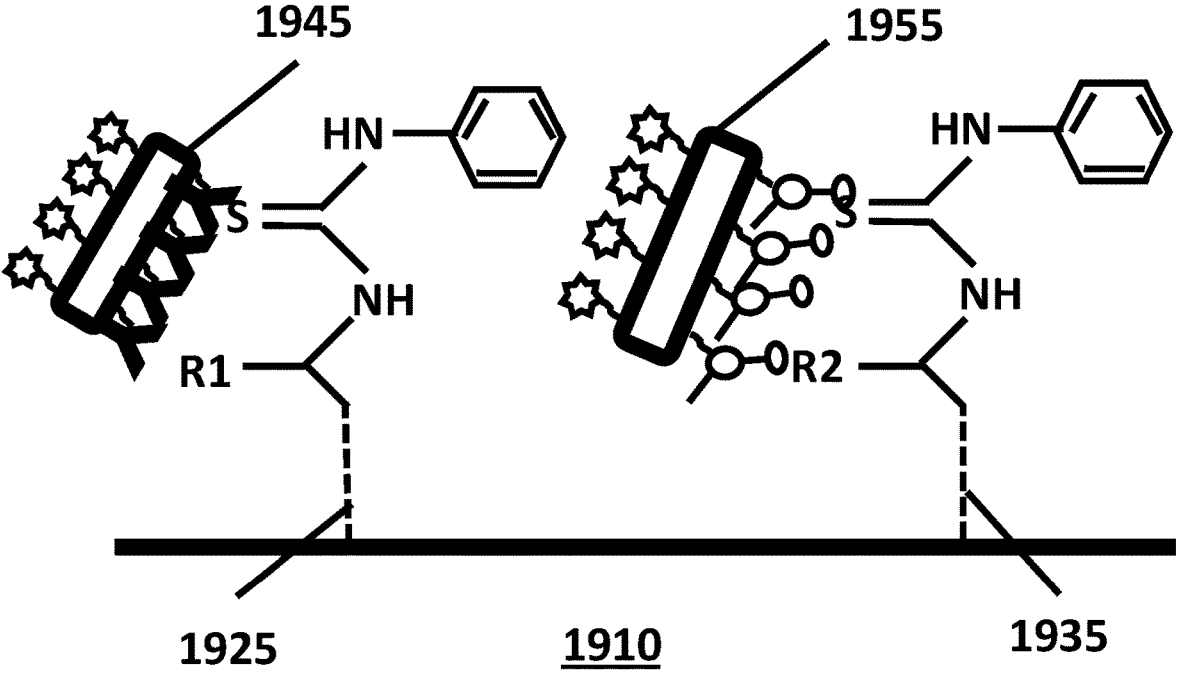
FIG. 19D shows a method of utilizing a detectable probe to determine a peptide sequence.

Detectable probes or affinity reagents may be applied to additional polypeptide characterization methods. Detectable probes or affinity reagents may be configured to enable single-molecule detection Edman degradation techniques. In general, Edman degradation may produce sequence reads for a plurality of peptides by step-wise removal and detection of single amino-acid residues from each peptide. A single-molecule approach to Edman degradation may be facilitated by the use of detectable probes or affinity reagents to detect a terminal amino acid or a terminal amino acid sequence. FIGS. 19A-19D depict possible approaches to Edman degradation utilizing detectable probes to increase the signal strength of each sequence read. FIG. 19A depicts a solid support 1910 with a plurality of polypeptides bound to the solid support 1910. A first polypeptide 1920 has a terminal amino acid residue with sidechain R1 and a second polypeptide 1930 has a terminal amino acid residue with sidechain R2. FIG. 19B depicts a contacting of the plurality of peptides with a detectable probe composition including a plurality of probe species with high binding specificity for each natural terminal amino acid residue (e.g., including at least 20 unique probe species). First polypeptide 1920 is bound by detectable probe 1940 which is configured to have a binding specificity for sidechain R1. Second polypeptide 1930 is bound by detectable probe 1950 which is configured to have a binding specificity for sidechain R2. Each detectable probe of the detectable probe composition has a unique detection signature or fingerprint, permitting each binding event to be uniquely identified. FIG. 19C depicts a typical intermediate step in an Edman degradation process after each peptide of the plurality of polypeptides has been reacted with an isothiocyanate compound to form a cleavable product. A first polypeptide 1925 has a terminal modified amino acid residue with sidechain R1 and a second polypeptide 1935 has a modified terminal amino acid residue with sidechain R2. FIG. 19D depicts a contacting of the plurality of modified peptides with a detectable probe composition including a plurality of probe species with high binding specificity for each modified natural terminal amino acid residue (e.g., including at least 20 unique probe species). First modified polypeptide 1925 is bound by detectable probe 1945 which is configured to have a binding specificity for sidechain R1. Second modified polypeptide 1935 is bound by detectable probe 1955 which is configured to have a binding specificity for sidechain R2. Each detectable probe of the detectable probe composition has a unique detection signature or fingerprint, permitting each binding event to be uniquely identified. In some configurations, detectable probe compositions may be contacted with detectable probe compositions before and after modification of the terminal amino acid residues to increase the confidence of the sequence reads.

The skilled person will readily recognize that many of the embodiments discussed may readily be configured to utilize other techniques discussed above, such as the use of concatenated barcodes as depicted in FIGS. 15A-15D, or the methods for forming weak secondary binding interactions like those depicted in FIGS. 8, 9A, and 9B.

EXAMPLES

Figure 23:
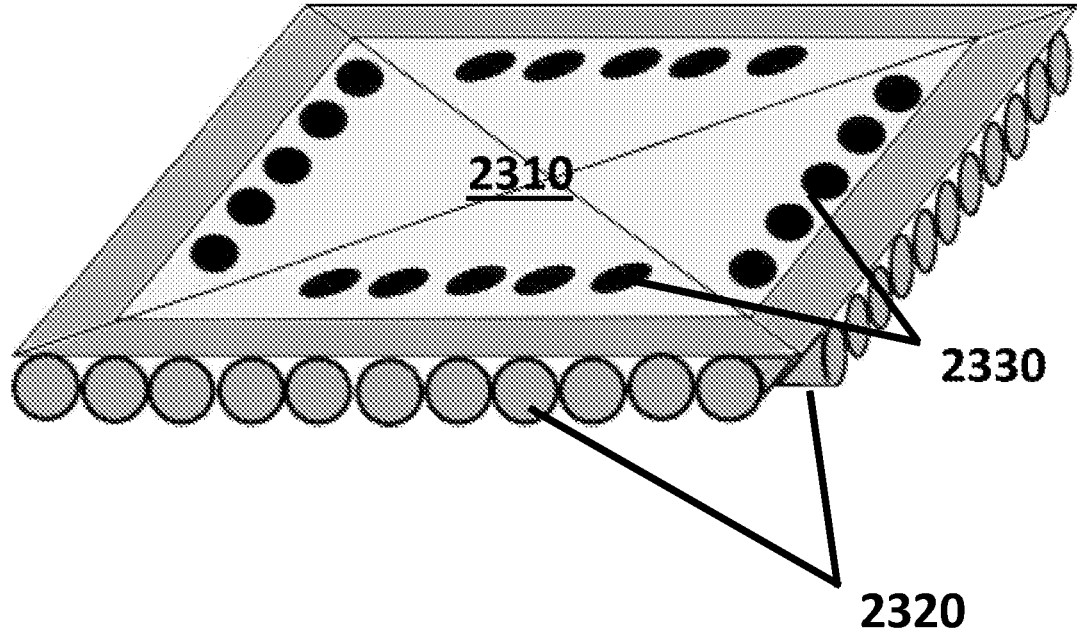
FIG. 23 shows a simplified schematic of a detectable probe or affinity reagent including a DNA origami retaining component.

Example 1: Design and Synthesis of Affinity Reagents Having Origami Tiles as Retaining Components Origami tile-based affinity reagents were designed utilizing CADNANO software with accompanying in-house python scripts. Tiles were designed as nucleic acid origami having an approximately square shape with a single layer. Tiles were designed to have 20 DNA aptamer binding sites on a top face of the tile, and 44 dye molecule attachment sites distributed uniformly along the sides of the tile molecule. FIG. 23 depicts a schematic representation of the tile-based affinity reagent 2310, with dots 2330 representing aptamer attachment locations and circles 2320 representing dye attachment locations. Tiles were designed to have a side length of approximately 83 nanometers (nm)

Origami tiles were prepared using a scaffold strand of M13 single-stranded circular DNA strand containing 7249 nucleotides. 217 single-stranded oligonucleotides were designed and synthesized for hybridization with the scaffold strand as 'staples' to permit assembly of the tile-based affinity reagents.

Origami tiles were assembled by combining scaffold strands with the 217 oligonucleotides. DNA strands were combined at 90° C. in a buffer containing 5 mM Tris-HCl, 5 mM NaCl, 1 mM EDTA, 12.5 mM MgCl$_2$ at pH8.0. The DNA strand mixture was cooled to a temperature of 20° C. and allowed to anneal for 1.5 hrs.

Annealed tile-based affinity reagents were purified via HPLC Size Exclusion Chromatography or 100 kDa size cutoff spin filters. Purified tile-based affinity reagents were resuspended in a buffer containing 5 mM Tris-HCl, 200 mM NaCl, 1 mM EDTA, 11 mM MgCl$_2$ at pH 8.0 and stored at 4° C.

Example 2: Image Analysis of Origami Tiles

Origami tile-based affinity reagents were prepared as described in Example 1. Tile probes were imaged via transmission electron microscopy (TEM) to confirm the success of the assembly method. Tile probe solution was spotted on a glow discharged carbon deposited copper grid and negatively stained using Uranyl Formate.

Tile probes were imaged on a FEI Tecnai T12 transmission electron microscope at magnifications of 30,000× under an acceleration voltage of 120 kilovolts (kV). The tile probes appear to have an approximately square shape, with a side length of about 83 nm, as predicted.

Figure 25:
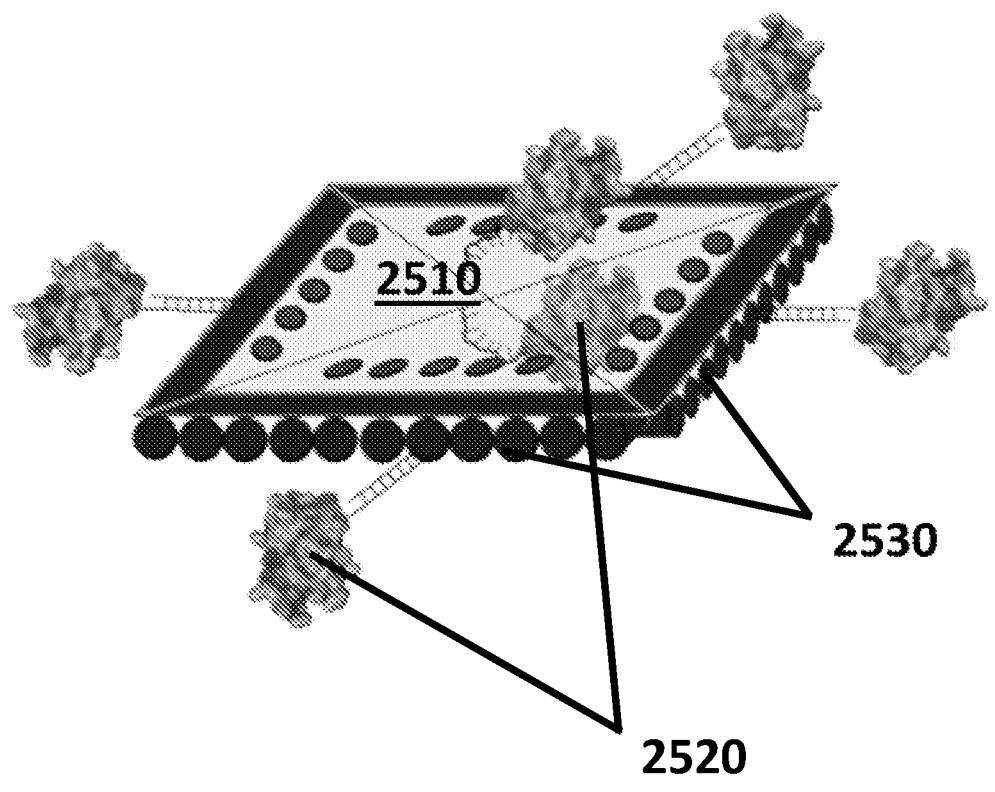
FIG. 25 shows a simplified schematic of a detectable probe or affinity reagent including a DNA origami retaining component.

Example 3: Design and Synthesis of Tile-Based Affinity Reagents Having Antibody-Based Binding Components Antibody tile detectable probes were designed utilizing CADNANO software with accompanying in-house python scripts. The origami tiles were designed to have an approximately square shape with a single layer. Tiles were designed to have 6 antibody binding sites (2 on a top face and 1 along each side of the tile) and 40 dye molecule attachment sites distributed uniformly along the sides of the tile molecule. FIG. 25 depicts a schematic representation of the tile-based affinity reagent 2510, with antibody components 2520 at respective attachment locations and circles 2530 representing attachment locations for label components. Tiles were designed to have a side length of approximately 83 nanometers (nm)

Origami tiles were prepared using a scaffold strand of M13 single-stranded circular DNA strand containing 7249 nucleotides. 217 single-stranded oligonucleotides were designed and synthesized for hybridization with the scaffold strand to permit assembly of the tile probes. 6 of the oligonucleotides were synthesized with transcyclooctene-modified nucleotides to enable attachment of antibody components via a click reaction.

Tiles were assembled by combining scaffold strands with the 217 oligonucleotides. DNA strands were combined at 90° C. in a buffer containing 5 mM Tris-HCl, 5 mM NaCl, 1 mM EDTA, 12.5 mM MgCl$_2$ at pH8.0. The DNA strand mixture was cooled to a temperature of 20° C. and allowed to anneal for 1.5 hrs.

Figure 26:
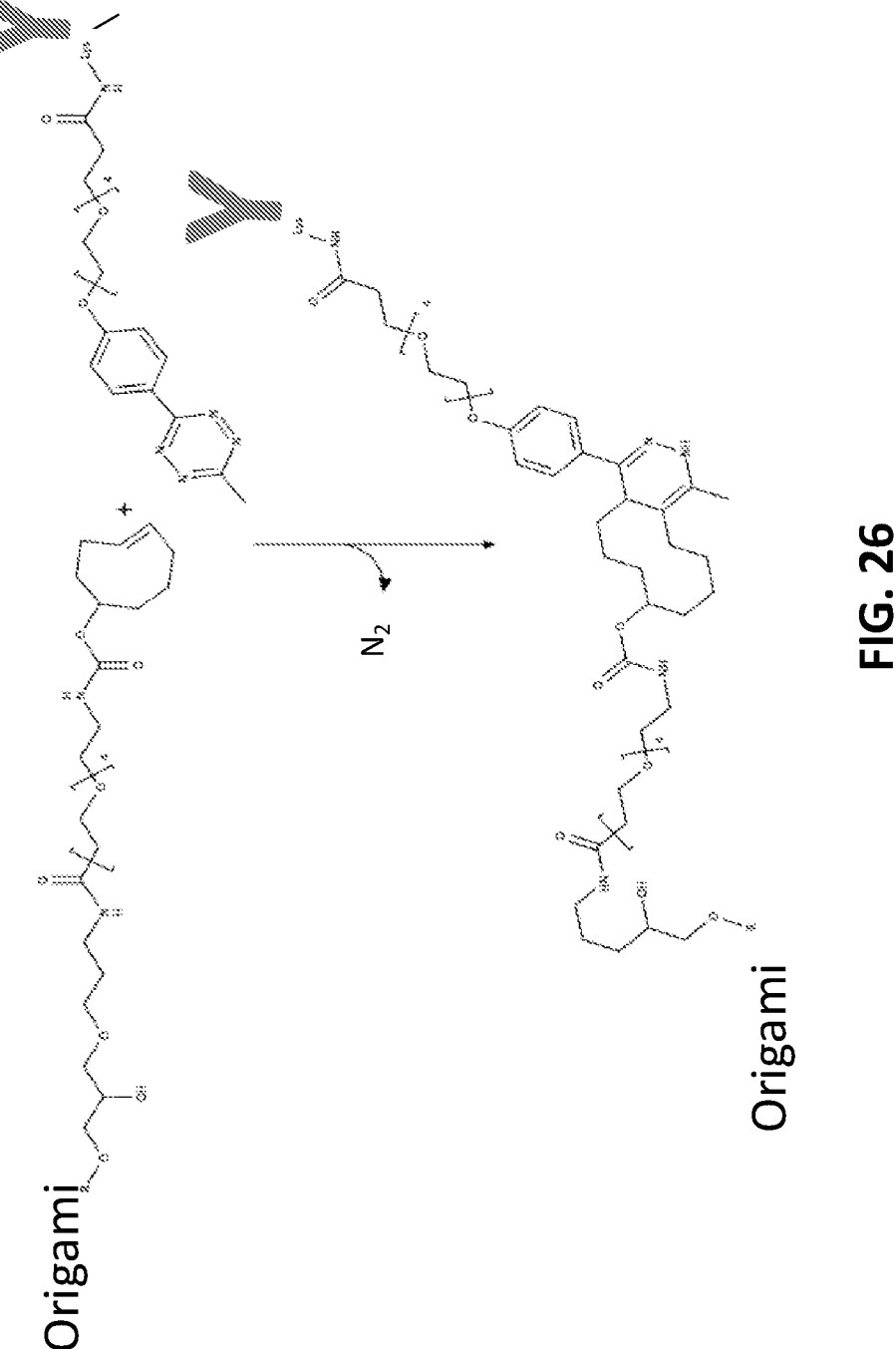
FIG. 26 shows a scheme for attaching an antibody-based binding component to an origami retaining component via a click reaction.

Annealed tiles were purified via HPLC Size Exclusion Chromatography or 100 kDa size cutoff spin filters. Purified tiles were resuspended in a buffer containing 5 mM Tris-HCl, 200 mM NaCl, 1 mM EDTA, 11 mM MgCl$_2$ at pH 8.0. Antibodies were attached to the tiles via a transcyclooctene (TCO)—methyltetrazine (mTz) click reaction. FIG. 26 depicts an exemplary reaction scheme for attachment of antibodies (or other binding components) to the origami tiles. Purified tile lobes with TCO modified nucleotides were combined with mTz-modified 10× Anti-His tag antibodies at a temperature of 20° C. and were allowed to react for 6 to 10 hrs. After the click reaction, tile probes were purified via HPLC Size Exclusion Chromatography.

Figure 27:
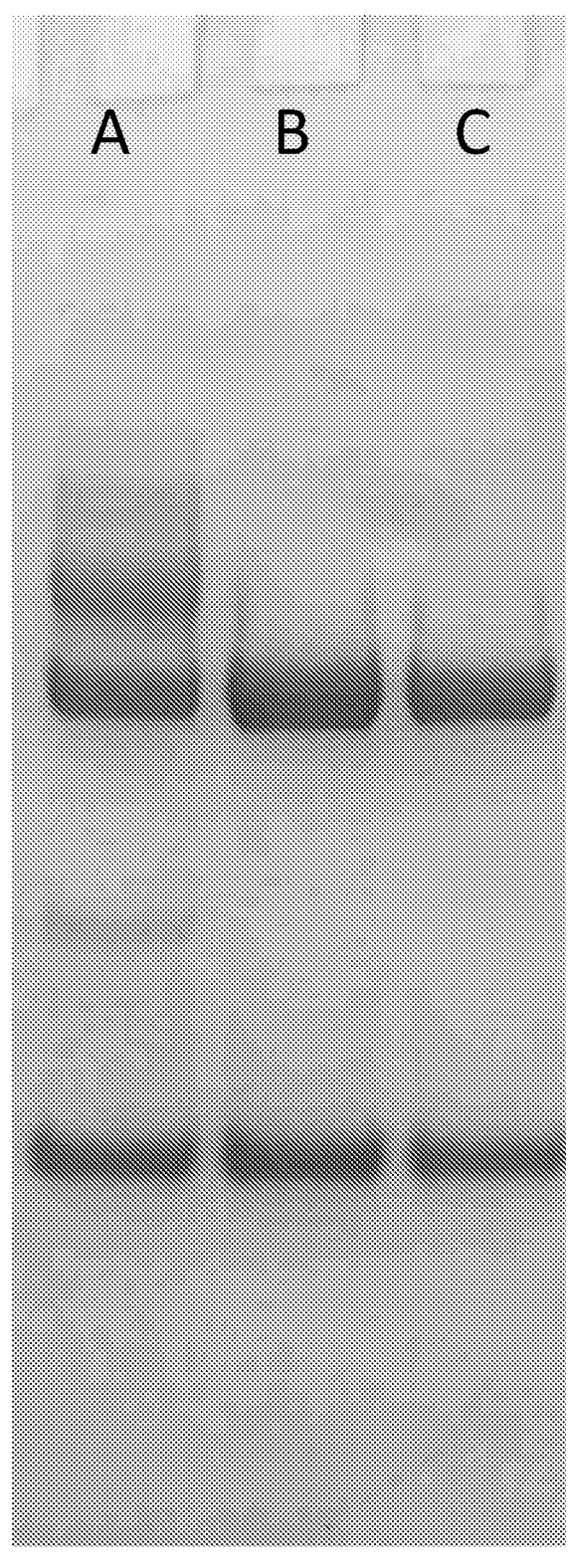
FIG. 27 shows an image of an SDS-Page gel containing antibody-oligonucleotide conjugates.

FIG. 27 shows an SDS-page gel for purified antibody-DNA oligo conjugates generated via TCO-mTz click reaction. Lane A contains antibody-DNA oligo conjugate. Lane B contains an mTz-modified antibody negative control. Lane C contains an unmodified antibody control. A dark, uppermost band is observed, confirming successful attachment of antibodies to DNA oligos.

Example 4: Binding of Tile-Based Affinity Reagents Having Aptamer-Based Binding Components Four different species of aptamer tile probe were prepared according to the method of Example 1. Each species of tile-based affinity reagent contained a different aptamer with varying binding affinities for terminal histidine tags. The four aptamers used were: B1 (highest affinity), A1 (moderate affinity), D1 (low affinity), and SC2 (no affinity). Each tile-based affinity reagent was assembled with 20 aptamers and 40 Alexa-Fluor® 647 dye molecules.

Each aptamer was screened for binding against single-molecule arrays of his-tagged ubiquitin. Protein arrays were prepared by depositing 10 nanogram/microliter solutions of ubiquitin conjugates (ubiquitin attached to a structured nucleic acid particle) on fluidic chips. Each fluidic chip contained 3 lanes, with each lane having a glass surface with a blanket coating of 3-aminopropyl triethoxysilane (APTMS). Three different types of protein arrays were prepared, 1 per lane on each chip: his-tagged ubiquitin; flag-tagged ubiquitin (negative control); and untagged ubiquitin (negative control). Each deposited protein conjugate contained an Alexa-Fluor® 488 dye molecule. Protein conjugate locations in the array were measured via fluorescence microscopy at 488 nm excitation. Prior to affinity reagent binding, fluidic chips were blocked for 60 minutes with a solution containing 1% BSA, 2 nM unlabeled DNA tiles, and 100 mg/ml dextran sulfate in a buffer containing.

To test binding, 15 µl of 20 nM affinity reagent solution was flowed into a fluidic chip. Probes were allowed to bind for 10 mins. After affinity reagent binding, fluidic chips were rinsed with a rinse solution. Binding was imaged on the surface using a ThorLab Microscope at 20× magnification and 647 nm excitation. Microscope images at 647 nm were compared to images at 488 nm to determine a fraction of proteins bound by the applied affinity reagents. All four affinity reagent species were tested against each of the 3 arrays. Each set of 12 experiments was duplicated.

Figures 28C, 28D:
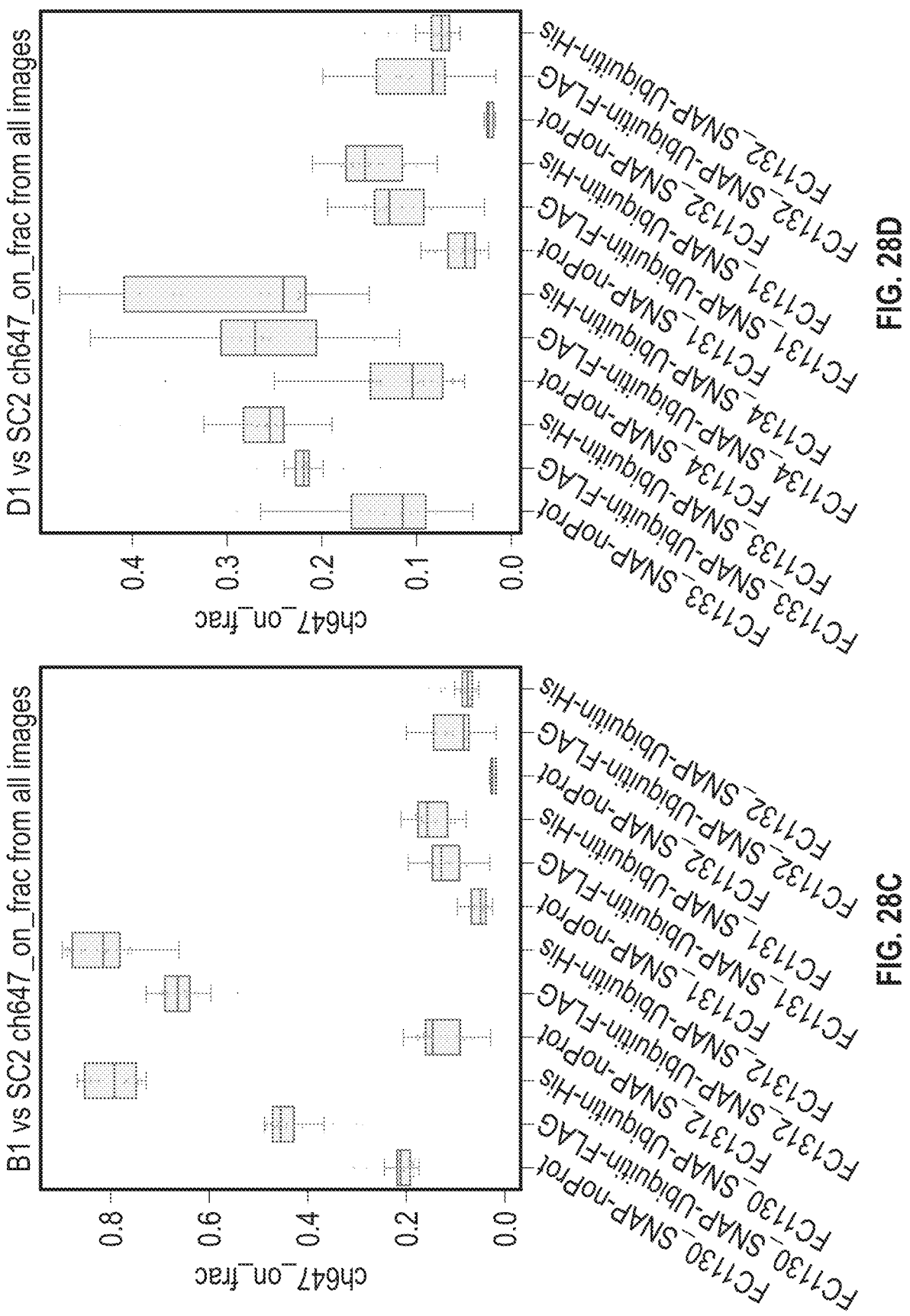
FIG. 28C shows binding data for a detectable probe against a polypeptide target.
FIG. 28D shows binding data for a detectable probe against a polypeptide target.

FIGS. 28A-28D depict occupancy rates for binding. Occupancy rate was determined as the ratio of observed locations with binding detected to total locations with a known protein conjugate. FIG. 28A shows occupancy rates for the B1 aptamer reagents against occupancy rates for the A1 aptamer reagents. Despite a lower binding affinity, the A1 aptamer reagents is shown to have nearly as high an occupancy rate as the B1 aptamer reagents. FIG. 28B shows occupancy rates for the B1 aptamer reagents against occupancy rates for the D1 aptamer reagents. FIGS. 28C and 28D compare occupancy for B1 vs. SC2 and D1 vs. SC2, respectively. As shown in FIGS. 28B and 28D, despite its low binding affinity for his-tagged proteins, the occupancy rate of the D1 aptamer reagents is observed to be nearly half that of the B1 aptamer reagents and notably higher than that of the negative control SC2 aptamer reagents, suggesting that the detectable probes can significantly improve the observed binding affinity of a weak binding aptamer through an avidity effect.

Example 5. Binding of Tile-Based Affinity Reagents Having Antibody-Based Binding Components Tile-based affinity reagents having antibody-based binding components were prepared according to Examples 2 and 3. Each affinity reagent was prepared with six 10× Anti-His antibodies and 40 Alexa-Fluor® 647 dye molecules. Binding was tested via the method described in Example 4, utilizing a 0.5 nM probe solution.

Figure 29A:
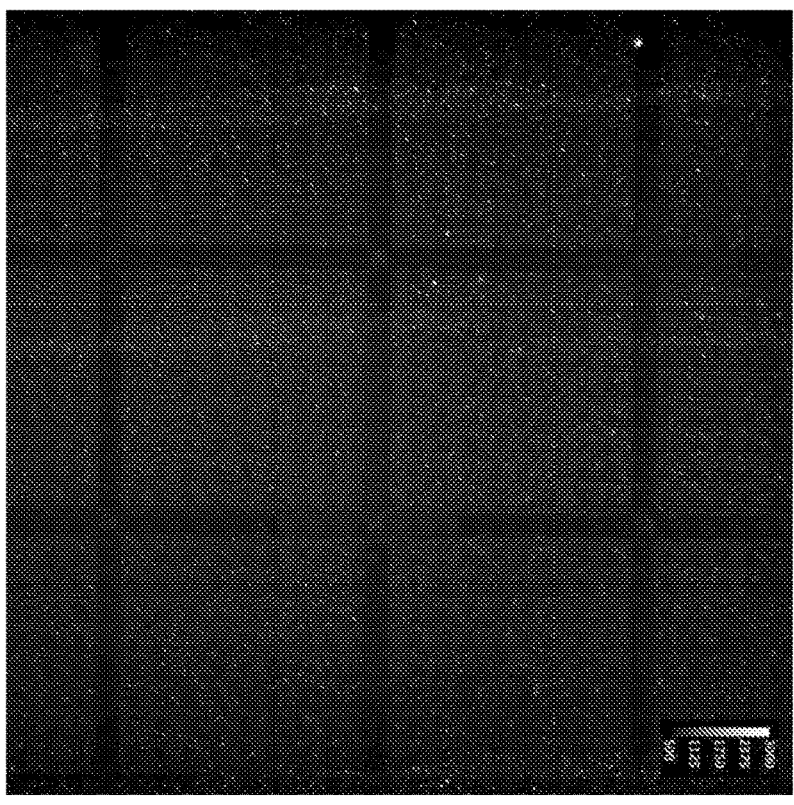
FIG. 29A shows a fluorescent microscope image of detectable probe binding against a negative control polypeptide array.
Figure 29B:
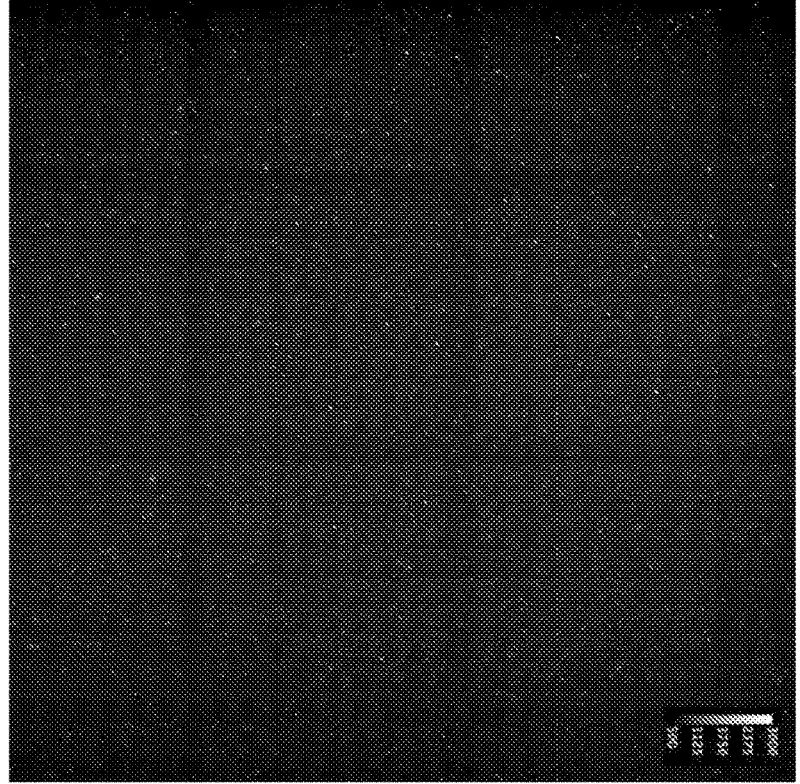
FIG. 29B shows a fluorescent microscope image of detectable probe binding against a negative control polypeptide array.
Figure 29C:
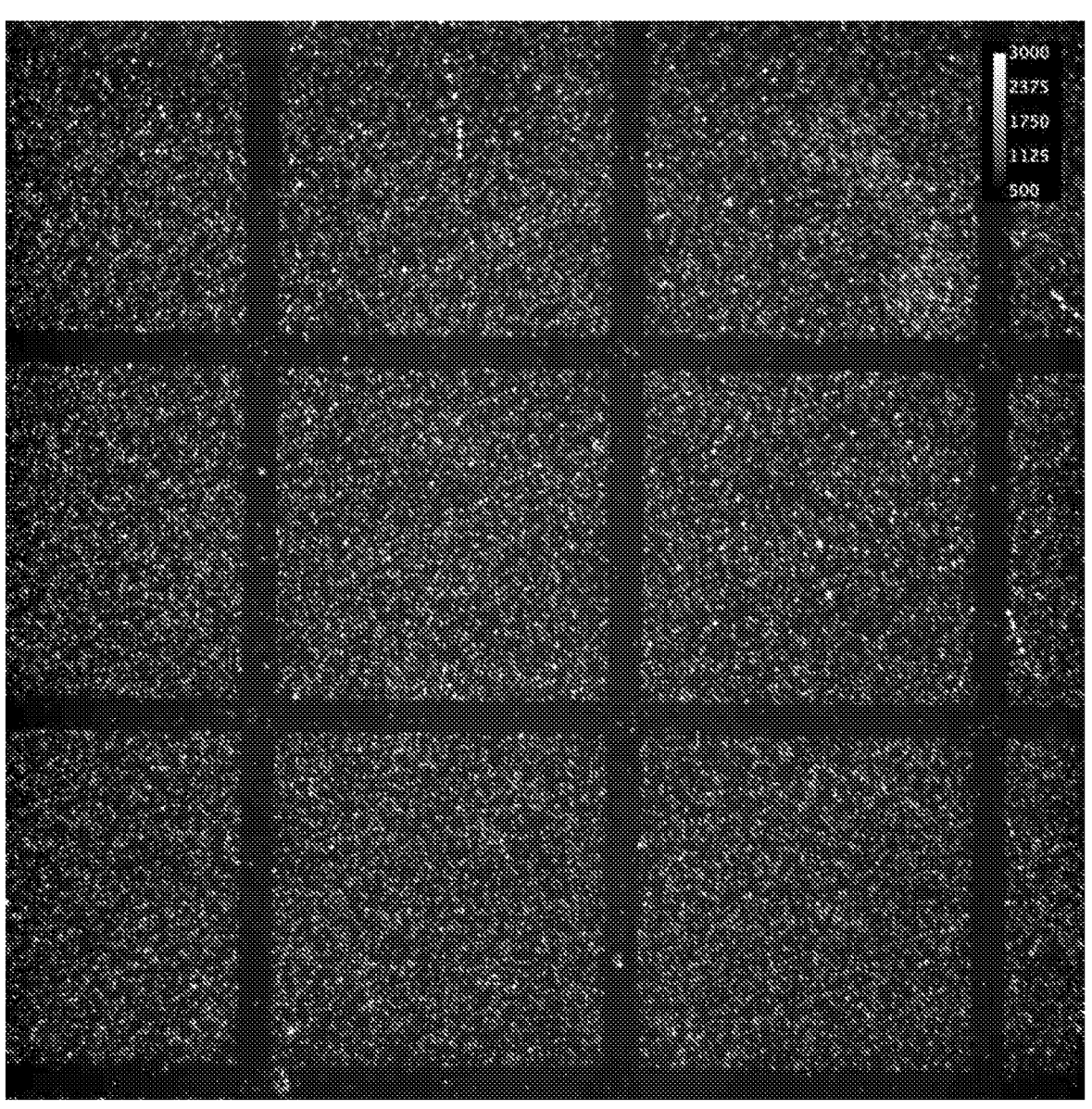
FIG. 29C shows a fluorescent microscope image of detectable probe binding against a polypeptide array.

FIGS. 29A-29C show fluorescence microscopy images for binding of the reagents. FIGS. 29A and 29B show binding of the reagents to untagged and flag-tagged ubiquitin arrays, respectively. FIG. 29C shows binding of the reagents to a his-tagged ubiquitin array. A higher level probe binding to the his-tagged array was observed.

Figure 30:
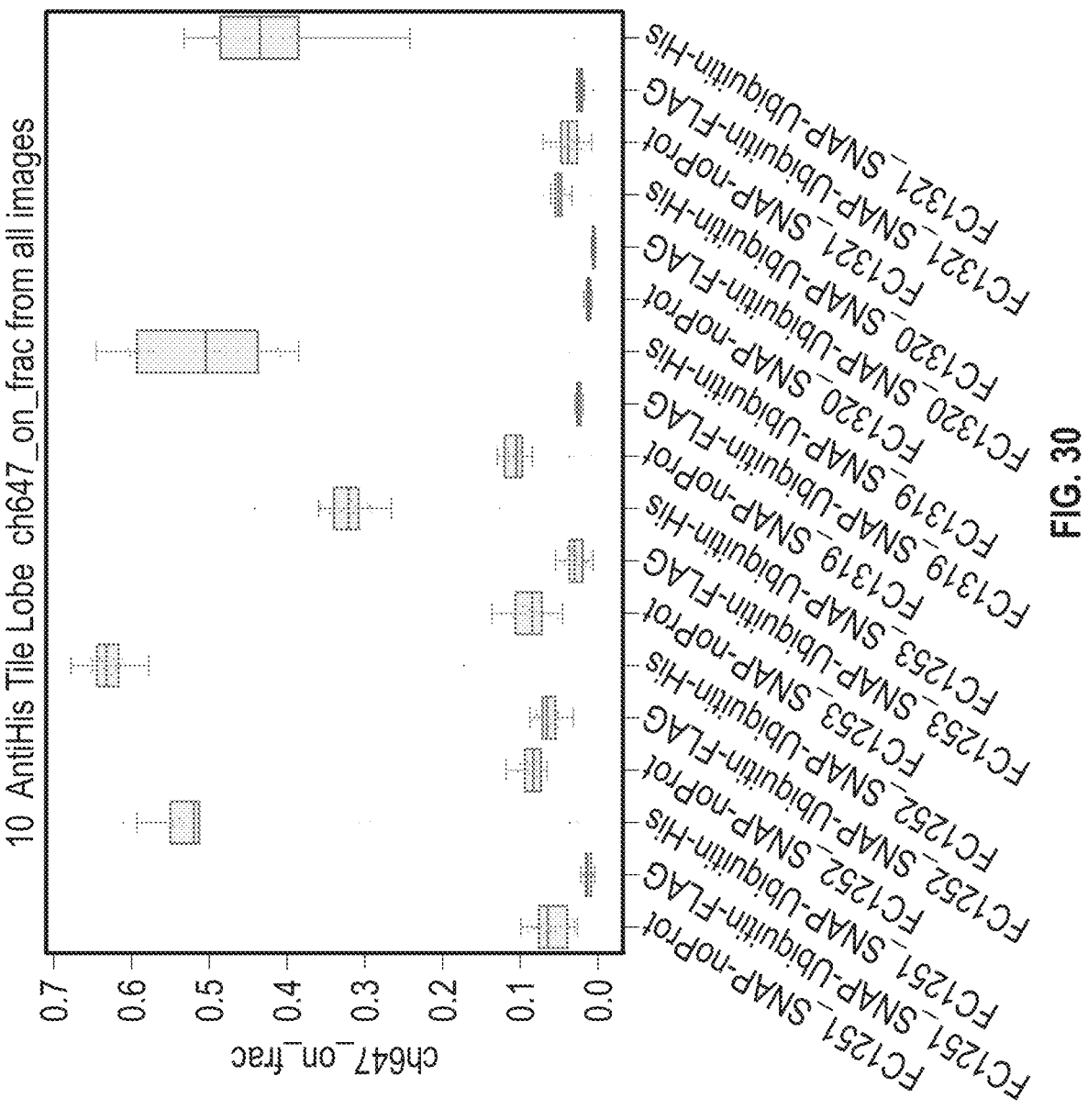
FIG. 30 shows binding data for a detectable probe against a polypeptide target.

FIG. 30 shows occupancy rates for the affinity reagents against the 3 different protein arrays on 6 different chips. High occupancy rates on his-tagged protein arrays are observed for all 6 chips, while much lower occupancy rates are observed for the other non-his tagged proteins on each fluidic chip.

Example 6. Multiplex Binding Assay

Detectable affinity reagents are assembled including either 1 or 2 types of fluorophore. Available fluorophores have emission in red, yellow, green, or blue wavelengths (R, Y, G, B). Each fluorophore is named to indicate the total number of each fluorophore on the detectable probe. For example, a detectable affinity reagent with 10 red fluorophores and 10 yellow fluorophores would be named "R10Y10." Each affinity reagent with a unique fluorophore combination is attached to a unique species of binding component having a unique binding specificity for a target moiety. Two unique pools of fluorophores are created, with compositions of each pool listed in Table 1 below.

TABLE 1

| Pool 1 | Pool 2 |
|--------|--------|
| R10Y10 | R20Y10 |
| R20Y20 | R10Y20 |
| B10G10 | B10G20 |
| G20B20 | B20G10 |
| B10 | B10 |
| G10 | G10 |
| R10 | R10 |
| Y10 | Y10 |

A pool of affinity reagents is contacted to a first binding partner. Fluorescence intensities are measured at wavelengths corresponding to the four possible fluorophores. Measured fluorescence intensities are correlated to the possible available number of fluorophores. Table 2 displays measured fluorophore counts based upon fluorescence intensities, as well as the combination of bound probes from each pool that would give rise to the unique combination of observed fluorescence intensities.

TABLE 2

| Observed Binding Intensities (in fluorophores) | | | |
|---|---|---|---|
| R | Y | G | B |
| 40 | 30 | 0 | 10 |

| Possible Observed Probe Combinations |
|---|
| Pool 1: R10Y10, R20Y20, R10, B10 |
| Pool 2: R10Y20, R20Y10, R10, B10 |

Based upon the observed fluorescence intensities, available target moieties can be predicted for the binding partner.

A pool of affinity reagents is contacted to a second binding partner. Fluorescence intensities are measured at wavelengths corresponding to the four possible fluorophores. Measured fluorescence intensities are correlated to the possible available number of fluorophores. Table 3 displays measured fluorophore counts based upon fluorescence intensities, as well as the combination of bound affinity reagents from each pool that would give rise to the unique combination of observed fluorescence intensities.

TABLE 3

| Observed Binding Intensities (in fluorophores) | | | |
|---|---|---|---|
| R | Y | G | B |
| 30 | 10 | 20 | 10 |

Possible Observed Probe Combinations
Pool 1: R10Y10, R10, R10, B10G10, G10
Pool 2: R20Y10, R10, B10G20

Based upon the observed fluorescence intensities, available target moieties can be predicted for the binding partner. Rational engineering of multiplex pools of detectable affinity reagents can give rise to unique binding signatures that predict the existence of multiple target moieties within a binding partner simultaneously.

Example 7. Affinity Chromatography

Three affinity chromatography columns are prepared. The first chromatography column includes a first chromatography resin including affinity reagents covalently attached to the resin. The affinity reagents in the first column have a general binding affinity for polypeptides regardless of amino acid sequence. The second chromatography column includes a second chromatography resin including affinity reagents covalently attached to the resin. The affinity reagents in the second column have a binding affinity for polypeptides including a lysine-arginine-alanine (KRA) amino acid trimer sequence within their amino acid sequences. The third chromatography column includes a third chromatography resin including affinity reagents coupled to the resin by oligonucleotide hybridization. The affinity reagents in the third column have a binding affinity for polypeptides including a lysine-glutamic acid-asparagine (KEN) amino acid trimer sequence within their amino acid sequences.

The three affinity chromatography column are arranged sequentially. A crude cellular lysate is applied to the first general separation column. Polypeptides are captured from the crude cellular lysate while the non-polypeptide fraction of the lysate passes through the column and is discarded. After discarding of the non-polypeptide of the lysate, the polypeptide fraction is eluted by the application of an elution buffer to the first column. The eluted fraction is captured and applied to the second KRA-specific chromatography column. A first fraction of polypeptides is captured on the KRA-specific resin while a second fraction passes through the column and is captured. After collection of the second fraction from the end of the column, the first fraction of polypeptides is eluted from the column by an elution buffer and collected at the column end.

The first collected polypeptide fraction from the KRA-specific chromatography column is added to the third KEN-specific chromatography column. A first fraction of polypeptides is captured on the KEN-specific resin while a second fraction passes through the column and is captured. After collection of the second fraction from the end of the column, the first fraction of polypeptides is eluted from the column by heating the column to melt the oligonucleotide hybridizations, thereby releasing the detectable probes from the column.

Figure 40:
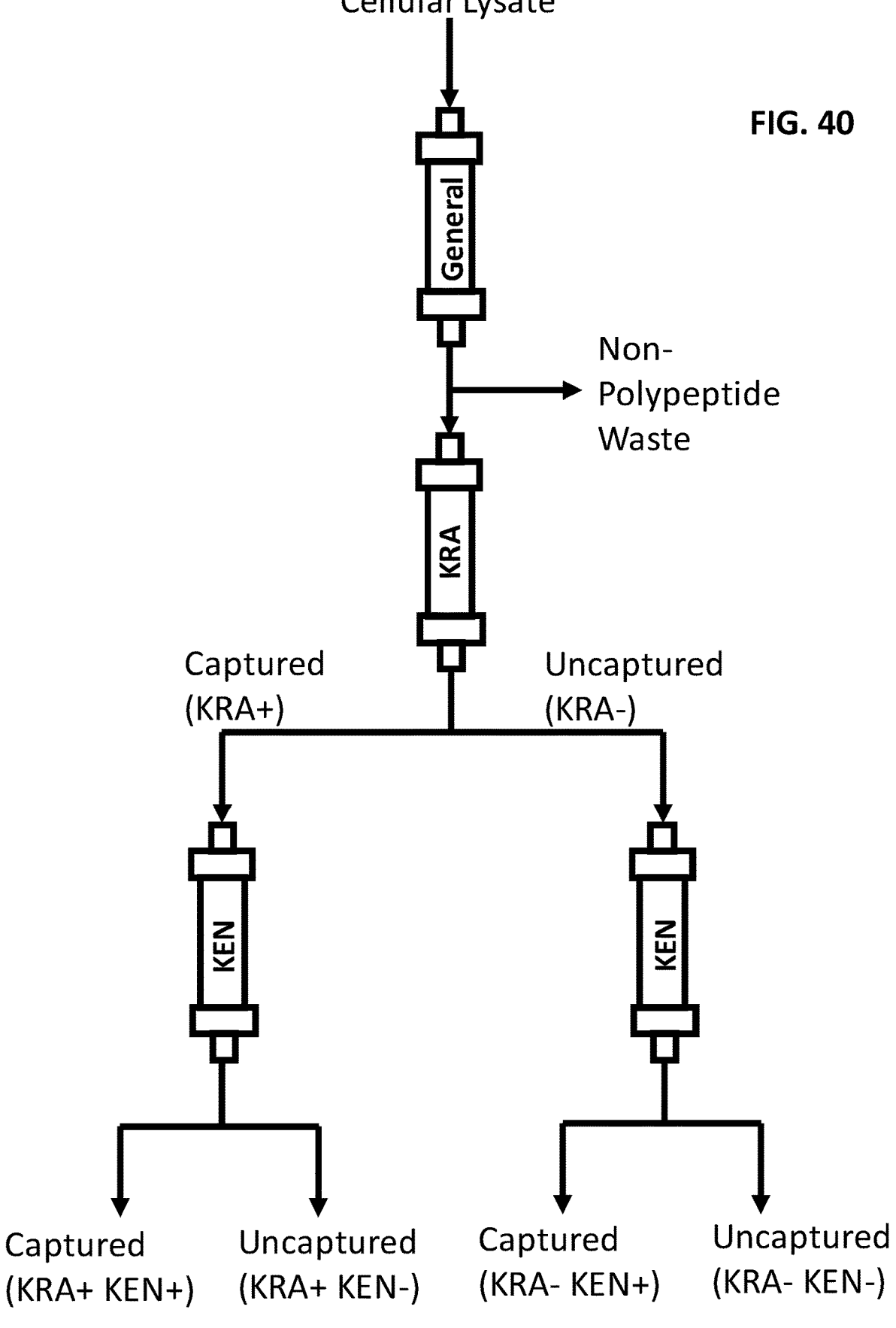
FIG. 40 shows an affinity chromatography system utilizing a detectable probe or affinity reagent as a capture agent.

The KEN-specific column is regenerated with a new batch of KEN-specific detectable affinity reagents to replenish the released affinity reagents from the separation of the first fraction. The separation is then repeated for the second collected fraction from the KRA-specific column. A first pass-through fraction is collected, followed by a second captured fraction. After separation of both fractions from the KRA-specific column, a total of four fractions are formed. FIG. 40 shows a schematic of the chromatographic process from the initial cellular lysate to the final four polypeptide fractions, with the preliminary determined characteristics of the four fractions listed at the bottom. The preliminary characterizations of the four fractions are evaluated based upon the chromatography behaviors of each fraction. The characterizations are considered preliminary due to the possibility of false negative or false positive capture interactions.

The two fractions of polypeptides captured on the KEN-specific column are collected as affinity reagent-polypeptide complexes. Each of the affinity reagent-bound polypeptide fractions is sequentially applied to a patterned silicon solid support including a plurality of attachment sites, with each site configured to capture and bind an affinity reagent. After each affinity reagent-bound fraction is applied to the chip, fluorescence microscopy is used to measure and record the location of each occupied attachment site on the solid support.

The two non-captured fractions from the KEN-specific column are attached to structured nucleic acid particles. Each non-captured fraction is applied to the silicon solid support, with occupied attachment sites observed by fluorescence microscopy as with the captured fractions. After all four fractions are bound to the solid support, a patterned array of polypeptides has been generated for a polypeptide assay.

Example 8. Synthesis of FluoSphere™-Based Affinity Reagents

Figure 41:
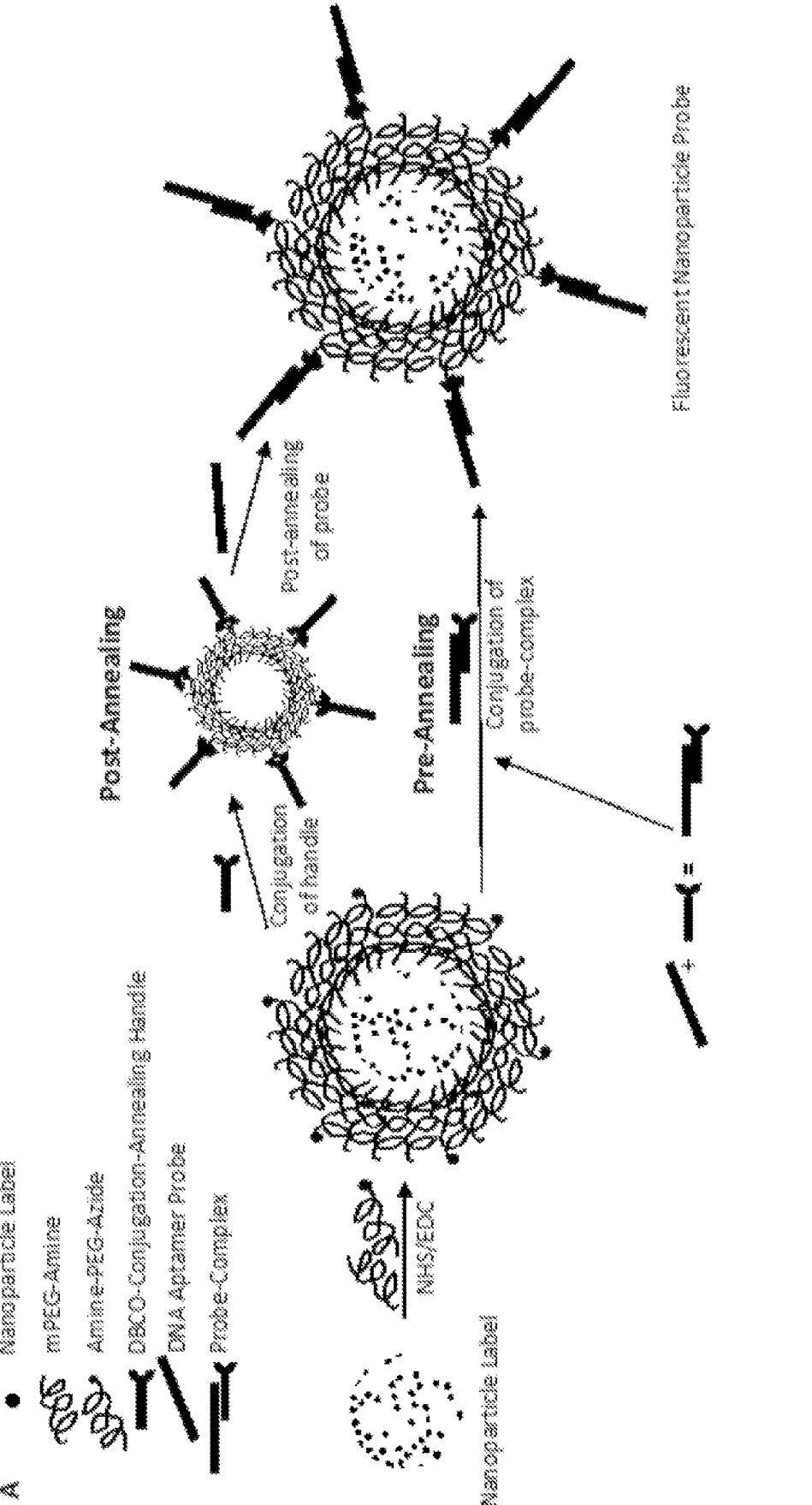
FIG. 41 shows a scheme for preparing FluoSphere™-based detectable probes.

Detectable affinity reagents were prepared using highly fluorescent organic nanoparticles including a modifiable surface chemistry. FIG. 41 illustrates a scheme for the preparation of FluoSphere™-based probes. 40 nm or 200 nm carboxylate-functionalized FluoSpheres™ (Thermo-Fisher) were modified with polyethylene glycol moieties to form a passivated layer surrounding the FluoSphere™ particles. FluoSpheres™ were activated by NHS-EDC activation prior to functionalization with PEG groups. The carboxylate functionalized FluoSpheres™ were combined with a 95:5 mixture of NH2—PEG and NH2—PEG-azide to form a PEGylated surface coating around the FluoSpheres™ containing azide functionalities. PEGylated FluoSpheres™ were incubated with 3'-dibenzocyclooctene (DBCO)-terminated oligonucleotides to covalently attach the oligonucleotide to the azide-terminated PEG moieties on the surface of the PEGylated layer. The incubation occurred in phosphate buffered solution (pH 7.4) overnight at about 24° C.

Following attachment of the oligonucleotides to the FluoSpheres™, attachment sites were provided for coupling of affinity reagents. The oligo-functionalized FluoSpheres™ were combined with an oligonucleotide including the complementary sequence to the functionalized oligo handle. The mixture was heated to 95° C. for 5 minutes, then annealed at 70° C. for 10 minutes before cooling to room temperature. Alternatively, the complementary oligonucleotide could be annealed to the DBCO-functionalized oligonucleotide before attachment to the FluoSpheres™. Sequences for the oligonucleotides are listed in Table 4.

TABLE 4

| Oligonucleotide Attachment Handle Sequences | |
|---|---|
| Oligo Name | Sequence |
| DBCO-terminated oligo | 3'-DBCO-GTTCGTCTTCTGCCGTATGCTCTA-5' (SEQ ID NO: 8) |
| Complementary oligo | 5'-CAA GCA GAA GAC GGC ATA CGA GAT CAT GCT TCC CCA GGG AGA TGG TTT GCC GGT GGG CAG GTT TAG GGT CTG CTC GGG ATT GCG GAG GAA CAT GCG TCG CAA ACG TGT AGA TCT CGG TGG TCG CCG TAT CAT T-3' (SEQ ID NO: 9) |

Example 9. Synthesis of Quantum Dot-Based Affinity Reagents

Detectable affinity reagents were prepared using highly fluorescent inorganic nanoparticles including a modifiable surface chemistry. 15 nm carboxylated quantum dots (Thermo Fisher) were modified with polyethylene glycol moieties to form a non-adhering layer surrounding the quantum dots particles. The quantum dots were combined with a 75:25 mixture of $NH_2$—PEG and $NH_2$—PEG-azide to form a PEGylated surface coating around the quantum dots containing azide functionalities. PEGylated quantum dots were incubated with 3'-DBCO-terminated oligonucleotides to covalently attach the oligonucleotide to the azide-terminated PEG moieties on the surface of the PEGylated layer. The incubation occurred in phosphate buffered solution (pH 7.4) overnight at about 24° C.

Following attachment of the oligonucleotides to the quantum dots, attachment sites were provided for coupling of affinity reagents. The oligo-functionalized quantum dots were combined with an oligonucleotide including the complementary sequence to the functionalized oligo handle. The mixture was heated to 95° C. for 5 minutes, then annealed at 70° C. for 10 minutes before cooling to room temperature. Alternatively, the complementary oligonucleotide could be annealed to the DBCO-functionalized oligonucleotide before attachment to the quantum dots. Sequences for the oligonucleotides are listed in Table 4.

Example 10. Optimization of FluoSphere™-Based Affinity Reagents

Various configurations of FluoSphere™-based detectable affinity reagents were examined to determine an optimal PEGylation strategy. Carboxylated FluoSpheres™ were PEGylated according to the method described in Example 8. Variables tested included PEG size, PEG types, and PEG surface density.

Figures 42A, 42B, 42C, 42D:
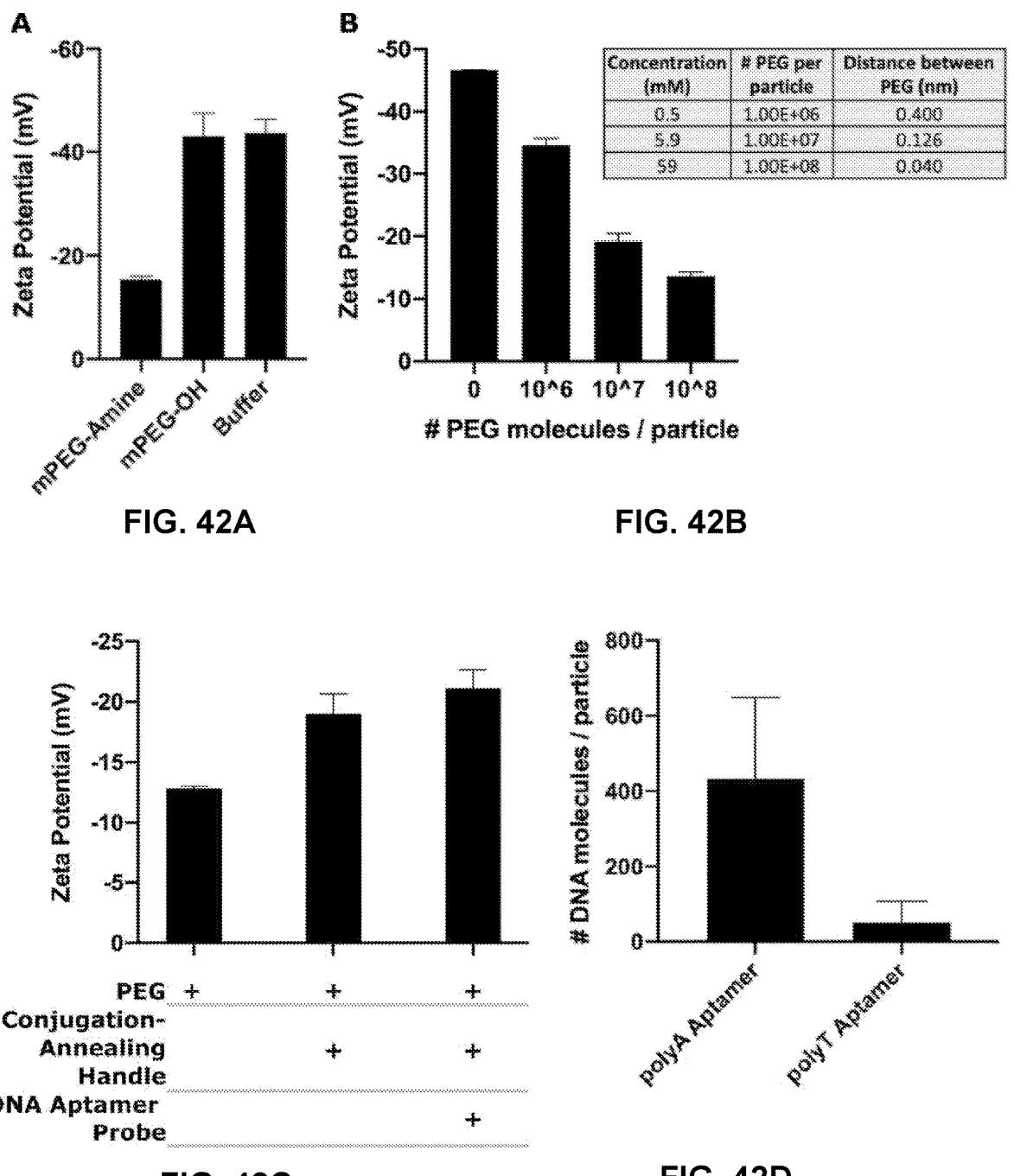
FIG. 42A shows characterization data for FluoSphere™-based detectable probes.
FIG. 42B shows characterization data for FluoSphere™-based detectable probes.
FIG. 42C shows characterization data for FluoSphere™-based detectable probes.
FIG. 42D shows characterization data for FluoSphere™-based detectable probes.

PEGylated FluoSpheres™ were characterized by measurement of Zeta potential to determine the extent of surface passivation. Zeta potential measurements were conducted in 2% phosphate buffer solution (PBS). FIG. 42A shows measured Zeta potential for FluoSpheres™ PEGylated with PEG-NH$_2$, PEG-OH, and NHS-activated FluoSpheres™. A reduction in magnitude of Zeta potential when reacted with the PEG-NH$_2$ demonstrates successful PEGylation and passivation of the FluoSphere™ surface. FIG. 42B shows Zeta potential as a function of the estimated surface density of PEG groups. FluoSpheres™ were prepared by the method of Example 8 with a varied PEG-NH$_2$ concentration of 0.5 mM, 5.9 mM or 59 mM PEG-NH$_2$. The Zeta potential is shown to decrease in magnitude as the estimated PEG surface density increases.

PEGylated FluoSpheres™ were coupled to oligonucleotides to provide attachment sites for coupling binding components. The strategy for providing attachment sites is described in Example 8. FIG. 42C shows measured Zeta potential for PEGylated FluoSpheres™ as oligonucleotides and attachment oligonucleotides are added to the FluoSphere™. Zeta potential is seen to increase in magnitude as nucleic acids are added, confirming successful coupling of the oligonucleotides to the FluoSpheres™. FIG. 42D shows coupling of aptamer components to oligo-coupled Fluo-Spheres™ FluoSpheres™ were coupled with poly-T oligonucleotides to form attachment sites that are configured to couple aptamer components displaying a poly-A annealing sequence. Average total number of annealed oligonucleotides was calculated by qPCR after annealing of the aptamer components. FIG. 42D shows successful coupling of poly-A-containing aptamer components, and little observed binding of poly-T-containing aptamers.

PEGylated FluoSpheres™ were prepared with differing sizes of PEG groups. FIG. 42E shows the measured Zeta potential for FluoSpheres™ PEGylated with mPEG-12, mPEG-24, mPEG-36, mPEG-45, or mPEG-112. Zeta potential is seen to decrease in magnitude as the size of the PEG group increases. FIG. 42F shows the polydispersity index (PDI) for PEGylated FluoSpheres™ as a function of PEG size. PDI was measured by dynamic light scattering. Beyond a PEG size of mPEG-36, the PDI is observed to increase, suggesting decreased colloidal stability.

Example 11. Binding Characterization of FluoSphere™-Based Affinity Reagents

Binding of FluoSphere™-based affinity reagents was tested to assess their target-binding characteristics. Fluo-Sphere™-based retaining components were prepared by the method described in Example 8. Aptamers were pre-annealed with the attachment oligonucleotide at 95° C. for 5 minutes, then coupled to the FluoSpheres™. FluoSpheres™ were prepared with the following aptamers: P7-B1-P5 (target histidine tag), P7-H3T-P5 (target histidine tag) and P7-VEGF Aptamer 89 (target VEGF).

Figure 43A:
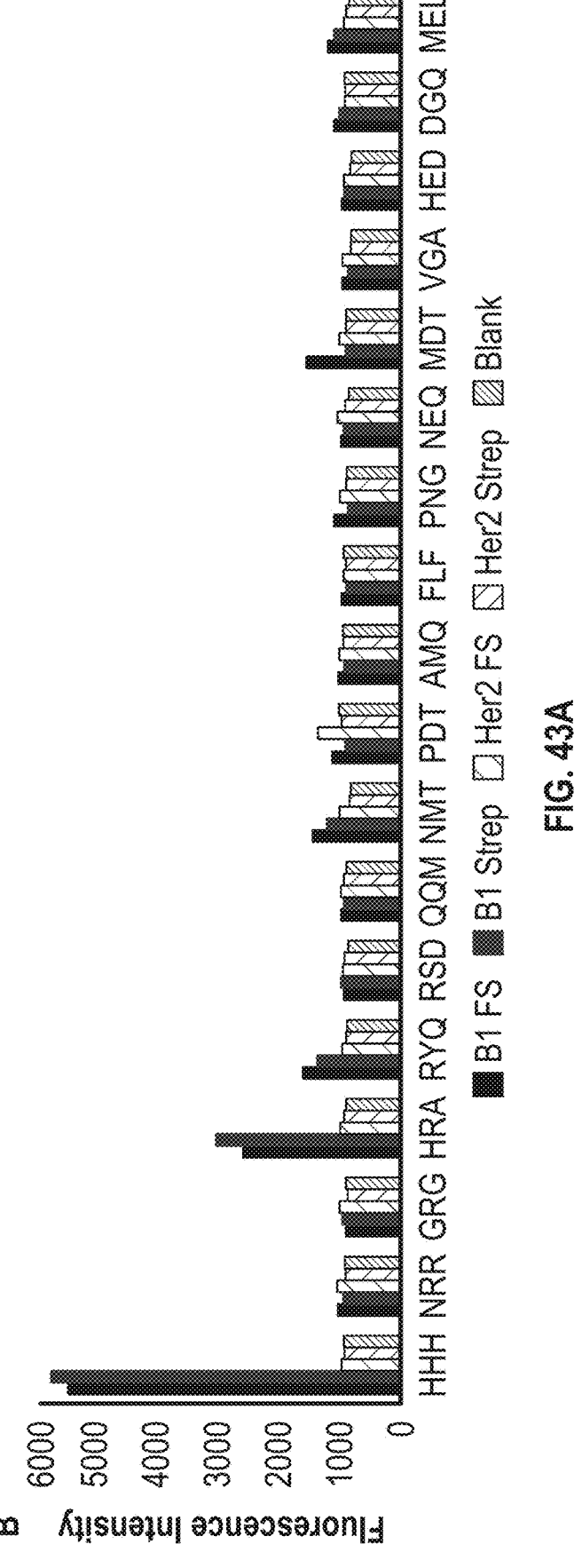
FIG. 43A shows binding characterization data for Fluo-Sphere™-based detectable probes.
Figure 45A:
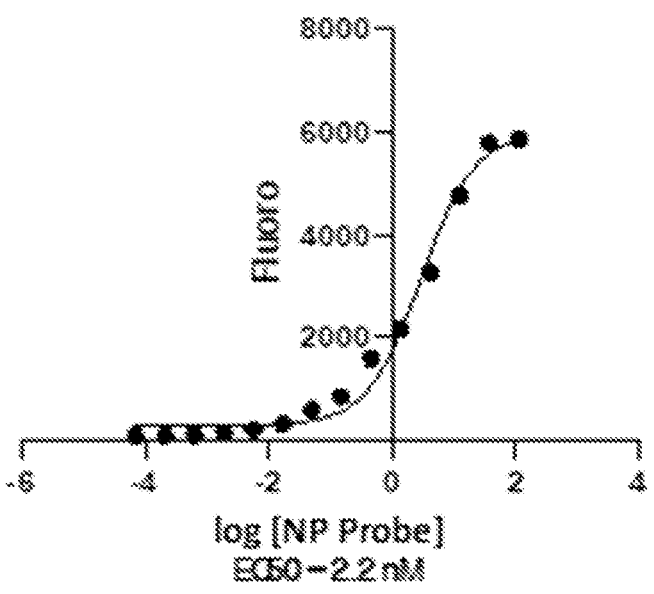
FIG. 45A shows binding characterization data for Fluo-Sphere™-based detectable probes.
Figure 45B:
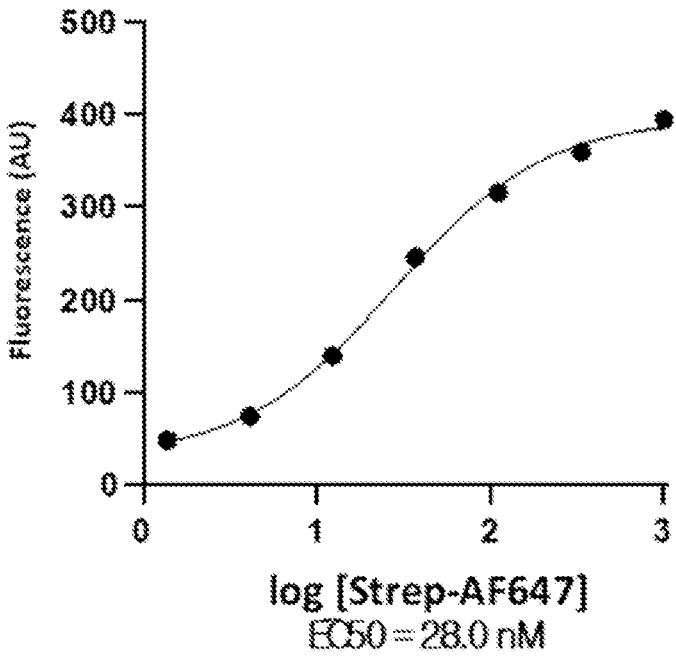
FIG. 45B shows binding characterization data for Alexa-Fluor®-based aptamers.
Figures 45C, 45D:
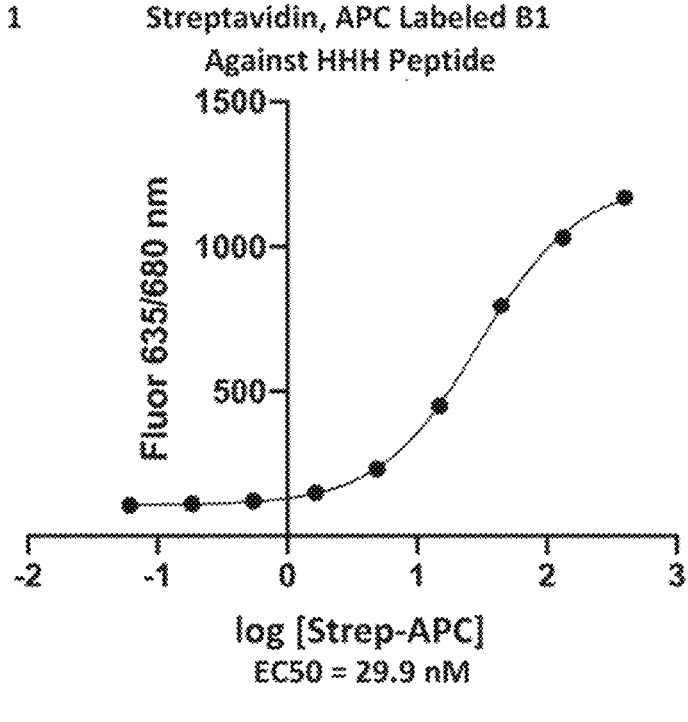
FIG. 45C shows binding characterization data for APC-based aptamers.
FIG. 45D shows binding characterization data for Sure-Light™ APC-based aptamers.

Peptide targets for binding studies were prepared by fixing biotinylated trimer amino-acid sequences to a streptavidin coated plate. FIG. 43A shows binding of various aptamer formulations (On-target: P7-B1-P5-FS are Fluo-Sphere™ probes, P7-B1-P5-strep are labeled with streptavidin-Alexa-Fluor® 647; Off-target: Her2-FS are Fluo-Sphere™ probes, Her2-strep are labeled with streptavidin Alexa-Fluor® 647) against various peptide trimer targets. P7-B1-P5-containing FluoSphere™ probes are observed to have a similar binding profile to P7-B1-P5-Strep and a dissimilar binding profile to Her2 specific affinity reagents.

Dissociation constants were measured for FluoSphere™-based affinity reagents against various targets. Targets were prepared by coupling biotinylated targets (protein or peptide) to streptavidin plates. FIG. 43B displays binding measurements for P7-B1-P5 aptamer-containing FluoSphere™ affinity reagents against a histidine-tagged Her2 protein target. The EC50 was measured to be 6.5 nM, suggesting that the FluoSphere™-based P7-B1-P5 affinity reagents are capable of successfully binding the histidine tag of the Her2-His conjugate. FIG. 43C displays binding measurements for P7-H3T-P5 aptamer against an HHH trimer peptide. The measured EC50 is 3.4 nM, suggesting that the FluoSphere™-based affinity reagents is capable of binding the trimer target. FIG. 43D shows measured binding as a function of probe concentration for a P7-VEGF-Aptamer 89-based FluoSphere™ affinity reagent against a VEGF target (on target) and myoglobin (off target). A much higher fluorescence intensity is measured as a function of affinity reagent concentration for binding with VEGF, suggesting that the FluoSphere™-based probe has binding affinity for its intended target.

Example 12. Stability Characterization of FluoSphere™-Based Affinity Reagents The stability of prepared FluoSphere™-based detectable affinity reagents was tested to determine the binding activity of the affinity reagents after extended storage at 4° C. in PBS buffer. Detectable affinity reagents were prepared by the method described in Example 8. Detectable affinity reagents were prepared with P7-B1-P5 aptamer (target histidine tag). Stability measurements were also performed for single P7-B1-P5 aptamers coupled to commercially available fluorescent labels Streptavidin-Alexa Fluor® 647 Conjugate (Thermo Fisher) and Streptavidin-APC (Thermo Fisher). FIGS. 44A-44C show affinity measurements for each detectable affinity reagent at indicated timepoints. At each time interval, the affinity of detectable affinity reagents was evaluated as described in Example 11. FluoSphere™-based detectable affinity reagents showed a stronger affinity to targets for a longer period of time than the streptavidin conjugates. Surprisingly, the P7-B1-P5 FluoSphere™-based detectable probes have substantially improved stability compared to commercial fluorescent alternative.

Example 13. Binding Characterization of FluoSphere™-Based Affinity Reagents

The binding affinity of P7-B1-P5-coupled FluoSphere™-based Affinity reagents was measured in comparison to the binding affinity of single-aptamer P7-B1-P5-fluorophore conjugates. P7-B1-P5-coupled FluoSphere™-based detectable affinity reagents were prepared according to the method of Example 8. Single-aptamer P7-B1-P5 conjugates were also prepared for the following fluorophores: Streptavidin-Alexa Fluor® 647 (Thermo Fisher), Streptavidin-APC (Thermo Fisher), and SureLight™ APC (Columbia Biosciences). Binding curves were measured against a histidine (HHH) peptide using various concentrations of probe or aptamer. Dissociation constants (EC50) were derived from the binding measurement data.

FIGS. 45A-45D show plots of the dissociation constant for the FluoSphere™-based affinity reagents, Alexa Fluor® aptamers, APC aptamers, and SureLight™ APC aptamers, respectively. The FluoSphere™-based affinity reagents were measured to have an EC50 of about 2.2 nM, The Alexa-Fluor® and APC aptamers had EC50 measurements of 28.0 nM and 29.9 nM, respectively. The SureLight™ APC aptamer had a measured EC50 of 2.3 nM. The Fluo-Sphere™-based affinity reagent appeared to bind the histidine peptide target comparably or better, depending upon the exact detectable probe system utilized.

Example 14. Binding Characterization of Quantum Dot-Based Affinity Reagents

Detectable affinity reagents containing a quantum dot fluorophore as a retaining component were prepared according to the method of Example 9. The quantum dot-based affinity reagents were coupled with P7-B1-P5 aptamers (target histidine tag). Binding measurements were made to determine the binding properties of the quantum dot-based affinity reagents.

Figure 24A:
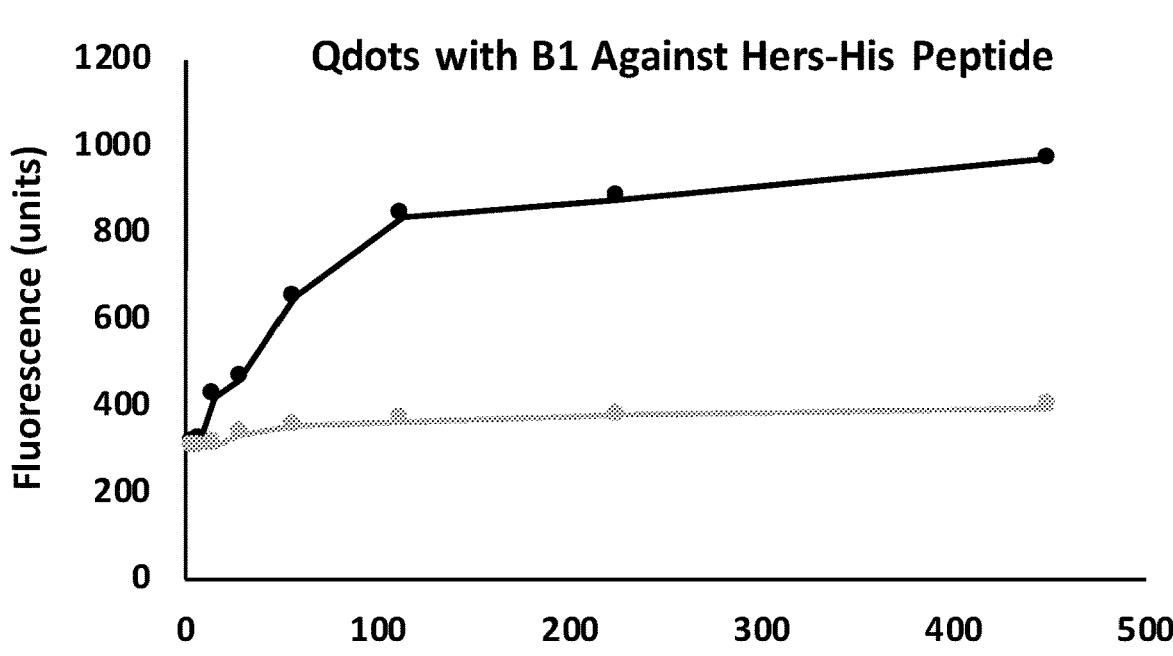
FIG. 24A shows binding characterization data for quantum dot-based detectable probes.
Figure 24B:
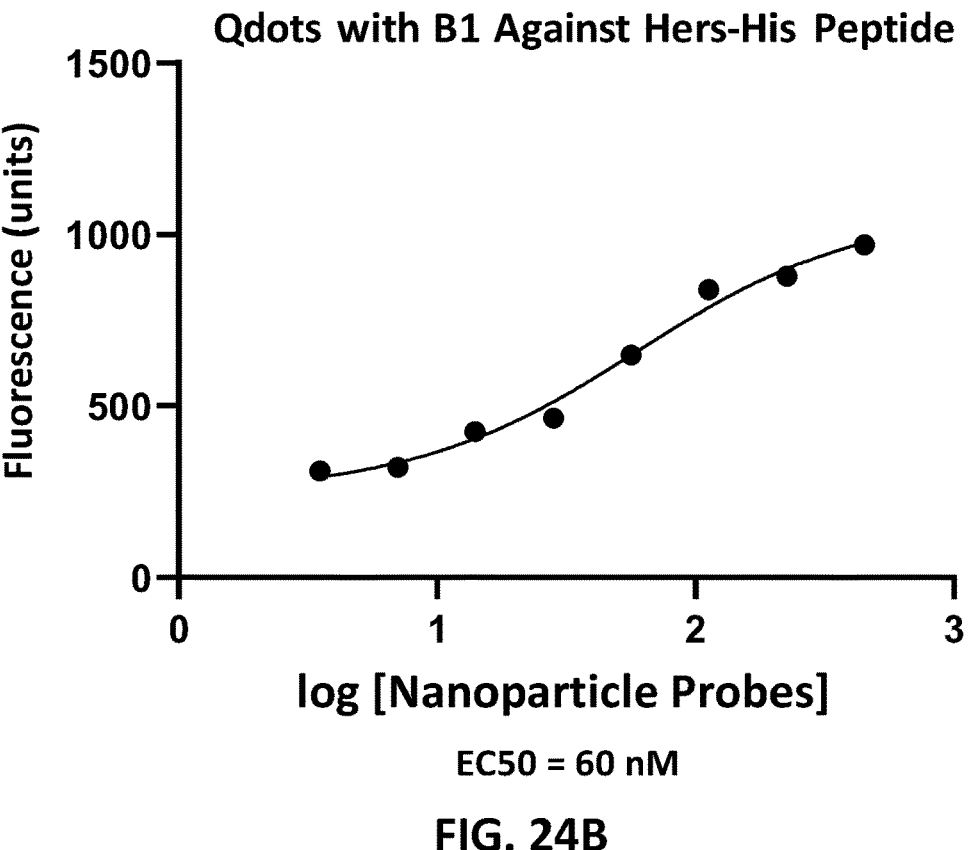
FIG. 24B shows binding characterization data for quantum dot-based detectable probes.

FIGS. 24A and 24B display binding measurement data for the P7-B1-P5-quantum dot-based affinity reagents. FIG. 24A displays fluorescence measurements for quantum dot-based P7-B1-P5 affinity reagents that were contacted with his-tagged Her2 proteins (on-target binding) and myoglobin (off-target control). Fluorescent signal is observed to increase with increasing affinity reagent concentration against the Her2-his target. Little change is observed in the fluorescent signal when affinity reagents are contacted to the myoglobin control, suggesting that the quantum-dot based P7-B1-P5 aptamers are capable of distinguishing and binding their intended target. FIG. 24B displays EC50 measurement data against HHH peptide for the quantum dot-based P7-B1-P5 affinity reagents. The EC50 is measured to be 60 nM, suggesting that the quantum dot-based affinity reagents bind with their intended target.

Example 15. Synthesis of FluoSphere™-Based Affinity Reagents

Figure 46:
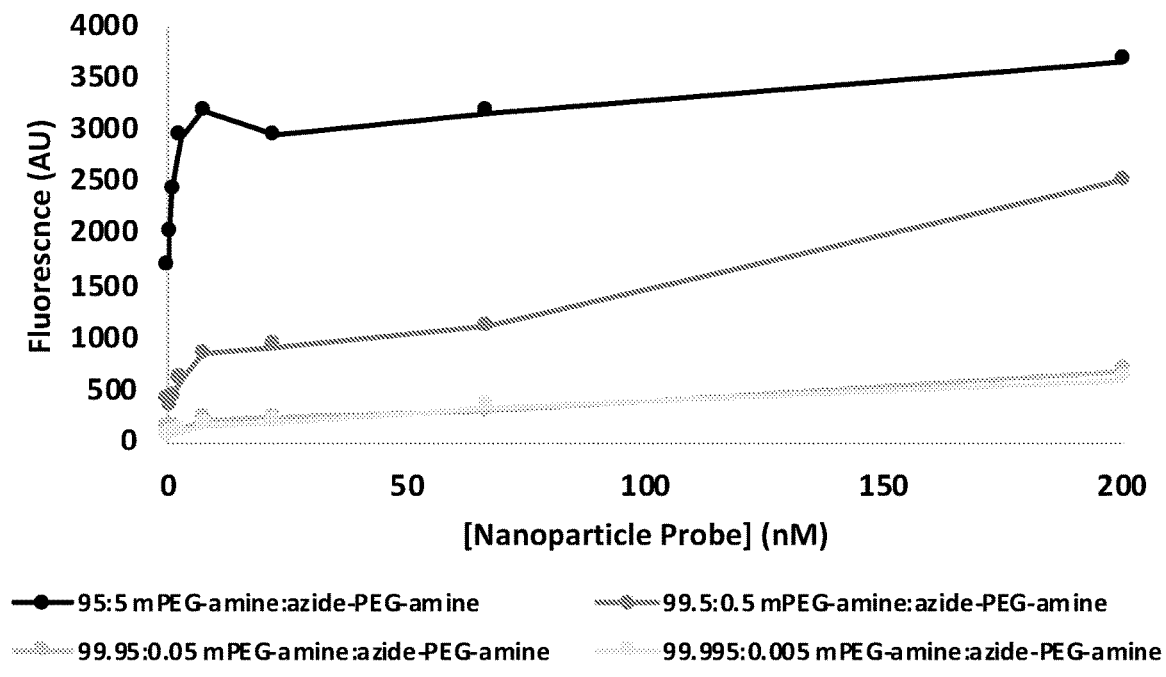
FIG. 46 shows binding data for FluoSphere™-based detectable probes with differing quantities of available affinity reagent attachment sites.

FluoSphere™-based affinity reagents with varying ratios of functionalized to non-functionalized groups were prepared. Binding of the FluoSphere™-based affinity reagents was tested to assess an optimal amount of functionalized amount of functionalized groups on the affinity reagent surface. FluoSphere™-based affinity reagents with ratios of mPEG-amine:amine-PEG-azide of 95:5, 99.5:0.5, 99.95:0.05, and 99.995:0.005 were fabricated. After fabrication, the affinity reagents were attached to B1 aptamers as described in Example 8, and evaluated in plate-based binding studies. The ratio of 95:5 showed about 1.5× higher signal than the ratio of 99.5:0.5 (see FIG. 46). An increase in the quantity of available azide groups (the attachment group for the attachment of oligonucleotides to which aptamers were annealed) increases the amount of on-target binding of the affinity reagent when fully fabricated.

Figure 47:
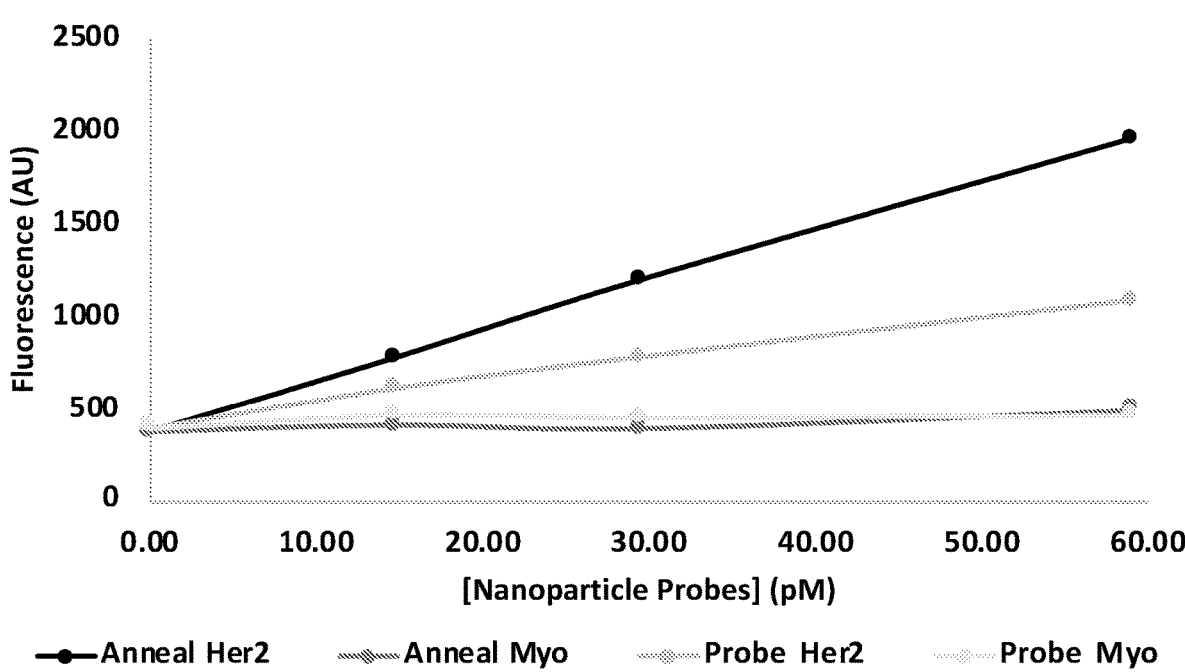

Example 16. Direct Conjugation of Affinity Reagents to FluoSphere™-Based Affinity Reagents FluoSphere™-based affinity reagents were prepared via the direct conjugation of binding components to the functionalized nanoparticles. B1 aptamers containing a 5'-DBCO functional group were contacted with functionalized Fluo-Spheres™ containing surface-displayed mPEG-azide groups. Detectable affinity reagents were formed by the reaction of azide moieties with DBCO moieties. Binding of FluoSphere™-based affinity reagents prepared by the direct conjugation strategy and FluoSphere™-based affinity reagents prepared via oligonucleotide annealing (see Example 8) was compared against a Her2-his tag target. FIG. 47 displays on-target Her2-his binding data for directly-conjugated affinity reagents and annealed affinity reagents, as well as binding for both affinity reagent types against a myoglobin (off-target) control. The observed binding of the directly-conjugated affinity reagents was observed to be lower than that of the annealed affinity reagents, but substantially exceeded the binding seen against the negative control.

Example 17. Enzymatic Incorporation of Fluorescent dUTP Nucleotides

AlexaFluor-647 dUTP nucleotides were enzymatically incorporated to the 3' end region of an aptamer, as described in FIG. 49B. Fluorophores incorporated to the aptamers were visualized at 647 nm, as illustrated in FIG. 52 showing successful incorporation of fluorophores.

Example 18. AlexaFluor-647 NHS Ester Conjugation to AminoAllyl dUTP

AAdUTP nucleotides were incorporated into an aptamer, using the method described in FIG. 49B. The resulting labeled aptamers were chemically conjugated to fluorophores, run on a gel, treated with SYBR and visualized at 488 nm to show doubled stranded DNA (FIG. 53A), and 647 nm to show the presence of fluorophores (FIG. 53B).

Example 19. dsDNA-647 Labeled Aptamer Concentration Measurements dsDNA-647 labeled aptamer concentration was measured using absorbance at 260 nm, the results are shown in FIG. 54. To examine the conjugation efficiency of AlexaFluor-647 to the aptamers a fluorophore standard curve was used (FIG. 55A), to determine the fluorophore concentration (FIG. 55B). The Fluorophore concentration measurement was used to determine the Fluorophore:DNA ratio which estimates the degree of labeling, as shown in FIG. 56.

Example 20. dsDNA-647 On-Target Binding and Imaging

To assess on target binding and imaging of a labeled aptamer an experiment was conducted using a dsDNA-647 labeled aptamer specific to the epitope HHH. HHH peptides were immobilized on a microplate surface and exposed to the labeled aptamer, as shown in FIG. 57A. FIG. 57B shows binding of the labeled aptamer to the HHH peptide, FIG. 57C shows lack of binding to a negative control peptide, MetGluThr.

To assess imaging the labeled aptamers were visualized on a custom 20× objective epifluorescent microscope at various concentrations, as shown in FIG. 57D.

While preferred embodiments of the present invention have been shown and described herein, it will be apparent to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

SEQUENCE LISTING

```
Sequence total quantity: 17
SEQ ID NO: 1            moltype = AA  length = 5
FEATURE                 Location/Qualifiers
REGION                  1..5
                        note = Description of unidentified: Target peptide sequence
source                  1..5
                        mol_type = protein
                        organism = unidentified
SEQUENCE: 1
AAAAA                                                        5

SEQ ID NO: 2            moltype = AA  length = 5
FEATURE                 Location/Qualifiers
REGION                  1..5
                        note = Description of unidentified: Target peptide sequence
source                  1..5
                        mol_type = protein
                        organism = unidentified
SEQUENCE: 2
AAAAC                                                        5

SEQ ID NO: 3            moltype = AA  length = 5
FEATURE                 Location/Qualifiers
REGION                  1..5
                        note = Description of unidentified: Target peptide sequence
source                  1..5
                        mol_type = protein
                        organism = unidentified
SEQUENCE: 3
CAAAA                                                        5

SEQ ID NO: 4            moltype = AA  length = 5
FEATURE                 Location/Qualifiers
REGION                  1..5
                        note = Description of unidentified: Target peptide sequence
source                  1..5
                        mol_type = protein
```

```
                        organism = unidentified
SEQUENCE: 4
CAAAC                                                                     5

SEQ ID NO: 5           moltype = AA   length = 5
FEATURE                Location/Qualifiers
REGION                 1..5
                       note = Description of unidentified: Target peptide sequence
source                 1..5
                       mol_type = protein
                       organism = unidentified
SEQUENCE: 5
CAAAD                                                                     5

SEQ ID NO: 6           moltype = AA   length = 4
FEATURE                Location/Qualifiers
REGION                 1..4
                       note = Description of synthetic construct: Synthetic peptide
source                 1..4
                       mol_type = protein
                       organism = synthetic construct
SEQUENCE: 6
RGDS                                                                     4

SEQ ID NO: 7           moltype = AA   length = 4
FEATURE                Location/Qualifiers
REGION                 1..4
                       note = Description of synthetic construct: Synthetic peptide
source                 1..4
                       mol_type = protein
                       organism = synthetic construct
SEQUENCE: 7
RGES                                                                     4

SEQ ID NO: 8           moltype = DNA   length = 24
FEATURE                Location/Qualifiers
misc_feature           1..24
                       note = Description of synthetic construct: Synthetic
                        oligonucleotide
source                 1..24
                       mol_type = other DNA
                       organism = synthetic construct
SEQUENCE: 8
atctcgtatg ccgtcttctg cttg                                              24

SEQ ID NO: 9           moltype = DNA   length = 133
FEATURE                Location/Qualifiers
misc_feature           1..133
                       note = Description of synthetic construct: Synthetic
                        polynucleotide
source                 1..133
                       mol_type = other DNA
                       organism = synthetic construct
SEQUENCE: 9
caagcagaag acggcatacg agatcatgct tccccaggga gatggtttgc cggtgggcag        60
gtttagggtc tgctcgggat tgcggaggaa catgcgtcgc aaacgtgtag atctcggtgg       120
tcgccgtatc att                                                          133

SEQ ID NO: 10          moltype = AA   length = 5
FEATURE                Location/Qualifiers
REGION                 1..5
                       note = Description of unidentified: Target peptide sequence
source                 1..5
                       mol_type = protein
                       organism = unidentified
SEQUENCE: 10
TAAAL                                                                     5

SEQ ID NO: 11          moltype = AA   length = 5
FEATURE                Location/Qualifiers
REGION                 1..5
                       note = Description of unidentified: Target peptide sequence
source                 1..5
                       mol_type = protein
                       organism = unidentified
SEQUENCE: 11
YAAAS                                                                     5

SEQ ID NO: 12          moltype = AA   length = 5
```

-continued

```
FEATURE            Location/Qualifiers
REGION             1..5
                   note = Description of unidentified: Target peptide sequence
source             1..5
                   mol_type = protein
                   organism = unidentified
SEQUENCE: 12
MAAAT                                                              5

SEQ ID NO: 13      moltype = AA   length = 5
FEATURE            Location/Qualifiers
REGION             1..5
                   note = Description of unidentified: Target peptide sequence
source             1..5
                   mol_type = protein
                   organism = unidentified
SEQUENCE: 13
AAAAD                                                              5

SEQ ID NO: 14      moltype = AA   length = 5
FEATURE            Location/Qualifiers
REGION             1..5
                   note = Description of unidentified: Target peptide sequence
source             1..5
                   mol_type = protein
                   organism = unidentified
SEQUENCE: 14
YAAAA                                                              5

SEQ ID NO: 15      moltype = AA   length = 5
FEATURE            Location/Qualifiers
REGION             1..5
                   note = Description of unidentified: Target peptide sequence
source             1..5
                   mol_type = protein
                   organism = unidentified
SEQUENCE: 15
YAAAC                                                              5

SEQ ID NO: 16      moltype = AA   length = 5
FEATURE            Location/Qualifiers
REGION             1..5
                   note = Description of unidentified: Target peptide sequence
source             1..5
                   mol_type = protein
                   organism = unidentified
SEQUENCE: 16
YAAAD                                                              5

SEQ ID NO: 17      moltype = AA   length = 5
FEATURE            Location/Qualifiers
REGION             1..5
                   note = Description of unidentified: Target peptide sequence
source             1..5
                   mol_type = protein
                   organism = unidentified
SEQUENCE: 17
YAAAY                                                              5
```

What is claimed is:

1. A method for detecting analytes comprising:

providing an array of different analytes attached to a solid support, wherein the different analytes are attached to the solid support by structured nucleic acid particles, delivering to the array of different analytes a fluidic medium comprising a plurality of detectable probes, each of the detectable probes comprising a retaining component attached to a binding component and a plurality of label components, each binding component of the plurality of detectable probes is configured to bind to two or more different analytes of the array of different analytes, and after delivering the fluidic medium to the array of different analytes, acquiring signals from label components of the detectable probes bound to analytes of the array of different analytes, thereby detecting at least two different analytes of the array of different analytes, wherein the retaining component comprises a first face and a second face, wherein the binding component is attached to the first face of the retaining component, and wherein the plurality of label components is attached to the second face of the retaining component.

2. The method of claim 1, wherein an analyte of the different analytes comprises a polypeptide, a protein, a peptide, an oligopeptide, a nucleic acid, or an oligonucleotide.

3. The method of claim 2, wherein the analyte comprises a polypeptide.

4. The method of claim 1, further comprising quantifying the different analytes.

5. The method of claim 1, further comprising determining the location of the different analytes on the solid support.

6. The method of claim 1, wherein the array of different analytes comprises at least $10^6$ analytes.

7. The method of claim 1, wherein an analyte of the different analytes comprises a single molecule.

8. The method of claim 1, wherein a label component of the plurality of label components comprises a fluorophore, luminophore, chromophore, nanoparticle, heavy atom, radioactive isotope, mass label, charge label, spin label, receptor, ligand, nucleic acid barcode, polypeptide barcode, or polysaccharide barcode.

9. The method of claim 8, wherein the label component comprises a fluorophore.

10. The method of claim 8, wherein the label component comprises a nucleic acid barcode.

11. The method of claim 10, wherein the signal from the nucleic acid barcode is amplified.

12. The method of claim 1, wherein the structured nucleic acid particles each comprise nucleic acid origami or a nucleic acid nanoball.

13. The method of claim 1, wherein the retaining component of each of the detectable probes comprises nucleic acid origami or a nucleic acid nanoball.

14. The method of claim 1, wherein each of the detectable probes comprise two or more binding components.

15. The method of claim 1, wherein the binding component comprises an antibody, antibody fragment, lectin, functional lectin fragment, avidin, streptavidin, or aptamer.

16. The method of claim 1, wherein the solid support is non-porous.

17. The method of claim 1, wherein the solid support comprises glass, plastic, nylon, ceramic, silica, silicon, carbon, metal, or a polymer.

18. The method of claim 1, wherein the array of different analytes comprises sites that are separated by less than 100 microns, 50 microns, 10 microns, 5 microns, 1 micron, or 0.5 micron.

19. A composition comprising:

an array of different analytes attached to a solid support, wherein the different analytes are attached to the solid support by structured nucleic acid particles, and a fluidic medium comprising a plurality of detectable probes contacted to the array of different analytes, detectable probes of the plurality of detectable probes being unattached to the solid support, each of the detectable probes comprising a retaining component attached to one or more binding components and a plurality of label components, each of the one or more binding components is configured to bind to two or more different analytes of the array of different analytes, wherein the retaining component comprises a first face and a second face, wherein the one or more binding component is attached to the first face of the retaining component, and wherein the plurality of label components is attached to the second face of the retaining component.

20. The method of claim 19, wherein each binding component of the plurality of detectable probes recognizes an epitope common to the two or more different analytes of the array of different analytes.

21. The method of claim 20, wherein the epitope contains a contiguous 3, 4, or 5 amino acid sequence.

22. The method of claim 20, wherein the epitope contains a post-translational modification.

23. A system, comprising:

an array of structured nucleic acid particles attached to a solid support, wherein structured nucleic acid particles of the array of structured nucleic acid particles are attached to a plurality of analytes, wherein each of the structured nucleic acid particles is detectable at single-analyte resolution;

a plurality of detectable probes, each of the detectable probes comprising a retaining component attached to one or more binding components and a plurality of label components, each of the one or more binding components is configured to bind to two or more different analytes of the plurality of analytes, wherein the retaining component comprises a first face and a second face, wherein the one or more binding components are attached to the first face of the retaining component, and wherein the plurality of label components is attached to the second face of the retaining component;

a fluidic device that is configured to deliver the plurality of detectable probes to the array of structured nucleic acid particles, and a detection system that is configured to detect signals from detectable probes bound to analytes on the array of structured nucleic acid particles at single-analyte resolution.

* * * * *